(12) United States Patent
Sligar et al.

(10) Patent No.: US 7,592,008 B2
(45) Date of Patent: *Sep. 22, 2009

(54) MEMBRANE SCAFFOLD PROTEINS

(75) Inventors: Stephen G. Sligar, Urbana, IL (US);
Timothy H. Bayburt, Urbana, IL (US);
Mary A. Schuler, Urbana, IL (US);
Natanya R. Civjan, Urbana, IL (US);
Ylena V. Grinkova, Urbana, IL (US);
Ilia G. Denisov, Urbana, IL (US);
Stephen James Grimme, Urbana, IL (US)

(73) Assignee: The Board of Trustees of the University of Illinois, a body corporate and politic of the State of Illinois, Urbana, IL (US)

( * ) Notice: Subject to any disclaimer, the term of this patent is extended or adjusted under 35 U.S.C. 154(b) by 50 days.

This patent is subject to a terminal disclaimer.

(21) Appl. No.: 11/033,489

(22) Filed: Jan. 11, 2005

(65) Prior Publication Data

US 2005/0182243 A1    Aug. 18, 2005

Related U.S. Application Data

(63) Continuation-in-part of application No. 10/465,789, filed on Jun. 18, 2003, now Pat. No. 7,083,958, which is a continuation-in-part of application No. 09/990,087, filed on Nov. 20, 2001, now Pat. No. 7,048,949.

(60) Provisional application No. 60/252,233, filed on Nov. 20, 2000, provisional application No. 60/536,281, filed on Jan. 13, 2004.

(51) Int. Cl.
A61K 39/00    (2006.01)
A61K 38/00    (2006.01)
A61K 39/12    (2006.01)
A61K 39/02    (2006.01)
A61K 39/002   (2006.01)

(52) U.S. Cl. ............. 424/184.1; 424/185.1; 424/204.1; 424/234.1; 424/265.1; 424/274.1; 424/277.1; 424/400

(58) Field of Classification Search ........................ None
See application file for complete search history.

(56) References Cited

U.S. PATENT DOCUMENTS

| | | | |
|---|---|---|---|
| 5,206,086 A | 4/1993 | Sparks et al. | |
| 5,652,339 A | 7/1997 | Lerch et al. | |
| 6,172,262 B1 | 1/2001 | McQuade et al. | |
| 6,248,353 B1 | 6/2001 | Singh | |
| 6,514,523 B1 | 2/2003 | Sparks | |
| 6,828,306 B2 | 12/2004 | Sparks | |
| 7,048,949 B2* | 5/2006 | Sligar et al. | 424/499 |
| 7,083,958 B2 | 8/2006 | Sligar et al. | |
| 2004/0053384 A1 | 3/2004 | Sligar et al. | |
| 2005/0182243 A1 | 8/2005 | Sligar et al. | |
| 2006/0211092 A1 | 9/2006 | Sligar et al. | |
| 2006/0211093 A1 | 9/2006 | Sligar et al. | |

FOREIGN PATENT DOCUMENTS

| | | |
|---|---|---|
| EP | 0663407 B1 | 7/2002 |
| WO | 9317031 A2 | 9/1993 |
| WO | 0075187 A1 | 12/2000 |
| WO | 0102551 A2 | 1/2001 |
| WO | 0240501 A2 | 5/2002 |

OTHER PUBLICATIONS

Bayburt et al., Reconstitution and imaging of a membrane protein in a nanometer-size phospholipid bilayer. Journal of Structural Biology 123:37-44, 1998.*

Koppaka et al., The structure of human lipoprotein A-I. J. Biol. Chem. 274: 14541-14544, 1999.*

McManus et al. (Feb 2000) "Distinct Central Amphipathic α-Helices in Apolipoprotein A-I Contribute to the in Vivo Maturation of High Density Lipoprotein by Either Activating Lechithin-Cholesterol Acyltransferase or Binding Lipids," J. Biol. Chem. 275(7):5043-5051.

Miller, J.P. et al. (1996) "X-ray Diffraction Analysis of Cytochrome P450 2B4 Reconstituted into Liposomes" Biochemistry 35:1466-1474.

Minnich et al. (1992) "Site-Directed Mutagenesis and Structure-Function Analysis of the Human Apolipoprotein A-I. Relation Between Lecithin-Cholesterol Acyltransferase Activation and Lipid Binding," J. Biol. Chem. 267(23) 16553-16560.

Mukhopadhyay, R. et al. (Mar. 31, 2000) "A scanning tunneling microscopy study of *Clostridium pasteurianum* rubredoxin" J. Inorg. Biochem. 78:251-254.

Phillips, J.C. et al. (1997) "Predicting the Structure of Apolipoprotein A-I in Reconstituted High-Density Lipoprotein Disks" Biophysics Journal 73:2337-2346.

(Continued)

*Primary Examiner*—Ruixiang Li
(74) *Attorney, Agent, or Firm*—Greenlee Winner and Sullivan, PC

(57) ABSTRACT

The membrane scaffold proteins (MSP) of the present invention assemble with hydrophobic or partially hydrophobic proteins to form soluble nanoscale particles which preserve native structure and function; they are improved over liposomes and detergent micelles, in terms of stability and preservation of biological activity and native conformation. In the presence of phospholipid, MSPs form nanoscopic phospholipid bilayer disks, with the MSP stabilizing the particle at the perimeter of the bilayer domain. The particle bilayer structure allows manipulation of incorporated proteins in solution or on solid supports, including for use with such surface-sensitive techniques as scanning probe microscopy or surface plasmon resonance. The nanoscale particles, which are robust in terms of integrity and maintenance of biological activity of incorporated proteins, facilitate pharmaceutical and biological research, structure/function correlations, structure determinations, bioseparations, and drug discovery.

13 Claims, 15 Drawing Sheets

OTHER PUBLICATIONS

Reardon et al. (Oct. 2001) "In Vivo Studies of HDL Assembly and Metabolism Using Adenovirus-Mediated Transfer of ApoA-I Mutants in ApoA-I-Deficient Mice," Biochem. 40(45):13670-13680.

Rezaie et al. (1992), "Expression and Purification of a Soluble Tissue Factor Fusion Protein with an Epitope for an Unusual Calcium-Dependent Antibody," Protein Expression and Purification 3:453-460.

Robinson, C.R. and Sligar, S.G. (1998) "Changes in solvation during DNA binding and cleavage are critical to altered specificity of the EcoRI endonuclease" Proc. Natl. Acad. Sci. USA 95:2186-2191.

Robinson, C.R. and Sauer, R.T. (May 1998) "Optimizing the stability of single-chain proteins by linker length and composition mutagenesis" Proc. Natl. Acad. Sci. USA 95(1):5929-5934.

Rogers et al. (1997) "Truncation of the Amino Terminus of Human Apolipoprotein A-I Substantially Alters Only the Lipid-Free Conformation," Biochem. 36(2):288-300.

Rogers, D.P. et al. (1998) "Structural Analysis of Apolipoproein A-I: Effects of Amino-and Carboxy-Terminal Deletions on the Lipid-Free Structure" Biochemistry 37:945-955.

Rogers, D.P. et al. (1998) "The Lipid-Free Structure of Apolipoprotein A-I: Effects of Amino-Terminal Deletions" Biochemistry 37(34):11714-11725.

Rosseneu et al. (1992) "Contribution of Helix-Helix Interactions to the Stability of Apolipoprotein-Lipid Complexes," International Congress Series 1001:(High Density Lipoproteins Atheroscler III) 105-114.

Salamon, Z. (1997) "Coupled Plasmon—Waveguide Resonators: A New Spectroscopic Tool for Probing Proteolipid Film Structure and Properties" Biophys. Journal 73:2791-2797.

Savelli, et al. (2000), "Enzyme activity and stability control by amphiphilic self-organizing systems in aqueous solutions," Curr. Opin. Colloid & Interface Science 5:111-117.

Schafmeister, C. et al. (1993) "Structure at 2.5 λof a Designed Peptide That Maintains Solubility of Membrane Proteins" Science 262:734-738.

Scott et al. (Dec. 2001) "The N-Terminal Globular Domain and the First Class A Amphipathic Helix of Apolioporotein A-I are Important for Lecithin: Cholesterol Acyltransferase Activation and the Maturation of High Density Lipoprotein in Vivo," J. Biol. Chem. 276(52):48716-48754.

Segrest, J.P. et al. (Nov. 1999) "A Detailed Molecular Belt Model for Apolipoprotein A-I in Discoidal High Density Lipoprotein" J. Biol. Chem. 274(45):31755-31758.

Shaw, A.W. et al., (Jan 2004) "Phospholipid Phase Transitions in Homogeneous Nanometer Scale Bilayer Discs"; FEBS Letters 556:260-264.

Sklar, L.A. et al. (May 2000) "Solubilization and Display of G Protein-Coupled Receptors on Beads for Real-Time Fluorescence and Flow Cytometric Analysis" Bio Techniques 28(5):976-985.

Sligar, S. (2003) "Finding a Single-Molecule Solution for Membrane Proteins"; Biochem. Biophys. Res. Comm. 312:115-119.

Sorci-Thomas et al. (1997) "Alteration in Apolipoprotein A-I 22-Mer Repeat Order Results in a Decrease in Lecithin: Cholesterol Acyltransferase Reactivity," J. Biol. Chem. 272(11):7278-7284.

Sorci-Thomas et al. (1998) "The Hydrophobic Face Orientation of Apolipoprotein A-I Amphipathic Helix Domain 143-164 Regulates Lecthin: Cholesterol Acyltransferase Activation," J. Biol. Chem. 273(19):11776-11782.

Supplementary European Report corresponding to EP 05 75 1008, dated Feb. 8, 2008.

Sviridov et al. (1996) "Efflux of Cellular Cholesterol and Phospholipid to Apolipoprotein A-I Mutants," J. Biol. Chem. 271(52):33277-33283.

Sviridov et al. (Jun. 2000) "Identification of a Sequence of Apolipoprotein A-I Associated with the Activation of Lecithin: Cholesterol Acyltransferase," J. Biol. Chem. 275(26)19707-19712.

Tocanne, J.F. et . (1994) "Lipid domains and lipid/protein interactions in biological membranes" Chemistry and Physics of Lipids 73:139-158.

Wald, J.H. et al. (1990) "Investigation of the Lipid Domains and Apolipoprotein Orientation in Reconstituted High Density Lipoproteins by Fluorescence and IR Methods" J. Biol. Chem. 265(32):20044-20050.

Wald, J. H. et al. (1990) "Structure of Apolipoprotein A-I in Three Homogeneous, Reconstituted High Density Lipoprotein Particles" J. Biol. Chem. 265(32):20037-20043.

Wang, M. et al. (1997) "Three -dimensional structure of NADPH-cytochrome P450 reductase: Prototype for FMN and FAD-containing enzymes" Proc. Natl. Acad. Sci. USA 94:8411-8416.

Wlodawer, A. et al. (1979) "High-Density Lipoprotein Recombinants: Evidence For A Bicycle Tire Micelle Structure Obtained By Neutron Scattering and Electron Microscopy" FEBS Lett. 104(2):231-235 Segr35.

Zuck, P. et al. (Sep. 1999) "Ligand-receptor binding measured by laser-scanning imaging" Proc. Natl. Acad. Sci. USA 96:11122-11127.

Barnes et al. (1999) "A review of central 5-HT receptors and their function," Neuropharmacology 38:1083-1152.

Shaw et al (2007) The Local Phospholipid Environment Modulates the Activation of Blood Clotting. J Biol. Chem. 282 (9):2556-6563.

Morrissey et al. (2008) Blood Clotting Reactions on Nanoscale Phospholipid Bilayers. Thromb. Research Suppl. 521-524.

Atkinson, D. and Small, D.M. (1986) "Recombinant Lipoproteins:Implications for Structure and Asemmbly of Native Lipoproteins" Ann. Rev. Biophys. Chem. 15:403-456.

Bolanos-Garcia et al (2003) On the Structure and Function of Apolipoproteins: More Than a Family of Lipid-Binding Proteins. Progress in Biophysics & Mol. Biol. 83:47-68.

Bayburt, T.H. et al., (Dec. 2002) "Self-Assembly of Discoidal Phospholipid Bilayer Nanoparticles with Membrane Scaffold Proteins"; Nano Letters 2:853-856.

Bayburt, T.H. et al., (May 2002) "Single Molecule Height Measurements on Microsomal Cytochrome P450 in nanometer-Scale Phospholipid Bilayer Disks"; Proceedings of the National Academy of Sciences 99:6725-6730.

Bayburt, T.H. et al. (Nov. 2003) "Self-Assembly of Single Integral Membrane Proteins into Soluble Nanoscale Phospholipid Bilayers"; Protein Science 12:2476-2481.

Bayburt, T.H. et al. (Nov. 2003) "Reconstitution and Imaging of a Membrane Protein in a Nanometer-Size Phospholipid bilayer" J. Struct. Biol. 123:37-44.

Bayburt, T.H. et al. (Jun. 2000) "Single Molecule Height Measurements on a Membrane Protein in Nanometer-Scale Phospholipid Bilayer Disks" Langmuir 16(14):5993-5997.

Bayley, H. et al. (1982), "Delipidation, Renaturation, and Reconstitution of Bacteriorhodopsin," Methods Enzymol. 88:74-81.

Bergeron et al. (1995) "Apolipoprotein A-I Confirmation in Reconstituted Discoidal Lipoproteins Varying in Phospholipid and Cholesterol Content," J. Biol. Chem. 270:27429-27438.

Bergeron et al. (1997) "Characterization of Human Apolipoprotein A-I Expressed in *Escherichia coli*," Biochim. Biophys. Acta. 1344:139-152.

Boguski, M.S. et al. (1986) "On computer-assisted analysis of biological sequences: proline punctuation, consensus sequences, and apolipoprotein repeats" J.of Lipid Research 27:1011-1034.

Borhani, D.W. et al. (1997) "Crystal structure of truncated human apolipoprotein A-I suggests a lipid-bound conformation" Proc. Natl. Acad. Sci. USA 94:12291-12296.

Brouillette, C. et al., (2001), "Structural models of human apolipoprotein A-I: a critical analysis and review," Biochim. Biophys. Acta 1531:4-46.

Brouillette, C.G. et al. (1984) "Structural Studies of Apolipoprotein A-I/Phosphatidylcholine Recombinants by High-Field Proton NMR, Nondenaturing Gradient Gel Electrophoresis, and Electron Microscopy" Biochemistry 23:359-367.

Bruhn et al. (1991) "An Approach to the Functional Analysis of Lecithin-Cholesterol Acryltransferase. Activation by Recombinant Normal and Mutagenized Apolipoprotein AI," Biological Chemistry Hoppee-Seyler 372(3):225-234.

Burgess et al. (Nov. 2, 1999) "Deletion of the C-Terminal Domain of Apolipoprotein A-I Impairs Cell Surface Binding and Lipid Efflux in Macrophage," Biochem. 38(44):14524-14533.

Carlson, J. W. et al. (Mar. 2000) "Nanopatterning Phospholipid Bilayers" Langmuir 16(8):3927-3931.

Carlson, J.W. et al. (Sep. 1997) "Imaging and Manipulation of High-Density Lipoproteins" Biophys. J. 73:1184-1189.

Chen, J.S. et al., (2002) Insect Molecular Biology 11:175-186.

Chromy et al. (2007) "Different Apolipoproteins Impact Nanolipoprotein Particle Formation," J. Am. Chem. Soc. Oct. 27, 2007; [Epub Ahead of Print], A-D, and supporting documents, S1-S8.

Civjan, N.R. et al., (2003) "Direct Solubilization of Heterologously Expressed Membrane Proteins by Incorporation into Nanoscale Lipid Bilayers"; BioTechniques 35:556-563.

Dalton, M.B. and Swaney, J.B. (Sep. 15, 1993) "Structural and Functional Domains of Apolipoprotein A-I within High Density Lipoproteins" J. Biol Chem. 268(26):19274-19283.

Dencher, N.A. and Heyn, M.P. (1982) Methods Enyzmol. 88:5-10.

Denisov, I.G., et al. (Mar. 2004) "Directed Self Assembly of Monodisperse Phospholipid Bilayer Nanodiscs with Controlled Size"; J. Am. Chem. Soc., In Press.

Duan, et al. (2004) Co-incorporation of Heterologously-Expressed Arabidopsis Cytochrome P450 and P450 Reductase into Soluble Nanoscale Lipid Bilayers'; Archives Biochemistry and Biophysics, In Press.

Durbin, D.M. and Jonas, A. (Dec. 1999) "Lipid-free apolipoproteins A-I and A-II promote remodeling of reconstituted high density lipoproteins and alter their reactivity with lecithin:cholesterol acyltransferase" J. Lipid Research 40(12):2293-2302.

Dubois et al. (Jun. 2001) "Self-Assembly or Regular Hollow Icosahedra in Salt-Free Catanionic Solutions," Nature 411:672-675.

Fidge, N.H. (Feb. 1999) "High density lipoprotein receptors, binding proteins, and ligands" J. Lipid Research 40 (2):187-201.

Fielding, P.E. and Fielding, C.J. (1991) "Dynamics of lipoprotein transport in the circulatory system" Biochemistry of Lipids, Lipoproteins, and Membranes. D.E. Vance and J. Vance. Amsterdam, Elsevier Press Chapter 15, pp. 427-459.

File History for U.S. Patent 7,048,949.

File History for U.S. Patent 7,083,958.

Forte, T.M. et al. (1971) "Electron microscopic study on reassembly of plasma high density apoprotein with various lipids" Biochim. Biophys. Acts 248:381-386.

Frank, P.G. et al. (1997) "Deletion of Central α-Helices in Human Apolipoprotein A-I: Effect on Phospholipid Association" Biochemistry 36:1798-1806.

Frank et al. (1998) "Importance of Central α-Helixes of Human Apolipoprotein A-I in the Maturation of High Density Lipoproteins," Biochem. 37(39):13902-13909.

Friis, E.P. et al. (Feb. 1999) "An approach to long-range electron transfer mechanisms in mettalloproteins: in situ scanning tunneling ,microscopy with submolecular resolution" Proc. Natl. Acad. Sci. USA 96:1379-1384.

Gillotte et al (1996) "Apolipoprotein A-I Structureal Modification and the Functionality of Reconstituted High Density Lipoprotein Particles in Cellular Cholesterol Efflux," J. Biol. Chem. 271(39):23729-23798.

Gillotte et al. (Jan. 1999) "Apolipoprotein0Mediated Plasma Membrane Microsolubilization. Role of Lipid Affinity and Membrane Penetration in the Efflux of Cellular Cholesterol and Phospholipid," J. Biol. Chen. 274(4):2021-2028.

Glomset, J.A. (1968) "The plasma lecithin:cholesterol acyltransferase reaction" J. Lipid Research 9:155-167.

Holvoet, P. et al. (1995) "Phospholipid Binding and Lecithin-Cholesterol Acyltransferase Activation Properties of Apolipoprotein A-I Mutants" (1995) Biochemistry 34:13334-13342.

Imaoka, S. et al., (1992), "Role of Phospholipids in Reconstituted Cytochrome P450 3A Form and Mechanism of Their Activation of Catalytic Activity," Biochemistry 31:6063-6069.

Jin, L et al. (1995) "Surface Plasmon Resonance Biosensor Studies of Human Wild-Type and Mutant Lecithin Cholesterol Acyltransferase Interactions with Lipoproteins" Biochemistry 38(47):15659-15665.

Jonas, A. (1986) "Reconstitution of High Density Lipoproteins" Methods Enzymol. 128:553-582.

Jonas, A. (1991) "Lecithin-cholesterol acyltransferase in the metabolism of high-density lipoproteins" Biochem,. Biophys. Acta 1084:205-220.

Jonas, A. et al. (1989) "Defined Apolipoprotein A-I Conformation in Reconstituted High Density Lipoprotein Discs" J. Biol. Chem. 264(9):4818-4824.

Koppaka, V. et al. (May 1999) "The Structure of Human Lipoprotein A-I" J. Biol. Chem. 274(21)14541-14544.

Laccotripe et al. (1997) "The Carboxly-Terminal Hydrophobic Residues of Apolipoprotein A-I Affects its Rate of Phospholipid Binding and its Association with High Density Lipoprotein," J. Biol. Chem. 272(28):17511-17522.

Liadaki et al. (Jul. 2000)"Binding of High Density Lipoprotein (HDL) and Discoidal Reconstituted HDL to the HDL Receptor Scavenger Receptor Class B Type I. Effect of Lipid Association and apoA-I Mutations on Receptor Binding," J. Biol. Chem. 275(28):21262-21271.

Marcel et al. (1998) "Definition of Apolipoprotein A-I Domains Involved in Reverse Cholesterol Transport," International Congress Series 1155:(Atherosclerosis XI)1149-1153.

Marheineke, K. et al., (1998), "Lipid composition of *Spodoptera frugiperda* (Sf9) and *Trichoplusia ni* (Tn) insect cells used for baculovirus infection," FEBS Letters 441:49-52.

McGregor, C-L. (Feb 2003), "Lipoprotein detergents designed for the structural study of membrane proteins," Nature Biotechnol. 21:171-176.

* cited by examiner

SEQUENCE LISTING

<160> NUMBER OF SEQ ID NOS: 136

<210> SEQ ID NO 1
<211> LENGTH: 762
<212> TYPE: DNA
<213> ORGANISM: Homo sapiens

<400> SEQUENCE: 1

```
ccatggccca tttctggcag caagatgaac cccccagag ccctgggat cgagtgaagg      60
acctggccac tgtgtacgtg gatgtgctca agacagcgg cagagactat gtgtcccagt    120
ttgaaggctc cgccttggga aaacagctaa acctaaagct ccttgacaac tgggacagcg    180
tgacctccac cttcagcaag ctgcgcgaac agctcggccc tgtgacccag gagttctggg    240
ataacctgga aaaggagaca gagggcctga ggcaagagat gagcaaggat ctggaggagg    300
tgaaggccaa ggtgcagccc tacctggacg acttccagaa gaagtggcag gaggagatgg    360
agctctaccg ccagaaggtg gagccgctgc gcgcagagct ccaagagggc gcgcgccaga    420
agctgcacga gctgcaagag aagctgagcc cactgggcga ggagatgcgc gaccgcgcgc    480
gcgcccatgt ggacgcgctg cgcacgcatc tggcccccta cagcgacgag ctgcgccagc    540
gcttggccgc gcgccttgag gctctcaagg agaacggcgg cgccagactg gccgagtacc    600
acgccaaggc caccgagcat ctgagcacgc tcagcgagaa ggccaagccc gcgctcgagg    660
acctccgcca aggcctgctg cccgtgctgg agagcttcaa ggtcagcttc ctgagcgctc    720
tcgaggagta cactaagaag ctcaacaccc agtaataagc tt                      762
```

<210> SEQ ID NO 2
<211> LENGTH: 250
<212> TYPE: PRT
<213> ORGANISM: Homo sapiens

<400> SEQUENCE: 2

```
Met Ala His Phe Trp Gln Gln Asp Glu Pro Pro Gln Ser Pro Trp Asp
1               5                   10                  15

Arg Val Lys Asp Leu Ala Thr Val Tyr Val Asp Val Leu Lys Asp Ser
                20                  25                  30

Gly Arg Asp Tyr Val Ser Gln Phe Glu Gly Ser Ala Leu Gly Lys Gln
            35                  40                  45

Leu Asn Leu Lys Leu Leu Asp Asn Trp Asp Ser Val Thr Ser Thr Phe
        50                  55                  60

Ser Lys Leu Arg Glu Gln Leu Gly Pro Val Thr Gln Glu Phe Trp Asp
65                  70                  75                  80

Asn Leu Glu Lys Glu Thr Glu Gly Leu Arg Gln Glu Met Ser Lys Asp
                85                  90                  95

Leu Glu Glu Val Lys Ala Lys Val Gln Pro Tyr Leu Asp Asp Phe Gln
                100                 105                 110

Lys Lys Trp Gln Glu Glu Met Glu Leu Tyr Arg Gln Lys Val Glu Pro
            115                 120                 125

Leu Arg Ala Glu Leu Gln Glu Gly Ala Arg Gln Lys Leu His Glu Leu
        130                 135                 140

Gln Glu Lys Leu Ser Pro Leu Gly Glu Glu Met Arg Asp Arg Ala Arg
145                 150                 155                 160

Ala His Val Asp Ala Leu Arg Thr His Leu Ala Pro Tyr Ser Asp Glu
                165                 170                 175
```

-continued

```
Leu Arg Gln Arg Leu Ala Ala Arg Leu Glu Ala Leu Lys Glu Asn Gly
            180                 185                 190

Gly Ala Arg Leu Ala Glu Tyr His Ala Lys Ala Thr Glu His Leu Ser
        195                 200                 205

Thr Leu Ser Glu Lys Ala Lys Pro Ala Leu Glu Asp Leu Arg Gln Gly
    210                 215                 220

Leu Leu Pro Val Leu Glu Ser Phe Lys Val Ser Phe Leu Ser Ala Leu
225                 230                 235                 240

Glu Glu Tyr Thr Lys Lys Leu Asn Thr Gln
                245                 250

<210> SEQ ID NO 3
<211> LENGTH: 61
<212> TYPE: DNA
<213> ORGANISM: Artificial Sequence
<220> FEATURE:
<223> OTHER INFORMATION: oligonucleotide primer

<400> SEQUENCE: 3
tataccatgg gccatcatca tcatcatcat atagaaggaa gactaaagct ccttgacaac    60
t                                                                    61

<210> SEQ ID NO 4
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 4
gcaagcttat tactgggtgt tgagcttctt                                     30

<210> SEQ ID NO 5
<211> LENGTH: 654
<212> TYPE: DNA
<213> ORGANISM: Artificial Sequence
<220> FEATURE:
<223> OTHER INFORMATION: nucleotide sequence encoding HIS-tagged MSP1

<400> SEQUENCE: 5
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga ggcaggagat gagcaaggat   180
ctggaggagg tgaaggccaa ggtgcagccc tacctggacg acttccagaa gaagtggcag   240
gaggagatgg agctctaccg ccagaaggtg gagccgctgc gcgcagagct ccaagagggc   300
gcgcgccaga agctgcacga gctgcaagag aagttgagcc cactgggcga ggagatgcgc   360
gaccgcgcgc gcgcccatgt ggacgcgctg cgcacgcatc tggcccccta cagcgacgag   420
ctgcgccagc gcttggccgc gcgccttgag gctctcaagg agaacggcgg cgccagactg   480
gccgagtacc acgccaaggc caccgagcat ctgagcacgc tcagcgagaa ggccaaaccc   540
gcgctcgagg acctccgcca aggcctgctg cccgtgctgg agagcttcaa ggtcagcttc   600
ctgagcgctc tcgaggagta cactaagaag ctcaacaccc agtaataagc ttgc        654

<210> SEQ ID NO 6
<211> LENGTH: 212
<212> TYPE: PRT
<213> ORGANISM: Artificial Sequence
<220> FEATURE:
```

<223> OTHER INFORMATION: HIS-tagged MSP1

<400> SEQUENCE: 6

```
Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 7
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 7
taccatggca aagctccttg acaactg                                       27

<210> SEQ ID NO 8
<211> LENGTH: 619
<212> TYPE: DNA
<213> ORGANISM: Artificial Sequence
<220> FEATURE:
<223> OTHER INFORMATION: nucleotide sequence encoding MSP1 without His-
      tag

<400> SEQUENCE: 8
taccatggca aagctccttg acaactggga cagcgtgacc tccaccttca gcaagctgcg    60
cgaacagctc ggccctgtga cccaggagtt ctgggataac ctggaaaagg agacagaggg   120
cctgaggcag gagatgagca aggatctgga ggaggtgaag gccaaggtgc agccctacct   180
ggacgacttc cagaagaagt ggcaggagga gatggagctc taccgccaga aggtggagcc   240
gctgcgcgca gagctccaag agggcgcgcg ccagaagctg cacgagctgc aagagaagtt   300

```
gagcccactg ggcgaggaga tgcgcgaccg cgcgcgcgcc catgtggacg cgctgcgcac    360
gcatctggcc ccctacagcg acgagctgcg ccagcgcttg gccgcgcgcc ttgaggctct    420
caaggagaac ggcggcgcca gactggccga gtaccacgcc aaggccaccg agcatctgag    480
cacgctcagc gagaaggcca aacccgcgct cgaggacctc cgccaaggcc tgctgcccgt    540
gctggagagc ttcaaggtca gcttcctgag cgctctcgag gagtacacta agaagctcaa    600
cacccagtaa taagcttgc                                                 619
```

```
<210> SEQ ID NO 9
<211> LENGTH: 201
<212> TYPE: PRT
<213> ORGANISM: Artificial Sequence
<220> FEATURE:
<223> OTHER INFORMATION: MSP1 without His-tag

<400> SEQUENCE: 9
```

Met Ala Lys Leu Leu Asp Asn Trp Asp Ser Val Thr Ser Thr Phe Ser
1               5                   10                  15

Lys Leu Arg Glu Gln Leu Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

```
<210> SEQ ID NO 10
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 10
taccatggca aagctccttg acaactg                                         27

<210> SEQ ID NO 11
<211> LENGTH: 61
<212> TYPE: DNA
<213> ORGANISM: Artificial Sequence
<220> FEATURE:
```

```
<223> OTHER INFORMATION: oligonucleotide primer

<400> SEQUENCE: 11
tataccatgg gccatcatca tcatcatcat atagaaggaa gactaaagct ccttgacaac    60
t                                                                    61

<210> SEQ ID NO 12
<211> LENGTH: 52
<212> TYPE: DNA
<213> ORGANISM: Artificial Sequence
<220> FEATURE:
<223> OTHER INFORMATION: oligonucleotide primer

<400> SEQUENCE: 12
taagaagctc aacacccagg gtaccggtgg aggtagtgga ggtggtaccc ta            52

<210> SEQ ID NO 13
<211> LENGTH: 50
<212> TYPE: DNA
<213> ORGANISM: Artificial Sequence
<220> FEATURE:
<223> OTHER INFORMATION: oligonucleotide primer

<400> SEQUENCE: 13
cagggtaccg gtggaggtag tggaggtggt accctaaagc tccttgacaa               50

<210> SEQ ID NO 14
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 14
gcaagcttat tactgggtgt tgagcttctt                                     30

<210> SEQ ID NO 15
<211> LENGTH: 9
<212> TYPE: PRT
<213> ORGANISM: artificial sequence
<220> FEATURE:
<223> OTHER INFORMATION: synthetic peptide of linker

<400> SEQUENCE: 15

Gly Thr Gly Gly Gly Ser Gly Gly Thr
1               5

<210> SEQ ID NO 16
<211> LENGTH: 1260
<212> TYPE: DNA
<213> ORGANISM: Artificial Sequence
<220> FEATURE:
<223> OTHER INFORMATION: nucleotide sequence encoding His-tagged MSP2

<400> SEQUENCE: 16
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga ggcaggagat gagcaaggat   180
ctggaggagg tgaaggccaa ggtgcagccc tacctgacg acttccagaa gaagtggcag    240
gaggagatgg agctctaccg ccagaaggtg agccgctgc gcgcagagct ccaagagggc   300
gcgcgccaga agctgcacga gctgcaagag aagctgagcc cactgggcga ggagatgcgc   360
```

-continued

```
gaccgcgcgc gcgcccatgt ggacgcgctg cgcacgcatc tggcccccta cagcgacgag    420
ctgcgccagc gcttggccgc gcgccttgag gctctcaagg agaacggcgg cgccagactg    480
gccgagtacc acgccaaggc caccgagcat ctgagcacgc tcagcgagaa ggccaagccc    540
gcgctcgagg acctccgcca aggcctgctg cccgtgctgg agagcttcaa ggtcagcttc    600
ctgagcgctc tcgaggagta cactaagaag ctcaacaccc agggtaccct aaagctcctt    660
gacaactggg acagcgtgac ctccaccttc agcaagctgc cgaacagct cggccctgtg     720
acccaggagt tctgggataa cctggaaaag gagacagagg gcctgaggca ggagatgagc    780
aaggatctgg aggaggtgaa ggccaaggtg cagccctacc tggacgactt ccagaagaag    840
tggcaggagg agatggagct ctaccgccag aaggtggagc cgctgcgcgc agagctccaa    900
gagggcgcgc gccagaagct gcacgagctg caagagaagc tgagcccact gggcgaggag    960
atgcgcgacc gcgcgcgcgc ccatgtggac gcgctgcgca cgcatctggc ccctacagc    1020
gacgagctgc gccagcgctt ggccgcgcgc cttgaggctc tcaaggagaa cggcggcgcc   1080
agactggccg agtaccacgc caaggccacc gagcatctga gcacgctcag cgagaaggcc   1140
aagcccgcgc tcgaggacct ccgccaaggc ctgctgcccg tgctggagag cttcaaggtc   1200
agcttcctga gcgctctcga ggagtacact aagaagctca cacccagta ataagcttgc    1260
```

<210> SEQ ID NO 17
<211> LENGTH: 414
<212> TYPE: PRT
<213> ORGANISM: Artificial Sequence
<220> FEATURE:
<223> OTHER INFORMATION: His-tagged MSP2

<400> SEQUENCE: 17

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205
```

```
Leu Asn Thr Gln Gly Thr Leu Lys Leu Leu Asp Asn Trp Asp Ser Val
    210                 215                 220
Thr Ser Thr Phe Ser Lys Leu Arg Glu Gln Leu Gly Pro Val Thr Gln
225                 230                 235                 240
Glu Phe Trp Asp Asn Leu Glu Lys Glu Thr Glu Gly Leu Arg Gln Glu
                245                 250                 255
Met Ser Lys Asp Leu Glu Glu Val Lys Ala Lys Val Gln Pro Tyr Leu
            260                 265                 270
Asp Asp Phe Gln Lys Lys Trp Gln Glu Glu Met Glu Leu Tyr Arg Gln
        275                 280                 285
Lys Val Glu Pro Leu Arg Ala Glu Leu Gln Glu Gly Ala Arg Gln Lys
    290                 295                 300
Leu His Glu Leu Gln Glu Lys Leu Ser Pro Leu Gly Glu Glu Met Arg
305                 310                 315                 320
Asp Arg Ala Arg Ala His Val Asp Ala Leu Arg Thr His Leu Ala Pro
                325                 330                 335
Tyr Ser Asp Glu Leu Arg Gln Arg Leu Ala Ala Arg Leu Glu Ala Leu
            340                 345                 350
Lys Glu Asn Gly Gly Ala Arg Leu Ala Glu Tyr His Ala Lys Ala Thr
        355                 360                 365
Glu His Leu Ser Thr Leu Ser Glu Lys Ala Lys Pro Ala Leu Glu Asp
    370                 375                 380
Leu Arg Gln Gly Leu Leu Pro Val Leu Glu Ser Phe Lys Val Ser Phe
385                 390                 395                 400
Leu Ser Ala Leu Glu Glu Tyr Thr Lys Lys Leu Asn Thr Gln
                405                 410

<210> SEQ ID NO 18
<211> LENGTH: 1282
<212> TYPE: DNA
<213> ORGANISM: Artificial Sequence
<220> FEATURE:
<223> OTHER INFORMATION: nucleotide sequence encoding His-tagged MSP2L

<400> SEQUENCE: 18
taccatgggc catcatcatc atcatcatat agaaggaaga ctaaagctcc ttgacaactg      60
ggacagcgtg acctccacct tcagcaagct gcgcgaacag ctcggccctg tgacccagga     120
gttctgggat aacctggaaa aggagacaga gggcctgagg caggagatga gcaaggatct     180
ggaggaggtg aaggccaagg tgcagcccta cctggacgac ttccagaaga gtggcagga     240
ggagatggag ctctaccgcc agaaggtgga gccgctgcgc gcagagctcc agagggcgc     300
gcgccagaag ctgcacgagc tgcaagagaa gctgagccca ctgggcgagg agatgcgcga     360
ccgcgcgcgc gcccatgtgg acgcgctgcg cacgcatctg gcccctaca gcgacgagct     420
gcgccagcgc ttggccgcgc gccttgaggc tctcaaggag aacggcggcg ccagactggc     480
cgagtaccac gccaaggcca ccgagcatct gagcacgctc agcgagaagg ccaagcccgc     540
gctcgaggac ctccgccaag gcctgctgcc cgtgctggag agcttcaagg tcagcttcct     600
gagcgctctc gaggagtaca ctaagaagct caacacccag ggtaccggtg aggtagtgg      660
aggtggtacc ctaaagctcc ttgacaactg ggacagcgtg acctccacct tcagcaagct     720
gcgcgaacag ctcggccctg tgacccagga gttctgggat aacctggaaa aggagacaga     780
gggcctgagg caggagatga gcaaggatct ggaggaggtg aaggccaagg tgcagcccta     840
cctggacgac ttccagaaga gtggcagga ggagatggag ctctaccgcc agaaggtgga     900
```

```
gccgctgcgc gcagagctcc aagagggcgc gcgccagaag ctgcacgagc tgcaagagaa    960
gctgagccca ctgggcgagg agatgcgcga ccgcgcgcgc gcccatgtgg acgcgctgcg   1020
cacgcatctg gccccctaca gcgacgagct gcgccagcgc ttggccgcgc gccttgaggc   1080
tctcaaggag aacggcggcg ccagactggc cgagtaccac gccaaggcca ccgagcatct   1140
gagcacgctc agcgagaagg ccaagcccgc gctcgaggac ctccgccaag gcctgctgcc   1200
cgtgctggag agcttcaagg tcagcttcct gagcgctctc gaggagtaca ctaagaagct   1260
caacacccag taataagctt gc                                            1282
```

<210> SEQ ID NO 19
<211> LENGTH: 422
<212> TYPE: PRT
<213> ORGANISM: Artificial Sequence
<220> FEATURE:
<223> OTHER INFORMATION: His-tagged MSP2L

<400> SEQUENCE: 19

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Gly Gly Ser Gly Gly Gly Thr Leu Lys
    210                 215                 220

Leu Leu Asp Asn Trp Asp Ser Val Thr Ser Thr Phe Ser Lys Leu Arg
225                 230                 235                 240

Glu Gln Leu Gly Pro Val Thr Gln Glu Phe Trp Asp Asn Leu Glu Lys
                245                 250                 255

Glu Thr Glu Gly Leu Arg Gln Glu Met Ser Lys Asp Leu Glu Glu Val
            260                 265                 270

Lys Ala Lys Val Gln Pro Tyr Leu Asp Asp Phe Gln Lys Lys Trp Gln
        275                 280                 285

Glu Glu Met Glu Leu Tyr Arg Gln Lys Val Glu Pro Leu Arg Ala Glu
```

-continued

```
                290                 295                 300
Leu Gln Glu Gly Ala Arg Gln Lys Leu His Glu Leu Gln Glu Lys Leu
305                 310                 315                 320

Ser Pro Leu Gly Glu Glu Met Arg Asp Arg Ala Arg Ala His Val Asp
                325                 330                 335

Ala Leu Arg Thr His Leu Ala Pro Tyr Ser Asp Glu Leu Arg Gln Arg
            340                 345                 350

Leu Ala Ala Arg Leu Glu Ala Leu Lys Glu Asn Gly Gly Ala Arg Leu
        355                 360                 365

Ala Glu Tyr His Ala Lys Ala Thr Glu His Leu Ser Thr Leu Ser Glu
370                 375                 380

Lys Ala Lys Pro Ala Leu Glu Asp Leu Arg Gln Gly Leu Leu Pro Val
385                 390                 395                 400

Leu Glu Ser Phe Lys Val Ser Phe Leu Ser Ala Leu Glu Glu Tyr Thr
                405                 410                 415

Lys Lys Leu Asn Thr Gln
            420

<210> SEQ ID NO 20
<211> LENGTH: 43
<212> TYPE: DNA
<213> ORGANISM: Artificial Sequence
<220> FEATURE:
<223> OTHER INFORMATION: oligonucleotide primer

<400> SEQUENCE: 20
tggagctcta ccgccagaag gtggagccct acagcgacga gct                43

<210> SEQ ID NO 21
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 21
gcaagcttat tactgggtgt tgagcttctt                                30

<210> SEQ ID NO 22
<211> LENGTH: 522
<212> TYPE: DNA
<213> ORGANISM: Artificial Sequence
<220> FEATURE:
<223> OTHER INFORMATION: nucleotide sequence encoding MSP1D5D6

<400> SEQUENCE: 22
tataccatgg gccatcatca tcatcatcat atagaaggaa gactaaagct ccttgacaac    60
tgggacagcg tgacctccac cttcagcaag ctgcgcgaac agctcggccc tgtgacccag   120
gagttctggg ataacctgga aaaggagaca gagggcctga ggcaggagat gagcaaggat   180
ctggaggagg tgaaggccaa ggtgcagccc tacctggacg acttccagaa gaagtggcag   240
gaggagatgg agctctaccg ccagaaggtg gagccctaca gcgacgagct cgccagcgc    300 ttggccgcgc gccttgaggc tctcaaggag aacggcggcg ccagactggc cgagtaccac   360
gccaaggcca ccgagcatct gagcacgctc agcgagaagg ccaaaccgc gctcgaggac    420 ctccgccaag gcctgctgcc cgtgctggag agcttcaagg tcagcttcct gagcgctctc   480
gaggagtaca ctaagaagct caacacccag taataagctt gc                     522
```

<210> SEQ ID NO 23
<211> LENGTH: 168
<212> TYPE: PRT
<213> ORGANISM: Artificial Sequence
<220> FEATURE:
<223> OTHER INFORMATION: His-tagged MSP1D5D6

<400> SEQUENCE: 23

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 24
<211> LENGTH: 29
<212> TYPE: DNA
<213> ORGANISM: Artificial Sequence
<220> FEATURE:
<223> OTHER INFORMATION: oligonucleotide primer

<400> SEQUENCE: 24
cagaattcgc tagccgagta ccacgccaa                                        29

<210> SEQ ID NO 25
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 25
gcaagcttat tactgggtgt tgagcttctt                                       30

<210> SEQ ID NO 26
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 26
ataccatggg ccatcatcat catcatcata                                       30

<210> SEQ ID NO 27
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 27
cagaattcgc tagcctggcg ctcaacttct ctt                                   33

<210> SEQ ID NO 28
<211> LENGTH: 522
<212> TYPE: DNA
<213> ORGANISM: Artificial Sequence
<220> FEATURE:
<223> OTHER INFORMATION: nucleotide sequence encoding His-tagged MSP1D6

<400> SEQUENCE: 28
tataccatgg gccatcatca tcatcatcat atagaaggaa gactaaagct ccttgacaac      60
tgggacagcg tgacctccac cttcagcaag ctgcgcgaac agctcggccc tgtgacccag     120
gagttctggg ataacctgga aaaggagaca gagggcctga ggcaggagat gagcaaggat     180
ctggaggagg tgaaggccaa ggtgcagccc tacctggacg acttccagaa aagtggcag      240 gaggagatgg agctctaccg ccagaaggtg gagccgctgc gcgcagagct ccaagagggc     300
gcgcgccaga agctgcacga gctgcaagag aagttgagcg ccaggctagc cgagtaccac     360
gccaaggcca ccgagcatct gagcacgctc agcgagaagg ccaaacccgc gctcgaggac     420
ctccgccaag gcctgctgcc cgtgctggag agcttcaagg tcagcttcct gagcgctctc     480
gaggagtaca ctaagaagct caacacccag taataagctt gc                        522

<210> SEQ ID NO 29
<211> LENGTH: 168
<212> TYPE: PRT
<213> ORGANISM: Artificial Sequence
<220> FEATURE:
<223> OTHER INFORMATION: His-tagged MSP1D6

<400> SEQUENCE: 29

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

<210> SEQ ID NO 30
<211> LENGTH: 77
<212> TYPE: DNA
<213> ORGANISM: Artificial Sequence
<220> FEATURE:
<223> OTHER INFORMATION: synthetic oligonucleotide

<400> SEQUENCE: 30
taccatgggt catcatcatc atcatcacat tgagggacgt ctgaagctgt tggacaattg    60
ggactctgtt acgtcta                                                   77

<210> SEQ ID NO 31
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 31
aggaattctg ggacaacctg gaaaagaaa ccgagggact gcgtcaggaa atgtccaaag    60
at                                                                   62

<210> SEQ ID NO 32
<211> LENGTH: 54
<212> TYPE: DNA
<213> ORGANISM: Artificial Sequence
<220> FEATURE:
<223> OTHER INFORMATION: synthetic oligonucleotide

<400> SEQUENCE: 32
tatctagatg actttcagaa aaaatggcag gaagagatgg aattatatcg tcaa          54

<210> SEQ ID NO 33
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 33
atgagctcca agagaagctc agcccattag gcgaagaaat gcgcgatcgc gcccgtgcac    60
atgttgatgc act                                                       73

<210> SEQ ID NO 34
<211> LENGTH: 65
<212> TYPE: DNA
<213> ORGANISM: Artificial Sequence
<220> FEATURE:
<223> OTHER INFORMATION: synthetic oligonucleotide

<400> SEQUENCE: 34
gtctcgaggc gctgaaagaa aacggggtg cccgcttggc tgagtaccac gcgaaagcga    60
cagaa                                                                65

<210> SEQ ID NO 35
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 35
gaagatctac gccagggctt attgcctgtt cttgagagct ttaaagtcag ttttct    56

<210> SEQ ID NO 36
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 36
cagaattcct gcgtcacggg gcccagttgt tcgcgaagtt tactgaaggt agacgtaaca    60
g    61

<210> SEQ ID NO 37
<211> LENGTH: 55
<212> TYPE: DNA
<213> ORGANISM: Artificial Sequence
<220> FEATURE:
<223> OTHER INFORMATION: synthetic oligonucleotide

<400> SEQUENCE: 37
tcatctagat atggctgaac cttggccttc acctcttcta aatctttgga cattt    55

<210> SEQ ID NO 38
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 38
tggagctcat ggagtttttg gcgtgccccc tcttgcagtt ccgcacgcag cggttccacc    60
ttttgacgat ataattccat    80

<210> SEQ ID NO 39
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 39
gcctcgagac gtgcggccaa acgctggcga agttcatccg aatacggcgc caaatgagtc    60
cggagtgcat caacat    76

<210> SEQ ID NO 40
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 40
gtagatcttc cagcgccggt ttcgcttttt cgctcaaggt gctcaggtgt tctgtcgctt    60
t    61

<210> SEQ ID NO 41
<211> LENGTH: 66
<212> TYPE: DNA
<213> ORGANISM: Artificial Sequence
<220> FEATURE:
<223> OTHER INFORMATION: synthetic oligonucleotide

<400> SEQUENCE: 41

```
ccaagcttat tactgggtat tcagcttttt agtatattct tccagagctg acagaaaact    60
gactтt                                                                66
```

<210> SEQ ID NO 42
<211> LENGTH: 651
<212> TYPE: DNA
<213> ORGANISM: Artificial Sequence
<220> FEATURE:
<223> OTHER INFORMATION: full synthetic sequence encoding MSP1

<400> SEQUENCE: 42

```
accatgggtc atcatcatca tcatcacatt gagggacgtc tgaagctgtt ggacaattgg    60
gactctgtta cgtctacctt cagtaaactt cgcgaacaac tgggccccgt gacgcaggaa   120
ttctgggaca acctggaaaa agaaaccgag ggactgcgtc aggaaatgtc caaagattta   180
gaagaggtga aggccaaggt tcagccatat ctagatgact ttcagaaaaa atggcaggaa   240
gagatggaat atatcgtca aaaggtggaa ccgctgcgtg cggaactgca agaggggca    300
cgccaaaaac tccatgagct ccaagagaag ctcagcccat aggcgaaga aatgcgcgat   360
cgcgcccgtg cacatgttga tgcactccgg actcatttgg cgccgtattc ggatgaactt   420
cgccagcgtt tggccgcacg tctcgaggcg ctgaaagaaa acgggggtgc ccgcttggct   480
gagtaccacg cgaaagcgac agaacacctg agcaccttga gcgaaaaagc gaaaccggcg   540
ctggaagatc tacgccaggg cttattgcct gttcttgaga gctttaaagt cagttttctg   600
tcagctctgg aagaatatac taaaaagctg aatacccagt aataagcttg g            651
```

<210> SEQ ID NO 43
<211> LENGTH: 201
<212> TYPE: PRT
<213> ORGANISM: Artificial Sequence
<220> FEATURE:
<223> OTHER INFORMATION: His-tagged MSP1D3

<400> SEQUENCE: 43

```
Met Gly His His His His His His Ile Glu Gly Arg Leu Lys Leu Leu
1               5                   10                  15
Asp Asn Trp Asp Ser Val Thr Ser Thr Phe Ser Lys Leu Arg Glu Gln
            20                  25                  30
Leu Gly Pro Val Thr Gln Glu Phe Trp Asp Asn Leu Glu Lys Glu Thr
        35                  40                  45
Glu Gly Leu Arg Gln Glu Met Ser Pro Tyr Leu Asp Asp Phe Gln Lys
    50                  55                  60
Lys Trp Gln Glu Glu Met Glu Leu Tyr Arg Gln Lys Val Glu Pro Leu
65                  70                  75                  80
Arg Ala Glu Leu Gln Glu Gly Ala Arg Gln Lys Leu His Glu Leu Gln
                85                  90                  95
Glu Lys Leu Ser Pro Leu Gly Glu Glu Met Arg Asp Arg Ala Arg Ala
            100                 105                 110
His Val Asp Ala Leu Arg Thr His Leu Ala Pro Tyr Ser Asp Glu Leu
        115                 120                 125
Arg Gln Arg Leu Ala Ala Arg Leu Glu Ala Leu Lys Glu Asn Gly Gly
    130                 135                 140
Ala Arg Leu Ala Glu Tyr His Ala Lys Ala Thr Glu His Leu Ser Thr
145                 150                 155                 160
```

-continued

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 44
<211> LENGTH: 201
<212> TYPE: PRT
<213> ORGANISM: Artificial Sequence
<220> FEATURE:
<223> OTHER INFORMATION: His-tagged MSP1D9

<400> SEQUENCE: 44

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 45
<211> LENGTH: 392
<212> TYPE: PRT
<213> ORGANISM: Artificial Sequence
<220> FEATURE:
<223> OTHER INFORMATION: His-tagged MSP2 delta 1

<400> SEQUENCE: 45

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

```
Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Leu Lys Leu Leu Asp
        195                 200                 205

Asn Trp Asp Ser Val Thr Ser Thr Phe Ser Lys Leu Arg Glu Gln Leu
    210                 215                 220

Gly Pro Val Thr Gln Glu Phe Trp Asp Asn Leu Glu Lys Glu Thr Glu
225                 230                 235                 240

Gly Leu Arg Gln Glu Met Ser Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
        355                 360                 365

Pro Val Leu Glu Ser Phe Lys Val Ser Phe Leu Ser Ala Leu Glu Glu
    370                 375                 380

Tyr Thr Lys Lys Leu Asn Thr Gln
385                 390

<210> SEQ ID NO 46
<211> LENGTH: 4
<212> TYPE: PRT
<213> ORGANISM: Artificial Sequence
<220> FEATURE:
<223> OTHER INFORMATION: synthetic peptide of linker
<220> FEATURE:
<221> NAME/KEY: MISC_FEATURE
<222> LOCATION: (1)..(4)
<223> OTHER INFORMATION: X is Ser or Thr

<400> SEQUENCE: 46

Gly Gly Gly Xaa
```

```
<210> SEQ ID NO 47
<211> LENGTH: 12
<212> TYPE: PRT
<213> ORGANISM: Artificial Sequence
<220> FEATURE:
<223> OTHER INFORMATION: artificial sequence of His-tag

<400> SEQUENCE: 47

Met Gly His His His His His His Ile Glu Gly Arg
1               5                   10

<210> SEQ ID NO 48
<211> LENGTH: 23
<212> TYPE: PRT
<213> ORGANISM: Artificial Sequence
<220> FEATURE:
<223> OTHER INFORMATION: artificial sequence of HisTEV

<400> SEQUENCE: 48

Met Gly His His His His His His His Asp Tyr Asp Ile Pro Thr Thr
1               5                   10                  15

Glu Asn Leu Tyr Phe Gln Gly
            20

<210> SEQ ID NO 49
<211> LENGTH: 22
<212> TYPE: PRT
<213> ORGANISM: Artificial Sequence
<220> FEATURE:
<223> OTHER INFORMATION: artificial sequence of Helix 1

<400> SEQUENCE: 49

Leu Lys Leu Leu Asp Asn Trp Asp Ser Val Thr Ser Thr Phe Ser Lys
1               5                   10                  15

Leu Arg Glu Gln Leu Gly
            20

<210> SEQ ID NO 50
<211> LENGTH: 22
<212> TYPE: PRT
<213> ORGANISM: Artificial Sequence
<220> FEATURE:
<223> OTHER INFORMATION: artificial sequence of Helix 2

<400> SEQUENCE: 50

Pro Val Thr Gln Glu Phe Trp Asp Asn Leu Glu Lys Glu Thr Glu Gly
1               5                   10                  15

Leu Arg Gln Glu Met Ser
            20

<210> SEQ ID NO 51
<211> LENGTH: 11
<212> TYPE: PRT
<213> ORGANISM: Artificial Sequence
<220> FEATURE:
<223> OTHER INFORMATION: artificial sequence of Helix 3

<400> SEQUENCE: 51

Lys Asp Leu Glu Glu Val Lys Ala Lys Val Gln
1               5                   10

<210> SEQ ID NO 52
<211> LENGTH: 22
```

```
<212> TYPE: PRT
<213> ORGANISM: Artificial Sequence
<220> FEATURE:
<223> OTHER INFORMATION: artificial sequence of Helix 4

<400> SEQUENCE: 52

Pro Tyr Leu Asp Asp Phe Gln Lys Lys Trp Gln Glu Glu Met Glu Leu
1               5                   10                  15

Tyr Arg Gln Lys Val Glu
            20

<210> SEQ ID NO 53
<211> LENGTH: 22
<212> TYPE: PRT
<213> ORGANISM: Artificial Sequence
<220> FEATURE:
<223> OTHER INFORMATION: artificial sequence of Helix 5

<400> SEQUENCE: 53

Pro Leu Arg Ala Glu Leu Gln Glu Gly Ala Arg Gln Lys Leu His Glu
1               5                   10                  15

Leu Gln Glu Lys Leu Ser
            20

<210> SEQ ID NO 54
<211> LENGTH: 22
<212> TYPE: PRT
<213> ORGANISM: Artificial Sequence
<220> FEATURE:
<223> OTHER INFORMATION: artificial sequence of Helix 6

<400> SEQUENCE: 54

Pro Leu Gly Glu Glu Met Arg Asp Arg Ala Arg Ala His Val Asp Ala
1               5                   10                  15

Leu Arg Thr His Leu Ala
            20

<210> SEQ ID NO 55
<211> LENGTH: 22
<212> TYPE: PRT
<213> ORGANISM: Artificial Sequence
<220> FEATURE:
<223> OTHER INFORMATION: artificial sequence of Helix 7

<400> SEQUENCE: 55

Pro Tyr Ser Asp Glu Leu Arg Gln Arg Leu Ala Ala Arg Leu Glu Ala
1               5                   10                  15

Leu Lys Glu Asn Gly Gly
            20

<210> SEQ ID NO 56
<211> LENGTH: 22
<212> TYPE: PRT
<213> ORGANISM: Artificial Sequence
<220> FEATURE:
<223> OTHER INFORMATION: artificial sequence of Helix 8

<400> SEQUENCE: 56

Ala Arg Leu Ala Glu Tyr His Ala Lys Ala Thr Glu His Leu Ser Thr
1               5                   10                  15

Leu Ser Glu Lys Ala Lys
            20

<210> SEQ ID NO 57
```

```
<211> LENGTH: 11
<212> TYPE: PRT
<213> ORGANISM: Artificial Sequence
<220> FEATURE:
<223> OTHER INFORMATION: artificial sequence of Helix 9

<400> SEQUENCE: 57

Pro Ala Leu Glu Asp Leu Arg Gln Gly Leu Leu
1               5                   10

<210> SEQ ID NO 58
<211> LENGTH: 24
<212> TYPE: PRT
<213> ORGANISM: Artificial Sequence
<220> FEATURE:
<223> OTHER INFORMATION: artificial sequence of Helix 10

<400> SEQUENCE: 58

Pro Val Leu Glu Ser Phe Lys Val Ser Phe Leu Ser Ala Leu Glu Glu
1               5                   10                  15

Tyr Thr Lys Lys Leu Asn Thr Gln
            20

<210> SEQ ID NO 59
<211> LENGTH: 11
<212> TYPE: PRT
<213> ORGANISM: Artificial Sequence
<220> FEATURE:
<223> OTHER INFORMATION: artificial sequence of Helix 0.5

<400> SEQUENCE: 59

Ser Thr Phe Ser Lys Leu Arg Glu Gln Leu Gly
1               5                   10

<210> SEQ ID NO 60
<211> LENGTH: 36
<212> TYPE: DNA
<213> ORGANISM: Artificial Sequence
<220> FEATURE:
<223> OTHER INFORMATION: sequence encoding His-tag

<400> SEQUENCE: 60
atgggtcatc atcatcatca tcacattgag ggacgt                         36

<210> SEQ ID NO 61
<211> LENGTH: 69
<212> TYPE: DNA
<213> ORGANISM: Artificial Sequence
<220> FEATURE:
<223> OTHER INFORMATION: sequence encoding His-TEV

<400> SEQUENCE: 61
atgggtcatc atcatcatca tcatcacgat tatgatattc ctactactga gaatttgtat    60
tttcagggt                                                            69

<210> SEQ ID NO 62
<211> LENGTH: 66
<212> TYPE: DNA
<213> ORGANISM: Artificial Sequence
<220> FEATURE:
<223> OTHER INFORMATION: sequence encoding Helix 1

<400> SEQUENCE: 62
ctgaagctgt tggacaattg ggactctgtt acgtctacct tcagtaaact tcgcgaacaa    60
ctgggc                                                               66
```

<210> SEQ ID NO 63
<211> LENGTH: 66
<212> TYPE: DNA
<213> ORGANISM: Artificial Sequence
<220> FEATURE:
<223> OTHER INFORMATION: sequence encoding Helix 2

<400> SEQUENCE: 63
cccgtgacgc aggaattctg ggacaacctg gaaaagaaa ccgagggact gcgtcaggaa    60
atgtcc                                                              66

<210> SEQ ID NO 64
<211> LENGTH: 33
<212> TYPE: DNA
<213> ORGANISM: Artificial Sequence
<220> FEATURE:
<223> OTHER INFORMATION: sequence encoding Helix 3

<400> SEQUENCE: 64
aaagatttag aagaggtgaa ggccaaggtt cag                                33

<210> SEQ ID NO 65
<211> LENGTH: 66
<212> TYPE: DNA
<213> ORGANISM: Artificial Sequence
<220> FEATURE:
<223> OTHER INFORMATION: sequence encoding Helix 4

<400> SEQUENCE: 65
ccatatctcg atgactttca gaaaaaatgg caggaagaga tggaattata tcgtcaaaag    60
gtggaa                                                              66

<210> SEQ ID NO 66
<211> LENGTH: 66
<212> TYPE: DNA
<213> ORGANISM: Artificial Sequence
<220> FEATURE:
<223> OTHER INFORMATION: sequence encoding Helix 5

<400> SEQUENCE: 66
ccgctgcgtg cggaactgca agagggggca cgccaaaaac tccatgagct ccaagagaag    60
ctcagc                                                              66

<210> SEQ ID NO 67
<211> LENGTH: 66
<212> TYPE: DNA
<213> ORGANISM: Artificial Sequence
<220> FEATURE:
<223> OTHER INFORMATION: sequence encoding Helix 6

<400> SEQUENCE: 67
ccattaggcg aagaaatgcg cgatcgcgcc cgtgcacatg ttgatgcact ccggactcat    60
ttggcg                                                              66

<210> SEQ ID NO 68
<211> LENGTH: 66
<212> TYPE: DNA
<213> ORGANISM: Artificial Sequence
<220> FEATURE:
<223> OTHER INFORMATION: sequence encoding Helix 7

<400> SEQUENCE: 68

```
ccgtattcgg atgaacttcg ccagcgtttg ccgcacgtc tcgaggcgct gaaagaaaac      60
gggggt                                                                66
```

<210> SEQ ID NO 69
<211> LENGTH: 66
<212> TYPE: DNA
<213> ORGANISM: Artificial Sequence
<220> FEATURE:
<223> OTHER INFORMATION: sequence encoding Helix 8

<400> SEQUENCE: 69

```
gcccgcttgg ctgagtacca cgcgaaagcg acagaacacc tgagcacctt gagcgaaaaa      60
gcgaaa                                                                66
```

<210> SEQ ID NO 70
<211> LENGTH: 33
<212> TYPE: DNA
<213> ORGANISM: Artificial Sequence
<220> FEATURE:
<223> OTHER INFORMATION: sequence encoding Helix 9

<400> SEQUENCE: 70

```
ccggcgctgg aagatctacg ccagggctta ttg                                   33
```

<210> SEQ ID NO 71
<211> LENGTH: 72
<212> TYPE: DNA
<213> ORGANISM: Artificial Sequence
<220> FEATURE:
<223> OTHER INFORMATION: sequence encoding Helix 10

<400> SEQUENCE: 71

```
cctgttcttg agagctttaa agtcagtttt ctgtcagctc tggaagaata tactaaaaag      60
ctgaataccc ag                                                         72
```

<210> SEQ ID NO 72
<211> LENGTH: 33
<212> TYPE: DNA
<213> ORGANISM: Artificial Sequence
<220> FEATURE:
<223> OTHER INFORMATION: sequence encoding Helix 0.5

<400> SEQUENCE: 72

```
tctaccttca gtaaacttcg cgaacaactg ggc                                   33
```

<210> SEQ ID NO 73
<211> LENGTH: 234
<212> TYPE: PRT
<213> ORGANISM: Artificial Sequence
<220> FEATURE:
<223> OTHER INFORMATION: artificial sequence of His-tagged MSP1E1

<400> SEQUENCE: 73

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu

```
                65                  70                  75                  80
Met Glu Leu Tyr Arg Gln Lys Val Glu Pro Tyr Leu Asp Asp Phe Gln
                    85                  90                  95

Lys Lys Trp Gln Glu Glu Met Glu Leu Tyr Arg Gln Lys Val Glu Pro
                100                 105                 110

Leu Arg Ala Glu Leu Gln Glu Gly Ala Arg Gln Lys Leu His Glu Leu
                115                 120                 125

Gln Glu Lys Leu Ser Pro Leu Gly Glu Met Arg Asp Arg Ala Arg
            130                 135                 140

Ala His Val Asp Ala Leu Arg Thr His Leu Ala Pro Tyr Ser Asp Glu
145                 150                 155                 160

Leu Arg Gln Arg Leu Ala Ala Arg Leu Glu Ala Leu Lys Glu Asn Gly
                165                 170                 175

Gly Ala Arg Leu Ala Glu Tyr His Ala Lys Ala Thr Glu His Leu Ser
                180                 185                 190

Thr Leu Ser Glu Lys Ala Lys Pro Ala Leu Glu Asp Leu Arg Gln Gly
                195                 200                 205

Leu Leu Pro Val Leu Glu Ser Phe Lys Val Ser Phe Leu Ser Ala Leu
                210                 215                 220

Glu Glu Tyr Thr Lys Lys Leu Asn Thr Gln
225                 230

<210> SEQ ID NO 74
<211> LENGTH: 256
<212> TYPE: PRT
<213> ORGANISM: Artificial Sequence
<220> FEATURE:
<223> OTHER INFORMATION: artificial sequence of His-tagged MSP1E2

<400> SEQUENCE: 74

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
                20                  25                  30

Leu Gly Pro Val Thr Gln Glu Phe Trp Asp Asn Leu Glu Lys Glu Thr
                35                  40                  45

Glu Gly Leu Arg Gln Glu Met Ser Lys Asp Leu Glu Glu Val Lys Ala
                50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
                100                 105                 110

Leu Arg Ala Glu Leu Gln Glu Gly Ala Arg Gln Lys Leu His Glu Leu
                115                 120                 125

Gln Glu Lys Leu Ser Pro Leu Arg Ala Glu Leu Gln Glu Gly Ala Arg
            130                 135                 140

Gln Lys Leu His Glu Leu Gln Glu Lys Leu Ser Pro Leu Gly Glu Glu
145                 150                 155                 160

Met Arg Asp Arg Ala Arg Ala His Val Asp Ala Leu Arg Thr His Leu
                165                 170                 175

Ala Pro Tyr Ser Asp Glu Leu Arg Gln Arg Leu Ala Ala Arg Leu Glu
                180                 185                 190

Ala Leu Lys Glu Asn Gly Gly Ala Arg Leu Ala Glu Tyr His Ala Lys
```

```
                      195                 200                 205
Ala Thr Glu His Leu Ser Thr Leu Ser Glu Lys Ala Lys Pro Ala Leu
        210                 215                 220

Glu Asp Leu Arg Gln Gly Leu Leu Pro Val Leu Glu Ser Phe Lys Val
225                 230                 235                 240

Ser Phe Leu Ser Ala Leu Glu Glu Tyr Thr Lys Lys Leu Asn Thr Gln
                245                 250                 255

<210> SEQ ID NO 75
<211> LENGTH: 278
<212> TYPE: PRT
<213> ORGANISM: Artificial Sequence
<220> FEATURE:
<223> OTHER INFORMATION: artificial sequence of His-tagged MSP1E3

<400> SEQUENCE: 75

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Tyr Leu Asp Asp Phe Gln
                85                  90                  95

Lys Lys Trp Gln Glu Glu Met Glu Leu Tyr Arg Gln Lys Val Glu Pro
            100                 105                 110

Leu Arg Ala Glu Leu Gln Glu Gly Ala Arg Gln Lys Leu His Glu Leu
        115                 120                 125

Gln Glu Lys Leu Ser Pro Leu Gly Glu Glu Met Arg Asp Arg Ala Arg
    130                 135                 140

Ala His Val Asp Ala Leu Arg Thr His Leu Ala Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
                245                 250                 255

Leu Glu Ser Phe Lys Val Ser Phe Leu Ser Ala Leu Glu Glu Tyr Thr
            260                 265                 270

Lys Lys Leu Asn Thr Gln
        275

<210> SEQ ID NO 76
<211> LENGTH: 223
<212> TYPE: PRT
```

```
<213> ORGANISM: Artificial Sequence
<220> FEATURE:
<223> OTHER INFORMATION: artificial sequence of His-tagged MSP1TEV

<400> SEQUENCE: 76

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
            20                  25                  30

Val Thr Ser Thr Phe Ser Lys Leu Arg Glu Gln Leu Gly Pro Val Thr
        35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Glu Tyr Thr Lys Lys Leu Asn Thr Gln
    210                 215                 220

<210> SEQ ID NO 77
<211> LENGTH: 200
<212> TYPE: PRT
<213> ORGANISM: Artificial Sequence
<220> FEATURE:
<223> OTHER INFORMATION: artificial sequence of MSP1NH

<400> SEQUENCE: 77

Leu Lys Leu Leu Asp Asn Trp Asp Ser Val Thr Ser Thr Phe Ser Lys
1               5                   10                  15

Leu Arg Glu Gln Leu Gly Pro Val Thr Gln Glu Phe Trp Asp Asn Leu
            20                  25                  30

Glu Lys Glu Thr Glu Gly Leu Arg Gln Glu Met Ser Lys Asp Leu Glu
        35                  40                  45

Glu Val Lys Ala Lys Val Gln Pro Tyr Leu Asp Asp Phe Gln Lys Lys
    50                  55                  60

Trp Gln Glu Glu Met Glu Leu Tyr Arg Gln Lys Val Glu Pro Leu Arg
65                  70                  75                  80

Ala Glu Leu Gln Glu Gly Ala Arg Gln Lys Leu His Glu Leu Gln Glu
                85                  90                  95

Lys Leu Ser Pro Leu Gly Glu Glu Met Arg Asp Arg Ala Arg Ala His
            100                 105                 110
```

```
Val Asp Ala Leu Arg Thr His Leu Ala Pro Tyr Ser Asp Glu Leu Arg
        115                 120                 125

Gln Arg Leu Ala Ala Arg Leu Glu Ala Leu Lys Glu Asn Gly Gly Ala
    130                 135                 140

Arg Leu Ala Glu Tyr His Ala Lys Ala Thr Glu His Leu Ser Thr Leu
145                 150                 155                 160

Ser Glu Lys Ala Lys Pro Ala Leu Glu Asp Leu Arg Gln Gly Leu Leu
                165                 170                 175

Pro Val Leu Glu Ser Phe Lys Val Ser Phe Leu Ser Ala Leu Glu Glu
            180                 185                 190

Tyr Thr Lys Lys Leu Asn Thr Gln
            195                 200

<210> SEQ ID NO 78
<211> LENGTH: 212
<212> TYPE: PRT
<213> ORGANISM: Artificial Sequence
<220> FEATURE:
<223> OTHER INFORMATION: artificial sequence of His-tagged MSP1T2

<400> SEQUENCE: 78

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 79
<211> LENGTH: 189
<212> TYPE: PRT
<213> ORGANISM: Artificial Sequence
<220> FEATURE:
<223> OTHER INFORMATION: artificial sequence of MSP1T2NH

<400> SEQUENCE: 79
```

```
Ser Thr Phe Ser Lys Leu Arg Glu Gln Leu Gly Pro Val Thr Gln Glu
1               5                   10                  15

Phe Trp Asp Asn Leu Glu Lys Glu Thr Glu Gly Leu Arg Gln Glu Met
            20                  25                  30

Ser Lys Asp Leu Glu Glu Val Lys Ala Lys Val Gln Pro Tyr Leu Asp
        35                  40                  45

Asp Phe Gln Lys Lys Trp Gln Glu Glu Met Glu Leu Tyr Arg Gln Lys
    50                  55                  60

Val Glu Pro Leu Arg Ala Glu Leu Gln Glu Gly Ala Arg Gln Lys Leu
65                  70                  75                  80

His Glu Leu Gln Glu Lys Leu Ser Pro Leu Gly Glu Glu Met Arg Asp
                85                  90                  95

Arg Ala Arg Ala His Val Asp Ala Leu Arg Thr His Leu Ala Pro Tyr
            100                 105                 110

Ser Asp Glu Leu Arg Gln Arg Leu Ala Ala Arg Leu Glu Ala Leu Lys
        115                 120                 125

Glu Asn Gly Gly Ala Arg Leu Ala Glu Tyr His Ala Lys Ala Thr Glu
    130                 135                 140

His Leu Ser Thr Leu Ser Glu Lys Ala Lys Pro Ala Leu Glu Asp Leu
145                 150                 155                 160

Arg Gln Gly Leu Leu Pro Val Leu Glu Ser Phe Lys Val Ser Phe Leu
                165                 170                 175

Ser Ala Leu Glu Glu Tyr Thr Lys Lys Leu Asn Thr Gln
            180                 185

<210> SEQ ID NO 80
<211> LENGTH: 201
<212> TYPE: PRT
<213> ORGANISM: Artificial Sequence
<220> FEATURE:
<223> OTHER INFORMATION: artificial sequence of MSP1T3

<400> SEQUENCE: 80

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175
```

```
Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 81
<211> LENGTH: 168
<212> TYPE: PRT
<213> ORGANISM: Artificial Sequence
<220> FEATURE:
<223> OTHER INFORMATION: artificial sequence of MSP1D4D5

<400> SEQUENCE: 81

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Leu Gly Glu Glu Met Arg Asp Arg Ala Arg Ala His
65                  70                  75                  80

Val Asp Ala Leu Arg Thr His Leu Ala Pro Tyr Ser Asp Glu Leu Arg
                85                  90                  95

Gln Arg Leu Ala Ala Arg Leu Glu Ala Leu Lys Glu Asn Gly Gly Ala
            100                 105                 110

Arg Leu Ala Glu Tyr His Ala Lys Ala Thr Glu His Leu Ser Thr Leu
        115                 120                 125

Ser Glu Lys Ala Lys Pro Ala Leu Glu Asp Leu Arg Gln Gly Leu Leu
    130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 82
<211> LENGTH: 168
<212> TYPE: PRT
<213> ORGANISM: Artificial Sequence
<220> FEATURE:
<223> OTHER INFORMATION: His-tagged MSP1D6D7

<400> SEQUENCE: 82

Met Gly His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Ala
```

```
                    100                 105                 110
Arg Leu Ala Glu Tyr His Ala Lys Ala Thr Glu His Leu Ser Thr Leu
            115                 120                 125

Ser Glu Lys Ala Lys Pro Ala Leu Glu Asp Leu Arg Gln Gly Leu Leu
        130                 135                 140

Pro Val Leu Glu Ser Phe Lys Val Ser Phe Leu Ser Ala Leu Glu Glu
145                 150                 155                 160

Tyr Thr Lys Lys Leu Asn Thr Gln
                165

<210> SEQ ID NO 83
<211> LENGTH: 190
<212> TYPE: PRT
<213> ORGANISM: Artificial Sequence
<220> FEATURE:
<223> OTHER INFORMATION: His-tagged MSP1D3D9

<400> SEQUENCE: 83

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Val Leu Glu Ser Phe Lys Val Ser Phe
                165                 170                 175

Leu Ser Ala Leu Glu Glu Tyr Thr Lys Lys Leu Asn Thr Gln
            180                 185                 190

<210> SEQ ID NO 84
<211> LENGTH: 201
<212> TYPE: PRT
<213> ORGANISM: Artificial Sequence
<220> FEATURE:
<223> OTHER INFORMATION: His-tagged MSP1D10.5

<400> SEQUENCE: 84

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45
```

```
Glu Gly Leu Arg Gln Glu Met Ser Lys Asp Leu Glu Val Lys Ala
        50                  55                  60

Lys Val Gln Pro Tyr Leu Asp Asp Phe Gln Lys Trp Gln Glu Glu
 65                  70                  75                  80

Met Glu Leu Tyr Arg Gln Lys Val Glu Pro Leu Arg Ala Glu Leu Gln
                 85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Ser Ala Leu Glu
            180                 185                 190

Glu Tyr Thr Lys Lys Leu Asn Thr Gln
        195                 200
```

<210> SEQ ID NO 85
<211> LENGTH: 190
<212> TYPE: PRT
<213> ORGANISM: Artificial Sequence
<220> FEATURE:
<223> OTHER INFORMATION: His-tagged MSP1D3D10.5

<400> SEQUENCE: 85

```
Met Gly His His His His His His Ile Glu Gly Arg Leu Lys Leu Leu
 1               5                  10                  15

Asp Asn Trp Asp Ser Val Thr Ser Thr Phe Ser Lys Leu Arg Glu Gln
                 20                  25                  30

Leu Gly Pro Val Thr Gln Glu Phe Trp Asp Asn Leu Glu Lys Glu Thr
             35                  40                  45

Glu Gly Leu Arg Gln Glu Met Ser Pro Tyr Leu Asp Asp Phe Gln Lys
 50                  55                  60

Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Ser Ala Leu Glu Glu Tyr Thr Lys Lys Leu Asn Thr Gln
            180                 185                 190
```

<210> SEQ ID NO 86
<211> LENGTH: 381

```
<212> TYPE: PRT
<213> ORGANISM: Artificial Sequence
<220> FEATURE:
<223> OTHER INFORMATION: His-tagged MSP2D1D1

<400> SEQUENCE: 86

Met Gly His His His His His His Asp Tyr Asp Ile Pro Thr Thr
1               5                   10                  15

Glu Asn Leu Tyr Phe Gln Gly Pro Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Gly Thr Pro Val Thr Gln Glu
        195                 200                 205

Phe Trp Asp Asn Leu Glu Lys Glu Thr Glu Gly Leu Arg Gln Glu Met
    210                 215                 220

Ser Lys Asp Leu Glu Glu Val Lys Ala Lys Val Gln Pro Tyr Leu Asp
225                 230                 235                 240

Asp Phe Gln Lys Lys Trp Gln Glu Glu Met Glu Leu Tyr Arg Gln Lys
                245                 250                 255

Val Glu Pro Leu Arg Ala Glu Leu Gln Glu Gly Ala Arg Gln Lys Leu
            260                 265                 270

His Glu Leu Gln Glu Lys Leu Ser Pro Leu Gly Glu Glu Met Arg Asp
        275                 280                 285

Arg Ala Arg Ala His Val Asp Ala Leu Arg Thr His Leu Ala Pro Tyr
    290                 295                 300

Ser Asp Glu Leu Arg Gln Arg Leu Ala Ala Arg Leu Glu Ala Leu Lys
305                 310                 315                 320

Glu Asn Gly Gly Ala Arg Leu Ala Glu Tyr His Ala Lys Ala Thr Glu
                325                 330                 335

His Leu Ser Thr Leu Ser Glu Lys Ala Lys Pro Ala Leu Glu Asp Leu
            340                 345                 350

Arg Gln Gly Leu Leu Pro Val Leu Glu Ser Phe Lys Val Ser Phe Leu
        355                 360                 365

Ser Ala Leu Glu Glu Tyr Thr Lys Lys Leu Asn Thr Gln
    370                 375                 380
```

```
<210> SEQ ID NO 87
<211> LENGTH: 13
<212> TYPE: PRT
<213> ORGANISM: Artificial Sequence
<220> FEATURE:
<223> OTHER INFORMATION: sequence of Helix 10.5

<400> SEQUENCE: 87

Ser Ala Leu Glu Glu Tyr Thr Lys Lys Leu Asn Thr Gln
1               5                   10

<210> SEQ ID NO 88
<211> LENGTH: 49
<212> TYPE: DNA
<213> ORGANISM: Artificial Sequence
<220> FEATURE:
<223> OTHER INFORMATION: nucleotide sequence of Helix 10.5

<400> SEQUENCE: 88 cagtttctg tcagctctgg aagaatatac taaaaagctg aatacccag              49

<210> SEQ ID NO 89
<211> LENGTH: 43
<212> TYPE: PRT
<213> ORGANISM: Artificial Sequence
<220> FEATURE:
<223> OTHER INFORMATION: sequence of GLOB

<400> SEQUENCE: 89

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn
        35                  40

<210> SEQ ID NO 90
<211> LENGTH: 66
<212> TYPE: DNA
<213> ORGANISM: Artificial
<220> FEATURE:
<223> OTHER INFORMATION: Oligonuceotide encoding H2S

<400> SEQUENCE: 90
tccgtgacgc aggaattctg ggacaacctg gaaaagaaa ccgagggact gcgtcaggaa   60
atgtcc                                                             66

<210> SEQ ID NO 91
<211> LENGTH: 201
<212> TYPE: PRT
<213> ORGANISM: Artificial
<220> FEATURE:
<223> OTHER INFORMATION: MSP1T4

<400> SEQUENCE: 91

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60
```

```
Lys Trp Gln Glu Glu Met Glu Leu Tyr Arg Gln Lys Val Glu Pro Leu
 65                  70                  75                  80

Arg Ala Glu Leu Gln Glu Gly Ala Arg Gln Lys Leu His Glu Leu Gln
                 85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
            115                 120                 125

Arg Gln Arg Leu Ala Ala Arg Leu Glu Ala Leu Lys Glu Asn Gly Gly
        130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln
        195                 200

<210> SEQ ID NO 92
<211> LENGTH: 190
<212> TYPE: PRT
<213> ORGANISM: Artificial
<220> FEATURE:
<223> OTHER INFORMATION: MSP1T5

<400> SEQUENCE: 92

Met Gly His His His His His His Asp Tyr Asp Ile Pro Thr Thr
  1               5                  10                  15

Glu Asn Leu Tyr Phe Gln Gly Lys Glu Thr Glu Gly Leu Arg Gln Glu
             20                  25                  30

Met Ser Lys Asp Leu Glu Glu Val Lys Ala Lys Val Gln Pro Tyr Leu
         35                  40                  45

Asp Asp Phe Gln Lys Lys Trp Gln Glu Glu Met Glu Leu Tyr Arg Gln
 50                  55                  60

Lys Val Glu Pro Leu Arg Ala Glu Leu Gln Glu Gly Ala Arg Gln Lys
 65                  70                  75                  80

Leu His Glu Leu Gln Glu Lys Leu Ser Pro Leu Gly Glu Glu Met Arg
                 85                  90                  95

Asp Arg Ala Arg Ala His Val Asp Ala Leu Arg Thr His Leu Ala Pro
            100                 105                 110

Tyr Ser Asp Glu Leu Arg Gln Arg Leu Ala Ala Arg Leu Glu Ala Leu
            115                 120                 125

Lys Glu Asn Gly Gly Ala Arg Leu Ala Glu Tyr His Ala Lys Ala Thr
        130                 135                 140

Glu His Leu Ser Thr Leu Ser Glu Lys Ala Lys Pro Ala Leu Glu Asp
145                 150                 155                 160

Leu Arg Gln Gly Leu Leu Pro Val Leu Glu Ser Phe Lys Val Ser Phe
                165                 170                 175

Leu Ser Ala Leu Glu Glu Tyr Thr Lys Lys Leu Asn Thr Gln
            180                 185                 190

<210> SEQ ID NO 93
<211> LENGTH: 179
<212> TYPE: PRT
<213> ORGANISM: Artificial
```

```
<220> FEATURE:
<223> OTHER INFORMATION: MSP1T6

<400> SEQUENCE: 93

Met Gly His His His His His His Asp Tyr Asp Ile Pro Thr Thr
1               5                   10                  15

Glu Asn Leu Tyr Phe Gln Gly Lys Asp Leu Glu Glu Val Lys Ala Lys
            20                  25                  30

Val Gln Pro Tyr Leu Asp Asp Phe Gln Lys Lys Trp Gln Glu Glu Met
        35                  40                  45

Glu Leu Tyr Arg Gln Lys Val Glu Pro Leu Arg Ala Glu Leu Gln Glu
    50                  55                  60

Gly Ala Arg Gln Lys Leu His Glu Leu Gln Glu Lys Leu Ser Pro Leu
65                  70                  75                  80

Gly Glu Glu Met Arg Asp Arg Ala Arg Ala His Val Asp Ala Leu Arg
                85                  90                  95

Thr His Leu Ala Pro Tyr Ser Asp Glu Leu Arg Gln Arg Leu Ala Ala
            100                 105                 110

Arg Leu Glu Ala Leu Lys Glu Asn Gly Gly Ala Arg Leu Ala Glu Tyr
        115                 120                 125

His Ala Lys Ala Thr Glu His Leu Ser Thr Leu Ser Glu Lys Ala Lys
    130                 135                 140

Pro Ala Leu Glu Asp Leu Arg Gln Gly Leu Leu Pro Val Leu Glu Ser
145                 150                 155                 160

Phe Lys Val Ser Phe Leu Ser Ala Leu Glu Glu Tyr Thr Lys Lys Leu
                165                 170                 175

Asn Thr Gln

<210> SEQ ID NO 94
<211> LENGTH: 289
<212> TYPE: PRT
<213> ORGANISM: Artificial
<220> FEATURE:
<223> OTHER INFORMATION: MSP1E3TEV

<400> SEQUENCE: 94

Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
            20                  25                  30

Val Thr Ser Thr Phe Ser Lys Leu Arg Glu Gln Leu Gly Pro Val Thr
        35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Leu Asp Asp Phe Gln Lys Lys Trp Gln Glu Glu Met Glu Leu
145                 150                 155                 160
```

Tyr Arg Gln Lys Val Glu Pro Leu Arg Ala Glu Leu Gln Gly Ala
                165                 170                 175

Arg Gln Lys Leu His Glu Leu Gln Glu Lys Leu Ser Pro Leu Gly Glu
            180                 185                 190

Glu Met Arg Asp Arg Ala Arg Ala His Val Asp Ala Leu Arg Thr His
        195                 200                 205

Leu Ala Pro Tyr Ser Asp Glu Leu Arg Gln Arg Leu Ala Ala Arg Leu
    210                 215                 220

Glu Ala Leu Lys Glu Asn Gly Gly Ala Arg Leu Ala Glu Tyr His Ala
225                 230                 235                 240

Lys Ala Thr Glu His Leu Ser Thr Leu Ser Glu Lys Ala Lys Pro Ala
                245                 250                 255

Leu Glu Asp Leu Arg Gln Gly Leu Leu Pro Val Leu Glu Ser Phe Lys
            260                 265                 270

Val Ser Phe Leu Ser Ala Leu Glu Glu Tyr Thr Lys Lys Leu Asn Thr
        275                 280                 285

Gln

<210> SEQ ID NO 95
<211> LENGTH: 278
<212> TYPE: PRT
<213> ORGANISM: Artificial
<220> FEATURE:
<223> OTHER INFORMATION: MSP1E3D1

<400> SEQUENCE: 95

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
                20                  25                  30

Leu Gly Pro Val Thr Gln Glu Phe Trp Asp Asn Leu Glu Lys Glu Thr
            35                  40                  45

Glu Gly Leu Arg Gln Glu Met Ser Lys Asp Leu Glu Glu Val Lys Ala
        50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Leu Asp Asp Phe Gln Lys Lys Trp Gln
    130                 135                 140

Glu Glu Met Glu Leu Tyr Arg Gln Lys Val Glu Pro Leu Arg Ala Glu
145                 150                 155                 160

Leu Gln Glu Gly Ala Arg Gln Lys Leu His Glu Leu Gln Glu Lys Leu
                165                 170                 175

Ser Pro Leu Gly Glu Glu Met Arg Asp Arg Ala Arg Ala His Val Asp
            180                 185                 190

Ala Leu Arg Thr His Leu Ala Pro Tyr Ser Asp Glu Leu Arg Gln Arg
        195                 200                 205

Leu Ala Ala Arg Leu Glu Ala Leu Lys Glu Asn Gly Gly Ala Arg Leu
    210                 215                 220

-continued

```
Ala Glu Tyr His Ala Lys Ala Thr Glu His Leu Ser Thr Leu Ser Glu
225                 230                 235                 240

Lys Ala Lys Pro Ala Leu Glu Asp Leu Arg Gln Gly Leu Leu Pro Val
            245                 250                 255

Leu Glu Ser Phe Lys Val Ser Phe Leu Ser Ala Leu Glu Glu Tyr Thr
            260                 265                 270

Lys Lys Leu Asn Thr Gln
        275
```

<210> SEQ ID NO 96
<211> LENGTH: 423
<212> TYPE: PRT
<213> ORGANISM: Artificial
<220> FEATURE:
<223> OTHER INFORMATION: MSP2TEV

<400> SEQUENCE: 96

```
Met Gly His His His His His His Asp Tyr Asp Ile Pro Thr Thr
1               5                   10                  15

Glu Asn Leu Tyr Phe Gln Gly Leu Lys Leu Leu Asp Asn Trp Asp Ser
                20                  25                  30

Val Thr Ser Thr Phe Ser Lys Leu Arg Glu Gln Leu Gly Pro Val Thr
            35                  40                  45

Gln Glu Phe Trp Asp Asn Leu Glu Lys Glu Thr Glu Gly Leu Arg Gln
    50                  55                  60

Glu Met Ser Lys Asp Leu Glu Glu Val Lys Ala Lys Val Gln Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Pro Val Leu Glu Ser Phe Lys Val Ser
        195                 200                 205

Phe Leu Ser Ala Leu Glu Tyr Thr Lys Lys Leu Asn Thr Gln Gly Thr
210                 215                 220

Leu Lys Leu Leu Asp Asn Trp Asp Ser Val Thr Ser Thr Phe Ser Lys
225                 230                 235                 240

Leu Arg Glu Gln Leu Gly Pro Val Thr Gln Glu Phe Trp Asp Asn Leu
                245                 250                 255

Glu Lys Glu Thr Glu Gly Leu Arg Gln Glu Met Lys Asp Leu Glu Glu
            260                 265                 270

Val Lys Ala Lys Val Gln Pro Tyr Leu Asp Asp Phe Gln Lys Lys Trp
        275                 280                 285

Gln Glu Glu Met Glu Leu Tyr Arg Gln Lys Val Glu Pro Leu Arg Ala
290                 295                 300
```

```
Glu Leu Gln Glu Gly Ala Arg Gln Lys Leu His Glu Leu Gln Glu Lys
305                 310                 315                 320

Leu Ser Pro Leu Gly Glu Met Arg Asp Arg Ala Arg Ala His Val
                325                 330                 335

Asp Ala Leu Arg Thr His Leu Ala Pro Tyr Ser Asp Glu Leu Arg Gln
            340                 345                 350

Arg Leu Ala Ala Arg Leu Glu Ala Leu Lys Glu Asn Gly Gly Ala Arg
        355                 360                 365

Leu Ala Glu Tyr His Ala Lys Ala Thr Glu His Leu Ser Thr Leu Ser
    370                 375                 380

Glu Lys Ala Lys Pro Ala Leu Glu Asp Leu Arg Gln Gly Leu Leu Pro
385                 390                 395                 400

Val Leu Glu Ser Phe Lys Val Ser Phe Leu Ser Ala Leu Glu Glu Tyr
                405                 410                 415

Thr Lys Lys Leu Asn Thr Gln
            420

<210> SEQ ID NO 97
<211> LENGTH: 199
<212> TYPE: PRT
<213> ORGANISM: Artificial
<220> FEATURE:
<223> OTHER INFORMATION: MSP1N1

<400> SEQUENCE: 97

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu
        195

<210> SEQ ID NO 98
<211> LENGTH: 401
<212> TYPE: PRT
<213> ORGANISM: Artificial
<220> FEATURE:
```

<223> OTHER INFORMATION: MSP2N1

<400> SEQUENCE: 98

```
Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Phe Ser Lys Leu Arg Glu Gln Leu Gly Pro
    210                 215                 220

Val Thr Gln Glu Phe Trp Asp Asn Leu Glu Lys Glu Thr Glu Gly Leu
225                 230                 235                 240

Arg Gln Glu Met Ser Lys Asp Leu Glu Glu Val Lys Ala Lys Val Gln
                245                 250                 255

Pro Tyr Leu Asp Asp Phe Gln Lys Lys Trp Gln Glu Glu Met Glu Leu
            260                 265                 270

Tyr Arg Gln Lys Val Glu Pro Leu Arg Ala Glu Leu Gln Glu Gly Ala
        275                 280                 285

Arg Gln Lys Leu His Glu Leu Gln Glu Lys Leu Ser Pro Leu Gly Glu
    290                 295                 300

Glu Met Arg Asp Arg Ala Arg Ala His Val Asp Ala Leu Arg Thr His
305                 310                 315                 320

Leu Ala Pro Tyr Ser Asp Glu Leu Arg Gln Arg Leu Ala Ala Arg Leu
                325                 330                 335

Glu Ala Leu Lys Glu Asn Gly Gly Ala Arg Leu Ala Glu Tyr His Ala
            340                 345                 350

Lys Ala Thr Glu His Leu Ser Thr Leu Ser Glu Lys Ala Lys Pro Ala
        355                 360                 365

Leu Glu Asp Leu Arg Gln Gly Leu Leu Pro Val Leu Glu Ser Phe Lys
    370                 375                 380

Val Ser Phe Leu Ser Ala Leu Glu Glu Tyr Thr Lys Lys Leu Asn Thr
385                 390                 395                 400
```

Gln

<210> SEQ ID NO 99
<211> LENGTH: 392
<212> TYPE: PRT
<213> ORGANISM: Artificial
<220> FEATURE:
<223> OTHER INFORMATION: MSP2N2

<400> SEQUENCE: 99

```
Met Gly His His His His His His Asp Tyr Asp Ile Pro Thr Thr
1               5                  10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Pro Val Thr Gln Glu Phe Trp Asp Asn Leu
    210                 215                 220

Glu Lys Glu Thr Glu Gly Leu Arg Gln Glu Met Ser Lys Asp Leu Glu
225                 230                 235                 240

Glu Val Lys Ala Lys Val Gln Pro Tyr Leu Asp Asp Phe Gln Lys Lys
                245                 250                 255

Trp Gln Glu Glu Met Glu Leu Tyr Arg Gln Lys Val Glu Pro Leu Arg
            260                 265                 270

Ala Glu Leu Gln Glu Gly Ala Arg Gln Lys Leu His Glu Leu Gln Glu
        275                 280                 285

Lys Leu Ser Pro Leu Gly Glu Glu Met Arg Asp Arg Ala Arg Ala His
    290                 295                 300

Val Asp Ala Leu Arg Thr His Leu Ala Pro Tyr Ser Asp Glu Leu Arg
305                 310                 315                 320

Gln Arg Leu Ala Ala Arg Leu Glu Ala Leu Lys Glu Asn Gly Gly Ala
                325                 330                 335

Arg Leu Ala Glu Tyr His Ala Lys Ala Thr Glu His Leu Ser Thr Leu
            340                 345                 350

Ser Glu Lys Ala Lys Pro Ala Leu Glu Asp Leu Arg Gln Gly Leu Leu
```

```
                355               360                365
Pro Val Leu Glu Ser Phe Lys Val Ser Phe Leu Ser Ala Leu Glu Glu
                    370                375                380

Tyr Thr Lys Lys Leu Asn Thr Gln
385                 390

<210> SEQ ID NO 100
<211> LENGTH: 603
<212> TYPE: DNA
<213> ORGANISM: Artificial
<220> FEATURE:
<223> OTHER INFORMATION: DNA encoding MSP1T4

<400> SEQUENCE: 100
atgggtcatc atcatcatca tcatcacgat tatgatattc ctactactga gaatttgtat      60
tttcagggtt ccgtgacgca ggaattctgg gacaacctgg aaaagaaaac cgagggactg     120
cgtcaggaaa tgtccaaaga tttagaagag gtgaaggcca aggttcagcc atatctcgat     180
gactttcaga aaaatggcag gaagagatgg aattatatcg tcaaaaggtg gaaccgctg      240 cgtgcggaac tgcaagaggg ggcacgccaa aaactccatg agctccaaga aagctcagc      300 ccattaggcg aagaaatgcg cgatcgcgcc cgtgcacatg ttgatgcact ccggactcat     360
ttggcgccgt attcggatga acttcgccag cgtttggccg cacgtctcga ggcgctgaaa     420
gaaaacgggg gtgcccgctt ggctgagtac cacgcgaaag cgacagaaca cctgagcacc     480
ttgagcgaaa aagcgaaacc ggcgctggaa gatctacgcc agggcttatt gcctgttctt     540
gagagcttta agtcagtttt ctgtcagctc tggaagaat atactaaaaa gctgaatacc      600
cag                                                                  603

<210> SEQ ID NO 101
<211> LENGTH: 570
<212> TYPE: DNA
<213> ORGANISM: Artificial
<220> FEATURE:
<223> OTHER INFORMATION: DNA encoding MSP1T5

<400> SEQUENCE: 101
atgggtcatc atcatcatca tcatcacgat tatgatattc ctactactga gaatttgtat      60
tttcagggta agaaaccga gggactgcgt caggaaatgt ccaaagattt agaagaggtg      120
aaggccaagg ttcagccata tctcgatgac tttcagaaaa atggcagga agagatggaa      180 ttatatcgtc aaaaggtgga accgctgcgt gcggaactgc aagaggggc acgccaaaaa     240 ctccatgagc tccaagagaa gctcagccca ttaggcgaag aaatgcgcga tcgcgcccgt     300
gcacatgttg atgcactccg gactcatttg gcgccgtatt cggatgaact tcgccagcgt    360
ttggccgcac gtctcgaggc gctgaaagaa aacgggggtg cccgcttggc tgagtaccac    420
gcgaaagcga cagaacacct gagcaccttg agcgaaaaag cgaaaccggc gctggaagat    480
ctacgccagg gcttattgcc tgttcttgag agctttaaag tcagttttct gtcagctctg    540
gaagaatata ctaaaaagct gaatacccag                                     570

<210> SEQ ID NO 102
<211> LENGTH: 537
<212> TYPE: DNA
<213> ORGANISM: Artificial
<220> FEATURE:
<223> OTHER INFORMATION: DNA encoding MSP1T6

<400> SEQUENCE: 102
```

```
atgggtcatc atcatcatca tcatcacgat tatgatattc ctactactga gaatttgtat      60 tttcaggqta agatttaga agaggtgaag gccaaggttc agccatatct cgatgacttt     120
cagaaaaaat ggcaggaaga gatgaatta tatcgtcaaa aggtggaacc gctgcgtgcg     180
gaactgcaag agggggcacg ccaaaaactc catgagctcc aagagaagct cagcccatta     240
ggcgaagaaa tgcgcgatcg cgcccgtgca catgttgatg cactccggac tcatttggcg     300
ccgtattcgg atgaacttcg ccagcgtttg gccgcacgtc tcgaggcgct gaaagaaaac     360
gggggtgccc gcttggctga gtaccacgcg aaagcgacag aacacctgag caccttgagc     420
gaaaaagcga accggcgct ggaagatcta cgccagggct tattgcctgt tcttgagagc     480
tttaaagtca gttttctgtc agctctggaa gaatatacta aaaagctgaa tacccag      537

<210> SEQ ID NO 103
<211> LENGTH: 597
<212> TYPE: DNA
<213> ORGANISM: Artificial
<220> FEATURE:
<223> OTHER INFORMATION: DNA encoding MSP1N1

<400> SEQUENCE: 103
atgggtcatc atcatcatca tcatcacgat tatgatattc ctactactga gaatttgtat      60 tttcaggqtt ccgtgacgca ggaattctgg gacaacctgg aaaagaaac cgagggactg     120 cgtcaggaaa tgtccaaaga tttagaagag gtgaaggcca aggttcagcc atatctcgat     180
gactttcaga aaaatggca ggaagagatg aattatatc gtcaaaaggt ggaaccatat     240
ctcgatgact tcagaaaaa atggcaggaa gagatggaat tatatcgtca aaaggtggaa     300
ccgctgcgtg cggaactgca agagggggca cgccaaaaac tccatgagct ccaagagaag     360
ctcagcccat aggcgaaga aatgcgcgat cgcgcccgtg cacatgttga tgcactccgg     420
actcatttgg cgccgtattc ggatgaactt cgccagcgtt tggccgcacg tctcgaggcg     480
ctgaaagaaa acgggggtgc ccgcttggct gagtaccacg cgaaagcgac agaacacctg     540
agcaccttga gcgaaaaagc gaaccggcg ctggaagatc tacgccaggg cttattg     597

<210> SEQ ID NO 104
<211> LENGTH: 4
<212> TYPE: PRT
<213> ORGANISM: Artificial
<220> FEATURE:
<223> OTHER INFORMATION: artificial peptide sequence

<400> SEQUENCE: 104

Asn Pro Gly Thr
1

<210> SEQ ID NO 105
<211> LENGTH: 867
<212> TYPE: DNA
<213> ORGANISM: Artificial
<220> FEATURE:
<223> OTHER INFORMATION: DNA encoding MSP1E3TEV

<400> SEQUENCE: 105
atgggtcatc atcatcatca tcatcacgat tatgatattc ctactactga gaatttgtat      60
tttcagggtc tgaagctgtt ggacaattgg gactctgtta cgtctacctt cagtaaactt     120
cgcgaacaac tgggccccgt gacgcaggaa ttctgggaca acctggaaaa agaaaccgag     180
ggactgcgtc aggaaatgtc caaagattta gaagaggtga aggccaaggt tcagccatat     240
```

| | |
|---|---|
| ctcgatgact tcagaaaaa atggcaggaa gagatggaat tatatcgtca aaaggtggaa | 300 |
| ccgctgcgtg cggaactgca agaggggca cgccaaaaac tccatgagct ccaagagaag | 360 |
| ctcagcccat taggcgaaga aatgcgcgat cgcgcccgtg cacatgttga tgcactccgg | 420 |
| actcatttgg cgccatatct cgatgacttt cagaaaaaat ggcaggaaga gatggaatta | 480 |
| tatcgtcaaa aggtggaacc gctgcgtgcg gaactgcaag aggggcacg ccaaaaactc | 540 |
| catgagctcc aagagaagct cagcccatta ggcgaagaaa tgcgcgatcg cgcccgtgca | 600 |
| catgttgatg cactccggac tcatttggcg ccgtattcgg atgaacttcg ccagcgtttg | 660 |
| gccgcacgtc tcgaggcgct gaaagaaaac gggggtgccc gcttggctga gtaccacgcg | 720 |
| aaagcgacag aacacctgag caccttgagc gaaaaagcga aaccggcgct ggaagatcta | 780 |
| cgccagggct tattgcctgt tcttgagagc tttaaagtca gttttctgtc agctctggaa | 840 |
| gaatatacta aaaagctgaa tacccag | 867 |

<210> SEQ ID NO 106
<211> LENGTH: 834
<212> TYPE: DNA
<213> ORGANISM: Artificial
<220> FEATURE:
<223> OTHER INFORMATION: DNA encoding MSP1E3D1

<400> SEQUENCE: 106

| | |
|---|---|
| atgggtcatc atcatcatca tcatcacgat tatgatattc ctactactga gaatttgtat | 60 |
| tttcagggtt ctaccttcag taaacttcgc gaacaactgg ccccgtgac gcaggaattc | 120 |
| tgggacaacc tggaaaaaga aaccgaggga ctgcgtcagg aaatgtccaa agatttagaa | 180 |
| gaggtgaagg ccaaggttca gccatatctc gatgactttc agaaaaaatg gcaggaagag | 240 |
| atggaattat atcgtcaaaa ggtggaaccg ctgcgtgcgg aactgcaaga ggggcacgc | 300 |
| caaaaactcc atgagctcca agagaagctc agcccattag gcgaagaaat gcgcgatcgc | 360 |
| gcccgtgcac atgttgatgc actccggact catttggcgc catatctcga tgactttcag | 420 |
| aaaaaatggc aggaagagat ggaattatat cgtcaaaagg tggaaccgct gcgtgcggaa | 480 |
| ctgcaagagg gggcacgcca aaaactccat gagctccaag agaagctcag cccattaggc | 540 |
| gaagaaatgc gcgatcgcgc ccgtgcacat gttgatgcac tccggactca tttggcgccg | 600 |
| tattcggatg aacttcgcca gcgtttggcc gcacgtctcg aggcgctgaa agaaaacggg | 660 |
| ggtgcccgct ggctgagta ccacgcgaaa gcgacagaac acctgagcac cttgagcgaa | 720 |
| aaagcgaaac cggcgctgga agatctacgc cagggcttat tgcctgttct tgagagcttt | 780 |
| aaagtcagtt tctgtcagc tctggaagaa tatactaaaa agctgaatac ccag | 834 |

<210> SEQ ID NO 107
<211> LENGTH: 1275
<212> TYPE: DNA
<213> ORGANISM: Artificial
<220> FEATURE:
<223> OTHER INFORMATION: DNA encoding MSP2TEV

<400> SEQUENCE: 107

| | |
|---|---|
| atgggtcatc atcatcatca tcatcacgat tatgatattc ctactactga gaatttgtat | 60 |
| tttcagggtc taaagctcct tgacaactgg gacagcgtga cctccacctt cagcaagctg | 120 |
| cgcgaacagc tcggccctgt gacccaggag ttctgggata acctggaaaa ggagacagag | 180 |
| ggcctgaggc aggagatgag caaggatctg gaggaggtga aggccaaggt gcagccctac | 240 |

```
ctggacgact tccagaagaa gtggcaggag gagatggagc tctaccgcca gaaggtggag      300
ccgctgcgcg cagagctcca agagggcgcg cgccagaagc tgcacgagct gcaagagaag      360
ctgagcccac tgggcgagga gatgcgcgac cgcgcgcgcg cccatgtgga cgcgctgcgc      420
acgcatctgg cccctacag cgacgagctg cgccagcgct tggccgcgcg ccttgaggct       480
ctcaaggaga acggcggcgc cagactggcc gagtaccacg ccaaggccac cgagcatctg      540
agcacgctca gcgagaaggc caagcccgcg ctcgaggacc tccgccaagg cctgctgccc      600
gtgctggaga gcttcaaggt cagcttcctg agcgctctcg aggagtacac taagaagctc      660
aacacccagg gtaccctaaa gctccttgac aactgggaca cgtgacctc caccttcagc       720 aagctgcgcg aacagctcgg ccctgtgacc caggagttct gggataacct ggaaaaggag      780
acagagggcc tgaggcagga gatgagcaag gatctggagg aggtgaaggc caaggtgcag      840
ccctacctgg acgacttcca gaagaagtgg caggaggaga tggagctcta ccgccagaag      900
gtggagccgc tgcgcgcaga gctccaagag ggcgcgcgcc agaagctgca cgagctgcaa      960
gagaagctga gcccactggg cgaggagatg cgcgaccgcg cgcgcgccca tgtggacgcg     1020
ctgcgcacga tctggcccc ctacagcgac gagctgcgcc agcgcttggc cgcgcgcctt      1080
gaggctctca aggagaacgg cggcgccaga ctggccgagt accacgccaa ggccaccgag     1140
catctgagca cgctcagcga gaaggccaag cccgcgctcg aggacctccg ccaaggcctg     1200
ctgcccgtgc tggagagctt caaggtcagc ttcctgagcg ctctcgagga gtacactaag     1260
aagctcaaca cccag                                                      1275

<210> SEQ ID NO 108
<211> LENGTH: 1203
<212> TYPE: DNA
<213> ORGANISM: Artificial
<220> FEATURE:
<223> OTHER INFORMATION: MSP2N1

<400> SEQUENCE: 108
atgggtcatc atcatcatca tcatcacgat tatgatattc ctactactga gaatttgtat       60
tttcagggtt ctaccttcag taaacttcgc gaacaactgg gccccgtgac gcaggaattc      120
tgggacaacc tggaaaaaga aaccgaggga ctgcgtcagg aaatgtccaa agatttagaa      180
gaggtgaagg ccaaggttca gccatatctc gatgactttc agaaaaaatg gcaggaagag      240
atggaattat atcgtcaaaa ggtggaaccg ctgcgtgcgg aactgcaaga gggggcacgc      300
caaaaactcc atgagctcca agagaagctc agcccattag gcgaagaaat gcgcgatcgc      360
gcccgtgcac atgttgatgc actccggact catttggcgc cgtattcgga tgaacttcgc      420
cagcgtttgg ccgcacgtct cgaggcgctg aaagaaaacg ggggtgcccg cttggctgag      480
taccacgcga aagcgacaga acacctgagc accttgagcg aaaaagcgaa accggcgctg      540
gaagatctac gccagggctt attgcctgtt cttgagagct ttaaagtcag ttttctgtca      600
gctctggaag aatatactaa aaagctgaat acccagggta ccttcagtaa acttcgcgaa      660
caactgggcc ccgtgacgca ggaattctgg gacaacctgg aaaaagaaac cgagggactg      720
cgtcaggaaa tgtccaaaga tttagaagag gtgaaggcca aggttcagcc atatctcgat      780
gactttcaga aaaaatggca ggaagagatg gaattatatc gtcaaaaggt ggaaccgctg      840
cgtgcggaac tgcaagaggg ggcacgccaa aaactccatg agctccaaga gaagctcagc      900
ccattaggcg aagaaatgcg cgatcgcgcc cgtgcacatg ttgatgcact ccggactcat      960
ttggcgccgt attcggatga acttcgccag cgtttggccg cacgtctcga ggcgctgaaa     1020
```

| | |
|---|---|
| gaaaacgggg gtgcccgctt ggctgagtac cacgcgaaag cgacagaaca cctgagcacc | 1080 |
| ttgagcgaaa aagcgaaacc ggcgctggaa gatctacgcc agggcttatt gcctgttctt | 1140 |
| gagagcttta aagtcagttt tctgtcagct ctggaagaat atactaaaaa gctgaatacc | 1200 |
| cag | 1203 |

<210> SEQ ID NO 109
<211> LENGTH: 1176
<212> TYPE: DNA
<213> ORGANISM: Artificial
<220> FEATURE:
<223> OTHER INFORMATION: DNA encoding MSP2N2

<400> SEQUENCE: 109

| | |
|---|---|
| atgggtcatc atcatcatca tcatcacgat tatgatattc ctactactga atttgtat | 60 |
| tttcagggtt ctaccttcag taaacttcgc gaacaactgg gccccgtgac gcaggaattc | 120 |
| tgggacaacc tggaaaaaga aaccgaggga ctgcgtcagg aaatgtccaa agatttagaa | 180 |
| gaggtgaagg ccaaggttca gccatatctc gatgactttc agaaaaaatg gcaggaagag | 240 |
| atggaattat atcgtcaaaa ggtggaaccg ctgcgtgcgg aactgcaaga gggggcacgc | 300 |
| caaaaactcc atgagctcca agagaagctc agcccattag cgaagaaat gcgcgatcgc | 360 |
| gcccgtgcac atgttgatgc actccggact catttggcgc cgtattcgga tgaacttcgc | 420 |
| cagcgtttgg ccgcacgtct cgaggcgctg aaagaaaacg ggggtgcccg cttggctgag | 480 |
| taccacgcga aagcgacaga cacctgagc accttgagcg aaaaagcgaa accggcgctg | 540 |
| gaagatctac gccagggctt attgcctgtt cttgagagct ttaaagtcag ttttctgtca | 600 |
| gctctggaag aatatactaa aaagctgaat acccagggta ccccgtgac gcaggaattc | 660 |
| tgggacaacc tggaaaaaga aaccgaggga ctgcgtcagg aaatgtccaa agatttagaa | 720 |
| gaggtgaagg ccaaggttca gccatatctc gatgactttc agaaaaaatg gcaggaagag | 780 |
| atggaattat atcgtcaaaa ggtggaaccg ctgcgtgcgg aactgcaaga gggggcacgc | 840 |
| caaaaactcc atgagctcca agagaagctc agcccattag cgaagaaat gcgcgatcgc | 900 |
| gcccgtgcac atgttgatgc actccggact catttggcgc cgtattcgga tgaacttcgc | 960 |
| cagcgtttgg ccgcacgtct cgaggcgctg aaagaaaacg ggggtgcccg cttggctgag | 1020 |
| taccacgcga aagcgacaga cacctgagc accttgagcg aaaaagcgaa accggcgctg | 1080 |
| gaagatctac gccagggctt attgcctgtt cttgagagct ttaaagtcag ttttctgtca | 1140 |
| gctctggaag aatatactaa aaagctgaat acccag | 1176 |

<210> SEQ ID NO 110
<211> LENGTH: 1198
<212> TYPE: DNA
<213> ORGANISM: Artificial
<220> FEATURE:
<223> OTHER INFORMATION: DNA encoding MSP2N3

<400> SEQUENCE: 110

| | |
|---|---|
| atgggtcatc atcatcatca tcatcacgat tatgatattc ctactactga atttgtat | 60 |
| tttcagggtt ctaccttcag taaacttcgc gaacaactgg gccccgtgac gcaggaattc | 120 |
| tgggacaacc tggaaaaaga aaccgaggga ctgcgtcagg aaatgtccaa agatttagaa | 180 |
| gaggtgaagg ccaaggttca gccatatctc gatgactttc agaaaaaatg gcaggaagag | 240 |
| atggaattat atcgtcaaaa ggtggaaccg ctgcgtgcgg aactgcaaga gggggcacgc | 300 |

```
caaaaactcc atgagctcca agagaagctc agcccattag gcgaagaaat gcgcgatcgc    360
gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga aagcgacaga cacctgagc accttgagcg aaaaagcgaa accggcgctg    540
gaagatctac gccagggctt attgcctgtt cttgagagct ttaaagtcag ttttctgtca    600
gctctggaag aatatactaa aaagctgaat acccagggta cccgcgaaca actgggcccc    660
gtgacgcagg aattctggga caacctggaa aaagaaaccg agggactgcg tcaggaaatg    720
tccaaagatt tagaagaggt gaaggccaag gttcagccat atctcgatga ctttcagaaa    780
aaatggcagg aagagatgga attatatcgt caaaaggtgg aaccgctgcg tgcggaactg    840 caagagggg cacgccaaaa actccatgag ctccaagaga agctcagccc attaggcgaa    900
gaaatgcgcg atcgcgcccg tgcacatgtt gatgcactcc ggactcattt ggcgccgtat    960
tcggatgaac ttcgccagcg tttggccgca cgtctcgagg cgctgaaaga aaacgggggt   1020
gcccgcttgg ctgagtacca cgcgaaagcg acagaacacc tgagcaccct tgagcgaaaaa   1080 gcgaaaccgg cgctggaaga tctacgccag ggcttattgc ctgttcttga gagctttaaa   1140
gtcagttttc tgtcagctct ggaagaatat actaaaaagc tgaatacccca gtaagctt    1198
```

<210> SEQ ID NO 111
<211> LENGTH: 397
<212> TYPE: PRT
<213> ORGANISM: Artificial
<220> FEATURE:
<223> OTHER INFORMATION: MSP2N3

<400> SEQUENCE: 111

```
Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205
```

```
Leu Asn Thr Gln Gly Thr Arg Glu Gln Leu Gly Pro Val Thr Gln Glu
    210                 215                 220

Phe Trp Asp Asn Leu Glu Lys Glu Thr Glu Gly Leu Arg Gln Glu Met
225                 230                 235                 240

Ser Lys Asp Leu Glu Glu Val Lys Ala Lys Val Gln Pro Tyr Leu Asp
                245                 250                 255

Asp Phe Gln Lys Lys Trp Gln Glu Glu Met Glu Leu Tyr Arg Gln Lys
            260                 265                 270

Val Glu Pro Leu Arg Ala Glu Leu Gln Glu Gly Ala Arg Gln Lys Leu
        275                 280                 285

His Glu Leu Gln Glu Lys Leu Ser Pro Leu Gly Glu Glu Met Arg Asp
    290                 295                 300

Arg Ala Arg Ala His Val Asp Ala Leu Arg Thr His Leu Ala Pro Tyr
305                 310                 315                 320

Ser Asp Glu Leu Arg Gln Arg Leu Ala Ala Arg Leu Glu Ala Leu Lys
                325                 330                 335

Glu Asn Gly Gly Ala Arg Leu Ala Glu Tyr His Ala Lys Ala Thr Glu
            340                 345                 350

His Leu Ser Thr Leu Ser Glu Lys Ala Lys Pro Ala Leu Glu Asp Leu
        355                 360                 365

Arg Gln Gly Leu Leu Pro Val Leu Glu Ser Phe Lys Val Ser Phe Leu
    370                 375                 380

Ser Ala Leu Glu Glu Tyr Thr Lys Lys Leu Asn Thr Gln
385                 390                 395

<210> SEQ ID NO 112
<211> LENGTH: 1149
<212> TYPE: DNA
<213> ORGANISM: Artificial
<220> FEATURE:
<223> OTHER INFORMATION: DNA encoding MSP2N4

<400> SEQUENCE: 112
atgggtcatc atcatcatca tcatcacgat tatgatattc ctactactga gaatttgtat     60
tttcagggtt ccgtgacgca ggaattctgg gacaacctgg aaaaagaaac cgagggactg    120
cgtcaggaaa tgtccaaaga tttagaagag gtgaaggcca aggttcagcc atatctcgat    180
gactttcaga aaaaatggca ggaagagatg gaattatatc gtcaaaaggt ggaaccgctg    240
cgtgcggaac tgcaagaggg ggcacgccaa aaactccatg agctccaaga gaagctcagc    300
ccattaggcg aagaaatgcg cgatcgcgcc cgtgcacatg ttgatgcact ccggactcat    360
ttggcgccgt attcggatga acttcgccag cgtttggccg cacgtctcga ggcgctgaaa    420
gaaaacgggg gtgcccgctt ggctgagtac cacgcgaaag cgacagaaca cctgagcacc    480
ttgagcgaaa aagcgaaacc ggcgctggaa gatctacgcc agggcttatt gcctgttctt    540
gagagcttta agtcagttt tctgtcagct ctggaagaat atactaaaaa gctgaatacc    600
cagaatccag gtaccccgt gacgcaggaa ttctgggaca acctggaaaa agaaaccgag    660
ggactgcgtc aggaaatgtc caagatttta gaagaggtga aggccaaggt tcagccatat    720
ctcgatgact ttcagaaaaa atggcaggaa gagatggaat tatatcgtca aaaggtggaa    780
ccgctgcgtg cggaactgca agagggggca cgccaaaaac tccatgagct ccaagagaag    840
ctcagcccat taggcgaaga aatgcgcgat cgcgcccgtg cacatgttga tgcactccgg    900
actcatttgg cgccgtattc ggatgaactt cgccagcgtt tggccgcacg tctcgaggcg    960
ctgaaagaaa acggggtgc cgcttggct gagtaccacg cgaaagcgac agaacacctg   1020
```

```
agcaccttga gcgaaaaagc gaaaccggcg ctggaagatc tacgccaggg cttattgcct   1080
gttcttgaga gctttaaagt cagttttctg tcagctctgg aagaatatac taaaaagctg   1140
aataccag                                                              1149
```

<210> SEQ ID NO 113
<211> LENGTH: 383
<212> TYPE: PRT
<213> ORGANISM: Artificial
<220> FEATURE:
<223> OTHER INFORMATION: MSP2N4

<400> SEQUENCE: 113

```
Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Leu
65                  70                  75                  80

Arg Ala Glu Leu Gln Glu Gly Ala Arg Gln Lys Leu His Glu Leu Gln
                85                  90                  95

Glu Lys Leu Ser Pro Leu Gly Glu Glu Met Arg Asp Arg Ala Arg Ala
            100                 105                 110

His Val Asp Ala Leu Arg Thr His Leu Ala Pro Tyr Ser Asp Glu Leu
        115                 120                 125

Arg Gln Arg Leu Ala Ala Arg Leu Glu Ala Leu Lys Glu Asn Gly Gly
    130                 135                 140

Ala Arg Leu Ala Glu Tyr His Ala Lys Ala Thr Glu His Leu Ser Thr
145                 150                 155                 160

Leu Ser Glu Lys Ala Lys Pro Ala Leu Glu Asp Leu Arg Gln Gly Leu
                165                 170                 175

Leu Pro Val Leu Glu Ser Phe Lys Val Ser Phe Leu Ser Ala Leu Glu
            180                 185                 190

Glu Tyr Thr Lys Lys Leu Asn Thr Gln Asn Pro Gly Thr Pro Val Thr
        195                 200                 205

Gln Glu Phe Trp Asp Asn Leu Glu Lys Glu Thr Glu Gly Leu Arg Gln
    210                 215                 220

Glu Met Ser Lys Asp Leu Glu Glu Val Lys Ala Lys Val Gln Pro Tyr
225                 230                 235                 240

Leu Asp Asp Phe Gln Lys Lys Trp Gln Glu Glu Met Glu Leu Tyr Arg
                245                 250                 255

Gln Lys Val Glu Pro Leu Arg Ala Glu Leu Gln Glu Gly Ala Arg Gln
            260                 265                 270

Lys Leu His Glu Leu Gln Glu Lys Leu Ser Pro Leu Gly Glu Glu Met
        275                 280                 285

Arg Asp Arg Ala Arg Ala His Val Asp Ala Leu Arg Thr His Leu Ala
    290                 295                 300

Pro Tyr Ser Asp Glu Leu Arg Gln Arg Leu Ala Ala Arg Leu Glu Ala
305                 310                 315                 320

Leu Lys Glu Asn Gly Gly Ala Arg Leu Ala Glu Tyr His Ala Lys Ala
                325                 330                 335
```

```
Thr Glu His Leu Ser Thr Leu Ser Glu Lys Ala Lys Pro Ala Leu Glu
        340                 345                 350

Asp Leu Arg Gln Gly Leu Leu Pro Val Leu Glu Ser Phe Lys Val Ser
        355                 360                 365

Phe Leu Ser Ala Leu Glu Glu Tyr Thr Lys Lys Leu Asn Thr Gln
    370                 375                 380

<210> SEQ ID NO 114
<211> LENGTH: 1137
<212> TYPE: DNA
<213> ORGANISM: Artificial
<220> FEATURE:
<223> OTHER INFORMATION: DNA encoding MSP2N5

<400> SEQUENCE: 114
atgggtcatc atcatcatca tcatcacgat tatgatattc ctactactga atttgtat     60 tttcagggtt ccgtgacgca ggaattctgg acaacctgg aaaaagaaac cgagggactg    120
cgtcaggaaa tgtccaaaga tttagaagag gtgaaggcca aggttcagcc atatctcgat    180
gactttcaga aaaatggca ggaagagatg gaattatatc gtcaaaaggt ggaaccatat    240
ctcgatgact ttcagaaaaa atggcaggaa gagatggaat tatatcgtca aaggtggaa    300 ccgctgcgtg cggaactgca gaggggggca cgccaaaaac tccatgagct ccaagagaag    360
ctcagcccat taggcgaaga aatgcgcgat cgcgcccgtg cacatgttga tgcactccgg    420
actcatttgg cgccgtattc ggatgaactt cgccagcgtt tggccgcacg tctcgaggcg    480
ctgaaagaaa cgggggtgc cgcttggct gagtaccacg cgaaagcgac agaacacctg    540
agcaccttga gcgaaaaagc gaaaccggcg ctggaagatc tacgccaggg cttattgaat    600
ccaggtacca agatttaga agaggtgaag gccaaggttc agccatatct cgatgacttt    660 cagaaaaat ggcaggaaga gatggaatta tatcgtcaaa aggtggaacc atatctcgat    720
gactttcaga aaaatggca ggaagagatg gaattatatc gtcaaaaggt ggaaccgctg    780
cgtgcggaac tgcaagaggg ggcacgccaa aaactccatg agctccaaga gaagctcagc    840
ccattaggcg aagaaatgcg cgatcgcgcc cgtgcacatg ttgatgcact ccggactcat    900
ttggcgccgt attcggatga acttcgccag cgtttggccg cacgtctcga ggcgctgaaa    960
gaaaacgggg gtgcccgctt ggctgagtac cacgcgaaag cgacagaaca cctgagcacc    1020
ttgagcgaaa aagcgaaacc ggcgctggaa gatctacgcc agggcttatt gcccgtgacg    1080
caggaattct gggacaacct ggaaaaagaa accgagggac tgcgtcagga atgtcc       1137

<210> SEQ ID NO 115
<211> LENGTH: 379
<212> TYPE: PRT
<213> ORGANISM: Artificial
<220> FEATURE:
<223> OTHER INFORMATION: MSP2n5

<400> SEQUENCE: 115

Met Gly His His His His His His Asp Tyr Asp Ile Pro Thr Thr
1               5                   10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60
```

Lys Trp Gln Glu Glu Met Glu Leu Tyr Arg Gln Lys Val Glu Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Asn Pro Gly Thr Lys Asp Leu Glu Glu
        195                 200                 205

Val Lys Ala Lys Val Gln Pro Tyr Leu Asp Asp Phe Gln Lys Lys Trp
    210                 215                 220

Gln Glu Glu Met Glu Leu Tyr Arg Gln Lys Val Glu Pro Tyr Leu Asp
225                 230                 235                 240

Asp Phe Gln Lys Lys Trp Gln Glu Glu Met Glu Leu Tyr Arg Gln Lys
                245                 250                 255

Val Glu Pro Leu Arg Ala Glu Leu Gln Glu Gly Ala Arg Gln Lys Leu
            260                 265                 270

His Glu Leu Gln Glu Lys Leu Ser Pro Leu Gly Glu Glu Met Arg Asp
        275                 280                 285

Arg Ala Arg Ala His Val Asp Ala Leu Arg Thr His Leu Ala Pro Tyr
    290                 295                 300

Ser Asp Glu Leu Arg Gln Arg Leu Ala Ala Arg Leu Glu Ala Leu Lys
305                 310                 315                 320

Glu Asn Gly Gly Ala Arg Leu Ala Glu Tyr His Ala Lys Ala Thr Glu
                325                 330                 335

His Leu Ser Thr Leu Ser Glu Lys Ala Lys Pro Ala Leu Glu Asp Leu
            340                 345                 350

Arg Gln Gly Leu Leu Pro Val Thr Gln Glu Phe Trp Asp Asn Leu Glu
        355                 360                 365

Lys Glu Thr Glu Gly Leu Arg Gln Glu Met Ser
370                 375

<210> SEQ ID NO 116
<211> LENGTH: 1143
<212> TYPE: DNA
<213> ORGANISM: Artificial
<220> FEATURE:
<223> OTHER INFORMATION: DNA encoding MSP2N6

<400> SEQUENCE: 116
atgggtcatc atcatcatca tcatcacgat tatgatattc ctactactga gaatttgtat    60
tttcagggtt ccgtgacgca ggaattctgg gacaacctgg aaaagaaaac cgagggactg   120
cgtcaggaaa tgtccaaaga tttagaagag gtgaaggcca aggttcagcc atatctcgat   180
gactttcaga aaaaatggca ggaagagatg gaattatatc gtcaaaaggt ggaaccatat   240

-continued

| | |
|---|---|
| ctcgatgact tcagaaaaaa atggcaggaa gagatggaat tatatcgtca aaggtggaa | 300 |
| ccgctgcgtg cggaactgca agaggggca cgccaaaaac tccatgagct ccaagagaag | 360 |
| ctcagcccat taggcgaaga aatgcgcgat cgcgcccgtg cacatgttga tgcactccgg | 420 |
| actcatttgg cgccgtattc ggatgaactt cgccagcgtt tggccgcacg tctcgaggcg | 480 |
| ctgaaagaaa acggggtgc cgcttggct gagtaccacg cgaaagcgac agaacacctg | 540 |
| agcaccttga gcgaaaaagc gaaaccggcg ctggaagatc tacgccaggg cttattgtcc | 600 |
| aatccaggta cccaaaaaga tttagaagag gtgaaggcca aggttcagcc atatctcgat | 660 |
| gactttcaga aaaaatggca ggaagagatg gaattatatc gtcaaaaggt ggaaccatat | 720 |
| ctcgatgact tcagaaaaaa atggcaggaa gagatggaat tatatcgtca aaggtggaa | 780 |
| ccgctgcgtg cggaactgca agaggggca cgccaaaaac tccatgagct ccaagagaag | 840 |
| ctcagcccat taggcgaaga aatgcgcgat cgcgcccgtg cacatgttga tgcactccgg | 900 |
| actcatttgg cgccgtattc ggatgaactt cgccagcgtt tggccgcacg tctcgaggcg | 960 |
| ctgaaagaaa acggggtgc cgcttggct gagtaccacg cgaaagcgac agaacacctg | 1020 |
| agcaccttga gcgaaaaagc gaaaccggcg ctggaagatc tacgccaggg cttattgccc | 1080 |
| gtgacgcagg aattctggga caacctggaa aaagaaaccg agggactgcg tcaggaaatg | 1140 |
| tcc | 1143 |

<210> SEQ ID NO 117
<211> LENGTH: 381
<212> TYPE: PRT
<213> ORGANISM: Artificial
<220> FEATURE:
<223> OTHER INFORMATION: MSP2N6

<400> SEQUENCE: 117

Met Gly His His His His His His Asp Tyr Asp Ile Pro Thr Thr
1               5                  10                  15

Glu Asn Leu Tyr Phe Gln Gly Ser Val Thr Gln Glu Phe Trp Asp Asn
            20                  25                  30

Leu Glu Lys Glu Thr Glu Gly Leu Arg Gln Glu Met Ser Lys Asp Leu
        35                  40                  45

Glu Glu Val Lys Ala Lys Val Gln Pro Tyr Leu Asp Asp Phe Gln Lys
    50                  55                  60

Lys Trp Gln Glu Glu Met Glu Leu Tyr Arg Gln Lys Val Glu Pro Tyr
65                  70                  75                  80

Leu Asp Asp Phe Gln Lys Lys Trp Gln Glu Glu Met Glu Leu Tyr Arg
                85                  90                  95

Gln Lys Val Glu Pro Leu Arg Ala Glu Leu Gln Glu Gly Ala Arg Gln
            100                 105                 110

Lys Leu His Glu Leu Gln Glu Lys Leu Ser Pro Leu Gly Glu Glu Met
        115                 120                 125

Arg Asp Arg Ala Arg Ala His Val Asp Ala Leu Arg Thr His Leu Ala
    130                 135                 140

Pro Tyr Ser Asp Glu Leu Arg Gln Arg Leu Ala Ala Arg Leu Glu Ala
145                 150                 155                 160

Leu Lys Glu Asn Gly Gly Ala Arg Leu Ala Glu Tyr His Ala Lys Ala
                165                 170                 175

Thr Glu His Leu Ser Thr Leu Ser Glu Lys Ala Lys Pro Ala Leu Glu
            180                 185                 190

Asp Leu Arg Gln Gly Leu Leu Ser Asn Pro Gly Thr Gln Lys Asp Leu

```
                195                 200                 205
Glu Glu Val Lys Ala Lys Val Gln Pro Tyr Leu Asp Asp Phe Gln Lys
    210                 215                 220

Lys Trp Gln Glu Glu Met Glu Leu Tyr Arg Gln Lys Val Glu Pro Tyr
225                 230                 235                 240

Leu Asp Asp Phe Gln Lys Lys Trp Gln Glu Glu Met Glu Leu Tyr Arg
                245                 250                 255

Gln Lys Val Glu Pro Leu Arg Ala Glu Leu Gln Glu Gly Ala Arg Gln
            260                 265                 270

Lys Leu His Glu Leu Gln Glu Lys Leu Ser Pro Leu Gly Glu Glu Met
        275                 280                 285

Arg Asp Arg Ala Arg Ala His Val Asp Ala Leu Arg Thr His Leu Ala
    290                 295                 300

Pro Tyr Ser Asp Glu Leu Arg Gln Arg Leu Ala Ala Arg Leu Glu Ala
305                 310                 315                 320

Leu Lys Glu Asn Gly Gly Ala Arg Leu Ala Glu Tyr His Ala Lys Ala
                325                 330                 335

Thr Glu His Leu Ser Thr Leu Ser Glu Lys Ala Lys Pro Ala Leu Glu
            340                 345                 350

Asp Leu Arg Gln Gly Leu Leu Pro Val Thr Gln Glu Phe Trp Asp Asn
        355                 360                 365

Leu Glu Lys Glu Thr Glu Gly Leu Arg Gln Glu Met Ser
    370                 375                 380

<210> SEQ ID NO 118
<211> LENGTH: 3282
<212> TYPE: DNA
<213> ORGANISM: Artificial
<220> FEATURE:
<223> OTHER INFORMATION: DNA encoding MSP2CPR

<400> SEQUENCE: 118
atgggtcatc atcatcatca tcacattgag gacgtctga agctgttgga caattgggac      60
tctgttacgt ctaccttcag taaacttcgc gaacaactgg ccccgtgac gcaggaattc     120 tgggacaacc tggaaaaaga aaccgaggga ctgcgtcagg aaatgtccaa agatttagaa    180
gaggtgaagg ccaaggttca gccatatctc gatgactttc agaaaaaatg cgaggaagag    240
atggaattat atcgtcaaaa ggtggaaccg ctgcgtgcgg aactgcaaga ggggcacgc     300 caaaaactcc atgagctcca agagaagctc agcccattag cgaagaaat gcgcgatcgc     360 gcccgtgcac atgttgatgc actccggact catttggcgc cgtattcgga tgaacttcgc    420
cagcgtttgg ccgcacgtct cgaggcgctg aaagaaaacg ggggtgcccg cttggctgag    480
taccacgcga agcgacaga cacctgagc accttgagcg aaaaagcgaa accggcgctg     540
gaagatctac gccagggctt attgcctgtt cttgagagct ttaaagtcag ttttctgtca    600
gctctggaag aatatactaa aaagctgaat acccagggta ccctgaagct gttggacaat    660
tgggactctg ttacgtctac cttcagtaaa cttcgcgaac aactgggccc cgtgacgcag    720
gaattctggg acaacctgga aaagaaacc gagggactgc gtcaggaaat gtccaaagat    780
ttagaagagg tgaaggccaa ggttcagcca tatctcgatg actttcagaa aaaatggcag    840
gaagagatgg aattatatcg tcaaaaggtg aaccgctgc gtgcggaact gcaagagggg    900
gcacgccaaa aactccatga gctccaagag aagctcagcc cattaggcga agaaatgcgc    960
gatcgcgccc gtgcacatgt tgatgcactc cggactcatt tggcgccgta ttcggatgaa   1020
```

```
cttcgccagc gtttggccgc acgtctcgag gcgctgaaag aaaacggggg tgcccgcttg    1080
gctgagtacc acgcgaaagc gacagaacac ctgagcacct tgagcgaaaa agcgaaaccg    1140
gcgctggaag atctacgcca gggcttattg cctgttcttg agagctttaa agtcagtttt    1200
ctgtcagctc tggaagaata tactaaaaag ctgaatacccc agtcgaccat gggagactct    1260
cacgaagaca ccagtgccac catgcctgag gccgtggctg aagaagtgtc tctattcagc    1320
acgacggaca tggttctgtt ttctctcatc gtggggtcc tgacctactg gttcatcttt    1380
agaaagaaga aagaagagat accggagttc agcaagatcc aaacaacggc cccacccgtc    1440
aaagagagca gcttcgtgga aaagatgaag aaaacgggaa ggaacattat cgtattctat    1500
ggctcccaga cgggaaccgc tgaggagttt gccaaccggc tgtccaagga tgcccaccgc    1560
tacgggatgc ggggcatgtc cgcagaccct gaagagtatg acttggccga cctgagcagc    1620
ctgcctgaga tcgacaagtc cctggtagtc ttctgcatgg ccacatacgg agagggcgac    1680
cccacggaca atgcgcagga cttctatgac tggctgcagg agactgacgt ggacctcact    1740
ggggtcaagt tgctgtatt tggtcttggg aacaagacct atgagcactt caatgccatg    1800
ggcaagtatg tggaccagcg gctggagcag cttggcgccc agcgcatctt tgagttgggc    1860
cttggtgatg atgacgggaa cttggaagag gatttcatca cgtggaggga gcagttctgg    1920
ccagctgtgt gcgagttctt tggggtagaa gccactgggg aggagtcgag cattcgccag    1980
tatgagctcg tggtccacga agacatggac gtagccaagg tgtacacggg tgagatgggc    2040
cgtctgaaga gctacgagaa ccagaaaccc ccttcgatg ctaagaatcc attcctggct    2100
gctgtcaccg ccaaccggaa gctgaaccaa ggcactgagc ggcatctaat gcacctggag    2160
ttggacatct cagactccaa gatcaggtat gaatctggag atcacgtggc tgtgtaccca    2220
gccaatgact cagccctggt caaccagatt ggggagatcc tgggagctga cctggatgtc    2280
atcatgtctc taaacaatct cgatgaggag tcaaacaaga agcatccgtt ccctgcccc    2340 accacctacc gcacggccct cacctactac ctggacatca ctaacccgcc acgcaccaat    2400
gtgctctacg aactggcaca gtacgcctca gagccctcgg agcaggagca cctgcacaag    2460
atggcgtcat cctcaggcga gggcaaggag ctgtacctga gctgggtggt ggaagcccgg    2520
aggcacatcc tagccatcct ccaagactac ccatcactgc ggccaccat cgaccacctg    2580 tgtgagctgc tgccacgcct gcaggcccga tactactcca ttgcctcatc ctccaaggtc    2640
caccccaact ccgtgcacat ctgtgccgtg gccgtggagt acgaagcgaa gtctggccga    2700
gtgaacaagg gggtggccac tagctggctt cgggccaagg aaccagcagg cgagaatggc    2760
ggccgcgccc tggtacccat gttcgtgcgc aaatctcagt tccgcttgcc tttcaagtcc    2820
accacacctg tcatcatggt gggccccggc actgggatta ccccttcat gggcttcatc    2880 caggaacgag cttggcttcg agagcaaggc aaggaggtgg gagagacgct gctatactat    2940
ggctgccggc gctcggatga ggactatctg taccgtgaag agctagcccg cttccacaag    3000
gacggtgccc tcacgcagct taatgtggcc ttttcccggg agcaggccca caagtctat    3060 gtccagcacc ttctgaagag agacagggaa cacctgtgga agctgatcca cgagggcggt    3120
gcccacatct atgtgtgcgg ggatgctcga aatatggcca agatgtgca aaacacattc    3180 tatgacattg tggctgagtt cgggcccatg gagcacaccc aggctgtgga ctatgttaag    3240
aagctgatga ccaagggccg ctactcacta gatgtgtgga gc                      3282
```

<210> SEQ ID NO 119
<211> LENGTH: 1094

<212> TYPE: PRT
<213> ORGANISM: Artificial
<220> FEATURE:
<223> OTHER INFORMATION: MSP2CPR

<400> SEQUENCE: 119

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr Leu Lys Leu Leu Asp Asn Trp Asp Ser Val
    210                 215                 220

Thr Ser Thr Phe Ser Lys Leu Arg Glu Gln Leu Gly Pro Val Thr Gln
225                 230                 235                 240

Glu Phe Trp Asp Asn Leu Glu Lys Glu Thr Glu Gly Leu Arg Gln Glu
                245                 250                 255

Met Ser Lys Asp Leu Glu Glu Val Lys Ala Lys Val Gln Pro Tyr Leu
            260                 265                 270

Asp Asp Phe Gln Lys Lys Trp Gln Glu Glu Met Glu Leu Tyr Arg Gln
        275                 280                 285

Lys Val Glu Pro Leu Arg Ala Glu Leu Gln Glu Gly Ala Arg Gln Lys
    290                 295                 300

Leu His Glu Leu Gln Glu Lys Leu Ser Pro Leu Gly Glu Glu Met Arg
305                 310                 315                 320

Asp Arg Ala Arg Ala His Val Asp Ala Leu Arg Thr His Leu Ala Pro
                325                 330                 335

Tyr Ser Asp Glu Leu Arg Gln Arg Leu Ala Ala Arg Leu Glu Ala Leu
            340                 345                 350

Lys Glu Asn Gly Gly Ala Arg Leu Ala Glu Tyr His Ala Lys Ala Thr
        355                 360                 365

Glu His Leu Ser Thr Leu Ser Glu Lys Ala Lys Pro Ala Leu Glu Asp
    370                 375                 380
```

```
Leu Arg Gln Gly Leu Leu Pro Val Leu Glu Ser Phe Lys Val Ser Phe
385                 390                 395                 400

Leu Ser Ala Leu Glu Glu Tyr Thr Lys Lys Leu Asn Thr Gln Ser Thr
            405                 410                 415

Met Gly Asp Ser His Glu Asp Thr Ser Ala Thr Met Pro Glu Ala Val
        420                 425                 430

Ala Glu Glu Val Ser Leu Phe Ser Thr Thr Asp Met Val Leu Phe Ser
            435                 440                 445

Leu Ile Val Gly Val Leu Thr Tyr Trp Phe Ile Phe Arg Lys Lys Lys
    450                 455                 460

Glu Glu Ile Pro Glu Phe Ser Lys Ile Gln Thr Thr Ala Pro Pro Val
465                 470                 475                 480

Lys Glu Ser Ser Phe Val Glu Lys Met Lys Lys Thr Gly Arg Asn Ile
                485                 490                 495

Ile Val Phe Tyr Gly Ser Gln Thr Gly Thr Ala Glu Glu Phe Ala Asn
            500                 505                 510

Arg Leu Ser Lys Asp Ala His Arg Tyr Gly Met Arg Gly Met Ser Ala
        515                 520                 525

Asp Pro Glu Glu Tyr Asp Leu Ala Asp Leu Ser Ser Leu Pro Glu Ile
530                 535                 540

Asp Lys Ser Leu Val Val Phe Cys Met Ala Thr Tyr Gly Glu Gly Asp
545                 550                 555                 560

Pro Thr Asp Asn Ala Gln Asp Phe Tyr Asp Trp Leu Gln Glu Thr Asp
                565                 570                 575

Val Asp Leu Thr Gly Val Lys Phe Ala Val Phe Gly Leu Gly Asn Lys
            580                 585                 590

Thr Tyr Glu His Phe Asn Ala Met Gly Lys Tyr Val Asp Gln Arg Leu
        595                 600                 605

Glu Gln Leu Gly Ala Gln Arg Ile Phe Glu Leu Gly Leu Gly Asp Asp
    610                 615                 620

Asp Gly Asn Leu Glu Glu Asp Phe Ile Thr Trp Arg Glu Gln Phe Trp
625                 630                 635                 640

Pro Ala Val Cys Glu Phe Phe Gly Val Glu Ala Thr Gly Glu Glu Ser
                645                 650                 655

Ser Ile Arg Gln Tyr Glu Leu Val Val His Glu Asp Met Asp Val Ala
            660                 665                 670

Lys Val Tyr Thr Gly Glu Met Gly Arg Leu Lys Ser Tyr Glu Asn Gln
        675                 680                 685

Lys Pro Pro Phe Asp Ala Lys Asn Pro Phe Leu Ala Ala Val Thr Ala
    690                 695                 700

Asn Arg Lys Leu Asn Gln Gly Thr Glu Arg His Leu Met His Leu Glu
705                 710                 715                 720

Leu Asp Ile Ser Asp Ser Lys Ile Arg Tyr Glu Ser Gly Asp His Val
                725                 730                 735

Ala Val Tyr Pro Ala Asn Asp Ser Ala Leu Val Asn Gln Ile Gly Glu
            740                 745                 750

Ile Leu Gly Ala Asp Leu Asp Val Ile Met Ser Leu Asn Asn Leu Asp
        755                 760                 765

Glu Glu Ser Asn Lys Lys His Pro Phe Pro Cys Pro Thr Thr Tyr Arg
    770                 775                 780

Thr Ala Leu Thr Tyr Tyr Leu Asp Ile Thr Asn Pro Pro Arg Thr Asn
785                 790                 795                 800

Val Leu Tyr Glu Leu Ala Gln Tyr Ala Ser Glu Pro Ser Glu Gln Glu
```

His Leu His Lys Met Ala Ser Ser Gly Glu Gly Lys Glu Leu Tyr
         805                 810                 815
                 820                 825                 830

Leu Ser Trp Val Val Glu Ala Arg Arg His Ile Leu Ala Ile Leu Gln
                 835                 840                 845

Asp Tyr Pro Ser Leu Arg Pro Pro Ile Asp His Leu Cys Glu Leu Leu
         850                 855                 860

Pro Arg Leu Gln Ala Arg Tyr Tyr Ser Ile Ala Ser Ser Ser Lys Val
865                 870                 875                 880

His Pro Asn Ser Val His Ile Cys Ala Val Ala Val Glu Tyr Glu Ala
                 885                 890                 895

Lys Ser Gly Arg Val Asn Lys Gly Val Ala Thr Ser Trp Leu Arg Ala
                 900                 905                 910

Lys Glu Pro Ala Gly Glu Asn Gly Gly Arg Ala Leu Val Pro Met Phe
         915                 920                 925

Val Arg Lys Ser Gln Phe Arg Leu Pro Phe Lys Ser Thr Thr Pro Val
         930                 935                 940

Ile Met Val Gly Pro Gly Thr Gly Ile Ala Pro Phe Met Gly Phe Ile
945                 950                 955                 960

Gln Glu Arg Ala Trp Leu Arg Glu Gln Gly Lys Glu Val Gly Glu Thr
                 965                 970                 975

Leu Leu Tyr Tyr Gly Cys Arg Arg Ser Asp Glu Asp Tyr Leu Tyr Arg
         980                 985                 990

Glu Glu Leu Ala Arg Phe His Lys Asp Gly Ala Leu Thr Gln Leu Asn
         995                 1000                1005

Val Ala Phe Ser Arg Glu Gln Ala His Lys Val Tyr Val Gln His
         1010                1015                1020

Leu Leu Lys Arg Asp Arg Glu His Leu Trp Lys Leu Ile His Glu
         1025                1030                1035

Gly Gly Ala His Ile Tyr Val Cys Gly Asp Ala Arg Asn Met Ala
         1040                1045                1050

Lys Asp Val Gln Asn Thr Phe Tyr Asp Ile Val Ala Glu Phe Gly
         1055                1060                1065

Pro Met Glu His Thr Gln Ala Val Asp Tyr Val Lys Lys Leu Met
         1070                1075                1080

Thr Lys Gly Arg Tyr Ser Leu Asp Val Trp Ser
         1085                1090

<210> SEQ ID NO 120
<211> LENGTH: 72
<212> TYPE: DNA
<213> ORGANISM: Artificial
<220> FEATURE:
<223> OTHER INFORMATION: DNA encoding His-TEV2 peptide

<400> SEQUENCE: 120
atgggtcatc atcatcatca tcatcacgat tatgatattc ctactactga gaatttgtat    60
tttcagggat cc                                                        72

<210> SEQ ID NO 121
<211> LENGTH: 24
<212> TYPE: PRT
<213> ORGANISM: Artificial
<220> FEATURE:
<223> OTHER INFORMATION: His-TEV2 peptide sequence

<400> SEQUENCE: 121

```
Met Gly His His His His His His Asp Tyr Asp Ile Pro Thr Thr
1               5                   10                  15

Glu Asn Leu Tyr Phe Gln Gly Ser
            20
```

<210> SEQ ID NO 122
<211> LENGTH: 714
<212> TYPE: DNA
<213> ORGANISM: Artificial
<220> FEATURE:
<223> OTHER INFORMATION: DNA encoding EGFP

<400> SEQUENCE: 122

```
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga cacccggtgg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga gcgcgatca catggtcctg      660
ctggagttcg tgaccgccgc cgggatcact ctcggcatgg acgagctgta caag           714
```

<210> SEQ ID NO 123
<211> LENGTH: 238
<212> TYPE: PRT
<213> ORGANISM: Artificial
<220> FEATURE:
<223> OTHER INFORMATION: EGFP sequence

<400> SEQUENCE: 123

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
```

```
                145                 150                 155                 160
Ile Lys Val Asn Phe Lys Ile Arg His Asn Ile Glu Asp Gly Ser Val
                    165                 170                 175

Gln Leu Ala Asp His Tyr Gln Gln Asn Thr Pro Ile Gly Asp Gly Pro
        180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Val Leu Leu Glu Phe Val
        210                 215                 220

Thr Ala Ala Gly Ile Thr Leu Gly Met Asp Glu Leu Tyr Lys
225                 230                 235

<210> SEQ ID NO 124
<211> LENGTH: 714
<212> TYPE: DNA
<213> ORGANISM: Artificial
<220> FEATURE:
<223> OTHER INFORMATION: DNA encoding EYFP

<400> SEQUENCE: 124
gtgagcaagg gcgaggagct gttcaccggg gtggtgccca tcctggtcga gctggacggc      60
gacgtaaacg gccacaagtt cagcgtgtcc ggcgagggcg agggcgatgc cacctacggc     120
aagctgaccc tgaagttcat ctgcaccacc ggcaagctgc ccgtgccctg gcccaccctc     180
gtgaccacct tcggctacgg cctgcagtgc ttcgcccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga caccctggtg     360
aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggtga acttcaagat ccgccacaac atcgaggacg gcagcgtgca gctcgccgac     540
cactaccagc agaacacccc catcggcgac ggccccgtgc tgctgcccga caaccactac     600
ctgagctacc agtccgccct gagcaaagac cccaacgaga gcgcgatca catggtcctg     660 ctggagttcg tgaccgccgc cgggatcact ctcggcatgg acgagctgta caag           714

<210> SEQ ID NO 125
<211> LENGTH: 238
<212> TYPE: PRT
<213> ORGANISM: Artificial
<220> FEATURE:
<223> OTHER INFORMATION: EYFP sequence

<400> SEQUENCE: 125

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Gly Tyr Gly Leu Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95
```

```
Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Tyr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 126
<211> LENGTH: 717
<212> TYPE: DNA
<213> ORGANISM: Artificial
<220> FEATURE:
<223> OTHER INFORMATION: DNA encoding ECFP

<400> SEQUENCE: 126
gtgagcaagg gcgaggagct gttcaccggg gtggtgccca tcctggtcga gctggacggc    60
gacgtaaacg gccacaagtt cagcgtgtcc ggcgagggcg agggcgatgc cacctacggc   120
aagctgaccc tgaagttcat ctgcaccacc ggcaagctgc ccgtgccctg gcccaccctc   180
gtgaccaccc tgacctgggg cgtgcagtgc ttcagccgct accccgacca catgaagcag   240
cacgacttct tcaagtccgc catgcccgaa ggctacgtcc aggagcgcac catcttcttc   300
aaggacgacg gcaactacaa gacccgcgcc gaggtgaagt tcgagggcga caccctggtg   360
aaccgcatcg agctgaaggg catcgacttc aaggaggacg gcaacatcct ggggcacaag   420
ctggagtaca actacatcag ccacaacgtc tatatcaccg ccgacaagca gaagaacggc   480
atcaaggcca acttcaagat ccgccacaac atcgaggacg gcagcgtgca gctcgccgac   540
cactaccagc agaacacccc catcggcgac ggccccgtgc tgctgcccga caaccactac   600
ctgagcaccc agtccgccct gagcaaagac cccaacgaga gcgcgatca catggtcctg   660 ctggagttcg tgaccgccgc cgggatcact ctcggcatgg acgagctgta caagtaa     717

<210> SEQ ID NO 127
<211> LENGTH: 238
<212> TYPE: PRT
<213> ORGANISM: Artificial
<220> FEATURE:
<223> OTHER INFORMATION: ECFP sequence

<400> SEQUENCE: 127

Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Leu
 50                  55                  60

Thr Trp Gly Val Gln Cys Phe Ser Arg Tyr Pro Asp His Met Lys Gln
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
130                 135                 140

Tyr Ile Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
210                 215                 220

Thr Ala Ala Gly Ile Thr Leu Gly Met Asp Glu Leu Tyr Lys
225                 230                 235

<210> SEQ ID NO 128
<211> LENGTH: 642
<212> TYPE: DNA
<213> ORGANISM: Artificial
<220> FEATURE:
<223> OTHER INFORMATION: DNA encoding MSP1T2-GT

<400> SEQUENCE: 128
atgggtcatc atcatcatca tcatcacgat tatgatattc ctactactga aatttgtat      60 tttcagggtt ctaccttcag taaacttcgc gaacaactgg ccccgtgac gcaggaattc     120 tgggacaacc tggaaaaaga aaccgaggga ctgcgtcagg aaatgtccaa agatttagaa     180
gaggtgaagg ccaaggttca gccatatctc gatgactttc agaaaaaatg caggaagag     240 atggaattat atcgtcaaaa ggtggaaccg ctgcgtgcgg aactgcaaga gggggcacgc     300
caaaaactcc atgagctcca agagaagctc agcccattag gcgaagaaat gcgcgatcgc     360
gcccgtgcac atgttgatgc actccggact catttggcgc cgtattcgga tgaacttcgc     420
cagcgtttgg ccgcacgtct cgaggcgctg aaagaaaacg ggggtgcccg cttggctgag     480
taccacgcga aagcgacaga acacctgagc accttgagcg aaaaagcgaa accggcgctg     540
gaagatctac gccagggctt attgcctgtt cttgagagct ttaaagtcag ttttctgtca     600
gctctggaag aatatactaa aaagctgaat acccagggta cc                       642

<210> SEQ ID NO 129
<211> LENGTH: 214
<212> TYPE: PRT
<213> ORGANISM: Artificial
<220> FEATURE:
<223> OTHER INFORMATION: MSP1T2-GT

<400> SEQUENCE: 129
```

Met Gly His His His His His His Asp Tyr Asp Ile Pro Thr Thr
1               5                   10                  15

Glu Asn Leu Tyr Phe Gln Gly Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln Gly Thr
    210

<210> SEQ ID NO 130
<211> LENGTH: 636
<212> TYPE: DNA
<213> ORGANISM: Artificial
<220> FEATURE:
<223> OTHER INFORMATION: DNA encoding MSP1RC12'

<400> SEQUENCE: 130
atgggtcatc atcatcatca tcacattgag ggatgtctga agctgttgga caattgggac    60
tctgttacgt ctaccttcag taaacttcgc gaacaactgg ccccgtgac gcaggaattc   120 tgggacaacc tggaaaaaga aaccgaggga ctgcgtcagg aaatgtccaa agatttagaa   180
gaggtgaagg ccaaggttca gccatatctc gatgactttc agaaaaaatg gcaggaagag   240
atggaattat atcgtcaaaa ggtggaaccg ctgcgtgcgg aactgcaaga gggggcacgc   300
caaaaactcc atgagctcca agagaagctc agcccattag gcgaagaaat gcgcgatcgc   360
gcccgtgcac atgttgatgc actccggact catttggcgc cgtattcgga tgaacttcgc   420
cagcgtttgg ccgcacgtct cgaggcgctg aaagaaaacg ggggtgcccg cttggctgag   480
taccacgcga aagcgacaga acacctgagc accttgagcg aaaaagcgaa accggcgctg   540
gaagatctac gccagggctt attgcctgtt cttgagagct ttaaagtcag ttttctgtca   600
gctctggaag aatatactaa aaagctgaat acccag    636

<210> SEQ ID NO 131
<211> LENGTH: 212
<212> TYPE: PRT
<213> ORGANISM: Artificial

<220> FEATURE:
<223> OTHER INFORMATION: MSP1RC12'

<400> SEQUENCE: 131

| | | | | | | | | | | | | | | |
|---|---|---|---|---|---|---|---|---|---|---|---|---|---|---|
| Met | Gly | His | His | His | His | His | Ile | Glu | Gly | Cys | Leu | Lys | Leu | Leu |
| 1 | | | 5 | | | | | 10 | | | | 15 | | |
| Asp | Asn | Trp | Asp | Ser | Val | Thr | Ser | Thr | Phe | Ser | Lys | Leu | Arg | Glu | Gln |
| | | | 20 | | | | 25 | | | | | 30 | | |
| Leu | Gly | Pro | Val | Thr | Gln | Glu | Phe | Trp | Asp | Asn | Leu | Glu | Lys | Glu | Thr |
| | | | 35 | | | | 40 | | | | 45 | | | |
| Glu | Gly | Leu | Arg | Gln | Glu | Met | Ser | Lys | Asp | Leu | Glu | Glu | Val | Lys | Ala |
| | 50 | | | | | 55 | | | | | 60 | | | |
| Lys | Val | Gln | Pro | Tyr | Leu | Asp | Asp | Phe | Gln | Lys | Lys | Trp | Gln | Glu | Glu |
| 65 | | | | | 70 | | | | | 75 | | | | | 80 |
| Met | Glu | Leu | Tyr | Arg | Gln | Lys | Val | Glu | Pro | Leu | Arg | Ala | Glu | Leu | Gln |
| | | | | 85 | | | | | 90 | | | | | 95 | |
| Glu | Gly | Ala | Arg | Gln | Lys | Leu | His | Glu | Leu | Gln | Glu | Lys | Leu | Ser | Pro |
| | | | | 100 | | | | | 105 | | | | | 110 | |
| Leu | Gly | Glu | Glu | Met | Arg | Asp | Arg | Ala | Arg | Ala | His | Val | Asp | Ala | Leu |
| | | | | 115 | | | | | 120 | | | | 125 | | |
| Arg | Thr | His | Leu | Ala | Pro | Tyr | Ser | Asp | Glu | Leu | Arg | Gln | Arg | Leu | Ala |
| | 130 | | | | | 135 | | | | | 140 | | | | |
| Ala | Arg | Leu | Glu | Ala | Leu | Lys | Glu | Asn | Gly | Gly | Ala | Arg | Leu | Ala | Glu |
| 145 | | | | | 150 | | | | | 155 | | | | | 160 |
| Tyr | His | Ala | Lys | Ala | Thr | Glu | His | Leu | Ser | Thr | Leu | Ser | Glu | Lys | Ala |
| | | | | 165 | | | | | 170 | | | | | 175 | |
| Lys | Pro | Ala | Leu | Glu | Asp | Leu | Arg | Gln | Gly | Leu | Leu | Pro | Val | Leu | Glu |
| | | | 180 | | | | | 185 | | | | | 190 | | |
| Ser | Phe | Lys | Val | Ser | Phe | Leu | Ser | Ala | Leu | Glu | Glu | Tyr | Thr | Lys | Lys |
| | | | 195 | | | | | 200 | | | | | 205 | | |
| Leu | Asn | Thr | Gln | | | | | | | | | | | | |
| | | | 210 | | | | | | | | | | | | |

<210> SEQ ID NO 132
<211> LENGTH: 636
<212> TYPE: DNA
<213> ORGANISM: Artificial
<220> FEATURE:
<223> OTHER INFORMATION: DNA encoding MSP1K9EC

<400> SEQUENCE: 132

| | |
|---|---|
| atgggtcatc atcatcatca tcacattgag gacgtctga agctgttgga caattgggac | 60 |
| tctgttacgt ctaccttcag taaacttcgc gaacaactgg ccccgtgac gcaggaattc | 120 |
| tgggacaacc tggaaaaaga aaccgaggga ctgcgtcagg aaatgtccaa agatttagaa | 180 |
| gaggtgaagg ccaaggttca gccatatctc gatgactttc agaaaaaatg gcaggaagag | 240 |
| atggaattat atcgtcaaaa ggtggaaccg ctgcgtgcgg aactgcaaga gggggcacgc | 300 |
| caatgtctcc atgagctcca agagaagctc agcccattag gcgaagaaat gcgcgatcgc | 360 |
| gcccgtgcac atgttgatgc actccggact catttggcgc cgtattcgga tgaacttcgc | 420 |
| cagcgtttgg ccgcacgtct cgaggcgctg aaagaaaacg ggggtgcccg cttggctgag | 480 |
| taccacgcga aagcgacaga acacctgagc accttgagcg aaaaagcgaa accggcgctg | 540 |
| gaagatctac gccagggctt attgcctgtt cttgagagct ttaaagtcag ttttctgtca | 600 |
| gctctggaag aatatactaa aaagctgaat acccag | 636 |

<210> SEQ ID NO 133
<211> LENGTH: 212
<212> TYPE: PRT
<213> ORGANISM: Artificial
<220> FEATURE:
<223> OTHER INFORMATION: MSP1K9EC

<400> SEQUENCE: 133

Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
    50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Cys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Lys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210

<210> SEQ ID NO 134
<211> LENGTH: 636
<212> TYPE: DNA
<213> ORGANISM: Artificial
<220> FEATURE:
<223> OTHER INFORMATION: DNA encoding MSP1D152C

<400> SEQUENCE: 134
atgggtcatc atcatcatca tcacattgag gacgtctga agctgttgga caattgggac      60
tctgttacgt ctaccttcag taaacttcgc gaacaactgg ccccgtgac gcaggaattc     120 tgggacaacc tggaaaaaga aaccgaggga ctgcgtcagg aaatgtccaa agatttagaa     180
gaggtgaagg ccaaggttca gccatatctc gatgactttc agaaaaaatg gcaggaagag     240
atggaattat atcgtcaaaa ggtggaaccg ctgcgtgcgg aactgcaaga gggggcacgc     300
caaaaactcc atgagctcca agagaagctc agcccattag gcgaagaaat gcgcgatcgc     360
gcccgtgcac atgttgatgc actccggact catttggcgc cgtattcgga tgaacttcgc     420
cagcgtttgg ccgcacgtct cgaggcgctg aaagaaaacg ggggtgcccg cttggctgag     480
taccacgcat gcgcgacaga acacctgagc accttgagcg aaaaagcgaa accggcgctg     540

-continued

```
gaagatctac gccagggctt attgcctgtt cttgagagct ttaaagtcag ttttctgtca    600
gctctggaag aatatactaa aaagctgaat acccag                              636
```

<210> SEQ ID NO 135
<211> LENGTH: 212
<212> TYPE: PRT
<213> ORGANISM: Artificial
<220> FEATURE:
<223> OTHER INFORMATION: MSP1K152C

<400> SEQUENCE: 135

```
Met Gly His His His His His His Ile Glu Gly Arg Leu Lys Leu Leu
1               5                   10                  15

Asp Asn Trp Asp Ser Val Thr Ser Thr Phe Ser Lys Leu Arg Glu Gln
            20                  25                  30

Leu Gly Pro Val Thr Gln Glu Phe Trp Asp Asn Leu Glu Lys Glu Thr
        35                  40                  45

Glu Gly Leu Arg Gln Glu Met Ser Lys Asp Leu Glu Glu Val Lys Ala
50                  55                  60

Lys Val Gln Pro Tyr Leu Asp Asp Phe Gln Lys Lys Trp Gln Glu Glu
65                  70                  75                  80

Met Glu Leu Tyr Arg Gln Lys Val Glu Pro Leu Arg Ala Glu Leu Gln
                85                  90                  95

Glu Gly Ala Arg Gln Lys Leu His Glu Leu Gln Glu Lys Leu Ser Pro
            100                 105                 110

Leu Gly Glu Glu Met Arg Asp Arg Ala Arg Ala His Val Asp Ala Leu
        115                 120                 125

Arg Thr His Leu Ala Pro Tyr Ser Asp Glu Leu Arg Gln Arg Leu Ala
    130                 135                 140

Ala Arg Leu Glu Ala Leu Lys Glu Asn Gly Gly Ala Arg Leu Ala Glu
145                 150                 155                 160

Tyr His Ala Cys Ala Thr Glu His Leu Ser Thr Leu Ser Glu Lys Ala
                165                 170                 175

Lys Pro Ala Leu Glu Asp Leu Arg Gln Gly Leu Leu Pro Val Leu Glu
            180                 185                 190

Ser Phe Lys Val Ser Phe Leu Ser Ala Leu Glu Glu Tyr Thr Lys Lys
        195                 200                 205

Leu Asn Thr Gln
    210
```

<210> SEQ ID NO 136
<211> LENGTH: 22
<212> TYPE: PRT
<213> ORGANISM: Artificial
<220> FEATURE:
<223> OTHER INFORMATION: Helix 2S peptide sequence

<400> SEQUENCE: 136

```
Pro Val Thr Gln Glu Phe Trp Asp Asn Leu Glu Lys Glu Thr Glu Gly
1               5                   10                  15

Leu Arg Gln Glu Met Ser
            20
```

MEMBRANE SCAFFOLD PROTEINS

CROSS REFERENCE TO RELATED APPLICATIONS

This application is a Continuation-in-Part of U.S. patent application Ser. No. 10/465,789, filed Jun. 18, 2003, now U.S. Pat. No. 7,038,958 which is a Continuation-in-Part of U.S. patent application Ser. No. 09/990,087, filed Nov. 20, 2001, now U.S. Pat. No. 7,048,949 which claims benefit of U.S. Provisional Application No. 60/252,233, filed Nov. 20, 2000, and the present application claims benefit of U.S. Provisional Application 60/536,281, filed Jan. 13, 2004. All prior applications are incorporated by reference in their entireties to the extent there is no inconsistency with the present disclosure.

ACKNOWLEDGMENT OF FEDERAL RESEARCH SUPPORT

This invention was made, at least in part, with funding from the National Institutes of Health (Grant Nos. R21GM63574, R01GM50007, R01GM31756, R01GM33775, and 5F32GM19024) and the National Science Foundation (Grant No. MCB 01-15068). Accordingly, the United States Government has certain rights in this invention.

BACKGROUND OF THE INVENTION

The field of the present invention encompasses molecular biology and membrane technology. Specifically, the present invention relates to membrane scaffold proteins (MSPs), especially artificial MSPs, and methods of using membrane scaffold proteins to stabilize, disperse and solubilize fully or partially hydrophobic proteins including but not limited to tethered, embedded or integral membrane proteins while maintaining the biological activities of those proteins or to stabilize, disperse and solubilize proteins which are purified and chemically solubilized, or directly from solubilized membrane fragments or membranes into a mimic of the native membrane environment. The hydrophobic proteins associate with the membrane scaffold proteins to form nanoscale disc-like structures termed Nanodiscs herein.

Several years ago we pursued structural and functional studies of lipids complexed with apolipoproteins (prepared from human plasma) and characterized these molecular assemblies by scanning probe microscopy, for example, using the adsorption of synthetic high density lipoprotein disks (rHDL, apo A-I) onto mica in an oriented manner (Carlson et al., 1997; Bayburt et al., 1998; Bayburt et al., 2000; Carlson et al., 2000). The diameters of the discoidal structures observed are approximately 10 nm with a height of 5.5 nanometers. The 5.5 nm high topology observed is most compatible with a single membrane bilayer epitaxially oriented on the atomically flat mica surface (Carlson et al., 1997).

We subsequently discovered that purified membrane proteins can be reconstituted into the phospholipid bilayer domain of certain such discoidal structures and studied in solution or subsequently adsorbed on a suitable surface for examination by structural or spectroscopic techniques that take advantage of a surface of oriented protein-bilayer assemblies. In the latter case, the underlying discoidal structures containing the membrane protein are easily recognizable and provide a point of reference for judging the quality of the sample and images.

High-density lipoproteins (HDL) are spherical assemblies of a protein component, termed apo A-l, and various phospholipids. HDL particles play an important role in mammalian cholesterol homeostasis by acting as the primary conduit for reverse cholesterol transport (Fielding and Fielding, 1991). The function of HDL as a cholesterol transporter relies upon the activity of the HDL-associated enzyme lecithin-cholesterol acyl transferase, or LCAT (Glomset, 1968; Jonas, 1991), which mediates the insertion of cholesterol esters into HDL lipoprotein particles. Certain portions of the apo A-I protein are required for the activity of this enzyme (Holvoet et al., 1995). In addition, a part of the apo A-I protein is thought to be in a globular domain at the N-terminus, and to be responsible for interactions with cell surface receptors. One nascent form of HDL particles has been assumed to be that of a discoid based on electron microscopy of stained preparations (Forte et al., 1971). Our laboratory has confirmed this using atomic force microscopy (AFM) studies of synthetic forms of rHDL under aqueous conditions. This form, however, is not the predominant form in circulation in vivo. Rather, the apo A-I sequence appears to have evolved to stabilize the more prevalent spherical structural form.

Two general models for the nascent structure of HDL disks have been proposed. One model has the apo A-I protein surrounding a circular bilayer section as a horizontal band or "belt" composed of a curving segmented alpha helical rod (Wlodawer et al., 1979). The other "picket fence" model has the protein traversing the edges of the bilayer vertically in a series of helical segments (Boguski et al., 1986). Both models are based primarily on indirect experimental evidence, and no three dimensional structure of the entire particle is available to distinguish between them.

The currently accepted model is the belt model, which is consistent with some electron microscopy and neutron scattering data (Wlodawer et al., 1979), where the helices are arranged longitudinally around the edge of the bilayer disks like a "belt" (Segrest et al. 1999). More recent infrared spectroscopy studies using a new method of sample orientation for dichroism measurements are more consistent with the belt model, in contrast to earlier studies (Wald et al., 1990; Koppaka et al., 1999). So far, there is no complete and direct evidence as to which model is correct, even though a low resolution x-ray crystal structure for apo A-I crystallized without lipid (Borhani et al., 1997) has been obtained. The low resolution crystal structure of an N-terminally truncated apo A-I shows a unit cell containing a tetrameric species composed of 4 helical rods which bend into a horseshoe shape and which combine to give a circular aggregate about 125× 80×40 Å. It was suggested that a dimeric species in this belt conformation is capable of forming discoidal particles.

The information collected to date concerning the reverse cholesterol transport cycle and the maturation of HDL particles suggests that the apo A-I protein has unique properties that allow it to interact spontaneously with membranes resulting in the formation of lipoprotein particles. Initial apo A-I lipid binding events have been proposed (Rogers et al., 1998), but the mechanism for conversion of bilayer-associated forms to discoidal particles remains unclear. The available evidence suggests that the energy of stabilization of lipid-free apo A-I is fairly low and that there is an equilibrium between two conformers (Atkinson and Small, 1986; Rogers et al., 1998). One conformer may be a long helical rod, and the other may be a helical "hairpin" structure about half as long. It has been suggested that the low stabilization energy and conformational plasticity allow apo A-I to structurally reorganize when it encounters a lipid membrane, thus facilitating the structural changes that would have to take place in-both the membrane and the protein to produce discrete lipoprotein particles (Rogers et al., 1998). Once these particles are formed, apo A-I may still undergo specific conformational changes that contribute to the dynamic functionality of the lipoprotein particles and interaction with enzymes and receptors. All of these interactions and changes take place at the protein-lipid interface and in specific topologies providing surface accessibility of critical residues. Thus, there is little reason to believe that apo A-I itself would be ideal for generating a stable, nanometer size phospholipid bilayer of controlled dimension.

Different types of lipid aggregates are used for reconstitution and study of purified membrane proteins; these include membrane dispersions, detergent micelles and liposomes (FIG. 1). Purified systems for biochemical and physical study require stability, which is not always inherent in or is limiting in these systems. Liposomes are closed spherical bilayer shells containing an aqueous interior. Reconstitution into liposomes by detergent dialysis or other methods typically results in random orientation of the protein with respect to outer and lumenal spaces. Since ligands or protein targets are usually hydrophilic or charged, they cannot pass through the liposomal bilayer as depicted in FIG. 1, although this may be advantageous in some instances. Since both sides of the liposomal bilayer are not accessible to bulk solvent, coupling effects between domains on opposite sides of the bilayer are difficult to study. Liposomes are also prone to aggregation and fusion and are usually unstable for long periods or under certain physical manipulations, such as stopped flow or vigorous mixing. The size of liposomes obtained by extruding through defined cylindrical pore sizes polydisperse in size distribution rather than exhibiting a uniform diameter.

Liposomes also may present difficulties due to light scattering, and aggregation of membrane proteins present in the bilayer and thermodynamic instability (Angrand et al., 1997; Savelli et al., 2000). The surface area of a liposome is relatively large ($10^5$ to $10^8$ $Å^2$). To obtain liposomes with single membrane proteins incorporated requires a large lipid to protein molar ratio.

Detergent micelles allow solubilization of membrane proteins by interaction with the membrane-embedded portion of the protein and are easy to use. Detergent micelles are dynamic and undergo structural fluctuations that promote subunit dissociation and often present difficulty in the ability to handle proteins in dilute solutions. An excess of detergent micelles, however, is necessary to maintain the protein in a non-aggregated and soluble state. Detergents can also be denaturing and often do not maintain the properties found in a phospholipid bilayer system. Specific phospholipid species are often necessary to support and modulate protein structure and function (Tocanne et al., 1994). Thus, the structure, function, and stability of detergent solubilized membrane proteins may be called into question. Since an excess of detergent micelles is needed, protein complexes can dissociate depending on protein concentration and the detergent protein ratio. By contrast, the MSP nanostructures of the present invention are more robust structurally, having a phospholipid bilayer mimetic domain of discrete size and composition and greater stability and smaller surface area than unilamellar liposomes. The disk structures allow access to both sides of the bilayer like detergents, and also provide a bilayer structure like that of liposomes.

There is a long felt need in the art for stable, defined compositions for the dispersion of membrane proteins and other hydrophobic or partially hydrophobic proteins, such that the native activities and properties of those proteins are preserved. Compounds other than proteins can also be dispersed in the nanoscale particles of the present invention.

SUMMARY OF THE INVENTION

Membrane Scaffold Proteins (MSPs) as used herein are artificial amphiphilic proteins which self-assemble with phospholipids and phospholipid mixtures into nanometer size membrane bilayers. A subset of these nanometer size assemblies are discoidal in shape, and are referred to as Nanodisc structures. These nanoscale particles can be from about 5 to about 500 nm, about 5 to about 100 nm, or about 5 to about 20 nm in diameter. These structures comprising phospholipid and MSP preserve the overall bilayer structure of normal membranes but provide a system which is both soluble in solution and which can be assembled or affixed to a variety of surfaces.

The amino acid sequences of specifically exemplified MSPs are given in SEQ ID NO:6, SEQ ID NO:9, SEQ ID NO:17, SEQ ID NO:19, SEQ ID NO:23, SEQ ID NO:29, SEQ ID NO:43, SEQ ID NO:44, SEQ ID NO:45 and SEQ ID NOS:73-86, SEQ ID NO:91-99, SEQ ID NO:111, SEQ ID NO:113, SEQ ID NO:115, SEQ ID NO:117, SEQ ID NO:119, SEQ ID NO:129, SEQ ID NO:131, SEQ ID NO:133 AND SEQ ID NO:135, and the corresponding sequences lacking the N-terminal 12 amino acid His tag or 23 amino acid HisTEV tag portion. Also within the scope of the present invention are artificial variant MSPs having conservative acid substitutions, insertions or deletions of up to five amino acids, or artificial variants having from 70 to 100% amino acid sequence identity with a specifically exemplified MSP sequence.

Within the scope of the present invention are those MSPs which contain a His-tag and/or a His-tag TEV sequence, as well as those MSPs which are the result of proteolytic or other cleavage to remove the "tag" portion of the protein, and which contain at the N-terminus one or more amino acids derived from the protease recognition sequence, which may be as specifically exemplified in the tables herein or with a functional modification (such as the TEV recognition sequence with either Ser or Gly in the P1' position, as discussed herein). It is also understood that certain amino acid substitutions at the P2' position are permitted in the His TEV-MSPs or the proteolytic cleavage products thereof; for example, the P2' amino acid can be Ser, Gly, Thr, Ala, Asn, Lys or Met. MSPs with such substitutions are within the scope of the present invention. In certain embodiments, naturally occurring membrane scaffold proteins, such as apolipoprotein A-1, A-II, C-I, C-II, C-III or E, apolipophorin III, among others, can be used in place of the artificial MSPs of the present invention (i.e., where the combination has not been reported in the prior art).

Methods for recombinantly producing the artificial MSPs are also within the scope of the present invention. Besides the specifically exemplified artificial MSPs, there can be additional helical domains included within the primary structure of an artificial MSP, for example, those derived from Apo A-II, apo C-I, apo C-II, apo C-III, apo E, apolipophorin III, myoglobin or hemoglobin. The numbers and orders of helical building blocks (See Table 19 for particular examples) can be varied, provided that the self assembly function of Nanodisc formation is preserved.

The present invention further provides the use of the nanometer scale phospholipid bilayer structures or Nanodiscs formed using MSPs for the incorporation of additional hydrophobic or partially hydrophobic molecules, including hydrophobic or partially hydrophobic proteins. Those additional proteins can be solubilized, for example, with the use of detergent, and the solubilized proteins can be added to a solution of MSP, with or without phospholipid(s), and the nanoscale particles self-assemble so that the MSPs and the additional "target" proteins are incorporated into a stable and soluble particle. Subsequently, any detergent can be removed by dialysis or treatment with such agents as ion exchange resins or macroporous polymeric adsorbent beads, e.g., Biobeads made of styrene divinylbenzene.

Detergents (or other solubilizing agents) useful in the dispersion of MSPs, membrane fragments, membranes or preparations of purified or partially purified hydrophobic or partially hydrophobic proteins include, without limitation, cholic acid, neutralized cholic acid, deoxycholic acid, sodium deoxycholate, including n-dodecyl-β-D-maltoside, t-octylphenoxypolyethoxyethanol (Triton X-100, Union Carbide Chemicals and Plastics Co., Inc.), n-octyl-beta-D-glucopyranoside (octylglucoside), octaethylene glycol monododecyl ether (C12E8), nonaethylene glycol monododecyl ether (C12E9), Emulgen 913, myristoyl sulfobetaine, dihexanoyl phosphatidylcholine, digitonin and JB3-14. Peptidetergents can be used as well. High hydrodynamic pressures (from about 200 to about 200,000 atmospheres) can also be used to solubilize (solvate) hydrophobic or partially hydrophobic proteins or other molecules.

Phospholipids which can be used in the Nanodisc assembly methods of the present invention include, without limitation, PC, phosphatidyl choline; PE, phosphatidyl ethanolamine, PI, phosphatidyl inositol; DPPC, dipalmitoyl-phosphatidylcholine; DMPC, dimyristoyl phosphatidyl choline; POPC, 1-palmitoyl-2-oleoyl-phosphatidyl choline; DHPC, dihexanoyl phosphatidyl choline, dipalmitoyl phosphatidyl ethanolamine, dipalmitoyl phosphatidyl inositol; dimyristoyl phosphatidyl ethanolamine; dimyristoyl phosphatidyl inositol; dihexanoyl phosphatidyl ethanolamine; dihexanoyl phosphatidyl inositol; 1-palmitoyl-2-oleoyl-phosphatidyl ethanolamine; 1-palmitoyl-2-oleoyl-phosphatidyl inositol; among others. The phospholipids can contain glycerol backbones or they can include sphingolipids. Generally, the phospholipid has two saturated fatty acids of from 6 to 20 carbon atoms with a commonly used head group exemplified by, but not limited to, phosphatidyl choline, phosphatidyl ethanolamine and phosphatidyl serine. The head group can be uncharged, positively charged, negatively charged or zwitterionic. The phospholipids can be natural (those which occur in nature) or synthetic (those which do not occur in nature), or mixtures of natural and synthetic. Desirably the molar ratio of MSPs to total membrane protein is that which produces about 100 to about 200 phospholipid molecules in each discoidal structure of about 10 nm in diameter. Those proteins, found in nature or associated with the various membrane structures of a living organism, are solubilized in the MSP supported nanobilayer or Nanodisc through the process of self-assembly, and the native structure and activity of the target protein are preserved in these MSP-supported structures.

Besides purified or solubilized hydrophobic or partially hydrophobic proteins, hydrophobic or partially hydrophobic proteins bound to or within membranes or membrane fragments or disrupted membranes can be assembled with the MSPs of the present invention, without the need for prepurification of the target protein. It is understood by the skilled artisan that the properties of a particular phospholipid determine its suitability for a particular application of a Nanodisc; for example, DPPC, which is gel-like in consistency, is not an appropriate choice for use in certain applications. Where membrane proteins are incorporated into Nanodiscs directly from intact or solubilized membranes or membrane fragments, the use of MSP1 is preferred over MSP2.

The MSP supported bilayers or Nanodiscs can be used in solutions or applied to a number of surfaces, such that the native structure and ligand binding, antigenic determinants and/or enzymatic activities of the protein incorporated in the MSP supported structure are maintained. As specifically exemplified, the MSP supported structures are affixed to a gold surface, e.g., for use in surface plasmon resonance technologies, to a multiwell plate or to solid surfaces including but not limited to, beads, magnetic particles, chromatography matrix materials and others. Solid materials to which the MSPs can be affixed include, but are not limited to, gold, silicon, polystyrene, quartz, silica, silicon oxides, silicon nitride, and other simple or complex materials. Where a polyhistidine sequence (His tag) is retained as part of the MSPs, the Nanodiscs can be bound to a nickel-NTA-coated surface, for example. Other oligopeptide tags which mediate binding to a surface or facilitate purification and which can be fused to a protein of interest, generally at the N- or C-terminus, by such techniques include, without limitation, strep-tag (Sigma-Genosys, The Woodlands, Tex.) which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); and a maltose binding protein fusion system allowing binding to an amylose resin (New England Biolabs, Beverly, Mass.).

It is noted that a His or other tag does not interfere with formation of helical domains and the ability to mediate assembly of a Nanodisc particle, nor is it required for helix formation and particle assembly. With appropriate modification of the MSP primary sequence, the polyhistidine or other tag) portion can be removed by specific proteolytic cleavage, for example using the Tobacco Etch Virus protease, where there is cognate recognition sequence between the tag and the first helical domain of the MSP.

The present invention further relates to methods for the incorporation of membrane-associated or other hydrophobic or partially hydrophobic proteins (or other hydrophobic or partially hydrophobic molecules) into nanoscale lipid bilayers or Nanodiscs comprising at least one MSP of the present invention. Membrane proteins (tethered, embedded or integral) can be used in the methods of the present invention. These proteins can be incorporated into nanoscale particles with MSPs from solubilized intact membrane preparations, intact cells (native or recombinant) or from disrupted membranes or membrane fragments, without prepurification or prefractionation of the membrane proteins, or the proteins can be purified prior to incorporation (with solubilization if needed).

Tethered membrane proteins, which are associated with the membrane bilayer via a relatively small portion of the protein, can be exemplified by cytochrome P450 reductases and cytochrome b5 proteins from various sources.

Embedded membrane proteins have a more extensive association with the bilayer, but typically the bulk of the protein is in contact with the extracellular environment or the cytoplasm. Examples of embedded membrane proteins include, without limitation, the general class of membrane associated cytochromes P450, for example, cytochrome P450 2B4 from rabbit liver microsomes, cytochrome P450 3A4 from human liver microsomes and cytochrome P450 6B1 from insect microsomes.

The integral membrane proteins are exemplified by the general class of proteins which include helical segments in the membrane bilayer, such as the 7-helix transmembrane proteins, including, but not limited to, bacteriorhodopsin (bR) from *Halobacterium halobium*, the human β-adrenergic receptor, the 5-hydroxy tryptamine 1A G-protein coupled receptor from *Homo sapiens* and other G-protein coupled protein receptors from human, plant, animal or other sources. In general an integral membrane protein has at least one portion which extends through the membrane bilayer. Other examples include, without limitation, channel-forming proteins, transporter proteins, signaling proteins, cytokine receptors (e.g., tumor necrosis factor receptors), interleukin receptors, Fas receptor, CD27, CD40, CD30, insulin and insulin family receptors, dopamine receptors, the lysophosphatidic acid receptors, and the chemokine receptors, such as CXCR4 and CCR5, dopamine receptors, and growth factor receptors (e.g., epidermal growth factor and/or HGF receptors). There can be from one to more than twenty domains of the protein passing through the membrane bilayer. An example of a one-pass protein which has been successfully incorporated into the nanoscale particles of the present invention is the aspartate receptor (Tar) from *Escherichia coli*; and an example of a twenty six-pass protein incorporated into Nanodiscs is an *E. coli* transhydrogenase. Members of each type of membrane protein have been successfully incorporated into the nanoscale structures using the MSPs and methods of the present invention. In particular, cell surface receptors, and especially G-protein coupled receptors, including but not limited to, beta-adrenergic, chemokine and other receptor proteins, can be incorporated into nanobilayer bilayer structures formed with the membrane scaffold proteins (MSPs) of the present invention. Where it is desired that a dimer or higher oligomer of a 7-helix transmembrane protein is incorporated into a Nanodisc, a Nanodisc of greater than 9 nm in diameter is preferred, which can be accomplished by the use of a relatively longer MSP sequence such as MSP1E1, MSP1E2 or MSP1E3.

The present invention further provides materials and methods using artificial or naturally occurring MSPs which increase the stability and monodispersity of the self-assembled nanoparticles. G-protein coupled receptors (GPCRs) are an important and diverse class of pharmaceutical targets in mammalian cellular membranes where they function as signal transducing elements, bind several classes of bioactive ligands and transmit information to the intracellular machinery. The artificial MSPs of the present invention stabilize and solubilize the membrane-associated form of GPCRs to allow purification and manipulation in solution or on a solid support for use in flow cytometry, high throughput screening applications, on surfaces for surface-plasmon biosensor and scanning-probe techniques, as well as other analytical applications. The methods for Nanodisc production of the present invention can be used to facilitate purification of naturally produced or recombinant membrane proteins in stable, biologically active and soluble form.

Also within the scope of the present invention are methods for adsorbing or binding a molecule or ion of interest to a protein (or other molecule) within a Nanodisc, where that protein (or other molecule) binds the compound or ion of interest with sufficient affinity so as to promote removal of the compound or ion of interest from a solution containing it. This application of Nanodisc technology can be used to remove contaminating materials or it can be use in separation or purification schemes. Similarly, Nanodiscs containing MSP and phospholipid can be used to separate hydrophobic materials from a solution by partitioning of the hydrophobic material into the phospholipid portion of the Nanodisc in a relatively nonspecific fashion. By way of nonlimiting example, lipophilic dyes have been shown to incorporate within Nanodiscs either during the self assembly process or by partitioning into the bilayer of the Nanodiscs from a solution.

The present invention further provides Nanodisc particles wherein proteins or carbohydrates of interest are attached (covalently or noncovalently) to the MSPs on the exterior of the Nanodisc. Alternatively, a carbohydrate or protein can be covalently bound to an alkane or phospholipid, which is then incorporated within the Nanodisc such that the carbohydrate is accessible to the outside, aqueous environment. Carbohydrates can also be in the form of glycoproteins which are incorporated within a Nanodisc. Such carbohydrate-carrying Nanodiscs can be used to positively or negatively modulate cellular responses, either in vivo or in vitro. This can be used also to direct the Nanodisc to a cell or surface displaying a lectin or the ligand of a lectin, or a receptor of the ligand of the receptor, depending on the choice of the carbohydrate or other molecule carried by the Nanodisc. Proteins which could be covalently or noncovalently linked to the Nanodisc include, without limitation, antibodies or antigen-binding fragments thereof, adhesins or other proteins or glycoproteins capable of binding to target molecules or cells of interest.

Yet another aspect of the present invention is the incorporation of a hydrophobic therapeutic or cosmetic molecule within the hydrophobic core of the Nanodisc. This strategy can prolong the circulating lifetime of the compound and it can also provide the benefits of slow release of a relatively insoluble and/or toxic molecule. Such a hydrophobic therapeutic can include, without limitation, photodynamic therapeutic agents such psoralens, porphyrins and phthalacyanin-related molecules, tamoxifen, paclitaxel, anticancer agents such as adriamycin, daunorubicin or doxorubicin, cholesterol-lowering drugs, antibacterial agents such as vancomycin, fat soluble vitamins such as D or E, and antifungal agents such as the azoles (e.g., ketoconazole) or polyenes (e.g., Amphotericin B). The Nanodiscs into which these compounds have been incorporated are also within the scope of the present invention.

Other molecules which can be incorporated within Nanodiscs or attached to Nanodiscs (such as by covalent attachment to the MSP) include antibodies, monoclonal antibodies, antibody fragments capable of binding to a cognate antigen, lectins, hormones, chemokines, lymphokines, peptides, lipids, albumin, amino sugars and lectins, nucleic acids, among others. Nanodiscs of the present invention can also be used to stabilize and deliver lipophilic agents which improve the appearance or quality of skin, including, but not limited to, vitamins A and/or E or retinol. Methods for improving the skin or for treating disease by administering or applying an effective amount of a therapeutic or cosmetically active composition comprising Nanodisc particles into which the therapeutic or cosmetically active ingredient has been incorporated are within the scope of the present invention. Such hydrophobic agents are packaged within Nanodiscs either directly or through self assembly with the hydrophobic (lipophilic) small molecule.

Drugs (therapeutic agents) discussed herein are exemplary, and are not meant to be limiting in any way. Hydrophobic anti-inflammatory agents include, but are not limited to, any known hydrophobic non-steroidal antiinflammatory agent, and any known hydrophobic steroidal antiinflammatory agent, any known non-steroidal antiinflammatory agent such as salicylic acid derivatives (aspirin), para-aminophenol derivatives (e.g., acetaminophen), indole and indene acetic acids (indomethacin), heteroaryl acetic acids (ketorolac), arylpropionic acids (ibuprofen), anthranilic acids (mefenamic acid), enolic acids (oxicams) and alkanones (nabumetone) and any known steroidal antiinflammatory agent which can include corticosteriods and biologically active synthetic analogs with respect to their relative glucocorticoid (metabolic) and mineralocorticoid (electrolyte-regulating) activities. Additionally, other drugs used in the therapy of inflammation or anti-inflammatory agents to be incorporated into Nanodiscs can include, but are not limited to, the autocoid antagonists such as all histamine and bradykinin receptor antagonists, leukotriene and prostaglandin receptor antagonists, and platelet activating factor receptor antagonists.

Antimicrobial agents include, without limitation, antibacterial agents, antiviral agents, antifungal agents, and antiprotozoan agents. Non-limiting examples of antimicrobial agents (antibiotics) are sulfonamides, trimethoprim-sulfamethoxazole, quinolones, penicillins, and cephalosporins. Antifungal agents include, without limitation azoles, and especially Amphotericin B and nystatin. Therapeutic compounds effective against protozoans can be similarly incorporated within Nanodiscs. Solubilization, reduction of potential toxicity and controlled release are advantages.

Antineoplastic agents include, but are not limited to, those which are suitable for treating tumors that may be present on or within an organ (such as carcinoma, sarcoma, hematopoietic cancers, e.g., myxoma, lipoma, papillary fibroelastoma, rhabdomyoma, fibroma, hemangioma, teratoma, mesothelioma of the AV node, lymphoma, and tumors that metastasize to the target organ, among others) including cancer chemotherapeutic agents, a variety of which are well known in the art, such as adriamycin, daunorubicin, doxorubicin, tamoxifen and paclitaxel. Antineoplastic agents can also include antibodies specific for the neoplastic cell and antibodies to which a therapeutic radionuclide or other therapeutic agent has been bound.

Angiogenic factors (e.g., to promote organ repair or for development of a biobypass to avoid a thrombosis) include, but are not limited to, basic fibroblast growth factor, acidic fibroblast growth factor, vascular endothelial growth factor, angiogenin, transforming growth factors, tumor necrosis factor, angiopoietin, platelet-derived growth factor, placental growth factor, hepatocyte growth factor, and proliferin.

Thrombolytic (clot dissolving) agents include, but are not limited to, urokinase, plasminogen activator, urokinase, streptokinase, inhibitors of α2-plasmin inhibitor, and inhibitors of plasminogen activator inhibitor-1, angiotensin converting enzyme (ACE) inhibitors, spironolactone, tissue plasminogen activator (tPA), an inhibitor of interleukin 1β-converting enzyme, anti-thrombin III, and the like.

Where the target organ is the heart, exemplary drugs for delivery include, but are not necessarily limited to drugs which are poorly soluble in water, growth factors, angiogenic agents, calcium channel blockers, antihypertensive agents, inotropic agents, antiatherogenic agents, anti-coagulants, beta-blockers, anti-arrhythmia agents, cardiac glycosides, antiinflammatory agents, antibiotics, antiviral agents and the like.

Calcium channel blockers include, but are not limited to, dihydropyridines such as nifedipine, nicardipine, nimodipine, and the like; benzothiazepines such as dilitazem; phenylalkylamines such as verapamil; diarylaminopropylamine ethers such as bepridil; and benzimidole-substituted tetralines such as mibefradil. Antihypertensive agents include, but are not limited to, diuretics, including thiazides such as hydroclorothiazide, furosemide, spironolactone, triamterene, and amiloride; antiadrenergic agents, including clonidine, guanabenz, guanfacine, methyldopa, trimethaphan, reserpine, guanethidine, guanadrel, phentolamine, phenoxybenzamine, prazosin, terazosin, doxazosin, propanolol, methoprolol, nadolol, atenolol, timolol, betaxolol, carteolol, pindolol, acebutolol, labetalol; vasodilators, including hydralizine, minoxidil, diazoxide, nitroprusside; and angiotensin converting enzyme inhibitors, including captopril, benazepril, enalapril, enalaprilat, fosinopril, lisinopril, quinapril, ramipril; angiotensin receptor antagonists, such as losartan; and calcium channel antagonists, including nifedine, amlodipine, felodipine XL, isadipine, nicardipine, benzothiazepines (e.g., diltiazem), and phenylalkylamines (e.g. verapamil). Anticoagulants include, but are not limited to, heparin, warfarin, hirudin, tick anti-coagulant peptide, low molecular weight heparins (such as enoxaparin, dalteparin, and ardeparin), ticlopidine, danaparoid, argatroban, abciximab and tirofiban.

Antiarrhythmic agents include, but are not limited to, sodium channel blockers (e.g., lidocaine, procainamide, encainide, flecanide, and the like), beta adrenergic blockers (e.g., propranolol), prolongers of the action potential duration (e.g., amiodarone), and calcium channel blockers (e.g., verpamil, diltiazem, nickel choride, and the like). Delivery of cardiac depressants (e.g., lidocaine), cardiac stimulants (e.g., isoproterenol, dopamine, norepinephrine, etc.) and combinations of multiple cardiac agents (e.g., digoxin/quinidine to treat atrial fibrillation) is possible using the Nanodiscs of the present invention.

Agents to treat congestive heart failure, include, but are not limited to, a cardiac glycoside, inotropic agents, a loop diuretic, a thiazide diuretic, a potassium ion sparing diuretic, an angiotensin converting enzyme inhibitor, an angiotensin receptor antagonist, a nitrovasodilator, a phosphodiesterase inhibitor, a direct vasodilator, an adrenergic receptor antagonist, a calcium channel blocker, and a sympathomimetic agent. Agents suitable for treating cardiomyopathies include, but are not limited to, dopamine, epinephrine, norepinephrine, and phenylephrine.

Also suitable are agents that prevent or reduce the incidence of restenosis including, but not limited to, taxol (paclataxane) and related compounds; and antimitotic agents. Other compounds that can be incorporated include vitamins A, D and E and cholesterol-controlling drugs such as the statins.

Small molecule therapeutic agents can be incorporated into the nanoscale discoid particles of the present invention. An advantageous plasma lifetime of Nanodiscs, the rendering of partially hydrophobic compounds soluble via the amphipathic membrane scaffold protein encircled Nanodisc, and the ability for potential targeting through modification of the MSP or phospholipid components of the Nanodisc, are important advantages provided. Examples 15-18 provide specific exemplification using Amphotericin B, ketoconazole and photodynamic agents, but other therapeutic molecules can be incorporated using the same or similar ratios and protocols. Similarly, the MSP specifically exemplified is MSP1T2, but others having the properties taught herein can substitute therefor.

Therapeutic Nanodisc compositions are desirably maintained as stable soluble solutions; solutions of Nanodiscs can also be lyophilized and stored as dry powders. Administration to a patient in need of the particular therapeutic compound contained in the Nanodiscs is preferably by a parenteral route, which can include intravenous, intraarterial, intramuscular, intradermal, subcutaneous, or there can be contact with a mucosal surface, for example by aerosolization (especially dry powder drug-Nanodisc preparations) and inhalation either intranasally or via the lower respiratory system, in a dosage sufficient for the intended patient response.

Nanodiscs of the present invention can also be used to stabilize and deliver lipophilic agents which improve the appearance and/or quality of skin, including but not limited to vitamin E or retinol. Methods for improving the appearance of skin or for treating disease are also within the scope of the present invention. Such hydrophobic agents are packaged within Nanodiscs either directly or through self-assembly of the lipid and phospholipid component. Administration is desirably by topical of an amount of composition comprising Nanodiscs into which the cosmetically active ingredient(s) has been incorporated application to an area of skin in need of improvement, in an amount (and at a frequency) effective for improving the appearance of the skin in need of improvement.

The scope of the present invention includes the use of Nanodiscs which carry a hydrophobic or partially hydrophobic antigen, which can be a protein, lipopolysaccharide, lipooligosaccharide or a lipoprotein. Such Nanodiscs can be used in immunogenic compositions, for example, as vaccine components. Viral proteins of interest include, without limitation, gp120 of Human Immunodeficiency Virus, envelope glycoproteins of Herpes simplex virus or measles virus, the "spike" protein of the SARS virus, hemagglutinin ligand of influenza virus or parainfluenza virus. Exemplary bacterial antigens include, but are not limited to, cell surface proteins such as the M6 protein or M proteins of *Streptococcus pyogenes*, fimbrillin of *Porphryomonas gingivalis*, InlB or ActA of *Listeria monocytogenes*, YadA of *Yersinia enterocolitica*, IcsA of *Shigella flexneri*, invasin of *Yersinia pseudotuberculosis*, products of the acf gene of Vibrio cholerae, capsular material comprising the poly-D-glutamate polypeptide of *Bacillus anthracis*, fibrinogen/fibrin binding protein of *Staphylococcus aureus*, V and/or W antigens of *Yersinia pestis* (especially from a vaccine strain such as EV76) or from *Yersinia enterocolytica* or *Yersinia pseudotuberculosis*, and flagellin or porin of *Campylobacter jejeuni*. Similarly, O antigens of *Salmonella typhi, Salmonella choleraesuis, Salmonella enteritidis* can be incorporated into nanodiscs, using the proteins and methods described herein.

The present invention further provides immunogenic compositions comprising Nanodiscs into which has been incorporated at least one hydrophobic or partially hydrophobic antigen, together with a pharmaceutically acceptable carrier. Optionally an adjuvant and/or an immune stimulant, such as a chemokine, can be incorporated into the composition. The Nanodiscs allow the stabilization and solubilization of a hydrophobic antigen, with the maintenance of the native conformation of the antigen, and with the presentation of hydrophilic regions of the antigen exposed to the aqueous environment, leading to an improved immune response in the human or animal to which the immunogenic composition has been administered.

An additional application of the present Nanodisc technology is in diagnostic and/or imaging procedures used in medical or veterinary settings. In this application, a targeting agent is embedded within or bound to the Nanodisc such that a binding site is accessible to the aqueous environment and an imaging compound, such as a dye, a radionuclide or a fluorescent or luminescent molecule, is incorporated within the Nanodisc. Imaging techniques useful with the Nanodiscs carrying the appropriate imaging agent, as well known to the art, can be used in magnetic resonance imaging, electron paramagnetic resonance imaging, optical imaging and ultrasound imaging. The binding site of the targeting agent is specific for a bacterial surface antigen, a tumor antigen, or other cell surface or tissue-specific marker. The discs are allowed to assembly from an aqueous mixture comprising imaging agent, MSP and target-specific protein. As for introduction of therapeutics, the MSP is desirably antigenically neutral, i.e., it should not trigger an immunological response within a human or animal to which it is administered.

Additional applications of antigen-containing Nanodiscs include assay kits and methods for the detection of an antibody specific for the particular antigen in a biological sample. Detection of the antibody bound to the Nanodisc-bound antigen can be by any means known to the art. Detection of the antibody in the biological sample indicates prior exposure of the human or animal to the antigen of interest, often this approach is used to recognize exposure to a pathogen. The biological sample can be blood, serum, plasma or tissue, especially from the lymph system.

We have developed Nanodiscs for use in structural, biochemical and pharmaceutical strategies by engineering the scaffold protein (MSP) for greater stability, size homogeneity through various size classes and useful functionalities in the resultant nanoscale lipoprotein particle. These particles can include tags for purification, binding to surfaces and physical manipulation of disks such as in hydrogels or on a gold biosensor surface, and they can serve as robust entities for rapid and reproducible assays and solution-based NMR screening and in solid state NMR structural studies. In NMR applications, the Nanodiscs provide a stable monodisperse environment for proteins and other hydrophobic molecules of interest, especially receptor proteins for which ligand binding is studied. For example, compounds that bind to the Nanodisc-supported receptor can exhibit broadened signals and hence, a difference spectrum between +/− target ligand can reveal the identity of bound ligands. The nanoparticles and membrane protein scaffolds are useful in biotechnology, the pharmaceutical industry as well as in basic research. In addition, the structural and functional principles uncovered through our discovery and the related techniques facilitate understanding the interactions of proteins with lipid bilayers at the molecular level.

The Nanodiscs can contain a single type of functional protein, or, where the MSP and the resulting Nanodiscs are large, they can contain macromolecular assemblies, for example cellular motility motors (flagella or cilia), multicomponent bioreactors such as multienzyme complexes, energy transduction complexes, or photosynthetic complexes. Where the incorporation of macromolecular assemblies, including a combination of a cytochrome and a reductase protein, a relatively large MSP is used to prepare the Nanodiscs, using for example, MSP1E1, MSP1E2 or MSP1E3. Where an MSP larger than MSP1 is used, the results are improved by the incorporation of a higher molar ratio of lipid to MSP (from 70:1 to 140:1, or from 90:1 to 115:1).

Also within the scope of the present invention are complexes in which more than one Nanodisc particles are associated with one another. The complexes can have longer time in circulation in a human or animal than single Nanodisc particles. These associations of particles can beheld together by electrostatic interactions (where different portions of the hydrophilic face of the helices have different charge) or they can be covalently bonded by disulfide bonds, for example, where the hydrophilic faces of at least some of the helices of the MSPs contain cysteine residues, or they can be constructed through genetic engineering of MSP fusion constructs. The particles in the complex can include therapeutic compounds, antibodies or imaging compounds. For example, gadolinium can be incorporated into Nanodiscs for use in ischemia imaging in humans.

The present invention further encompasses compositions and methods useful in detoxification and/or remediation of certain chemicals, where the appropriate binding protein or enzyme is incorporated within a Nanodisc in its bioactive conformation. An example is a cytochrome P450 coding sequence which encodes a protein capable of oxidizing (and/or dehalogenating) at least one halogenated hydrocarbon or light hydrocarbon. Examples include, but are not limited to, trichloroethylene, ethylene dibromide, chloroform, carbon tetrachloride, styrene, benzene, 1,2-dichloropropane, vinyl chloride, dichloromethane, methyl chloride, methyl chloroform, 1,2-dichloroethane, 1,2-dichloropropane, perchloroethylene, dichloroethylene, vinyl bromide, acrylonitrile, vinyl carbonate, ethyl carbamate, acetaminophen and methyl tertyl-butyl ether. The incorporation of human cytochrome P450s, either with our without membrane bound redox transfer partners, into Nanodiscs, in which the overall stoichiometry and homo- and hetero-oligomerization state can be controlled, is a significant improvement on the crude membrane preparations now used by the pharmaceutical industry for quantitation of drug metabolism, pharmacokinetics, and metabolite toxicity studies of lead compounds and drug candidates. In such examples, the Nanodiscs can be used in solution or they can be covalently or noncovalently bound to a solid support.

BRIEF DESCRIPTION OF THE DRAWINGS

FIG. 4A: MSP1 showing positions of half-repeats. Half-repeat 1 is disordered based on molecular dynamics simulation (Phillips, 1997). FIG. 4B: Hinge domain movement. FIG. 4C: Removal of half-repeats. FIG. 4D: Hinge domain replacement with helices 3 and 4. FIG. 4E: MSP2, with a tandem duplication of the sequence of MSP1. FIG. 4F: Removal of half-repeat 1 to make MSP1D1. FIG. 4G: Tandem repeat of MSP1D1 to form MSP2D1.

FIG. 7A: Disk-associated receptor and ligand-induced assembly of receptor-target complex on gold. FIG. 7B: Disk-associated receptor in a gel matrix.

FIG. 16A: Chromatogram showing the size separation of the reconstituted particles (Superdex™ 200). Dotted line shows size separation of a membrane sample in the absence of MSP showing the presence of high molecular weight non-specific and non-functional aggregates. FIG. 16B: Re-chromatogram of the CYP6B1 containing fraction demonstrating the homogeneity of the self-assembled CYP6B1-bilayer structure.

DETAILED DESCRIPTION OF THE INVENTION

Figure 1:
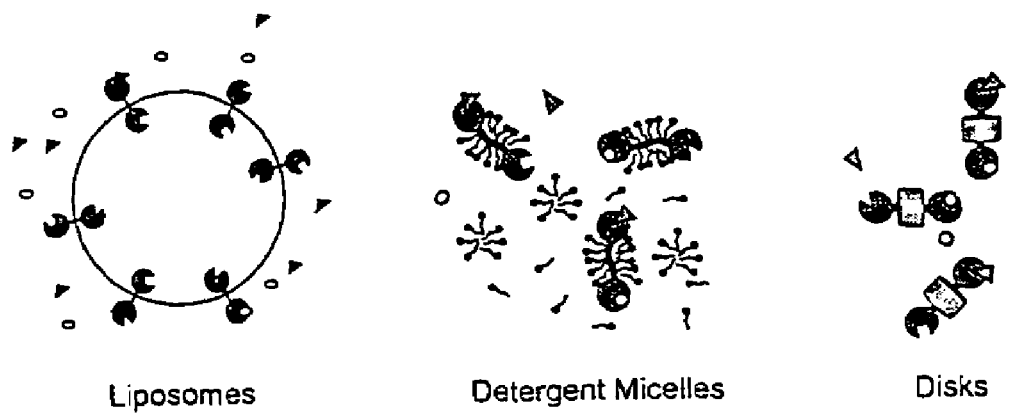
FIG. 1 schematically illustrates different types of lipid aggregates incorporating a membrane protein. Small circles and triangles represent ligand for intracellular and extracellular domains of the receptor proteins, respectively.

Abbreviations used in this application include A, Ala, Alanine; M, Met, Methionine; C, Cys, Cysteine; N, Asn, Asparagine; D, Asp, Aspartic Acid; P, Pro, Proline; E, Glu, Glutamic Acid; Q, Gln, Glutamine; F, Phe, Phenylalanine; R, Arg, Arginine; G, Gly, Glycine; S, Ser, Serine; H, His, Histidine; T, Thr, Threonine; I, lie, Isoleucine; V, Val, Valine; K, Lys, Lysine; W, Try, Tryptophan; L, Leu, Leucine; Y, Tyr, Tyrosine; MSP, membrane scaffold protein; DPPC, dipalmitoyl phosphatidylcholine; PC, phosphatidylcholine; PS, phosphatidyl serine; BR, bacteriorhodopsin; apo A-I, apolipoprotein A-I; GABA, gamma aminobutyric acid; PACAP, pituitary adenylate cyclase-activating polypeptide.

The simplest single-celled organisms are composed of central regions filled with an aqueous material and a variety of soluble small molecules and macromolecules. Enclosing this region is a membrane which is composed of phospholipids arranged in a bilayer structure. In more complex living cells, there are internal compartments and structures that are also enclosed by membranes. There are numerous protein molecules embedded or associated within these membrane structures, and these so-called membrane proteins are often the most important for determining cell functions including communication and processing of information and energy. The largest problem in studying membrane proteins is that the inside of the phospholipid bilayer is hydrophobic and the embedded or anchored part of the membrane protein is itself also hydrophobic. In isolating these membrane proteins from their native membrane environments, it is very difficult to prevent them from forming aggregates, which may be inactive or insoluble in the aqueous environments commonly used for biochemical investigations. The present invention provides ways to generate a soluble nanoparticle that provides a native-like phospholipid bilayer into which hydrophobic proteins of interest (target proteins) can be incorporated to maintain the target protein or smaller hydrophobic molecule as a soluble and monodisperse entity. This is accomplished by incorporating hydrophobic proteins such as membrane proteins into nanometer scale structures using the MSPs as described herein.

Solubilizing Agents

In the context of the present application, a solubilizing agent is one which disrupts hydrophobic interactions which lead to assembly or aggregation of hydrophobic and/or amphiphilic molecules into three dimension structures. For example, a solubilizing agent such as a detergent is used to put into solution hydrophobic proteins within membranes or membrane fragments. Detergents useful in the present context include, but are not limited to, cholate, deoxycholate, 1-palmitoyl-2-oleoyl-sn-glycerophosphocholate, 1-palmitoyl-2-oleoyl-sn-glycerophosphoserine, 1-palmitoyl-2-oleoyl-sn-glycerophosphoethanolamine, CHAPS, n-dodecyl-β-D-maltoside, octyl-glucopyranoside, Triton X-100, myristoyl sulfobetaine, dihexanoyl-phosphotidylcholine, digitonin, emulgen 913 o4r JB3-14. Peptidetergents can also be used; see, for example, Schafmeister et al. (1993).

Membrane Scaffold Proteins

Membrane Scaffold Proteins (MSPs) as used herein may be artificial (non-naturally occurring, those which do not occur in nature, i.e., those which differ in amino acid sequence from any naturally occurring proteins) amphiphilic proteins which self-assemble with phospholipids and phospholipid mixtures into nanometer size membrane bilayers. A subset of these nanometer size assemblies are discoidal in shape, and are referred to as Nanodiscs or Nanodisc structures. Desirably the MSPs comprise several helical domains, where the pairs of helical domains are separated by a punctuation region, made up of one to five amino acids which do not favor helix formation or which tend to stop helix formation of adjacent amino acids. Exemplary helical regions are provided in Table 19. These building blocks can be combined in orders and numbers other than those specifically exemplified, provided that the function of self assembly into stable, soluble nanoscale disc-like particles is maintained. Similarly, these specifically exemplified building blocks can be combined with other helical building blocks from other proteins such as other apolipoproteins, apolipophorins and the like. These assembled structures of MSP and phospholipid preserve the overall bilayer structure of normal membranes but provide a system which is both soluble and can be assembled or affixed to a variety of surfaces. A naturally occurring example of an MSP is human apo-A1. In addition, MSPs can be designed using helical segments of proteins other than human apoprotein A-1, for example, apo A-1 of other species, or apo C, apo E, myoglobin or hemoglobin proteins of various species. Helical segments from more than one protein can be combined, with the appropriate punctuation sequences, to form a MSP having the useful properties described herein. Additionally, functional MSPs can be generated by de novo protein design wherein the desired traits of amphipathic helical protein structures are generated. It is also understood that conservative amino acid substitutions can be made in the sequences specifically exemplified, with the proviso that the self-association function is maintained. Such substitution variants can be termed homologs of the specifically exemplified sequences. Various proteins of interest are described in Bolanos-Garcia et al. (2003) Progress in Biophys. Molec. Biol. 83:47-68.

Hydrophobic or partially hydrophobic proteins, e.g., membrane proteins, or membrane fragments can associate with these particles such that the hydrophobic proteins or membrane fragments are effectively solubilized in a stable structure which maintains the functionality of the protein with respect to enzymatic activity or ligand binding. Similarly, other hydrophobic or partially hydrophobic molecules of interest can also be incorporated within the nanoscale discoid particles of the present invention.

The Nanodisc particles are stable in solution or they can be fixed to a surface, advantageously in a uniform orientation with respect to the surface. As used herein, a nanoparticle comprising MSPs (with or without another hydrophobic or a partially hydrophobic protein) can be from about 5 to about 500 nm, desirably about 5 to about 100 nm, or about 5 to about 20 nm in diameter. Nanoparticles (disks) of about 5 to about 15 nm in diameter are especially useful.

It is also readily within the grasp of the skilled artisan to design MSPs for packaging hydrophobic passenger compounds, proteins or complexes where the MSP assumes an amphiphilic conformation based on beta sheets, where the amino acid sequence of the protein is punctuated so that there are regions of beta sheet forming portions separated by a flexible (hinge) region of amino acids. The region of beta sheet-forming sequence is desirably from about 10 to about 30 amino acids, and the punctuation region can include from 3 to 10 amino acids, where there are antiparallel beta sheets in the MSP or from about 10 to about 30 amino acids where the beta sheets are parallel.

Functional MSPs may or may not have punctuation between domains of secondary structure. The punctuation region disrupts regions of secondary structure within a protein. Proline and/or glycine residues are preferred punctuation regions in a protein having helical domains. Besides disrupting a domain with a particular characteristic secondary structure, the punctuation regions can provide flexibility to a protein's structure, serving to create a hinge region, especially in the case of two to three amino acids, desirably including proline, glycine and alanine residues. A punctuation region (or punctuation sequence, hinge region or hinge sequence) can include from 1 to 30 amino acids, desirably 1 to 2 amino acids when the domains of secondary structure are alpha helices, and, where there are antiparallel beta sheets in the MSP, 5 to 30, and especially 3 to 10 amino acids.

The necessary properties of the linker (punctuation, hinge) sequence between fused MSPs are flexibility and solubility so that the fused proteins assemble into particles in a manner similar to two separate MSP molecules. Linker sequences consisting of repeats of Gly-Gly-Gly-Ser/Thr-(SEQ ID NO:46) have these properties. It is also desirable, in at least some MSPs, to minimize the length of the linker. We constructed a fusion with the minimal linker sequence-GT-, which corresponds to the consensus DNA restriction site for Kpn I, as described herein below. The Kpn I site provides an easy way of inserting any desired linker sequence by restriction with Kpn I and insertion of double-stranded synthetic DNA encoding any desired linker (Robinson et al. 1998). We have also made a fusion construct with the longer linker sequence-GTGGGSGGGT-(SEQ ID NO:15). The MSP2 with the minimal linker, however, assembles into particles very similar to particles containing two MSP1 proteins, but which are more stable than those comprised of two MSP1 proteins. It is understood that the best choice of the particular MSP depends on the particular protein with which is to be assembled. In general, the assembly with larger proteins or protein complexes requires the use of larger MSPs.

One important goal in utilizing a membrane scaffold protein (MSP) to provide membrane proteins in general, and G-protein Coupled Receptors (GPCRs) in particular, with a suitable environment for homogeneous biochemical assay or crystallization is to have homogeneous preparations of particles. The engineered membrane scaffold proteins we have described, including, but not limited to, truncated human apo A-I (MSP1) where the amino terminal soluble domain has been removed, deletion or insertion mutants where one or more protein segments are removed or inserted, tandem repeats of MSP1 or deletion mutants, respectively, and any of the above materials where a histidine tag is incorporated, primarily form 8-10 nm (in diameter) particles when self-assembled with phospholipids in solution. Desirably the MSP does not include the helix H1. However, upon assembly with non-optimal stoichiometry of MSP and phospholipid, particles of other sizes may be present. While standard size separation chromatography can be used to purify a single size class of particle, it is preferable to minimize the size distribution of the initial reconstitution mixture of target protein, MSP and phospholipid. Engineered Nanodiscs of various sizes can be formed by appropriate choice of the length of the membrane scaffold protein. The particle 8-10 nm in diameter nominally comprises two MSP proteins.

Apolipoprotein Sequences

Sequences of several apolipoproteins, hemoglobins and myoglobins are available on the internet at the site of The National Center for Biotechnology Information (NCIB), National Institutes of Health. The coding sequences can be found on the internet and used in the construction of artificial MSP coding sequences or the sequences can be tailored to optimize expression in the recombinant host cell of choice. There is a large body of information about codon choice and nontranslated sequences in the art. Apolipoprotein C sequences include, without limitation, bovine, XP 77416; mouse, AAH 28816; human NP 000032; and monkey, Q28995. Myoglobin sequences include, for example, those of mouse, NP 038621; bovine, NP 776306; rat, NP 067599; and human, NP 005359. Hemoglobin alpha chain sequences include human, AAH 32122 or NP 000549; beta chain sequences include human, NP 000509 or P02023; rat, NP 150237; mouse NP032246; bovine, NP 776342, all of which are incorporated by reference herein. Others may be found at the NCBI website and in the scientific literature as well.

As used herein, amphiphilic and amphipathic are used synonymously in reference to membrane scaffold proteins. An amphiphilic protein or an amphiphilic helical region of a protein is one which has both hydrophobic and hydrophilic regions.

MSP Design

Figure 2:
FIG. 2 shows the wheel structure of an alpha helix, with the placement of hydrophobic and hydrophilic amino acid side chains that give the helix its amphipathic character.
Figure 2:
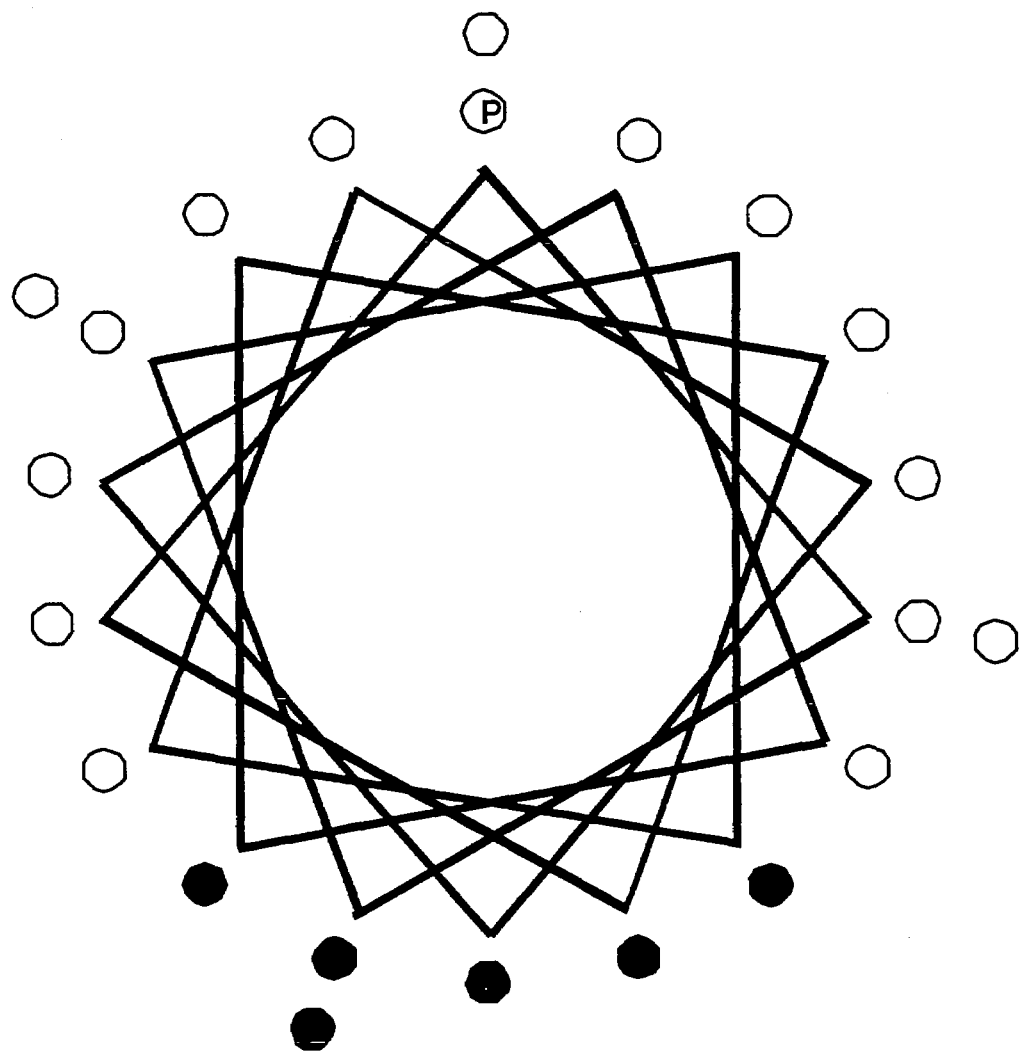

The MSPs of the present invention must be amphipathic, with one part of its structure more or less hydrophilic and facing the aqueous solvent and another part more or less hydrophobic and facing the center of the hydrophobic bilayer that is to be stabilized. The elements of secondary structure of the protein generate the hydrophilic and hydrophobic regions in three dimensional space. Examination of the basic biochemical literature reveals two candidate protein structures that can have this required amphipathic character: the helix and the pleated sheet. We designed the MSPs described herein to have a helix as the fundamental amphipathic building block. Each MSP has an amino acid sequence which forms amphipathic helices with more hydrophobic residues (such as A, C, F, I, L, M, V, W or Y) predominantly on one face of the helix and more polar or charged residues (such as D, E, N, Q, S, T, H, K or R and sometimes C) on the other face of the helix. See FIG. 2 for a schematic representation. In addition, each helical building block can be, but is not necessarily, punctuated with residues such as proline (P) or glycine (G) periodically, which can introduce flexibility into the overall structure by interrupting the general topology of the helix. In one embodiment, these punctuations occur about every 20-25 amino acids to form "kinks" or to initiate turns to facilitate the "wrapping" of the MSP around the edge of a discoidal phospholipid bilayer. The punctuation region (or sequence) can include from one to 10 amino acids, especially 3 to 10 where there are antiparallel beta sheets in the MSP. See FIG. 2, which depicts a generalized linear amino acid sequence and a helical wheel diagram showing the placement of predominantly hydrophobic amino acids on one face of the helix.

Figure 4A:
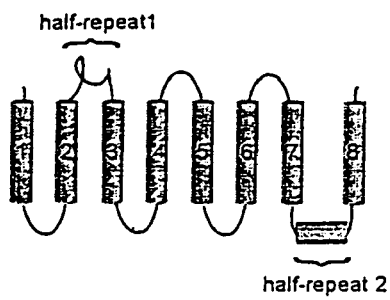
FIGS. 4A-4G illustrate various engineered MSP structures, shown with picket fence topology and helical assignments based on sequence analysis.
Figure 4B:
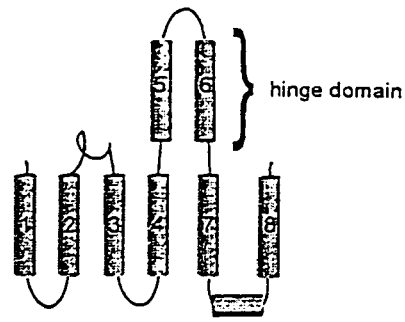
Figure 4C:
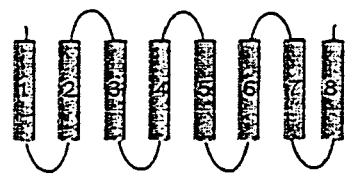
Figure 4D:
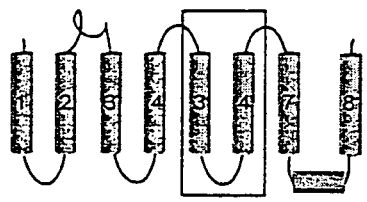
Figure 4E:
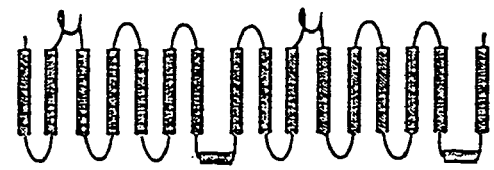
Figure 4F:
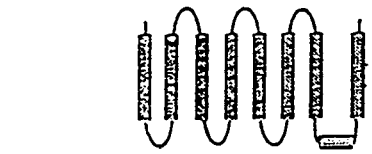
Figure 4G:
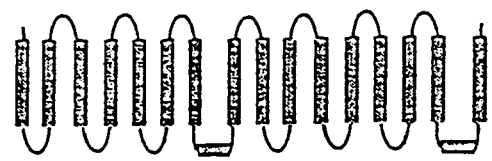
Figure 5A:
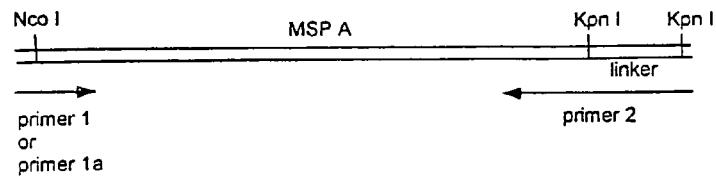
FIGS. 5A-5B diagrammatically illustrate the PCR strategy used to amplify artificial MSPs.
Figure 5B:
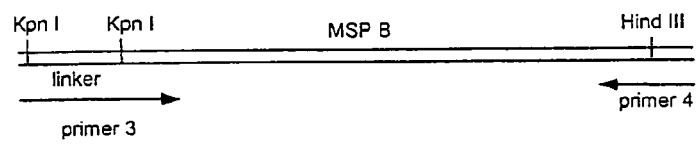

We created an additional artificial variant MSP (MSP2) by designing a tandem repeat of MSP1 connected by a short linker sequence to create a new molecule. This type of artificial MSP is termed a tandem repeat MSP. See FIG. 4G and SEQ ID NO:17. Relatively large quantities (tens of milligrams/liter cell culture) of the artificial MSPs of the present invention are produced in a bacterial expression system. Our constructs reduce the number of size classes that can be formed (those corresponding to three MSP1 molecules). As used herein a tandem repeat membrane scaffold protein is one in which at least four helices of a membrane scaffold are repeated in linear order in a new membrane scaffold protein (e.g., H1-H2-H3-H4-H5-H6-H7-H8-spacer-H1-H2-H3-H4-H5-H6-H7-H8). Examples of tandem repeat MSPs are also given in FIGS. 4E and 4G. See also SEQ ID NO:17 and SEQ ID NO:19, among others.

Nanodiscs made with tandem repeats (two) of MSP1 sequences were larger, but less stable, than those using certain other MSP structures, at least in some instances. Designing MSPs lacking at least one copy of H1 allowed the preparation of stable Nanodiscs which are also larger in size. In particular, the absence of the first helix in the second half of dimeric structure plays an important role in the improved results.

The complete amino acid and nucleic acid sequences for the MSP2 tandem repeat scaffold protein is shown in Tables 7 and 8; see also SEQ ID NO:16 and SEQ ID NO:17. The MSP2 fusion protein was expressed in *E. coli* and purified to homogeneity using basically the same procedure as described for the single MSPs. The MSP2 protein serves as an effective scaffold protein, self-assembling with phospholipid upon removal of solubilizing detergent. At a lipid/dimer ratio of 200 corresponding to nominally 10 nm particles, there is the much greater monodispersivity afforded by the MSP2 protein. Importantly, the overall stability of the disks, as monitored by chemically induced unfolding and exposure of tryptophan residues to solvent, is not altered by the fusion of the monomeric membrane scaffold proteins.

We have generated two new membrane scaffold protein dimers described below and self-assembled these with phospholipids. The resultant Nanodiscs have an overall Stokes diameter determined by small angle x-ray scattering of approximately 15.5 nm which corresponds to a calculated overall physical diameter of a discoid of 17 nm. These are the largest Nanodiscs constructed to date. The modular sequences (see also Table 19) of these new tandem repeat MSPs are as follows:

```
MSP2N2: HisTev-H1/2-H2-H3-H4-H5-H6-H7-H8-H9-H10-
        GT-H2-H3-H4-H5-H6-H7-H8-H9-H10

MSP2N3: HisTev-H1/2-H2-H3-H4-H5-H6-H7-H8-H9-H10-
        GTREQLG-H2-H3-H4-H5-H6-H7-H8-H9-H10
```

Figure 19:
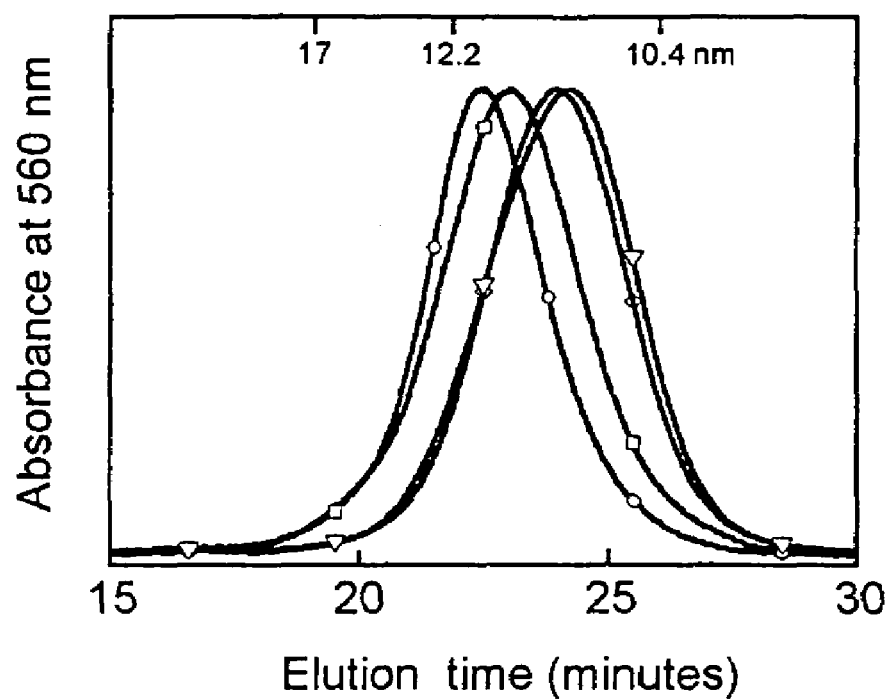
FIG. 19 shows the stoichiometry of phospholipid:MSP for various MSPs. The H1 helix domain does not play a significant role in the formation of the protein "belt" surrounding the Nanodiscs. We have found that the sizes of Nanodiscs constructed with MSP1 and those Nanodiscs constructed with MSPs missing either half or all of H1 are the same and have the same number of phospholipid molecules incorporated per Nanodisc.

Other MSPs have also been made and characterized. We have optimized the conditions of self-assembly to obtain the monodisperse nanoparticles with MSP1E1, MSP1E2 and MSP1E3, shown that the length of the protein is the determinant of the particle diameter, measured the stoichiometry of lipid/protein ratio in these particles and demonstrated the structural difference between the particles formed with lipids above or below melting point (270 K for POPC, 314 K for DPPC). We also prepared the series of deletion mutant membrane scaffold proteins, in which one quarter, one half, or the whole first helix (residues 44-65) was deleted. Experiments with Nanodiscs formed with the truncated proteins indicated that the first helix is of not required for the self-assembly of these Nanodiscs. This observation is believed to explain the earlier disagreement about the size of discoidal particles formed with apo A-1 and their heterogeneity. SAXS data for these Nanodiscs formed with scaffold proteins of different sizes are consistent with the structural model shown in FIG. 19. FIG. 19 also shows that H1 does not play a significant role in the formation of the "belt" of MSP around the outside of the Nanodisc.

Figure 3:
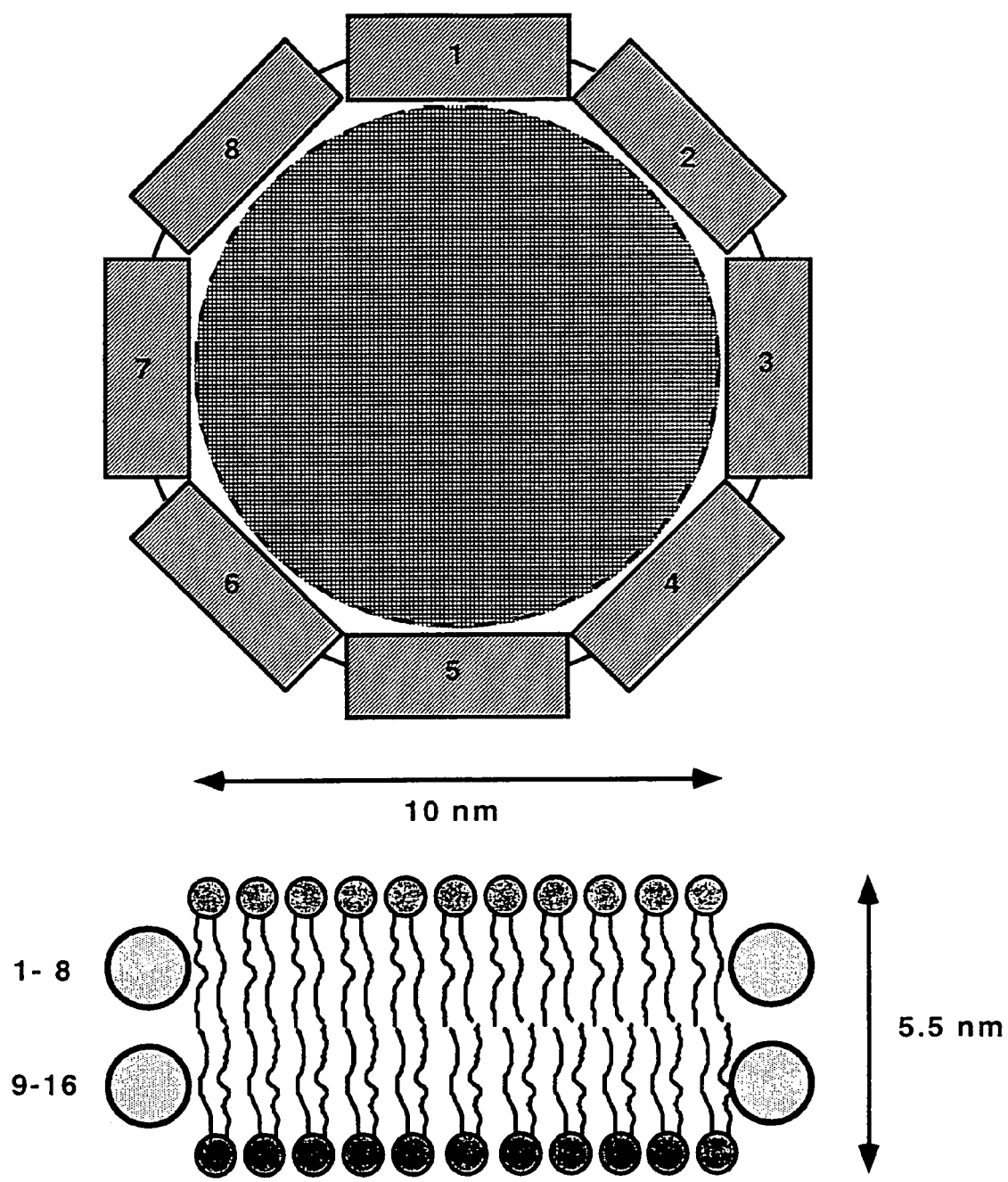
FIG. 3 is a schematic of a "belt" model of an MSP supported bilayer. The rectangles represent single helices with a diameter of about 1.5 nm and a helix length of about 3.9 nm.

In order to generate smaller belts around the bilayer structure, the overall length of the helical building blocks can be reduced, and the punctuations may be introduced more frequently. The exact amino acid sequence can vary in the positioning and number of the hydrophobic amino acids within the designed linear sequence. Simple models in which either the helical axis is parallel or perpendicular to the normal of the Nanodisc bilayer can be generated. To generate a disk with a diameter of roughly 10 nm, an MSP comprises about 12 to about 20 or more repeating units having this generalized amphipathic sequence. Preferably, this protein would be composed of amphipathic alpha helices each with a length of between 14 and 25 amino acids, punctuated in the linear sequence by a residue unfavorable for helix formation, such as proline or glycine or a sequence from about 1 to 5 amino acids which does not favor helix formation, which form small helical building blocks that stabilize the hydrophobic core of the phospholipid bilayer. A helix of about 20-25 amino acids (a helical building block, in the context of the present application) has a height comparable to the thickness of a membrane bilayer. These small helical segments are linked together (punctuated) with from 0 to about 5 amino acid residues, especially G or P. To cover the edge of a 10 nm discoidal particle in either the "belt" model presented, one would need between 10-20 such helices, with 16 being a useful number based on the simple graphic analysis of FIG. 3. Desirably, the helix contains from about 3 to about 18 amino acids per turn, and the type of helix can be an alpha, pi or 3, 10 helix, among others. Helices with three to sixteen, three to eight, desirably three to four, amino acids per turn of the helix. An MSP of the present invention can comprise from 50 to 400 turns. Secondary structure predictions can be determined using programs readily accessible to the art; see, for example, on the internet at the ExPASy proteomics server of the Swiss Institute of Bioinformatics. Guidance in predicting secondary structure is also given in publications such as Chou et al. (1974) Biochemistry 13:211, 222; Chou et al. (1978) Ann. Rev Biochem. 47:251-278; Fasman (1987) Biopolymers 26(supp.):S59-S79. Where there is a dimer or higher oligomer of a protein such as a 7-TM membrane protein or where more than one protein is to be incorporated within a single Nanodisc, for example a reductase and a cytochrome, the MSP used must be capable of forming a Nanodisc particle with a diameter greater than 9-10 nm. The larger Nanodiscs are prepared using longer MSP sequences, such as MSP1E1, MSP1E2 or MSP1E3.

In an alternative embodiment, the engineered amphiphilic MSP contain regions of secondary structure in three dimensional space, such as parallel or antiparallel beta sheets, with spacer regions of appropriate length to allow association of hydrophobic regions with a target hydrophobic target molecule which is protected from the aqueous milieu, and thus stabilized and solubilized.

Certain critical systems controlling cellular function are located in membrane compartments. Many of these membrane protein assemblies represent important pharmaceutical targets that are typically difficult to isolate in soluble and active form because particular phospholipid environments are often essential for maintaining optimal enzymatic turnover or ligand binding activity. Several pharmacologically significant examples indicate specific phospholipid requirements for individual enzymes and receptors, which are perturbed by detergents typically used to solubilize membrane proteins. Examples include the human β-adrenergic receptor that requires neutral lipids for efficient receptor hormone response (Kirolovsky et al., 1985) and the human cytochrome P450 monooxygenase (P450) superfamily that requires several phospholipid types for efficient drug metabolism (Imaoka et al., 1992). An inability to faithfully reconstitute the lipid requirements of detergent solubilized protein in purified systems can, and often does, affect the measured activity of these enzymes.

One of the most widely used alternatives for characterization of these native proteins involves the sub-fractionation of natural cellular membranes and incorporation into micron-sized liposomes. However, liposomes are compromised by thermodynamic instability, size heterogeneity and sequestration of target membrane proteins on the solvent-inaccessible side of the bilayer (Angrand et al., 1997; Savelli et al., 2000). Other convenient methods for obtaining large quantities of soluble functional membrane proteins assembled in phospholipid bilayers have not been available and, as a consequence, our understanding of the numerous protein complexes functioning within cell membranes has been hindered. In this application, we report a rapid method for compartmentalizing heterologously-expressed or native membrane proteins into stable, soluble nanometer-scale bilayer structures which are characterized by sufficient target stability, biological activity and sufficient robustness to survive operation in high-throughput analyses.

The MSPs of the present invention can be used to solubilize tethered, embedded or integral membrane proteins in nanoscale structures. A tethered membrane protein is composed mostly of a single relatively soluble globular domain external to the bilayer and a relatively simple (e.g., a single membrane-spanning or membrane-inserting domain) which anchors this simple globular domain to the membrane bilayer. The globular domain, in nature, can be extracellular or cytoplasmic in orientation.

Tethered membrane proteins are exemplified by NADPH-cytochrome P450 reductases (e.g., from rat liver endoplasmic reticulum or from insect) and cytochrome b5. NADPH-Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, insects etc Cytochrome b5 is a membrane-anchored (tethered) heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis (PAGE). Formation of Nanodiscs through the self-assembly process using MSPs taught in our invention,, wherein cytochrome b5 is added to the preparation of MSP and phospholipid results in incorporation of cytochrome b5 into disk structures. The disk complexes containing cytochrome b5 can be chromatographically separated and purified from undesired aggregated material. The optical absorption properties of the heme chromophore of the purified material show that the heme active site is in a native conformation. Tethered membrane proteins can be incorporated into Nanodiscs either during disc formation, or they can associate with preformed Nanodiscs.

Embedded membrane proteins, as defined herein, are those which include a membrane anchoring segment of the polypeptide, but which also have groupings of hydrophobic amino acids on the surface of the protein, which hydrophobic domains are embedded within the membrane bilayer. Examples of embedded membrane proteins include, without limitation, the interferon receptor superfamily, the nerve growth factor/tumor and the necrosis factor receptor superfamily as well as the cytochrome P450 proteins.

Tissue factor (TF), or thromboplastin, is a 30,000 Da type-I membrane protein critical to initiation of the blood coagulation cascade. This membrane-bound protein acts as an activation cofactor for factor VII, the soluble serine protease which carries out the first enzymatic step in blood coagulation. Expression of tissue factor is limited to cells that are not in direct contact with blood plasma, which cells form a "hemostatic envelope." The TF:VII complex must be assembled on a membrane surface to exhibit high activity, and optimal activity is seen only when the membrane contains phospholipids with negatively charged headgroups.

Another integral membrane protein which has been incorporated into Nanodiscs is a bacterial aspartate receptor. In *E. coli* and *Salmonella* the chemoreceptors Tsr and Tar mediate taxis towards serine and aspartate, respectively, mediated through stereospecific binding of those amino acids. In *E. coli* the Tar receptor protein mediates taxis towards maltose via recognition of a ligand-occupied soluble maltose-binding protein. Membranes from *E. coli* containing over-expressed Tar protein (provided by Gerald Hazelbauer, University of Missouri, Columbia, Mo.) were solubilized with CHAPS detergent and mixed with the scaffold protein MSP1T2. Detergent was removed by adsorption (using Biobead treatment as described herein below). The Tar receptor was incorporated into Nanodiscs, which were then purified by Ni-affinity column chromatography and analyzed by HPLC size-exclusion chromatography. Incorporation of the target was verified by SDS PAGE.

Examples of embedded cytochrome P450 membrane proteins include, without limitation, cytochrome P450 2B4 from rabbit liver microsomes, cytochrome P450 3A4 from human liver microsomes, cytochrome P450 6B1 from insect fat bodies, and cytochrome P450 86A1, 73A5 and 86A8 from plants the cytochromes P450 are a superfamily of enzymes that are found in all forms of life. One role of many P450s is to detoxify xenobiotics; for instance, human liver P450s detoxify most endogenous and exogenous compounds, and these enzymes determine the mean plasma lifetime of all drugs ingested. One of the most widely studied human liver cytochrome P450s is cytochrome P450 3A4 (CYP 3A4). This membrane bound P450 is the most highly expressed P450 in human liver and is responsible for metabolizing almost 50% of all pharmaceuticals (Guengerich, F. P., *Cytochrome* P450. Cytochrome P450, ed. P. R. Ortiz de Montellano, 1995, New York: Plenum Press. 473-535). In order to demonstrate the utility of Nanodisc technology for the study of the cytochrome P450, we incorporated CYP 3A4 into MSP supported nanobilayer discs. Further evidence from size separation chromatography and PAGE analysis supports the conclusion of incorporation of CYP 3A4 into Nanodiscs.

Cytochrome P450 6B1 (CYP 6B1) is a member of the large cytochrome P450 monooxygenase protein superfamily, and it is another example of an embedded membrane protein. CYP 6B1 has been isolated from *Papilio polyxenes*, the black swallow tail, which feeds exclusively on plants producing furanocoumarins, plant psoralen derivatives that are phototoxic to most organisms. CYP 6B1 catalyzes the detoxification of furanocoumarins by what is believed to be an epoxidation reaction (Ma et al. (1994)).

Integral membrane proteins have predominant and critical regions of structure located within the membrane bilayer. Alternatively, there can be relatively large soluble domains on both sides of the bilayer which are linked by one or more passes of the primary sequence through the hydrophobic bilayer core, especially cytokine-type molecules and receptors, which have simple one-pass connectivity but with soluble domains on both sides of the bilayer. As used herein, integral membrane proteins are exemplified by the general class of proteins in which there one or more helical segment in the membrane bilayer, including but not limited to the well known 7 helix transmembrane proteins (e.g., GPCRs).

We have shown that MSP1, MSP2, MSP1E1, MSP1E2, MSP1E3 and MSP2 assemble with bacteriorhodopsin. From the initial reconstitution mixture, two bacteriorhodopsin-containing species are observed when particles are formed with MSP1 or MSP2 in the absence of added phospholipid. MSP is absolutely required for the solubilization of bacteriorhodopsin to form these species because omission of an MSP from the formation mixture results in large non-specific bacteriorhodopsin aggregates that elute in the void volume of the gel filtration column. The majority of bacteriorhodopsin appeared solubilized in the presence of MSPs.

An especially valuable advantage of the MSP-containing nanoparticles of the present invention as a means to solubilize hydrophobic or partially hydrophobic "target" proteins is that the protein incorporated into the nanoparticle has a naturalistic presentation. Native target protein conformation is maintained, the native target protein-membrane interaction and topology are preserved, the target protein is maintained in a native-like environment, thereby increasing the stability of the target protein to inactivation and denaturation, and the topology of the target protein is maintained relative to the membrane. The maintenance of target protein topology relative to the membrane is especially important for screening targets for cell-cell or cell-virus interaction, elicitation of ligand or antibody binding to extra-membrane regions of the target protein or delivery of the target protein through specific trafficking pathways.

Incorporation from Membranes and Membrane Fragments

We have demonstrated that membranes or membrane fragments containing their natural repertoire of membrane proteins and lipids can be incorporated into Nanodiscs comprising MSPs. This can be effected directly without pre-purification or solubilization of the membrane protein populations. A particularly important embodiment is the use of this technology in a variety of commonly used heterologous expression systems for membrane proteins. These include, but are not limited to, insect cells, yeast cells, mammalian cells such as HEK cells, Vero cells and CHO cells, and bacterial cells. Virus envelope proteins or cell membranes of pathogens (e.g., bacteria), either of which can contain multiple copies of antigenic proteins or other molecules, can also be used. A specifically exemplified embodiment is the use of the common insect cell-baculovirus expression system. We used a commercially available Sf9 insect cell line co-infected such that a microsomal preparation containing over-expressed insect CYP6B1 and an over-expressed insect NADPH cytochrome P450 reductase was produced. Hence, we not only demonstrated that MSP Nanodiscs can be used to incorporate another cytochrome P450 system into soluble monodisperse particles, but also that the source of this P450 could be the whole membranes from the Sf9 cell line that was infected with a baculovirus carrying a cloned CYP6B1 gene.

The Nanodiscs generated by the procedure described herein contain the fatty acids and phospholipids from the original native membrane starting material and therefore provide a reliable in vitro environment in which to assay any membrane-bound enzyme or receptor of interest. Thus, MSP-supported Nanodiscs can be used in high-throughput screening ventures such as the identification of ligands for membrane-associated proteins, for example, using combinatorial libraries of peptides, proteins or chemical compounds, and for the identification of new pharmaceuticals. Additionally, the simple procedure of incorporation into Nanodiscs can be used to generate samples for structure determination using x-ray crystallography or NMR spectroscopy. A particular advantage of the Nanodisc system over alternative methods for membrane protein solubilization is the increase in sensitivity of optical measurements due to a significant decrease in light scattering of the particles. The methods of the present invention can be extended to any other source of membrane fragments containing target proteins of interest, such as any yeast, insect, bacterial or mammalian cell culture system or expression system.

High Throughput Screening

An important utility of the Nanodisc technology of the present invention is in high throughput screening for enzymatic or ligand binding activity. In many such systems, it is advantageous to have more than one target membrane protein incorporated into the Nanodiscs, for example, the electron transfer partner needed for P450 monooxygenase catalysis or the corresponding G-protein incorporated with a G-protein coupled receptor.

In order to demonstrate the utility of the MSP Nanodisc technology in these situations, we successfully incorporated the NADPH cytochrome P450 reductase and a cytochrome P450 6B1 into Nanodiscs. As demonstrated herein, each target membrane protein can be individually incorporated into Nanodiscs using MSPs or they can be incorporated in combinations. The endogenous relative amount of cytochrome P450 to reductase is about 10-20 P450 molecules per reductase molecule (Feyereisen, R. (1999) Ann. Rev. Entomol. 44, 501-533). To obtain activity of CYP6B1 after reconstitution into disks, an excess amount of reductase can be added to the reconstitution mixture.

BR, an integral membrane protein, has been incorporated into the MSP Nanodiscs as described herein, and we have also used a commercially available insect cell expression system that provides a membrane fraction hosting the G-protein coupled receptor human for 5-HT-1A (serotonin). The ligand binding activity documented for 5-HT-1A incorporation into Nanodiscs proves that the protein is in the active conformation in the Nanodiscs of the present invention. Subsequent experiments show that the beta-2 adrenergic receptor, the dopamine D2 and D1 receptors and the cytokine receptors CXCR4 and CCR5, all of which belong to the 7-transmembrane protein family and G-protein coupled receptor type, are easily incorporated into Nanodiscs by the methods of the present invention.

Other examples of membrane proteins and membrane protein complexes which have successfully been incorporated into Nanodiscs include cytochrome P450 reductases from rat, insects and plants, a bacteriorhodopsin trimer, a photosynthetic reaction center complex, a twenty-six transmembrane domain *Escherichia coli* transhydrogenase and integrin.

Stoichiometry of protein and lipid is an important factor in the formation of monodisperse discs with all MSPs. The set of extended MSPs shows that there is a well-defined optimum of lipid/protein ratio, which is crucial for quantitative assembly of monodisperse discoidal particles. In addition, the stoichiometric ratio is determined by the MSP length, because of the well-defined topology of discoidal structure with a cylindrical lipid bilayer surrounded by the scaffold protein (FIG. 19), which determines the lipid/protein ratio. The lipid/protein stoichiometry ratios for discs of different sizes were calculated as shown at FIG. 19 and tested experimentally. Concentrations of lipids were measured using tritiated lipids of the same chemical structure and scintillation counting of the column fractions, as described (Bayburt et al. (2002) supra). Concentrations of scaffold proteins were determined spectrophotometrically (Jones et al. (1990) *J. Biol. Chem.* 274: 22123-22129), using the molar absorption coefficients calculated for the known amino acid sequences according to the modified method of Gill-von Hippel, as described in Pace et al. (1995) *Protein Science* 4:2411-2423. All measurements were done on the narrow fractions after separation of the assembled lipid-protein particles by HPLC (Millenium System, Waters, Milford, Mass.) on the calibrated Superdex 200 (size exclusion chromatography) column.

Small angle X-ray scattering (SAXS) was measured at an ambient temperature of 295 K at the vacuum chamber with 1500 mm distance from the sample to the 2D detector at the photon energy 15 keV (wavelength 0.826 Å). The solutions of the Nanodiscs were sealed in glass capillaries with a diameter of 1.5 mm and placed on the holder in the sample chamber, together with calibrant (Ag behenate, spacing 58.38 Å,) and reference buffer solvents. The raw data were processed using the program FIT2D (Hammersley, A. P. (1998) *ESRF Internal Report, ESRF98HA01T, FIT2D V9. 129 Reference Manual V3*.1; Hammersley et al. (1996) *High Pressure Research* 14:235-248) to give the scattering curves in the form 1 g($I/I_0$) vs. Q=$4\pi$ sin(q)/2. Analysis of SAXS data was with the program CRYSOL (Svergun et al. (1995) *J. Appl. Cryst.* 28:768-773) and home written modeling and fitting subroutines using MATLAB (MathWorks, Natick, Mass.). The fitting program is based on the Debye equation and modeling of the nanoparticle by close packed spherical beads with different contrast, as it is done in other popular programs CRYSOL, DUMMIN, SAXS3D and DALAI_GA, reviewed in Takahasi et al. (2003) *J. Appl. Cryst.* 36:549-552; Koch et al. (2003) *Quart. Rev. Biophys.* 36:147-227. The models for fitting were constructed using the information on size and composition of Nanodiscs obtained by other methods described in this paper. The initial estimate for the scattering contrast, i.e. the difference between the electron density for water, 0.334 e/$Å^{-3}$, and the average electron density for the methylene groups in the central part of bilayer, lipid acyl chains, lipid polar head groups (Wiener et al (1989) *Biophys. J.* 55:315-325), and scaffold protein at the circumference of the particle (Svergun et al. (1998) *Proc. Natl. Acad. Sci. USA* 95:2267-2272), was assigned to each bead representing a correspondent phase. Experimental curves for each type of Nanodisc were fitted using five parameters, four electron densities and the radius of the disc. No attempt to made to introduce size or shape heterogeneity into the fitting. Modeling of such heterogeneity within 5% (as suggested by other experimental data) did not give a large difference in the calculated scattering curves, more significant variance in size and shape resulted in the loss of observed features on the scattering curves and gave considerably worse fits.

MSPs have been engineered to minimize the variability in the structure of the discoidal phospholipid bilayer entities, provide greater structural stability and increased size homogeneity of the disk structures, and incorporate useful functionalities such as peptide tags for purification and physical manipulation of disks. Such oligopeptide tags which can be fused to a protein of interest (by molecular biological or chemical methods) include, without limitation, strep-tag (Sigma-Genosys, The Woodlands, Tex.) which directs binding to streptavidin or its derivative streptactin (Sigma-Genosys); a glutathione-S-transferase gene fusion system which directs binding to glutathione coupled to a solid support (Amersham Pharmacia Biotech, Uppsala, Sweden); a calmodulin-binding peptide fusion system which allows purification using a calmodulin resin (Stratagene, La Jolla, Calif.); a maltose binding protein fusion system allowing binding to an amylose resin (New England Biolabs, Beverly, Mass.); and the oligo-histidine fusion peptide system which allows purification using a $Ni^{2+}$-NTA column (Qiagen, Valencia, Calif.).

Disk homogeneity is necessary for efficient incorporation of single membrane proteins or single membrane protein complexes into a single size class of disk. The parent molecule, apo A-I, has functions beyond disk structure stabilization (Forte et al., 1971; Holvoet et al., 1995; Fidge, 1999). These functional regions are unnecessary and often deleterious in the artificial bilayer systems of the present invention.

Secondary structure prediction allows assessment of structural features of the scaffold protein. The apo A-I structure consists of mostly helix, sometimes punctuated by proline or glycine residues in the repeat sequences. Eight to nine helices are believed to associate with lipid in the form of disks. The N-terminal "GLOB" region (SEQ ID NO:89) of apo A-I is predicted to be more globular in character. This portion of the molecule has been removed to produce the engineered MSP1. An MSP that produces disk assemblies with high monodispersity is desirable. To ascertain the roles of half repeats and to further characterize and optimize the MSP structure and function, mutagenesis was used to generate variants as described herein below. See Tables 2-21 below.

Hydrophobic or partially hydrophobic receptors incorporated into MSP disks are useful in structural, biochemical and pharmaceutical research. Membrane protein study was previously limited to insoluble membrane dispersions, detergent micelles, and liposomes. Purified systems for biochemical and physical study require stability, which may or may not be obtainable with detergents. Detergent micelles are dynamic and undergo structural fluctuations that promote subunit dissociation and present difficulties in the handling of proteins in dilute solution. MSP nanobilayers (Nanodiscs) are more robust structurally, having a phospholipid bilayer mimetic domain of discrete size and composition, and greater stability and smaller surface area than unilamellar liposomes. The particles of the present invention are stable in size, conformation and biological activity for at least a month at 4° C.

Surface Technology

The MSPs of the present invention, when formulated into Nanodiscs, can be used in analyses in surface technology such as biosensor chips for high throughput screening or solid phase assay techniques, including but not limited to multiwell plates made, for example, of polystyrene. Where the MSP comprises a His tag, the Nanodiscs can be bound to an immobilized metal, for example divalent nickel cation. Our work on disk scaffolds has also involved surface-associated assemblies.

Figure 7A:
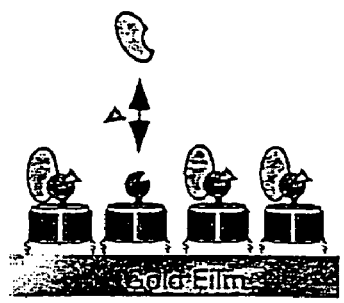
FIGS. 7A-7B show the membrane proteins incorporated into disks and attached to solid supports.
Figure 7B:
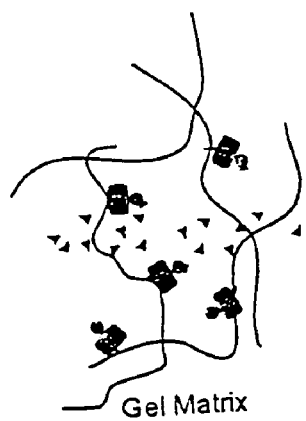
Figure 8:
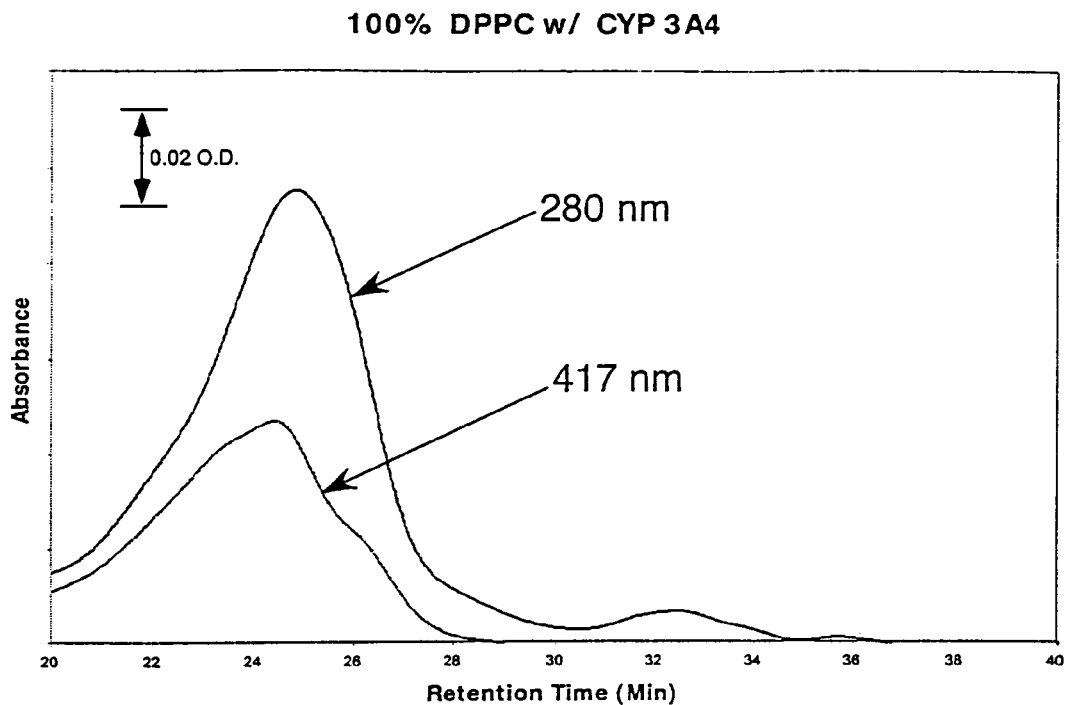
FIG. 8 is a chromatogram of cytochrome P450 3A4 incorporated into 10 nm bilayer disks composed of 100% DPPC as phospholipid.

For instance, the surface plasmon resonance (SPR) biosensor utilizes an approximately 50 nm gold film on an optical component to couple surface plasmons to a dielectric component (sample) at the surface of the gold film. MSP-stabilized bilayers can be attached to the surface for use as a biomimetic layer containing proteins or other targets of interest by engineering cysteines into the MSP (FIG. 7A). The use of thiols is well known for attaching molecules to gold surfaces. Based on the belt model, cysteine residues can be placed along the polar side of the amphipathic helix axis, provided that a cysteine residue is not positioned at the helix-helix interface. In cases wherein the MSP is so engineered, multiple cysteine residues can form disulfide-linked dimers (Segrest et al., 1999). An alternative is to introduce cysteines within a flexible N- or C-terminal linker. Such a construct is, in theory, capable of associating the belt (or the picket fence) model of disk to a gold surface. Alternatively, thiol lipids can be incorporated within the bilayer domain. Methodologies which utilize differences in optical refractive index with layered structures, such as total internal reflection spectroscopy, resonant mirrors, optical diffraction grating engineered on optical surfaces, and the like, can be likewise utilized by direct extrapolation. In addition to SPR, surface-associated disks on gold can be used in STM and electrochemical studies, for example, such as with membrane associated redox proteins, e.g. cytochrome P450 and its flavoprotein, as well as ion channels.

SPR data can also be obtained from measurements made using a thin film of dielectric such as silicon dioxide applied over the metal film normally used as the substrate in SPR. This variation of the technique has been termed coupled plasmon waveguide resonance (CPWR) (Salamon et al., 1997a). Because silica can be used as the active surface in these plasmon resonance experiments, the process of producing a self-assembled bilayer can be adapted according to the procedures used to produce surfaces on mica or other silicon oxide surfaces. This has the added advantage of making the conditions used for the SPR experiments directly comparable to those used for AFM experiments. The CPWR technique can easily be performed on an SPR instrument by simply adding the silica coating to the metal film slides that are presently used for SPR spectroscopy.

MSPs with available cysteine groups also enable specific labeling with chemically reactive groups or affinity tags for immobilization in gel matrices. Hydrogels with reactive coupling groups are useful for immobilizing proteins for SPR measurements. In a hydrogel configuration, the disk serves as a carrier for bilayer-embedded membrane proteins in a monodisperse form with both intra- and extracellular domains available for ligand binding. We have already demonstrated that disks containing a His tag bind to a metal chelate matrix, which can be used to immobilize Nanodiscs containing a His-tagged MSP. His tag vectors are commercially available (e.g., from Qiagen, Valencia, Calif.) and are described in U.S. Pat. Nos. 5,284,933 and 5,130,663. Other tag peptide sequences known to the art, including but not limited to, Flag tag (flagellar antigen) or Step tag (streptavidin binding), can be engineered into the MSP by molecular biological methods. Besides mediating attachment to a support of choice, the tag sequences can facilitate purification of the MSPs or of Nanodiscs containing them. Nanodiscs can also be used in preparing affinity matrices for bioseparation processes and measurements of ligand affinities. The particles produced by the methods of the present invention are useful for drug discovery, structure/function correlation, and structure determination of membrane proteins.

Membrane Protein Structure and Function Analysis

Structure determination of membrane proteins has been limited by the abilities to produce large amounts of membrane proteins and to crystallize these proteins. Nanodiscs and MSPs are useful as carriers for membrane protein stabilization and expression. MSP can serve to solubilize membrane proteins for crystallization in lieu of detergents. Indeed, where the lipid bound form of MSP is structurally stable and rigid, crystallization can be enhanced by introduction of crystal contacts through the MSP. We have demonstrated that MSP1, the extended forms of MSP1, and MSP2 or other tandem repeat MSPs can be used to solubilize BR from purple membranes in the presence and absence of exogenous lipid.

Fusion constructs with a membrane (or other) protein and an MSP region can be expressed in *Escherichia coli* using any of a number of art-known vectors to produce a stable and soluble form of the membrane protein that contains a membrane anchor in large quantity. The exciting discovery that MSP solubilizes BR in the absence of added phospholipid allows the use of the artificial MSP to stabilize membrane proteins in the absence of detergents or lipid additives. The (artificial) MSPs disclosed herein can be used in solubilization of other membrane proteins including, but not limited to, cytochrome P450, cytochrome P450 reductase, and the 5-HT-1A receptor, as well as other membrane-associated receptor proteins and enzymes.

Signal transducing elements occur across membranes, while vesicles render one side of membrane inaccessible to hydrophilic reagents and effector proteins. A specific embodiment of the present invention uses disks to solubilize and stabilize pharmaceutical targets such as GPCRs, ion channels, receptor kinases, and phosphatases in a naturalistic presentation. We have incorporated proteins with multiple membrane spanning domains into the disks of the present invention, with a focus on GPCRs. We had successfully incorporated the model serpentine membrane protein, bacteriorhodopsin, into Nanodiscs. Bacteriorhodopsin is a model for GPCRs, which are current targets for drug discovery. Currently, over 1000 probable G-protein receptors from various organisms have been cloned and many of the so-called "orphan" receptors await identification of natural (or synthetic) ligands. Ligand classes include peptide hormones, neurotransmitters, eicosanoids, lipids, calcium, nucleotides, and biogenic amines. GPCRs are believed be targets for more than half of currently marketed pharmaceuticals. This structural class of membrane proteins can readily be incorporated into Nanodiscs when contacted with MSPs as pre-solubilized proteins or as membrane-associated proteins. G-protein coupled receptors inserted into Nanodiscs are completely functional in this trans-membrane signaling process. Structural characterization of the reconstituted receptors is performed using chemical analysis, spectroscopy and atomic force microscopy.

Cytochrome proteins and reductases can be derived from plant, insect, mammalian, avian or other sources. Specific examples include, insect cytochrome P450 reductase and cytochrome P450 CYP6B1 and plant cytochrome P450 CYP7B12, CYP7B13, CYP73A5, CYP86A1, CYP86A2, CYP86A4, CYP86A7 or CYP86A8. "Derived from" can mean that the target protein is present in a natural (native) membrane when contacted with MSP to produce Nanodiscs, or the target protein can be isolated, purified or presolublized, or the target protein can be associated with the membranes of cells in which it is recombinantly produced.

GPCRs which can be solubilized in nanoscale phospholipid bilayers include the Class A (Rhodopsin-like) GPCRs which bind amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and lysophosphatidic acid (LPA), among other compounds. GPCRs with amine ligands include, without limitation, acetylcholine or muscarinic, adrenoceptors, dopamine, histamine, serotonin or octopamine receptors; peptide ligands include, but are not limited to, angiotensin, bombesin, bradykinin, anaphylatoxin, Fmet-leu-phe, interleukin-8, chemokine, cholecystokinin, endothelin, melanocortin, neuropeptide Y, neurotensin, opioid, somatostatin, tachykinin, thrombin vasopressin-like, galanin, proteinase activated, orexin and neuropeptide FF, adrenomedullin (G10D), GPR37/endothelin B-like, chemokine receptor-like and neuromedin U.

Other exemplary proteins include mammalian, especially human, CCR5 and CXCR4 chemokine receptors. These were incorporated into Nanodiscs by contacting membranes containing native or recombinant protein. The native protein conformation is maintained, as evidenced by the reaction of the CCR5-containing and CXCR4-containing Nanodiscs with CCR5- and CXCR4-specific antibodies. Nanodiscs containing the human bet-2 adrenergic receptor have also been made.

Ligands of other specific GPCRs include hormone proteins, rhodopsin, olfactory compounds, prostanoid, nucleotide-like (adenosine, purinoceptors), cannabinoid, platelet activating factor, gonadotropin-releasing hormone, thyrotropin-releasing hormone and secretagogue, melatonin and lysosphingolipid and LPA, among others. Class B secretin-like GPCRs include, without limitation, those which bind calcitonin, corticotropin releasing factor, gastric inhibitory peptide, glucagon, growth hormone-releasing hormone, parathyroid hormone, pituitary adenylate cyclase activating polypeptide (PACAP), secretin, vasoactive intestinal polypeptide, diuretic hormone, EMR1 and latrophilin. Class C metabotropic glutamate receptors include those which bind metabotropic glutamate, extracellular calcium-sensing receptors or GABA-B receptors, among others. "Orphan" receptors whose ligands are not yet known are also potential targets of assays of the present invention.

In the assays of the present invention which demonstrate binding of a particular ligand or which are used to identify inhibitors or competitors of ligand binding to an MSP-supported GPCR, a variety of detectable moieties (labels) can be incorporated within the ligand molecule (such as radioactive isotope, e.g., $^3H$, $^{14}C$, $^{35}S$, $^{32}P$, $^{125}I$, $^{131}I$, fluorescent compounds, luminescent compounds, etc.) can be attached to the ligand molecule provided that binding to the cognate receptor is not significantly reduced due to the label.

Scanning Probe Microscopy

An important technique used in the characterization of disk structures and associated proteins is scanning probe microscopy (SPM). SPM is an umbrella term for any microscope that utilizes the scanning principles first pioneered in the scanning tunneling microscope (STM), but these microscopes can vary so greatly they are best discussed in terms of their guiding central principle. The technology has been used in the analysis of biological membranes and their associated proteins, bilayer structures and incorporated membrane proteins surfaces. SPM combines independent mobility in all three spatial directions (scanning) with a detection system capable of detecting some characteristic of the surface (probing). The various surface characteristics that can be probed (conductivity, surface forces, compressibility, capacitance, magnetic, fluorescence emission) demonstrate the wealth of information that can be obtained. The excellent z-axis sensitivity of atomic force microscopy makes the presence of proteins binding to an rHDL monolayer or in Nanodiscs easily detectable (Bayburt et al., 1998). Precise height measurements are possible with AFM, and membrane protein height measurements obtained by modulating the force of the AFM probe on various Nanodisc assemblies (Bayburt et al., 2000). The surface association of disks formed from MSPs allows direct investigation of the biophysical properties of single membrane proteins incorporated into phospholipid bilayers on surfaces by SPM. The ability to attach disks to atomically flat conductive surfaces (such as gold or silica) is necessary for scanning tunneling microscopy (STM). Without wishing to be bound by theory, it is believed that tunneling through a redox-active system can be used to probe the functional state of an enzyme (Friis et al., 1999; Mukhopadhyay et al., 2000). These two techniques provide complementary data and can be used in concert to study events occurring at the bilayer/solution interface. The ability to place disks on a gold surface also allows the use of surface plasmon resonance (SPR). Insertion of membrane proteins into such artificial lipid bilayers, or their interaction with surface-associated proteins can be detected and quantified by SPR.

Other useful solid surfaces onto which Nanodiscs can be bound include, without limitation, quartz, silica, silicon, silicon oxide, silicon nitride, polystyrene, plastic and resins.

Disc Stability and Size Dispersion

Measurements of disk stabilities and determination of size dispersion among classes are necessary to evaluate the constructs and Nanodiscs. Gel filtration and native gel electrophoresis are used to separate and quantitate sizes of particles. Spectroscopy is used to quantitate secondary structure (CD) and lipid association (fluorescence) characteristics of the engineered MSPs, including stabilities based on thermal and chemical denaturation. Compositions and stoichiometries of components in disks can be quantitated by traditional methods, using radioactive or fluorescent labels, mass spectrometry, etc. of protein and lipid components.

Advances in the incorporation of fluorophores into the lipid bilayer of Nanodiscs have been accomplished. Such experiments provide important information for the incorporation of small molecules into Nanodiscs for therapeutic use and in the generation of labeled structures for tissue localization and ADME/toxicology studies. Fluorescence is one of the most widely used techniques to track proteins and to analyze protein binding events. Nanodiscs can be prepared to contain lipophilic fluorescent dyes and to label proteins. Several different fluorophores have been incorporated into the lipid bilayer of Nanodiscs during or after self-assembly. Due to the small size of the lipid bilayer of Nanodiscs (~8 nm in diameter) the dye is held within a few nanometers of a protein incorporated into the bilayer. In addition, the protein-to-dye stoichiometry can be strictly controlled. This methodology allows a desired number of dyes to label a protein without directly attaching the dyes through mutations or other invasive or potentially destructive techniques.

In related experiments, numerous fluorescein-labeled lipids were used in the formation of Nanodiscs. Results have suggested that as many as 30 to 40 small molecule organic molecules can be incorporated into a single Nanodiscs without perturbing the discoidal bilayer structure, as monitored hydromatically. These highly fluorescent Nanodiscs are useful in optical sensing and sorting applications, including use in microfluidic arrays and on-chip analytical systems for diagnostics.

As an example of this technology, Nanodiscs were assembled using DPPC doped with DHPE-fluorescein lipids and MSP1. Lipid mixtures containing 10 and 20% DHPE-fluorescein yielded Nanodiscs as shown by size exclusion chromatography. These percentages correspond to 16 and 32 fluorescently labeled lipids per Nanodisc which have been shown to contain 160 DPPCs when assembled with MSP1. A variety of lipophilic fluorophores have been incorporated into Nanodiscs. These include a lipophilic derivative of fluorescein, the lipid phase state marker laurdan and a derivative of hydroxycoumarin, a pH sensitive probe. These fluorophores have been incorporated into Nanodiscs both during and after the assembly process. Laurdan has been incorporated into Nanodiscs containing DPPC and DMPC. All of the fluorophores have been incorporated into Nanodiscs containing DMPC as well as into Nanodiscs which have been preassembled to incorporate an integral membrane protein target.

Incorporation of Hydrophobic or Amphipathic Compounds

Hydrophobic or amphipathic organic compounds, for example fluorescent and/or lipophilic dyes such as those used to probe membrane structure, can be readily incorporated into Nanodiscs in one of two ways. Most commonly, such a compound can be added to the detergent solubilized mixture. The compound of interest is then assembled naturally into the final structure during the Nanodisc assembly which is initiated by detergent removal. Alternately, these compounds can be incorporated into pre-formed Nanodiscs by simple incubation. In this case, there is an expected more facile incorporation into a fluid phospholipid state which is determined by the incubation temperature relative to the phase transition temperature of the phospholipid mixture. However, strong partitioning of such compounds into the hydrophobic bilayer structure allows successful incorporation even at room temperature (about 25° C.) with DPPC (phase transition temperature about 42° C.). Lipophilic dyes which partition into Nanodiscs can include, without limitation, diphenylhexatriene, octyldecylindocarbocyanine (DiI), C1-BODIPY 500/510, dihexadecanoylglycerophosphoethanolamine fluorescein.

Hydrophobic or partially hydrophobic imaging agents, therapeutic and/or cosmetically active molecules and the like can also be incorporated using the same or similar protocols.

Atomic Force Microscopy

AFM is used to provide molecular resolution data on the structural organization of the lipid and protein components of the Nanodiscs of the present invention. This technique can be used in air, vacuum, and under aqueous and non-aqueous fluids. The latter capability has made it the most important scanning probe technique in the biological sciences. The AFM is a very versatile instrument as it is capable of acquiring images and other forms of force data in contact, tapping, phase, and lateral force modes (Sarid, 1994). These scanning modes are available on the Digital Instruments Multimode Scanning Probe Microscope (Digital Instruments, Plainview, N.Y.), and they have been successfully used to image rHDL and proteins associated with Nanodiscs both with and without incorporated proteins. This instrument can also be used in STM and electrochemical modes to study characteristics of gold-associated Nanodiscs and incorporated redox proteins.

Modifications of MSP primary structure can generate alternative and more effective and stable membrane scaffold proteins. For instance, we have deleted and/or duplicated helical regions of MSP1 to produce novel artificial membrane scaffold proteins. See Table 21 herein below for examples of such membrane scaffold protein constructs.

Careful attention to the concentrations of MSP in the reconstitution mixture is necessary to insure homogeneity with respect to the sizes of Nanodiscs produced. The optimal phospholipid to MSP ratio depends on the overall size Nanodisc generated, which is in turn determined by the overall length of the encircling membrane scaffold protein. For example, the MSP1 scaffold protein self assembles to form a nominally 9.7 nm diameter disc with 163 DPPC phospholipid (PL) molecules incorporated per Nanodisc (81.6 per MSP1). For Nanodiscs which are engineered to be larger by adding additional helical segments within the MSP, more phospholipids (PL) are enclosed. MSPE1 with an additional 22-mer helix generates particles of diameter 10.4 nm and 105.7 PL per MSP1E1. With two 22-mer helices inserted into the MSP, a Nanodisc of diameter 11.1 nm is generated with 138.2 PL molecules per MSP1E2. With three 22-mer helices added, a 12 nm particle is produced with 176.6 DPPC molecules per resulting Nanodisc.

Figure 17:
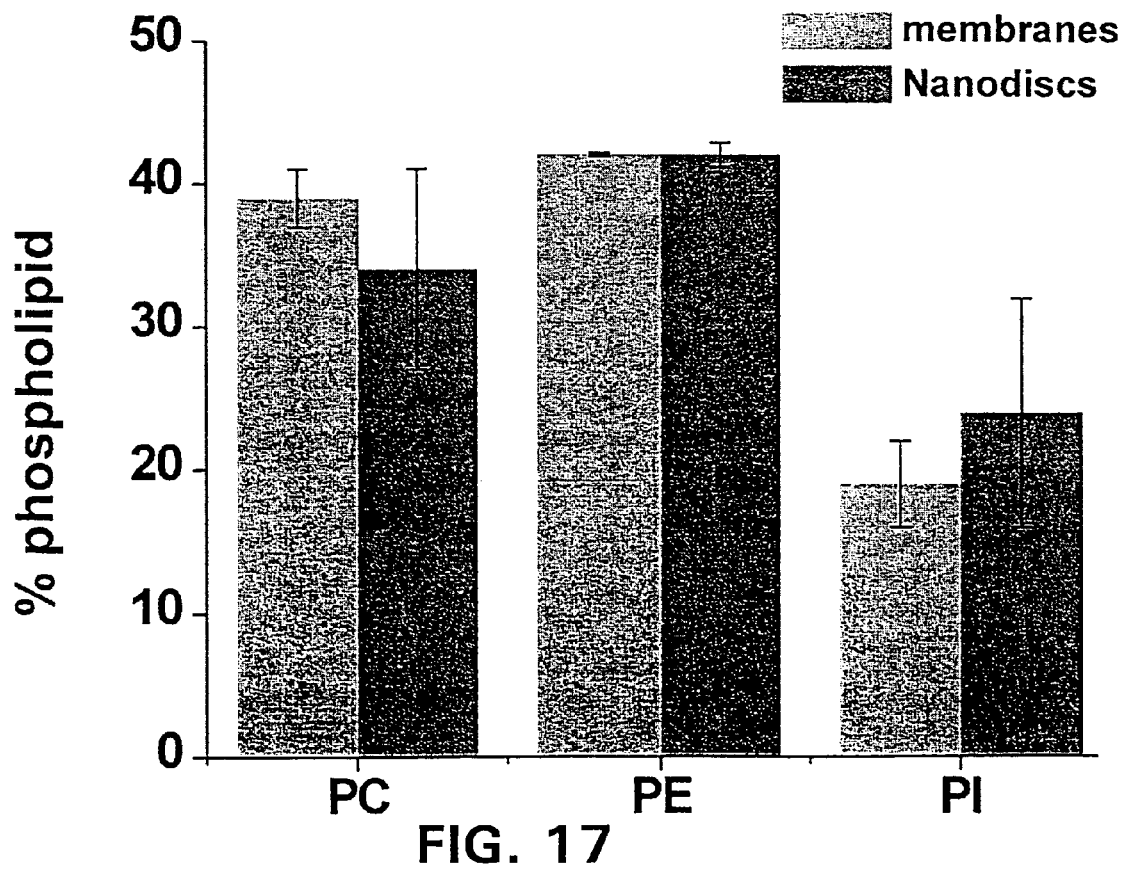
FIG. 17 shows the preservation of phospholipid content of starting membrane preparation in the resulting soluble Nanodisc bilayers. Vertical bars represent phospholipid type determined from three replicate samples of starting membranes or self-assembled Nanodiscs. PC: phosphatidylcholine, PE: phosphatidylethanolamine, PI: phosphatidylinositol.

We have studied the lipid composition of Nanodiscs formed with natural cell membranes. The successful application of MSP technology to the assembly of nanobilayers from natural biological membranes provides a unique opportunity for the direct isolation of membrane proteins from cells and their solubilization and dispersal into a system that closely mimics the native cell environment. To further clarify the extent to which the phospholipid content of the isolated Nanodiscs mimics that of the original Sf9 microsomal membranes, nickel affinity-purified nanostructures assembled with Sf9 microsomal membranes were analyzed by thin-layer chromatography. Comparisons of these Nanodisc phospholipid populations with the major phospholipid types found in insect cell membranes, which are phosphatidylcholine, phosphatidylinositol, and phosphatidylethanolamine (Marheineke et al., 1998) (FIG. 17), clearly indicate that the phospholipid composition of endogenous Sf9 microsomal membranes is preserved in assembled Nanodiscs.

Functional Proteomics

Figure 14:
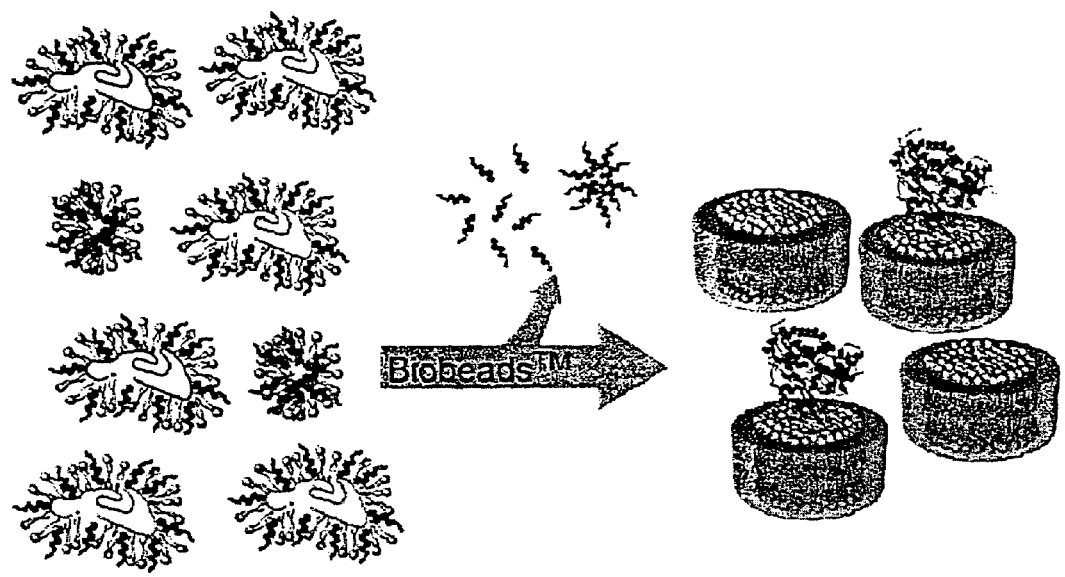
FIG. 14 provides a schematic describing the formation of nanoscale supported lipid bilayers (Nanodiscs) through self-assembly. A cell membrane preparation containing the target membrane protein is solubilized with detergent in the presence of membrane scaffold protein (MSP) (see herein below). Upon removal of the detergent, by dialysis or Biobeads™, a soluble MSP-supported Nanodisc, is formed with the target incorporated into the resulting phospholipid bilayer.
Figure 15A:
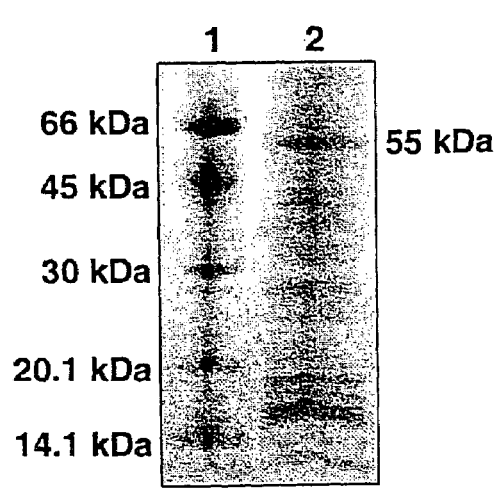
FIG. 15 shows the results of one dimensional SDS-PAGE of Nanodisc mixture. Lanes 1, low molecular weight markers. Lane 2 (left panel), Sf9 insect cell membranes from insect cells genetically modified for the overexpression of CYP6B1. The band at 55 kDa represents the overexpressed target membrane-bound protein. Lane 2 (right panel) illustrates the Nanodisc mixture assembled from Sf9 insect cell membranes overexpressing CYP6B1. MSP1 and CYP6B1 run at molecular weights of 25 kDa and 55 kDa, respectively.
Figure 15B:
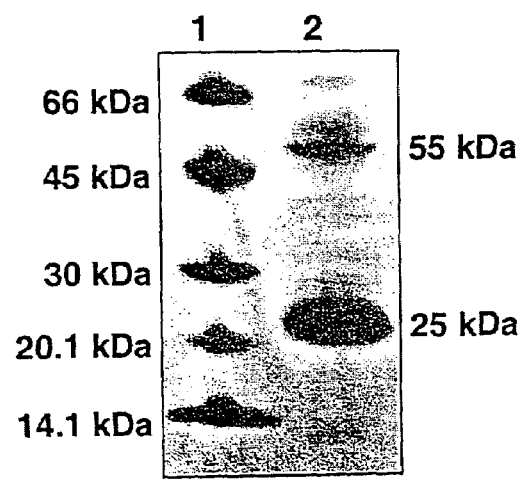

To adapt MSP technology to a format compatible with a functional proteomic analysis of heterologously-expressed membrane proteins, membranes from Sf9 cells overexpressing CYP6B1 were completely solubilized with detergent in the presence of the engineered membrane scaffold protein MSP1. Removal of the detergent (using Biobeads®) initiated self-assembly, allowing for the incorporation of the membrane protein population into MSP-supported phospholipid nanobilayers, as outlined in FIG. 14. The MSP1-containing particles were subsequently isolated using a nickel-chelating resin to bind the His6-tag on the N-terminus of the scaffold protein. Analysis of the affinity-purified soluble nanobilayers by denaturing polyacrylamide gel electrophoresis confirmed the presence of the CYP6B1 target protein as well as an array of endogenous proteins present in the original Sf9 cell membranes (FIG. 15). The nickel affinity-purified sample was fractionated by size exclusion chromatography (FIG. 16A) and analyzed by absorbance at 417 nm to identify a 10 nm fraction containing over 90% of the solubilized heme-containing target protein.

Figure 16A:
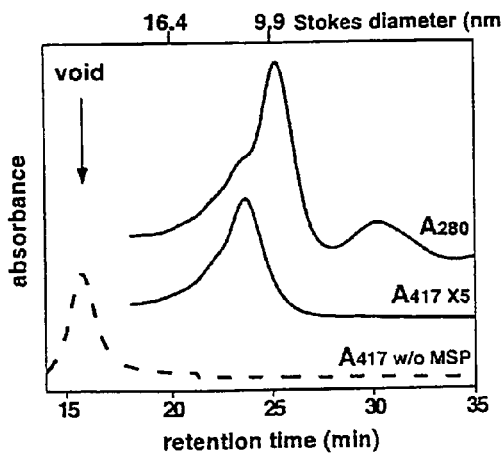
FIGS. 16A-16B show the results of size exclusion chromatography of Nanodiscs made using MSP1 and containing a heterologously expressed cytochrome P450, CYP6B1. The target protein is incorporated into the Nanodisc through the simple self-assembly process described in the text.

Size exclusion chromatography of CYP6B1-expressing Sf9 cell membranes treated and fractionated in the absence of the membrane scaffold protein shows that the target elutes as large, non-specific aggregates (FIG. 16A, dotted line). The homogeneity of the MSP1-supported Nanodiscs generated is dependent on the identity of lipid and its ratio of lipid to the amount of MSP used in the reconstitution procedure (Bayburt et al., 2002) supra). Our analysis of MSP disks assembled with the natural lipid pool from Sf9 insect cell membranes indicates other size populations in the initial nickel affinity-purified Nanodiscs (FIG. 16A). These variations are due to the difficulty in determining a priori the precise concentration of MSP protein ideally matched to the lipid composition in membrane preparations expressing variable amounts of the heterologous P450 protein and to the significant size distribution of the endogenous membrane proteins that are also assembled into nanostructures in this process. These other size classes represent non-specific aggregates that are easily separated from the about 10 nm diameter nanobilayer assemblies. Size-fractionated populations of Nanodiscs containing the P450 target protein are uniform and stable through re-fractionation on a sizing column, such as Superdex™ 200.

Figure 16B:
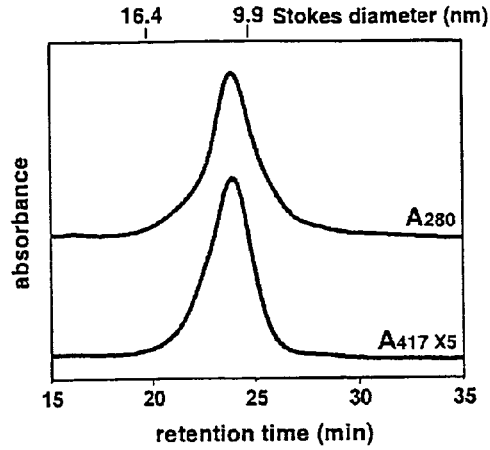

The final CYP6B1-containing population displays a stoichiometry of approximately one CYP6B1 protein per 10 Nanodiscs (FIG. 16B).

Figure 18:
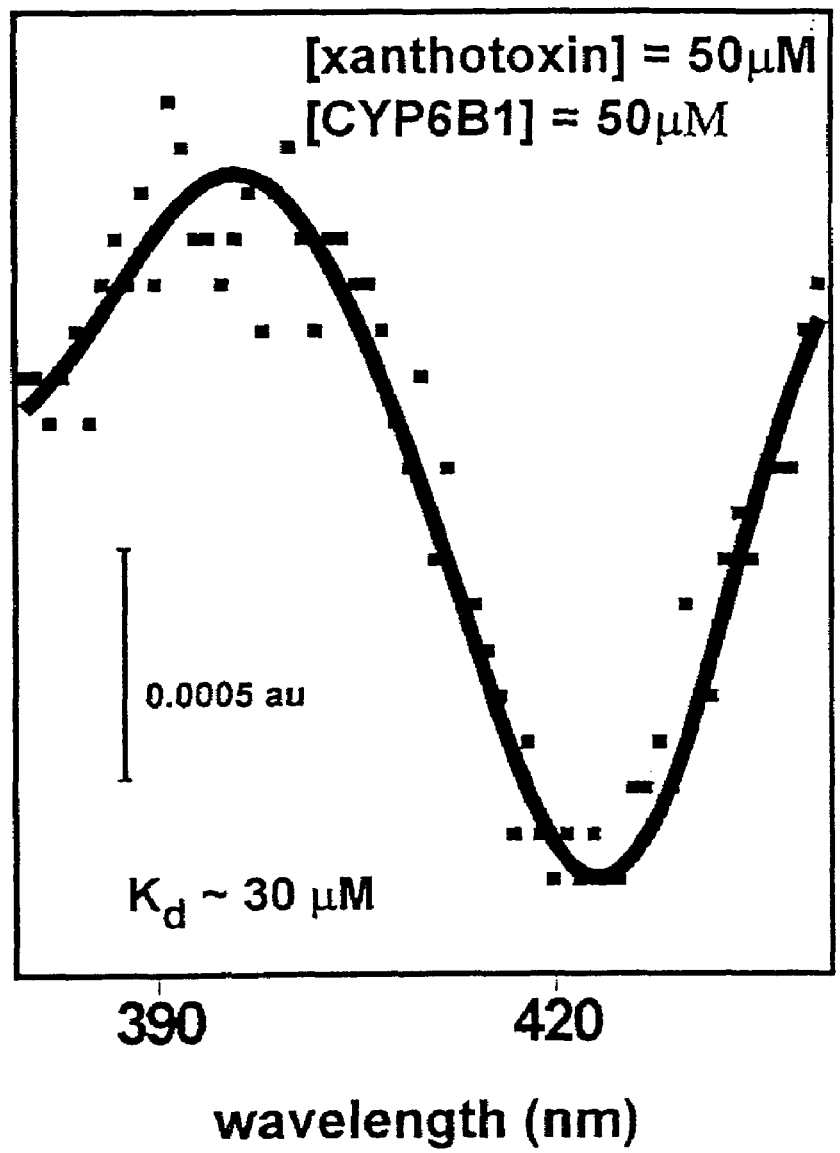
FIG. 18 shows ligand binding to CYP6B1 incorporated into Nanodisc membrane bilayers with MSP1. The characteristic "Type I" binding spectra (decrease in substrate low spin cytochrome with absorbance at about 417 nm and concomitant increase in the high spin fraction absorbing at about 390 nm) is obtained in microtiter plates using high-throughput plate reader following incremental addition of the environmental furanocoumarin xanthotoxin. A dissociation constant of roughly 30 μM was calculated.

We have examined the integrity of the membrane protein assembled into Nanodiscs. CYP6B1-containing nanostructures were assayed by reduction of the iron and binding of carbon monoxide (CO), which monitors via an absorbance maximum at 450 nm the quantity of protein that is intact and correctly configured for P450-mediated catalysis (Omura and Sato (1964) (See FIG. 18). This spectral assay indicates a clear absence of absorbance at 420 nm and documents the fact that normally labile proteins, such as P450s, are incorporated in their native form into Nanodiscs suitable for subsequent fractionation and biochemical analysis. To further demonstrate that the solubilized membrane protein is accessible for binding substrate and suitable for use in high-throughput optical analysis, binding of xanthotoxin, one of several furanocoumarin substrates metabolized by this P450, to MSP1- and CYP6B1-containing Nanodiscs was analyzed in 96-well microtiter plates using a sample volume of only 200 μl Nanodiscs (10 picomoles enzyme) and varying concentrations of substrate. The Type-I binding spectra (Estabrook and Werringloer, 1978) obtained at varying concentrations of xanthotoxin show an absorbance shift from 420 nm to 390 nm that is characteristic of substrates effectively displacing water as the sixth ligand to the heme iron in the P450 catalytic site and converting the iron from low spin to high spin. The data presented in FIG. 18 clearly illustrate that the ability of CYP6B1 to bind substrate is maintained throughout the Nanodisc assembly and subsequent fractionation process.

In summary, the present invention provides an important tool for the study of membrane protein targets as well as the complicated multi-component assemblies present in cellular bilayers. When coupled with our ability to express individual cloned P450s or other membrane proteins in the frequently used baculovirus, yeast and mammalian expression systems, these technologies present the opportunity to display single membrane proteins supported in native membrane bilayers in the development of biochemical methodologies previously restricted to soluble proteins. The lipid composition of the particles derived from MSP and membranes or membrane fragments mimics that of the starting membranes or fragments, especially where solubilized membrane or membrane fragment preparations are used as the source of the phospholipid(s) and hydrophobic protein or other hydrophobic molecule of interest. This contributes to maintaining the native conformation and activity of the membrane (or other hydrophobic) protein which becomes incorporated into the particles with MSP.

The ability to bind substrates, inhibitors and other interacting molecules with these solubilized membrane proteins using sensitive optical difference spectra in microtiter plates enables the development of high throughput screening methods for many different types of membrane proteins. For instance, cytochrome P450 and its reductase stabilized in a functional state through incorporation into Nanodiscs offer an attractive means for measurements of drug metabolism and pharmokinetics, with applications in the pharmaceutical industry. The fact that the Nanodisc solubilization procedures can be applied nonspecifically to all membrane proteins means that this technology can be used to solubilize and fractionate many pharmacological target proteins directly out of cellular membranes. Coupled with the histidine (or other) tag on the MSP molecule, this technology enables the immobilization of target proteins on surfaces suitable for high throughput screening. All the MSPs described herein can be used in preparing Nanodiscs with purified and solubilized hydrophobic or partially hydrophobic proteins or with hydrophobic or partially hydrophobic membrane proteins solubilized from membrane or membrane fragment preparations.

Immunogenic Compositions

Antigens which are hydrophobic or partially hydrophobic can be formulated into immunogenic compositions for administration to a human or animal in which an immune response, either cellular or humoral, is desired. The incorporation of the antigen into a Nanodisc with a MSP of the present invention allows the preparation of stable aqueous preparations which do not have a tendency to aggregate. At least one antigenic determinant of the antigen is presented to the aqueous phase, with the more hydrophobic portions of the antigen being buried within the hydrophobic central region of the Nanodisc. The antigen incorporated within the Nanodisc can be a protein, such as a cell membrane protein or a viral envelope protein, or it can be a lipopolysaccharide or a lipooligosaccharide.

The antigen can be derived from a virus, especially an enveloped virus, a bacterium including, but not limited to, a bacterium, fungus, protozoan, parasite, or it can be derived from a particular type of tumor or cancer. The antigen-containing Nanodisc preparation can be administered in prophylactic or therapeutic treatment regimens to generate an immune response, and administration of these Nanodiscs can be carried out in combination with other vaccine preparations for priming and/or boosting.

Cancers (neoplastic conditions) from which cells can be obtained for use as an antigen source in the methods of the present invention include carcinomas, sarcomas, leukemias and cancers derived from cells of the nervous system. These include, but are not limited to bone cancers (osteosarcoma), brain cancers, pancreatic cancers, lung cancers such as small and large cell adenocarcinomas, rhabdosarcoma, mesiothelioma, squamous cell carcinoma, basal cell carcinoma, malignant melanoma, other skin cancers, bronchoalveolar carcinoma, colon cancers, other gastrointestinal cancers, renal cancers, liver cancers, breast cancers, cancers of the uterus, ovaries or cervix, prostate cancers, lymphomas, myelomas, bladder cancers, cancers of the reticuloendothelial system (RES) such as B or T cell lymphomas, melanoma, and soft tissue cancers.

The terms "neoplastic cell", "tumor cell", or "cancer cell", used either in the singular or plural form, refer to cells that have undergone a malignant transformation that makes them harmful to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound, or palpation. Biochemical or immunologic findings alone may be insufficient to meet this definition.

Pathogens to which multiple antigen immunological responses are advantageous include viral, bacterial, fungal and protozoan pathogens. Viruses to which immunity is desirable include, but are not limited to, hemorrhagic fever viruses (such as Ebola virus), immune deficiency viruses (such as feline or human immunodeficiency viruses), herpesviruses, coronaviruses, adenoviruses, poxviruses, picornaviruses, orthomyxoviruses, paramyxoviruses, rubella, togaviruses, flaviviruses, bunyaviruses, reoviruses, oncogenic viruses such as retroviruses, pathogenic alphaviruses (such as Semliki forest virus or Sindbis virus), rhinoviruses, hepatitis viruses (Group B, C, etc), influenza viruses, among others. Bacterial pathogens to which immune responses are helpful include, without limitation, *staphylococci, streptococci, pneumococci, salmonellae, escherichiae, yersiniae, enterococci, clostridia, corynebacteria, hemophilus, neisseriae, bacteroides, francisella, legionella, pasteurellae, brucellae, mycobacteriae, bordetella, spirochetes, actinomycetes, chlamydiae, mycoplasmas, rickettsias*, and others. Pathogenic fungi of interest include but are not limited to *Candida, cryptococci, blastomyces, histoplasma, coccidioides, phycomycetes, trichodermas, aspergilli, pneumocystis*, and others. Protozoans to which immunity is useful include, without limitation, *toxoplasma, plasmodia, schistosomes, amoebae, giardia, babesia, leishmania*, and others. Other parasites include the roundworms, hookworms and tapeworms, filiaria and others.

A further object of the present invention is the administration of the antigen-containing immunogenic Nanodisc compositions of the present invention to a human or animal (e.g. horse, pig, cow, goat, rabbit, mouse, hamster) to generate immune responses, such as production of antibody specific to the antigen or a cellular response such that cells or tissues sharing the antigen are the subject of a cellular or cytotoxic immune response. Sera or cells collected from such humans or animals are useful in providing polyclonal sera or cells for the production of hybridomas that generate monoclonal sera, such antibody preparations being useful in research, diagnostic, and therapeutic applications.

While the generation of an immune response includes at least some level of protective immunity directed to the tumor cell (or neoplastic condition), pathogen or parasite, the clinical outcome in the patient suffering from such a neoplastic condition or infection with a parasite or a pathogen can be improved by also treating the patient with a suitable chemotherapeutic agent, as known to the art. Where the pathogen is viral, an anti-viral compound such as acyclovir can be administered concomitantly with antigen-containing Nanodisc vaccination in patients with herpes virus infection, or HAART (highly active anti-retroviral therapy) in individuals infected with HIV. Where the pathogen is a bacterial pathogen, an antibiotic to which that bacterium is susceptible is desirably administered and where the pathogen is a fungus, a suitable antifungal antibiotic is desirably administered.

Similarly, chemical agents for the control and/or eradication of parasitic infections are known and are advantageously administered to the human or animal patients using dosages and schedules well known to the art. Where the patient is suffering from a neoplastic condition, for example, a cancer, the administration of the immunogenic composition comprising the Nanodiscs carrying one or more multiplicity of cancer-associated antigens in the patient to which it has been administered is desirably accompanied by administration of antineoplastic agent(s), including, but not limited to, such chemotherapeutic agents as daunorubicin, taxol, thioureas, cancer-specific antibodies linked with therapeutic radionuclides, with the proviso that the agent(s) do not ablate the ability of the patient to generate an immune response to the administered Nanodiscs and the antigens whose expression they direct in the patient. Nucleic acids for modulating gene expression or for directing expression of a functional protein can be incorporated within Nanodiscs, especially where the nucleic acid molecules are complexed with a cationic lipids, many of which are commercially available.

Pharmaceutical formulations, such as vaccines or other immunogenic compositions, of the present invention comprise an immunogenic amount of the antigen-bearing Nanodiscs in combination with a pharmaceutically acceptable carrier. An "immunogenic amount" is an amount of the antigen-bearing Nanodiscs which is sufficient to evoke an immune response in the subject to which the pharmaceutical formulation is administered. An amount of from about $10^3$ to about $10^{11}$ particles per dose, preferably $10^5$ to $10^9$, is believed suitable, depending upon the age and species of the subject being treated. Depending on the setting for administration (i.e., disease treatment or prevention), the dose (and repetition of administration) can be chosen to be therapeutically effective or prophylactically effective.

Exemplary pharmaceutically acceptable carriers include, but are not limited to, sterile pyrogen-free water and sterile pyrogen-free physiological saline solution. Subjects which may be administered immunogenic amounts of the antigen-carrying Nanodiscs of the present invention include, but are not limited to, human and animal (e.g., dog, cat, horse, pig, cow, goat, rabbit, donkey, mouse, hamster, monkey) subjects. Immunologically active compounds such as cytokines and/or BCG can also be added to increase the immune response to the administered immunogenic preparation.

Immunogenic compositions comprising the Nanodiscs which incorporate antigens of interest produced using the methods of the present invention may be formulated by any of the means known in the art. Such compositions, especially vaccines, are typically prepared as injectables, either as liquid solutions or suspensions. Solid forms suitable for solution in, or suspension in, liquid prior to injection may also be prepared.

The active immunogenic ingredients (the Nanodiscs) are advantageously mixed with excipients or carriers that are pharmaceutically acceptable and compatible with the active ingredient. Suitable excipients include but are not limited to sterile water, saline, dextrose, glycerol, ethanol, or the like and combinations thereof.

In addition, if desired, the immunogenic compositions, including vaccines, may contain minor amounts of auxiliary substances such as wetting or emulsifying agents, pH buffering agents, and/or adjuvants which enhance the effectiveness of the vaccine. Examples of adjuvants which may be effective include but are not limited to aluminum hydroxide; N-acetylmuramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic component of the nanoscale particles after administration. Such additional formulations and modes of administration as known in the art may also be used.

The immunogenic (or otherwise biologically active) antigen-containing Nanodisc compositions are administered in a manner compatible with the dosage formulation, and in such amount as will be prophylactically and/or therapeutically effective. The quantity to be administered, which is generally in the range of about $10^3$ to about $10^{10}$ particles, preferably $10^5$ to $10^8$, in a dose, depends on the subject to be treated, the capacity of the individual's immune system to synthesize antibodies, and the degree of protection desired. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at weekly, monthly or 1 to 4 months for a second dose, and if needed, a subsequent dose(s) after several months or years. Hydrophobic or partially hydrophobic antigens can be incorporated into Nanodiscs as described for other molecules (such as membrane proteins or small molecules). Where the antigen is in nature associated with or is within a membrane, either a solubilized pure or partially pure preparation or a solubilized membrane or membrane fragment preparation can be used as the source of the input antigen in the Nanodisc assembly mixture.

Nuclear Magnetic Resonance

A current method for the diagnosis of myocardial ischemia utilizes an NMR relaxation agent containing gadolinium (Gd). The current market leader is Magnevist (Trademark of Berlex). The Gd metal is chelated in the form of gadopentetate dimeglumine. Unfortunately, the half life of this compound is only a few minutes in humans, due to its small size and rapid clearance. Nanodiscs are believed to have a half life of several hours in human plasma.

Various organic and inorganic complexes can be incorporated into the Nanodisc bilayer by conjugation (covalent attachment) with fatty-acid like chains that then partition into the Nanodisc bilayer. We have used this technique to affix fluorescent molecules to the Nanodisc at various loadings. For a typical 10 nm diameter Nanodisc containing about 160 DPPC phospholipid molecules, up to about 40-50 such alkyl chain-anchored species can be incorporated, replacing the native phospholipids, without comprising the Nanodisc structure. This same procedure can be used to affix other organics or inorganics to the Nanodisc, wherein the Nanodisc then becomes a carrier of the compound and conveys the advantageously controlled circulation lifetime while providing small and robust size. Such compounds include sugars, imaging agents, lipophilic dyes, photoactive (photodynamic) agents, etc. Photodynamic agents include, but are not limited to, those useful for treating tumors or atherosclerotic plaques, for example, porphyrins and phthalacyanin-related molecules.

Various chelating agents can be so constructed to provide a Nanodisc with approximately 50 Gd relaxation agents in a 10 nm diameter package. This should have great benefit in providing a longer lifetime imaging agent for cardiovascular imaging. We have completed a first experiment along these lines using a commercially available chelating agent, but which provides an incomplete coordination of the Gd molecule. This compound then is prone to precipitation. It is straightforward chemistry (J. Med. Chem 42, 2852 (1999)) to affix a long alkyl chain to the Magnevist structure, for example at the methylene carbon position, to have the same chelating properties as Magnevist but now in a more concentrated entity with increased plasma lifetime.

Functional Equivalents

It is understood that a variant of a specifically exemplified MSP can be made with an amino acid sequence which is substantially identical (at least about 80 to 99% identical, and all integers therebetween) to the amino acid sequence to an MSP of the present invention and it forms a functionally equivalent, amphiphilic, three dimensional structure and retains the ability to form Nanodiscs with phospholipid and/or a passenger molecule such as a hydrophobic or partially hydrophobic protein, among others. It is well known in the biological arts that certain amino acid substitutions can be made in protein sequences without affecting the function of the protein.

Generally, conservative amino acid substitutions or substitutions of similar amino acids are tolerated without affecting protein function. Similar amino acids can be those that are similar in size and/or charge properties, for example, aspartate and glutamate and isoleucine and valine are both pairs of similar amino acids. Nonpolar amino acids include alanine, valine, leucine, phenylalanine, tryptophan, methionine, isoleucine, cysteine and glycine. Uncharged polar amino acids include serine, threonine, asparagine, glutamine and tyrosine. Charged polar basic amino acids include lysine, arginine and histidine. Substitutions of one for another are permitted when helix formation is not disrupted except as intended. Similarity between amino acid pairs has been assessed in the art in a number of ways. For example, Dayhoff et al. (1978) in Atlas of Protein Sequence and Structure, Volume 5, Supplement 3, Chapter 22, pages 345-352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

Substitution mutation, insertional, and deletional variants of the disclosed nucleotide (and amino acid) sequences can be readily prepared by methods which are well known to the art. These variants can be used in the same manner as the exemplified MSP sequences so long as the variants have substantial sequence identity with a specifically exemplified sequence of the present invention. As used herein, substantial sequence identity refers to homology (or identity) which is sufficient to enable the variant polynucleotide or protein to function in the same capacity as the polynucleotide or protein from which the variant is derived. Preferably, this sequence identity is greater than 70% or 80%, more preferably, this identity is greater than 85%, or this identity is greater than 90%, and or alternatively, this is greater than 95%, and all integers between 70 and 100%. It is well within the skill of a person trained in this art to make substitution mutation, insertional, and deletional mutations which are equivalent in function or are designed to improve the function of the sequence or otherwise provide a methodological advantage. No variants which may read on any naturally occurring proteins or which read on a prior art variant are intended to be within the scope of the present invention as claimed.

It is well known in the art that the polynucleotide sequences of the present invention can be truncated and/or mutated such that certain of the resulting fragments and/or mutants of the original full-length sequence can retain the desired characteristics of the full-length sequence. A wide variety of restriction enzymes which are suitable for generating fragments from larger nucleic acid molecules are well known. In addition, it is well known that Ba/31 exonuclease can be conveniently used for time-controlled limited digestion of DNA. See, for example, Maniatis (1982) *Molecular Cloning: A Laboratory Manual*, Cold Spring Harbor Laboratory, New York, pages 135-139, incorporated herein by reference. See also Wei et al. (1983 *J. Biol. Chem.* 258:13006-13512. By use of Ba/31 exonuclease (commonly referred to as "erase-a-base" procedures), the ordinarily skilled artisan can remove nucleotides from either or both ends of the subject nucleic acids to generate a wide spectrum of fragments which are functionally equivalent to the subject nucleotide sequences. One of ordinary skill in the art can, in this manner, generate hundreds of fragments of controlled, varying lengths from locations all along the original MSP-encoding sequence. The ordinarily skilled artisan can routinely test or screen the generated fragments for their characteristics and determine the utility of the fragments as taught herein. It is also well known that the mutant sequences of the full length sequence, or fragments thereof, can be easily produced with site directed mutagenesis. See, for example, Larionov, O. A. and Nikiforov, V. G. (1982) *Genetika* 18(3):349-59; Shortle, D, DiMaio, D., and Nathans, D. (1981) *Annu. Rev. Genet.* 15:265-94; both incorporated herein by reference. The skilled artisan can routinely produce deletion-, insertion-, or substitution-type mutations and identify those resulting mutants which contain the desired characteristics of the full length wild-type sequence, or fragments thereof, i.e., those which retain GlcNAc T-Vb activity.

DNA sequences having at least 70, 80, 85, 90 or 95% or greater identity to the recited DNA coding sequence of Tables 1, 3, 4 or 5 (SEQ ID NOs:1, 3, 7 or 9) and functioning to encode a GlcNAc T-Vb protein are within the scope of the present invention. Functional equivalents are included in the definition of a GlcNAc T-Vb encoding sequence. Following the teachings herein and using knowledge and techniques well known in the art, the skilled worker will be able to make a large number of operative embodiments having equivalent DNA sequences to those listed herein without the expense of undue experimentation.

As used herein percent sequence identity of two nucleic acids is determined using the algorithm of Altschul et al. (1997) *Nucl. Acids Res.* 25: 3389-3402; see also Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See the National Center for Biotechnology Information on the internet.

Antibody Technology

Monoclonal or polyclonal antibodies, preferably monoclonal, specifically reacting with an MSP of the present invention (or to another protein of interest) can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1993) *Current Protocols in Molecular Biology*, Wiley Interscience, New York, N.Y.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecuiar Biology*, Greene/Wiley, New York, N.Y. Abbreviations and nomenclature, where employed, are deemed standard in the field and commonly used in professional journals such as those cited herein.

All references cited in the present application are incorporated by reference herein to the extent that there is no inconsistency with the present disclosure.

The description provided herein is not intended to limit the scope of the invention as claimed herein. Any variations in the exemplified articles and methods which occur to the skilled artisan are intended to fall within the scope of the present invention.

EXAMPLES

Example 1

Construction of Recombinant DNA Molecules for Expression of MSPs

The human proapo A-I coding sequence as given below was inserted between Ncol and Hindlul sites (underlined) in pET-28 (Novagen, Madison, Wis.). Start and stop codons are in bold type. The restriction endonuclease recognition sites used in cloning are underlined.

TABLE 1

ProApo A-I coding sequence (SEQ ID NO:1) Restriction sites used in cloning are underlined, and the translation start and stop signals are shown in bold.

<u>CCATGG</u>CCCATTTCTGGCAGCAAGATGAACCCCCCCAGAGCCCCTGGGATCGA
GTGAAGGACCTGGCCACTGTGTACGTGGATGTGCTCAAAGACAGCGGCAGAG
ACTATGTGTCCCAGTTTGAAGGCTCCGCCTTGGGAAAACAGCTAAACCTAAAGC
TCCTTGACAACTGGGACAGCGTGACCTCCACCTTCAGCAAGCTGCGCGAACAG
CTCGGCCCTGTGACCCAGGAGTTCTGGGATAACCTGGAAAAGGAGACAGAGG
GCCTGAGGCAAGAGATGAGCAAGGATCTGGAGGAGGTGAAGGCCAAGGTGCA
GCCCTACCTGGACGACTTCCAGAAGAAGTGGCAGGAGGAGATGGAGCTCTAC
CGCCAGAAGGTGGAGCCGCTGCGCGCAGAGCTCCAAGAGGGCGCGCGCCAG
AAGCTGCACGAGCTGCAAGAGAAGCTGAGCCCACTGGGCGAGGAGATGCGCG
ACCGCGCGCGCCCATGTGGACGCGCTGCGCACGCATCTGGCCCCCTACAG
CGACGAGCTGCGCCAGCGCTTGGCCGCGCGCCTTGAGGCTCTCAAGGAGAAC
GGCGGCGCCAGACTGGCCGAGTACCACGCCAAGGCCACCGAGCATCTGAGCA
CGCTCAGCGAGAAGGCCAAGCCCGCGCTCGAGGACCTCCGCCAAGGCCTGCT
GCCCGTGCTGGAGAGCTTCAAGGTCAGCTTCCTGAGCGCTCTCGAGGAGTACA
CTAAGAAGCTCAACACCCAGTAA<u>AAGCTT</u>-3'

TABLE 2

ProApo A-I amino acid sequence (SEQ ID NO:2)

MAHFWQQDEPPQSPWDRVKDLATVYVDVLKDSGRDYVSQFEGSALGKQLNLKLL
DNWDSVTSTFSKLREQLGPVTQEFWDNLEKETEGLRQEMSKDLEEVKAKVQPYL
DDFQKKWQEEMELYRQKVEPLRAELQEGARQKLHELQEKLSPLGEEMRDRARAH
VDALRTHLAPYSDELRQRLAARLEALKENGGARLAEYHAKATEHLSTLSEKAKPAL
EDLRQGLLPVLESFKVSFLSALEEYTKKLNTQ

The construction of the MSP1 coding sequence was accomplished as follows. Primers were designed to produce DNA encoding MSP1, the truncated protein lacking the N-terminal domain of proApo A-I, by polymerase chain reaction (PCR) mutagenesis (Higuchi et al., 1988).
Primer 1 (SEQ ID NO:3)
(5'-TATACCATGGGCCATCATCATCATCATCAT-CATATAGAAGGAA GACTAAAGCTCCTTGA-CAACT-3') introduces an N-terminal 6-histidine tag for purification and manipulation of MSP1, and a factor Xa cleavage site for removal of the histidine tag. Factor Xa cleaves after R in the protein sequence IEGR.

Primer 2 (SEQ ID NO:4) (5'-GCAAGCTTATTACTGGGT-GTTGAGCTTCTT-3') was used as a reverse primer.

TABLE 3

Histidine-tagged MSP1 coding sequence (SEQ ID NO:5). Restriction sites used in cloning are underlined, and the translation start and stop signals are shown in bold.

TATA<u>CCATGG</u>GCCATCATCATCATCATCATATAGAAGGAAGACTAAAGCTCCTT
GACAACTGGGACAGCGTGACCTCCACCTTCAGCAAGCTGCGCGAACAGCTCG
GCCCTGTGACCCAGGAGTTCTGGGATAACCTGGAAAAGGAGACAGAGGGCCT
GAGGCAGGAGATGAGCAAGGATCTGGAGGAGGTGAAGGCCAAGGTGCAGCCC
TACCTGGACGACTTCCAGAAGAAGTGGCAGGAGGAGATGGAGCTCTACCGCCA
GAAGGTGGAGCCGCTGCGCGCAGAGCTCCAAGAGGGCGCGCGCCAGAAGCT
GCACGAGCTGCAAGAGAAGTTGAGCCCACTGGGCGAGGAGATGCGCGACCGC
GCGCGCGCCCATGTGGACGCGCTGCGCACGCATCTGGCCCCCTACAGCGACG
AGCTGCGCCAGCGCTTGGCCGCGCGCCTTGAGGCTCTCAAGGAGAACGGCGG
CGCCAGACTGGCCGAGTACCACGCCAAGGCCACCGAGCATCTGAGCACGCTC
AGCGAGAAGGCCAAACCCGCGCTCGAGGACCTCCGCCAAGGCCTGCTGCCCG
TGCTGGAGAGCTTCAAGGTCAGCTTCCTGAGCGCTCTCGAGGAGTACACTAAG
AAGCTCAACACCCAGTAA<u>AAGCTT</u>GC

TABLE 4

Histidine-tagged MSP1 amino acid sequence (SEQ ID NO:6)

```
MGHHHHHHIEGRLKLLDNWDSVTSTFSKLREQLGPVTQEFWDNLEKETEGLRQE
MSKDLEEVKAKVQPYLDDFQKKWQEEMELYRQKVEPLRAELQEGARQKLHELQE
KLSPLGEEMRDRARAHVDALRTHLAPYSDELRQRLAARLEALKENGGARLAEYHA
KATEHLSTLSEKAKPALEDLRQGLLPVLESFKVSFLSALEEYTKKLNTQ
```

For production of MSP1 without a N-terminal histidine tag, primer 1 was replaced with primer 1a: 5'-TACCATG-GCAAAGCTCCTTGACAACTG-3' (SEQ ID NO:7) to produce the sequence provided in SEQ ID NO:8.

TABLE 5

Non-Histidine-tagged MSP1 DNA sequence (SEQ ID NO:8). Restriction sites used in cloning are underlined, and the translation start and stop signals are shown in bold.

```
TACCATGGCAAAGCTCCTTGACAACTGGGACAGCGTGACCTCCACCTTCAGCA
AGCTGCGCGAACAGCTCGGCCCTGTGACCCAGGAGTTCTGGGATAACCTGGA
AAAGGAGACAGAGGGCCTGAGGCAGGAGATGAGCAAGGATCTGGAGGAGGTG
AAGGCCAAGGTGCAGCCCTACCTGGACGACTTCCAGAAGAAGTGGCAGGAGG
AGATGGAGCTCTACCGCCAGAAGGTGGAGCCGCTGCGCGCAGAGCTCCAAGA
GGGCGCGCGCCAGAAGCTGCACGAGCTGCAAGAGAAGTTGAGCCCACTGGGC
GAGGAGATGCGCGACCGCGCGCGCGCCCATGTGGACGCGCTGCGCACGCAT
CTGGCCCCCTACAGCGACGAGCTGCGCCAGCGCTTGGCCGCGCGCCTTGAGG
CTCTCAAGGAGAACGGCGGCGCCAGACTGGCCGAGTACCACGCCAAGGCCAC
CGAGCATCTGAGCACGCTCAGCGAGAAGGCCAAACCCGCGCTCGAGGACCTC
CGCCAAGGCCTGCTGCCCGTGCTGGAGAGCTTCAAGGTCAGCTTCCTGAGCG
CTCTCGAGGAGTACACTAAGAAGCTCAACACCCAGTAATAAGCTTGC
```

TABLE 6

Non-Histidine-tagged MSP1 amino acid sequence (SEQ ID NO:9).

```
MAKLLDNWDSVTSTFSKLREQLGPVTQEFWDNLEKETEGLRQEMSKDLEEVKAK
VQPYLDDFQKKWQEEMELYRQKVEPLRAELQEGARQKLHELQEKLSPLGEEMRD
RARAHVDALRTHLAPYSDELRQRLAARLEALKENGGARLAEYHAKATEHLSTLSEK
AKPALEDLRQGLLPVLESFKVSFLSALEEYTKKLNTQ
```

Figure 6A:
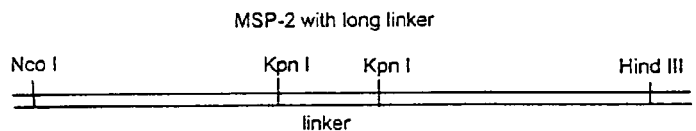
FIGS. 6A-6B show diagrams of the tandem repeat MSP2 with a long linker (FIG. 6A) and with a short linker sequence (FIG. 6B).
Figure 6B:
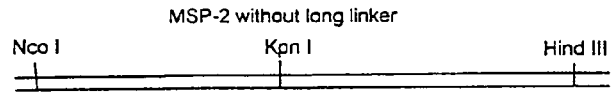

The production of an MSP with tandem repeats (MSP2) was carried at as described below. The following primers were used to generate MSP2 (see FIGS. 6A-6B):

```
Primer 3 (SEQ ID NO:10):
5'-TACCATGGCAAAGCTCCTTGACAACTG-3' primer3a (SEQ ID NO:11):
5'-TATACCATGGGCCATCATCATCATCATCATATAGAAGGA
AGACTAAAGCTCCTTGACAACT-3'

Primer 4 (SEQ ID NO:12):
5'-TAAGAAGCTCAACACCCAGGGTACCGGTGGAGGTAGTGGAGGTGGTACCCTA-3'

Primer 5 (SEQ ID NO:13):
5'-CAGGGTACCGGTGGAGGTAGTGGAGGTGGTACCCTAAAGCTCCTTGACAA-3'

Primer 6 (SEQ ID NO:14):
5'-GCAAGCTTATTACTGGGTGTTGAGCTTCTT-3'
```

In a first PCR, primer 2 (or primer 2a for N-terminal histidine tag) and primer 4 were used to add a linker sequence (encoding the amino acid sequence GTGGGSGGGT; SEQ ID NO:15) to the 3' end of the MSP gene to produce MSP-A. In a second PCR, the linker was added to the 5' end of the MSP constructs, one with and one without the linker. The Kpn I site gene to produce MSP-B. Treatment of MSP-A and MSP-B with KpnI and subsequent ligation produced the following provides an easy way to inserting any desired linker sequence by restriction with Kpn I and religation with double-stranded synthetic DNA encoding desired linker. See FIGS. 6A-6B.

TABLE 7

MSP2 (with histidine tag, without long linker) DNA sequence (SEQ ID NO:16). The translation start and stop codons are in bold type, and the restriction endonuclease recognition sites used in cloning are underlined.

TATA<u>CCATGG</u>GCCATCATCATCATCATCATATAGAAGGAAGACTAAAGCTCCTTGA
CAACTGGGACAGCGTGACCTCCACCTTCAGCAAGCTGCGCGAACAGCTCGGCCCT
GTGACCCAGGAGTTCTGGGATAACCTGGAAAAGGAGACAGAGGGCCTGAGGCAG
GAGATGAGCAAGGATCTGGAGGAGGTGAAGGCCAAGGTGCAGCCCTACCTGGAC
GACTTCCAGAAGAAGTGGCAGGAGGAGATGGAGCTCTACCGCCAGAAGGTGGAG
CCGCTGCGCGCAGAGCTCCAAGAGGGCGCGCGCCAGAAGCTGCACGAGCTGCAA
GAGAAGCTGAGCCCACTGGGCGAGGAGATGCGCGACCGCGCGCGCGCCCATGT
GGACGCGCTGCGCACGCATCTGGCCCCCTACAGCGACGAGCTGCGCCAGCGCTT
GGCCGCGCGCCTTGAGGCTCTCAAGGAGAACGGCGGCGCCAGACTGGCCGAGTA
CCACGCCAAGGCCACCGAGCATCTGAGCACGCTCAGCGAGAAGGCCAAGCCCGC
GCTCGAGGACCTCCGCCAAGGCCTGCTGCCCGTGCTGGAGAGCTTCAAGGTCAG
CTTCCTGAGCGCTCTCGAGGAGTACACTAAGAAGCTCAACACCCAGGGTACCCTA
AAGCTCCTTGACAACTGGGACAGCGTGACCTCCACCTTCAGCAAGCTGCGCGAAC
AGCTCGGCCCTGTGACCCAGGAGTTCTGGGATAACCTGGAAAAGGAGACAGAGG
GCCTGAGGCAGGAGATGAGCAAGGATCTGGAGGAGGTGAAGGCCAAGGTGCAGC
CCTACCTGGACGACTTCCAGAAGAAGTGGCAGGAGGAGATGGAGCTCTACCGCCA
GAAGGTGGAGCCGCTGCGCGCAGAGCTCCAAGAGGGCGCGCGCCAGAAGCTGC
ACGAGCTGCAAGAGAAGCTGAGCCCACTGGGCGAGGAGATGCGCGACCGCGCGC
GCGCCCATGTGGACGCGCTGCGCACGCATCTGGCCCCCTACAGCGACGAGCTGC
GCCAGCGCTTGGCCGCGCGCCTTGAGGCTCTCAAGGAGAACGGCGGCGCCAGAC
TGGCCGAGTACCACGCCAAGGCCACCGAGCATCTGAGCACGCTCAGCGAGAAGG
CCAAGCCCGCGCTCGAGGACCTCCGCCAAGGCCTGCTGCCCGTGCTGGAGAGCT
TCAAGGTCAGCTTCCTGAGCGCTCTCGAGGAGTACACTAAGAAGCTCAACACCCA
GTAA<u>AAGCTT</u>GC

TABLE 8

MSP2 (with histidine tag, without long linker) amino acid sequence (SEQ ID NO:17)

MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPALEDLRQGLLPVLESFKVSFLSALEEYTKKLNTQGTLKLLDNWDSVTSTFS
KLREQLGPVTQEFWDNLEKETEGLRQEMSKDLEEVKAKVQPYLDDFQKKWQEEMEL
YRQKVEPLRAELQEGARQKLHELQEKLSPLGEEMRDRARAHVDALRTHLAPYSDELR
QRLAARLEALKENGGARLAEYHAKATEHLSTLSEKAKPALEDLRQGLLPVLESFKVSFL
SALEEYTKKLNTQ

TABLE 9

MSP2L (with histidine tag, with long linker) DNA sequence (SEQ ID NO:18). Translation start and stop codons are in bold type; restriction endonuclease sites used in cloning are underlined.

TA<u>CCATGG</u>GCCATCATCATCATCATCATATAGAAGGAAGACTAAAGCTCCTTGACA
ACTGGGACAGCGTGACCTCCACCTTCAGCAAGCTGCGCGAACAGCTCGGCCCTGT
GACCCAGGAGTTCTGGGATAACCTGGAAAAGGAGACAGAGGGCCTGAGGCAGGA
GATGAGCAAGGATCTGGAGGAGGTGAAGGCCAAGGTGCAGCCCTACCTGGACGA
CTTCCAGAAGAAGTGGCAGGAGGAGATGGAGCTCTACCGCCAGAAGGTGGAGCC
GCTGCGCGCAGAGCTCCAAGAGGGCGCGCGCCAGAAGCTGCACGAGCTGCAAGA
GAAGCTGAGCCCACTGGGCGAGGAGATGCGCGACCGCGCGCGCGCCCATGTGG
ACGCGCTGCGCACGCATCTGGCCCCCTACAGCGACGAGCTGCGCCAGCGCTTGG
CCGCGCGCCTTGAGGCTCTCAAGGAGAACGGCGGCGCCAGACTGGCCGAGTACC
ACGCCAAGGCCACCGAGCATCTGAGCACGCTCAGCGAGAAGGCCAAGCCCGCGC
TCGAGGACCTCCGCCAAGGCCTGCTGCCCGTGCTGGAGAGCTTCAAGGTCAGCTT
CCTGAGCGCTCTCGAGGAGTACACTAAGAAGCTCAACACCCAGGGTACCGGTGGA
GGTAGTGGAGGTGGTACCCTAAAGCTCCTTGACAACTGGGACAGCGTGACCTCCA
CCTTCAGCAAGCTGCGCGAACAGCTCGGCCCTGTGACCCAGGAGTTCTGGGATAA
CCTGGAAAAGGAGACAGAGGGCCTGAGGCAGGAGATGAGCAAGGATCTGGAGGA
GGTGAAGGCCAAGGTGCAGCCCTACCTGGACGACTTCCAGAAGAAGTGGCAGGA
GGAGATGGAGCTCTACCGCCAGAAGGTGGAGCCGCTGCGCGCAGAGCTCCAAGA
GGGCGCGCGCCAGAAGCTGCACGAGCTGCAAGAGAAGCTGAGCCCACTGGGCGA
GGAGATGCGCGACCGCGCGCGCGCCCATGTGGACGCGCTGCGCACGCATCTGG
CCCCCTACAGCGACGAGCTGCGCCAGCGCTTGGCCGCGCGCCTTGAGGCTCTCA

TABLE 9-continued

MSP2L(with histidine tag, with long linker) DNA sequence (SEQ ID NO:18). Translation start and stop codons are in bold type; restriction endonuclease sites used in cloning are underlined.

AGGAGAACGGCGGCGCCAGACTGGCCGAGTACCACGCCAAGGCCACCGAGCATC
TGAGCACGCTCAGCGAGAAGGCCAAGCCCGCGCTCGAGGACCTCCGCCAAGGCC
TGCTGCCCGTGCTGGAGAGCTTCAAGGTCAGCTTCCTGAGCGCTCTCGAGGAGTA
CACTAAGAAGCTCAACACCCAGTAATAAGCTTGC

TABLE 10

MSP2 (with histidine tag, with long linker, in bold type) amino acid sequence (SEQ ID NO:19).

MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPALEDLRQGLLPVLESFKVSFLSALEEYTKKLNTQGTGGGSGGGTLKLLDN
WDSVTSTFSKLREQLGPVTQEFWDNLEKETEGLRQEMSKDLEEVKAKVQPYLDDFQ
KKWQEEMELYRQKVEPLRAELQEGARQKLHELQEKLSPLGEEMRDRARAHVDALRT
HLAPYSDELRQRLAARLEALKENGGARLAEYHAKATEHLSTLSEKAKPALEDLRQGLL
PVLESFKVSFLSALEEYTKKLNTQ

To delete hinge regions, deletion of helices 4 and 5 was carried out by constructing the C-terminal portion of MSP1 using the following PCR primers and the Sac I and Hind III fragment of the MSP1 coding sequence as template.

Primer A (SEQ ID NO:20):
5'-TGGAGCTCTACCGCCAGAAGGTGGAGCCCTACAGCGACGAGCT-3'

Primer B (SEQ ID NO:21):
5'-GCAAGCTTATTACTGGGTGTTGAGCTTCTT-3'.

This amplification product was digested with SacI and HindIII and ligated into pLitmus 28 for sequencing. The Sac I+HindIII treated histidine-tagged MSP1 construct in pET 28 vector was then ligated with the above fragment to produce MSP1Da.

TABLE 11

MSP1D5D6 DNA sequence (SEQ ID NO:22). Translations start and stop codons are in bold type; restriction endonuclease recognition sites are underlined.

TATA<u>CCATGG</u>GCCATCATCATCATCATCATATAGAAGGAAGACTAAAGCTCCTTGA
CAACTGGGACAGCGTGACCTCCACCTTCAGCAAGCTGCGCGAACAGCTCGGCCCT
GTGACCCAGGAGTTCTGGGATAACCTGGAAAAGGAGACAGAGGGCCTGAGGCAG
GAGATGAGCAAGGATCTGGAGGAGGTGAAGGCCAAGGTGCAGCCCTACCTGGAC
GACTTCCAGAAGAAGTGGCAGGAGGAGATGGAGCTctaccgccagaaggtggagcCCTAC
AGCGACGAGCTGCGCCAGCGCTTGGCCGCGCCTTGAGGCTCTCAAGGAGAAC
GGCGGCGCCAGACTGGCCGAGTACCACGCCAAGGCCACCGAGCATCTGAGCACG
CTCAGCGAGAAGGCCAAACCCGCGCTCGAGGACCTCCGCCAAGGCCTGCTGCCC
GTGCTGGAGAGCTTCAAGGTCAGCTTCCTGAGCGCTCTCGAGGAGTACACTAAGA
AGCTCAACACCCAGTAA<u>AAGCTT</u>GC

TABLE 12

MSP1D5D6 amino acid sequence (SEQ ID NO:23).

MGHHHHHHIEGRLKLLDNWDSVTSTFSKLREQLGPVTQEFWDNLEKETEGLRQEMS
KDLEEVKAKVQPYLDDFQKKWQEEMELYRQKVEPYSDELRQRLAARLEALKENGGAR
LAEYHAKATEHLSTLSEKAKPALEDLRQGLLPVLESFKVSFLSALEEYTKKLNTQ

Deletion of helices 5 and 6 was performed in a similar manner, but two separate PCR steps using the following primers were employed in a first reaction (Reaction 1,

```
Primer C: 5'-CAGAATTCGCTAGCCGAGTACCACGCCAA-3', SEQ ID NO:24; and

Primer D: 5'-GCAAGCTTATTACTGGGTGTTGAGCTTCTT-3', SEQ ID NO:25) and a
second reaction (Reaction 2, Primer E: 5'-ATACCATGGGCCATCATCATCATCATCATA-3', SEQ ID
NO:26; and Primer F: 5'-CAGAATTCGCTAGCCTGGCGCTCAACTTCTCTT-3', SEQ ID
NO:27.
```

The PCR products encode the N- and C-terminal portions of an MSP both lacking helices 5 and 6 and each contain a NheI restriction site. After digestion of the PCR products with NheI, NcoI and HindIII, the fragments was ligated into NcoI+ HindIII treated pET 28 to produce the DNA sequence of MSP1D6D7 See FIGS. 9A-9B.

TABLE 13

MSP1D6D7 DNA sequence (SEQ ID NO:28). Translation start and stop codons are shown in bold type, and restriction endonuclease recognition sites used in cloning are underlined.

TATA<u>CCATGG</u>GCCATCATCATCATCATCATATAGAAGGAAGACTAAAGCTCCTTGA
CAACTGGGACAGCGTGACCTCCACCTTCAGCAAGCTGCGCGAACAGCTCGGCCCT
GTGACCCAGGAGTTCTGGGATAACCTGGAAAAGGAGACAGAGGGCCTGAGGCAG
GAGATGAGCAAGGATCTGGAGGAGGTGAAGGCCAAGGTGCAGCCCTACCTGGAC
GACTTCCAGAAGAAGTGGCAGGAGGAGATGGAGCTCTACCGCCAGAAGGTGGAG
CCGCTGCGCGCAGAGCTCCAAGAGGGCGCGCGCCAGAAGCTGCACGAGCTGCAA
GAGAAGTTGAGCGCCAGGCTAGCCGAGTACCACGCCAAGGCCACCGAGCATCTG
AGCACGCTCAGCGAGAAGGCCAAACCCGCGCTCGAGGACCTCCGCCAAGGCCTG
CTGCCCGTGCTGGAGAGCTTCAAGGTCAGCTTCCTGAGCGCTCTCGAGGAGTACA
CTAAGAAGCTCAACACCCAGTAA<u>TAAGCTT</u>GC

TABLE 14

MSP1D6D7 amino acid sequence (SEQ ID NO:29).

MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSAR
LAEYHAKATEHLSTLSEKAKPALEDLRQGLLPVLESFKVSFLSALEEYTKKLNTQ

Example 2

Construction of Synthetic MSP Gene

A synthetic gene for MSP1 is made using the following overlapping synthetic oligonucleotides which are filled in using PCR. The codon usage has been optimized for expression in *E. coli*, and restriction sites have been introduced for further genetic manipulations of the gene.

```
Synthetic nucleotide taps1a (SEQ ID NO:30)
TACCATGGGTCATCATCATCATCATCACATTGAGGGACGTCTGAAGCTGTTGGACA
ATTGGGACTCTGTTACGTCTA Synthetic nucleotide taps2a (SEQ ID NO:31)
AGGAATTCTGGGACAACCTGGAAAAAGAAACCGAGGGACTGCGTCAGGAAATGTC
CAAAGAT Synthetic nucleotide taps3a (SEQ ID NO:32)
TATCTAGATGACTTTCAGAAAAAATGGCAGGAAGAGATGGAATTATATCGTCAA
```

-continued

Synthetic nucleotide taps4a (SEQ ID NO:33)
ATGAGCTCCAAGAGAAGCTCAGCCCATTAGGCGAAGAAATGCGCGATCGCGCCCG
TGCACATGTTGATGCACT Synthetic nucleotide taps5a (SEQ ID NO:34)
GTCTCGAGGCGCTGAAAGAAAACGGGGGTGCCCGCTTGGCTGAGTACCACGCGA
AAGCGACAGAA Synthetic nucleotide taps6a (SEQ ID NO:35)
GAAGATCTACGCCAGGGCTTATTGCCTGTTCTTGAGAGCTTTAAAGTCAGTTTTCT Synthetic nucleotide taps1b (SEQ ID NO:36)
CAGAATTCCTGCGTCACGGGGCCCAGTTGTTCGCGAAGTTTACTGAAGGTAGACG
TAACAG Synthetic nucleotide taps2b (SEQ ID NO:37)
TCATCTAGATATGGCTGAACCTTGGCCTTCACCTCTTCTAAATCTTTGGACATTT Synthetic nucleotide taps3b (SEQ ID NO:38)
TGGAGCTCATGGAGTTTTTGGCGTGCCCCCTCTTGCAGTTCCGCACGCAGCGGTT
CCACCTTTTGACGATATAATTCCAT Synthetic nucleotide taps4b (SEQ ID NO:39)
GCCTCGAGACGTGCGGCCAAACGCTGGCGAAGTTCATCCGAATACGGCGCCAAAT
GAGTCCGGAGTGCATCAACAT Synthetic nucleotide taps5b (SEQ ID NO:40)
GTAGATCTTCCAGCGCCGGTTTCGCTTTTTCGCTCAAGGTGCTCAGGTGTTCTGTC
GCTTT Synthetic nucleotide taps6b (SEQ ID NQ:41)
CCAAGCTTATTACTGGGTATTCAGCTTTTTAGTATATTCTTCCAGAGCTGACAGAAA
ACTGACTTT

TABLE 15

Full synthetic gene sequence for MSP1 (SEQ ID NO:42).
Restriction sites used in cloning are underlined, and
the translation start and stop signals are shown in bold.

ACCATGGGTCATCATCATCATCATCACATTGAGGGACGTCTGAAGCTGTTGGACAA
TTGGGACTCTGTTACGTCTACCTTCAGTAAACTTCGCGAACAACTGGGCCCCGTGA
CGCAGGAATTCTGGGACAACCTGGAAAAAGAAACCGAGGGACTGCGTCAGGAAAT
GTCCAAAGATTTAGAAGAGGTGAAGGCCAAGGTTCAGCCATATCTAGATGACTTTC
AGAAAAAATGGCAGGAAGAGATGGAATTATATCGTCAAAAGGTGGAACCGCTGCG
TGCCGGAACTGCAAGAGGGGGCACGCCAAAAACTCCATGAGCTCCAAGAGAAGCTC
AGCCCATTAGGCGAAGAAATGCGCGATCGCGCCCGTGCACATGTTGATGCACTCC
GGACTCATTTGGCGCCGTATTCGGATGAACTTCGCCAGCGTTTGGCCGCACGTCT
CGAGGCGCTGAAAGAAAACGGGGGTGCCCGCTTGGCTGAGTACCACGCGAAAGC
GACAGAACACCTGAGCACCTTGAGCGAAAAAGCGAAACCGGCGCTGGAAGATCTA
CGCCAGGGCTTATTGCCTGTTCTTGAGAGCTTTAAAGTCAGTTTTCTGTCAGCTCT
GGAAGAATATACTAAAAAGCTGAATACCCAGTAAAAGCTTGG

The following is the amino acid sequence of a MSP polypeptide in which half repeats are deleted:

TABLE 16

MSP1D3 (SEQ ID NO:43).

MGHHHHHHIEGRLKLLDNWDSVTSTFSKLREQLGPVTQEFWDNLEKETEGLRQEMS
PYLDDFQKKWQEEMELYRQKVEPLRAELQEGARQKLHELQEKLSPLGEEMRDRARA
HVDALRTHLAPYSDELRQRLAARLEALKENGGARLAEYHAKATEHLSTLSEKAKPALE
DLRQGLLPVLESFKVSFLSALEEYTKKLNTQ

TABLE 17

MSP1D9 (SEQ ID NO:44).

MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPVLESFKVSFLSALEEYTKKLNTQ

TABLE 18

MSP tandem repeat with first half-repeats deleted (MSP2delta1) (SEQ ID NO:45)

MGHHHHHHIEGRLKLLDNWDSVTSTFSKLREQLGPVTQEFWDNLEKETEGLRQEMS
PYLDDFQKKWQEEMELYRQKVEPLRAELQEGARQKLHELQEKLSPLGEEMRDRARA
HVDALRTHLAPYSDELRQRLAARLEALKENGGARLAEYHAKATEHLSTLSEKAKPALE
DLRQGLLPVLESFKVSFLSALEEYTKKLNTQGTLKLLDNWDSVTSTFSKLREQLGPVT
QEFWDNLEKETEGLRQEMSPYLDDFQKKWQEEMELYRQKVEPLRAELQEGARQKLH
ELQEKLSPLGEEMRDRARAHVDALRTHLAPYSDELRQRLAARLEALKENGGARLAEY
HAKATEHLSTLSEKAKPALEDLRQGLLPVLESFKVSFLSALEEYTKKLNTQ

Plasmids for the expression of extended MSPs were constructed from plasmid for MSP1 described in Bayburt et al. (2002) *Nanoletters* 2:853-856 using a "Seamless" cloning kit (Stratagene) according to the manufacturer recommendations. An alternative N-terminus for MSP1TEV was added by PCR; the primers were designed to include Nco I and Hind III restriction sites. The PCR product was cloned into the pET28a plasmid (Novagen). Truncated mutants of MSP were produced with a Quick-change kit (Stratagene) using the MSP1TEV plasmid as a template. The presence of the desired insertions or deletions and absence of PCR-induced mutations were verified by DNA sequencing.

Expression and purification of the MSP proteins was performed as described herein. Protein purity was characterized by SDS-PAGE and Electrospray Mass Spectrometry; it was found to be greater than 95%. The TEV protease expression system was purchased (Science Reagents, Inc., Atlanta, Ga.) and used after some minor modifications. The sequences of new scaffold proteins were optimized with respect to salt link scores for the belt model of the antiparallel dimer as described in Segrest et al. (1999) *J. Biol. Chem.* 274:31755-31758. At first, the amino acid sequences of the extended mutants were generated so that each of the central helices (from H3 to H7) (see FIG. 19), was inserted sequentially at every position between other central helices, i.e. after H3, H4, H5, and H6, and the number of favorable salt links minus number of unfavorable contacts of the same charges was calculated for all possible configurations of antiparallel dimers in the resulting scaffold protein (Segrest (1999) supra). As a result, the insertion mutants shown at FIG. 20 were selected as optimal for maximum salt link scores. These extended scaffold proteins, as well as truncated scaffold proteins, also containing different tag sequences at the N. terminus, were engineered in *E. coli* and expressed with a high yield and purified by standard procedures.

With reference to the following protein and DNA sequences, the MSPs we have utilized can be summarized as the following linked structures. Note H1, H2 refer to the sequences of Helix #1 etc. His is a (His)6 tag, TEV is the tobacco viral protease, X is the Factor X (ten) protease site.

TABLE 19

Amino Acid Sequences of MSP Building Blocks

| | | |
|---|---|---|
| GLOB | DEPPQSPWDRVKDLATVYVDVLKDSGRDYVSQFEGSALGKQLN | (SEQ ID NO:89) |
| HisX | MGHHHHHHIEGR | (SEQ ID NO:47) |
| HisTEV | MGHHHHHHHDYDIPTTENLYFQG | (SEQ ID NO:48) |
| Helix 1 (H1): | LKLLDNWDSVTSTFSKLREQLG | (SEQ ID NO:49) |
| Helix 2 (H2): | PVTQEFWDNLEKETEGLRQEMS | (SEQ ID NO:50) |
| Helix 3 (H3): | KDLEEVKAKVQ | (SEQ ID NO:51) |
| Helix 4 (H4): | PYLDDFQKKWQEEMELYRQKVE | (SEQ ID NO:52) |
| Helix 5 (H5): | PLRAELQEGARQKLHELQEKLS | (SEQ ID NO:53) |
| Helix 6 (H6): | PLGEEMRDRARAHVDALRTHLA | (SEQ ID NO:54) |
| Helix 7 (H7): | PYSDELRQRLAARLEALKENGG | (SEQ ID NO:55) |
| Helix 8 (H8): | ARLAEYHAKATEHLSTLSEKAK | (SEQ ID NO:56) |
| Helix 9 (H9): | PALEDLRQGLL | (SEQ ID NO:57) |
| Helix 10 (H10): | PVLESFKVSFLSALEEYTKKLNTQ | (SEQ ID NO:58) |
| Helix 0.5 (H0.5): | STFSKLREQLG | (SEQ ID NO:59) |
| Helix 10.5 (H10.5): | SALEEYTKKLNTQ | (SEQ ID NO:87) |
| Helix 2S (H2): | PVTQEFWDNLEKETEGLRQEMS | (SEQ ID NO:136) |

TABLE 20

Sequences encoding the MSP Building Blocks of TABLE 19.

| | |
|---|---|
| HisX | ATGGGTCATCATCATCATCATCACATTGAG (SEQ ID NO:60)<br>GGACGT |
| HisTEV | ATGGGTCATCATCATCATCATCATCACGA (SEQ ID NO:61)<br>TTATGATATTCCTACTACTGAGAATTTGT<br>ATTTTCAGGGT |
| Helix 1 (H1): | CTGAAGCTGTTGGACAATTGGGACTCTGT (SEQ ID NO:62)<br>TACGTCTACCTTCAGTAAACTTCGCGAAC<br>AACTGGGC |
| Helix 2 (H2): | CCCGTGACGCAGGAATTCTGGGACAACCT (SEQ ID NO:63)<br>GGAAAAAGAAACCGAGGGACTGCGTCAGG<br>AAATGTCC |
| Helix 3 (H3): | AAAGATTTAGAAGAGGTGAAGGCCAAGGT (SEQ ID NO:64)<br>TCAG |
| Helix 4 (H4): | CCATATCTCGATGACTTTCAGAAAAAATG (SEQ ID NO:65)<br>GCAGGAAGAGATGGAATTATATCGTCAAA<br>AGGTGGAA |
| Helix 5 (H5): | CCGCTGCGTGCGGAACTGCAAGAGGGGGC (SEQ ID NO:66)<br>ACGCCAAAAACTCCATGAGCTCCAAGAGA<br>AGCTCAGC |
| Helix 6 (H6): | CCATTAGGCGAAGAAATGCGCGATCGCGCC (SEQ ID NO:67)<br>CGTGCACATGTTGATGCACTCCGGACTCA<br>TTTGGCG |
| Helix 7 (H7): | CCGTATTCGGATGAACTTCGCCAGCGTTTG (SEQ ID NO:68)<br>GCCGCACGTCTCGAGGCGCTGAAAGAAAAC<br>GGGGGT |
| Helix 8 (H8): | GCCCGCTTGGCTGAGTACCACGCGAAAGC (SEQ ID NO:69)<br>GACAGAACACCTGAGCACCTTGAGCGAAA<br>AAGCGAAA |
| Helix 9 (H9): | CCGGCGCTGGAAGATCTACGCCAGGGCTT (SEQ ID NO:70)<br>ATTG |
| Helix 10 (H10): | CCTGTTCTTGAGAGCTTTAAAGTCAGTTT (SEQ ID NO:71)<br>TCTGTCAGCTCTGGAAGAATATACTAAAA<br>AGCTGAATACCCAG |
| Helix 0.5 (H0.5): | TCTACCTTCAGTAAACTTCGCGAACAACT (SEQ ID NO:72)<br>GGGC |
| Helix 10.5 (H10.5): | CAGTTTTCTGTCAGCTCTGGAAGAATATA (SEQ ID NO:88)<br>CTAAAAAGCTGAATACCCAG |
| Helix 2S (H2S): | TCCGTGACGCAGGAATTCTGGGACAACCT (SEQ ID NO:90)<br>GGAAAAAGAAACCGAGGGACTGCGTCAGG<br>AAATGTCC |

Several particular MSP sequences useful in the present invention are the following combinations of the above sequences, as given in Table 21 and others.

TABLE 21

Engineered MSPs Useful in Nanodisc Preparation.

| | | |
|---|---|---|
| MSP1 | HisX-H1-H2-H3-H4-H5-H6-H7-H8-H9-H10 | (SEQ ID NO:6) |
| MSP1E1 | HisX-H1-H2-H3-H4-H4-H5-H6-H7-H8-H9-H10 | (SEQ ID NO:73) |
| MSP1E2 | HisX-H1-H2-H3-H4-H5-H4-H5-H6-H7-H8-H9-H10 | (SEQ ID NO:74) |

TABLE 21-continued

Engineered MSPs Useful in Nanodisc Preparation.

| | | |
|---|---|---|
| MSP1E3 | HisX-H1-H2-H3-H4-H5-H6-H4-H5-H6-H7-H8-H9-H10 | (SEQ ID NO:75) |
| MSP1TEV | HisTev-H1-H2-H3-H4-H5-H6-H7-H8-H9-H10 | (SEQ ID NO:76) |
| MSP1NH | H1-H2-H3-H4-H5-H6-H7-H8-H9-H10 | (SEQ ID NO:77) |
| MSP1T2 | HisTev-H0.5-H2-H3-H4-H5-H6-H7-H8-H9-H10 | (SEQ ID NO:78) |
| MSP1T2NH | H0.5-H2-H3-H4-H5-H6-H7-H8-H9-H10 | (SEQ ID NO:79) |
| MSP1T3 | HisTev-H2-H3-H4-H5-H6-H7-H8-H9-H10 | (SEQ ID NO:80) |
| MSP1D3 | HisX-H1-H2-H4-H5-H6-H7-H8-H9-H10 | (SEQ ID NO:43) |
| MSP1D9 | HisX-H1-H2-H3-H4-H5-H6-H7-H8-H10 | (SEQ ID NO:44) |
| MSP1D5D6 | HisX-H1-H2-H3-H4-H7-H8-H9-H10 | (SEQ ID NO:23) |
| MSP1D6D7 | HisX-H1-H2-H3-H4-H5-H8-H9-H10 | (SEQ ID NO:82) |
| MSP1D3D9 | HisX-H1-H2-H4-H5-H6-H7-H8-H10 | (SEQ ID NO:83) |
| MSP1D10.5 | HisX-H1-H2-H3-H4-H5-H6-H7-H8-H9-H10.5 | (SEQ ID NO:84) |
| MSP1D3D10.5 | HisX-H1-H2-H4-H5-H6-H7-H8-H9-H10.5 | (SEQ ID NO:85) |
| MSP1T4 | HisTEV-H2S-H3-H4-H5-H6-H7-H8-H9-H10 | (SEQ ID NO:91) |
| Apo A-I | GLOB-H1-H2-H3-H4-H4-H5-H6-H5-H6-H7-H8-H9-H10 | |
| MSP1T5 | HisTev-H2.5-H3-H4-H5-H6-H7-H8-H9-H10 | (SEQ ID NO:92) |
| MSP1T6 | HisTev-H3-H4-H5-H6-H7-H8-H9-H10 | (SEQ ID NO:93) |
| MSP1E3TEV: | HisTev-H1-H2-H3-H4-H5-H6-H4-H5-H6-H7-H8-H9-H10 | (SEQ ID NO:94) |
| MSP1E3D1: | HisTev-H0.5-H2-H3-H4-H5-H6-H4-H5-H6-H7-H8-H9-H10 | (SEQ ID NO:95) |
| MSP2TEV: | HisTev-H1-H2-H3-H4-H5-H6-H7-H8-H9-H10-GT-H1-H2-H3-H4-H5-H6-H7-H8-H9-H10 | (SEQ ID NO:96) |
| MSP1N1: | His-TEV-H2S-H3-H4-H4-H5-H6-H7-H8-H9 | (SEQ ID NO:97) |
| MSP2N1: | HisTev-H0.5-H2-H3-H4-H5-H6-H7-H8-H9-H10-GT-H0.5-H2-H3-H4-H5-H6-H7-H8-H9-H10 | (SEQ ID NO:98) |
| MSP2N2: | HisTev-H0.5-H2-H3-H4-H5-H6-H7-H8-H9-H10-GT-H2-H3-H4-H5-H6-H7-H8-H9-H10 | (SEQ ID NO:99) |

In addition to these sequences, there are two fusion protein (tandem repeat MSP) constructs of reference. These are composed of two MSP1 constructs linked by a Gly-Thr linker:

```
MSP2 (MSP1-Gly-Thr-MSP1, SEQ ID NO:17) and MSP2D1D1 (MSP1T3-Gly-Thr-
H2-H3-H4-H5-H6-H7-H8-H9-H10, SEQ ID NO:86).
```

Other constructs that can be readily produced include permutations of the above, i.e., MSP1 or a tandemly repeated MSP with either a short or long linker sequence with any combination of the following: hinge deletion, hinge replacement, half-repeat deletion, histidine tag, different linkers for MSP2 analogs.

The coding and amino acid sequences of MSP1T4 are given in Tables 22 and 23, respectively.

TABLE 22

DNA sequence encoding MSP1T4 (SEQ ID NO:100)

atgggtcatcatcatcatcatcac-
gattatgatattcctactactgagaatttgtattttcagggttccgtgacgcaggaattc
tgggacaacctggaaaaagaaaccgagggactgcgtcaggaaatgtccaaagatttagaagaggtgaaggccaaggt
tcagccatatctcgatgactttcagaaaaaatggcaggaagagatggaattatatcgtcaaaaggtggaaccgctgcgtg
cggaactgcaagaggggcacgccaaaaactccatgagctccaagagaagctcagcccattaggcgaagaaatgcg
cgatcgcgcccgtgcacatgttgatgcactccggactcatttggcgcgtattcggatgaacttcgccagcgtttggccgcac
gtctcgaggcgctgaaagaaaacgggggtgcccgcttggctgagtaccacgcgaaagcgacagaacacctgagcacc
ttgagcgaaaaagcgaaaccggcgctggaagatctacgccagggcttattgcctgttcttgagagctttaaagtcagttttct
gtcagctctggaagaatatactaaaaagctgaatacccag

TABLE 23

Amino acid sequence of MSP1T4 (SEQ ID NO:91)

MGHHHHHHHDYDIPTTENLYFQGSVTQEFWDNLEKETEGLRQEMSKDLEEVKAKVQ
PYLDDFQKKWQEEMELYRQKVEPLRAELQEGARQKLHELQEKLSPLGEEMRDRARA
HVDALRTHLAPYSDELRQRLAARLEALKENGGARLAEYHAKATEHLSTLSEKAKPALE
DLRQGLLPVLESFKVSFLSALEEYTKKLNTQ

In the schematic for MSP1T5, H2.5 indicates the second half of the H2 helical sequence, i.e. the last 33 nucleotides or 11 amino acids is not included in the MSP sequence. The coding and amino acid sequence for this protein is given in Tables 24 and 25, respectively.

TABLE 24

DNA sequence encoding MSP1T5 (SEQ ID NO:101)

atgggtcatcatcatcatcatcatcacgattatgatattcctactactgagaatttgtattttcagggtaaagaaaccgaggga
ctgcgtcaggaaatgtccaaagatttagaagaggtgaaggccaaggttcagccatatctcgatgactttcagaaaaaatg
gcaggaagagatggaattatatcgtcaaaaggtggaaccgctgcgtgcggaactgcaagaggggcacgccaaaaa
ctccatgagctccaagagaagctcagcccattaggcgaagaaatgcgcgatcgcgcccgtgcacatgttgatgcactcc
ggactcatttggcgccgtattcggatgaacttcgccagcgtttggccgcacgtctcgaggcgctgaaagaaaacgggggt
gcccgcttggctgagtaccacgcgaaagcgacagaacacctgagcaccttgagcgaaaaagcgaaaccggcgctgg
aagatctacgccagggcttattgcctgttcttgagagctttaaagtcagttttctgtcagctctggaagaatatactaaaaagct
gaatacccag

TABLE 25

Amino acid sequence of MSP1T5 (SEQ ID NO:92)

MGHHHHHHHDYDIPTTENLYFQGKETEGLRQEMSKDLEEVKAKVQPYLDDFQKKWQ
EEMELYRQKVEPLRAELQEGARQKLHELQEKLSPLGEEMRDRARAHVDALRTHLAPY
SDELRQRLAARLEALKENGGARLAEYHAKATEHLSTLSEKAKPALEDLRQGLLPVLESF
KVSFLSALEEYTKKLNTQ

TABLE 26

DNA sequence encoding MSP1T6 (SEQ ID NO:102)

atgggtcatcatcatcatcatcatcacgattatgatattcctactactgagaatttgtattttcagggtaaagatttagaagaggt
gaaggccaaggttcagccatatctcgatgactttcagaaaaaatggcaggaagagatggaattatatcgtcaaaaggtgg
aaccgctgcgtgcggaactgcaagaggggcacgccaaaaactccatgagctccaagagaagctcagcccattaggc
gaagaaatgcgcgatcgcgcccgtgcacatgttgatgcactccggactcatttggcgccgtattcggatgaacttcgccag

TABLE 26-continued

DNA sequence encoding MSP1T6 (SEQ ID NO:102)

cgtttggccgcacgtctcgaggcgctgaaagaaaacgggggtgcccgcttggctgagtaccacgcgaaagcgacagaa
cacctgagcaccttgagcgaaaaagcgaaaccggcgctggaagatctacgccagggcttattgcctgttcttgagagcttt
aaagtcagtttttctgtcagctctggaagaatatactaaaaagctgaatacccag

TABLE 27

Amino acid sequence of MSP1T6 (SEQ ID NO:93)

MGHHHHHHHDYDIPTTENLYFQGKDLEEVKAKVQPYLDDFQKKWQEEMELYRQKVE
PLRAELQEGARQKLHELQEKLSPLGEEMRDRARAHVDALRTHLAPYSDELRQRLAAR
LEALKENGGARLAEYHAKATEHLSTLSEKAKPALEDLRQGLLPVLESFKVSFLSALEEY
TKKLNTQ

MSP1T5 and MSP1T6 discs preps are not homogeneous under all assembly conditions. The results are highly dependent on the particular assembly conditions.

In the following MSP construct (MSP1N1), H10 is not included, and two H4 motifs are inserted. The coding and amino acid sequences are given in Tables 28 and 29, respectively. This MSP is designed to increase the number of possible salt bridges on the interhelical interface.

TABLE 28

DNA sequence encoding MSP1N1 (SEQ ID NO:103)

atgggtcatcatcatcatcatcatcacgattatgatattcctactactgagaatttgtattttcagggttccgtgacgcaggaattc
tgggacaacctggaaaaagaaaccgagggactgcgtcaggaaatgtccaaagatttagaagaggtgaaggccaaggt
tcagccatatctcgatgactttcagaaaaaatggcaggaagagatggaattatatcgtcaaaaggtggaaccatatctcga
tgactttcagaaaaaatggcaggaagagatggaattatatcgtcaaaaggtggaaccgctgcgtgcggaactgcaagag
ggggcacgccaaaaactccatgagctccaagagaagctcagcccattaggcgaagaaatgcgcgatcgcgcccgtgc
acatgttgatgcactccggactcatttggcgccgtattcggatgaacttcgccagcgtttggccgcacgtctcgaggcgctga
aagaaaacgggggtgcccgcttggctgagtaccacgcgaaagcgacagaacacctgagcaccttgagcgaaaaagc
gaaaccggcgctggaagatctacgccagggcttattg

TABLE 29

Amino acid sequence of MSP1N1 (SEQ ID NO:97)

MGHHHHHHHDYDIPTTENLYFQGSVTQEFWDNLEKETEGLRQEMSKDLEEVKAKVQ
PYLDDFQKKWQEEMELYRQKVEPYLDDFQKKWQEEMELYRQKVEPLRAELQEGARQ
KLHELQEKLSPLGEEMRDRARAHVDALRTHLAPYSDELRQRLAARLEALKENGGARLA
EYHAKATEHLSTLSEKAKPALEDLRQGLL

The following "extended" MSPs incorporate a cleavable His-tag and use a TEV protease recognition site.

TABLE 30

DNA sequence encoding MSP1E3TEV (HisTev-H1-H2-H3-H4-H5-H6-H4-H5-H6-H7-H8-H9-H10) (SEQ ID NO:105)

atgggtcatcatcatcatcatcatcacgattatgatattcctactactgagaatttgtattttcagggtctgaagctgttggacaat
tgggactctgttacgtctaccttcagtaaacttcgcgaacaactgggccccgtgacgcaggaattctgggacaacctggaa
aaagaaaccgagggactgcgtcaggaaatgtccaaagatttagaagaggtgaaggccaaggttcagccatatctcgat
gactttcagaaaaaatggcaggaagagatggaattatatcgtcaaaaggtggaaccgctgcgtgcggaactgcaagag
ggggcacgccaaaaactccatgagctccaagagaagctcagcccattaggcgaagaaatgcgcgatcgcgcccgtgc
acatgttgatgcactccggactcatttggcgccatatctcgatgactttcagaaaaaatggcaggaagagatggaattatat
cgtcaaaaggtggaaccgctgcgtgcggaactgcaagagggggcacgccaaaaactccatgagctccaagagaagc
tcagcccattaggcgaagaaatgcgcgatcgcgcccgtgcacatgttgatgcactccggactcatttggcgccgtattcgg
atgaacttcgccagcgtttggccgcacgtctcgaggcgctgaaagaaaacgggggtgcccgcttggctgagtaccacgc
gaaagcgacagaacacctgagcaccttgagcgaaaaagcgaaaccggcgctggaagatctacgccagggcttattgc
ctgttcttgagagctttaaagtcagtttttctgtcagctctggaagaatatactaaaaagctgaatacccag

TABLE 31

Amino acid sequence of MSP1E3TEV (SEQ ID NO:94)

MGHHHHHHHDYDIPTTENLYFQGLKLLDNWDSVTSTFSKLREQLGPVTQEFWDNLEK
ETEGLRQEMSKDLEEVKAKVQPYLDDFQKKWQEEMELYRQKVEPLRAELQEGARQK
LHELQEKLSPLGEEMRDRARAHVDALRTHLAPYLDDFQKKWQEEMELYRQKVEPLRA
ELQEGARQKLHELQEKLSPLGEEMRDRARAHVDALRTHLAPYSDELRQRLAARLEAL
KENGGARLAEYHAKATEHLSTLSEKAKPALEDLRQGLLPVLESFKVSFLSALEEYTKKL
NTQ

TABLE 32

DNA sequence encoding MSP1E3D1 (SEQ ID NO:106)
(HisTev-H0.5-H2-H3-H4-H5-H6-H4-H5-H6-H7-H8-H9-H10)

atgggtcatcatcatcatcatcatcacgattatgatattcctactactgagaatttgtattttcagggttctaccttcagtaaacttc
gcgaacaactgggccccgtgacgcaggaattctgggacaacctggaaaaagaaaccgagggactgcgtcaggaaat
gtccaaagatttagaagaggtgaaggccaaggttcagccatatctcgatgactttcagaaaaaatggcaggaagagatg
gaattatatcgtcaaaaggtggaaccgctgcgtgcggaactgcaagaggggggcacgccaaaaactccatgagctccaa
gagaagctcagcccattaggcgaagaaatgcgcgatcgcgcccgtgcacatgttgatgcactccggactcatttggcgcc
atatctcgatgactttcagaaaaaatggcaggaagagatggaattatatcgtcaaaaggtggaaccgctgcgtgcggaac
tgcaagaggggcacgccaaaaactccatgagctccaagagaagctcagcccattaggcgaagaaatgcgcgatcg
cgcccgtgcacatgttgatgcactccggactcatttggcgccgtattcggatgaacttcgccagcgtttggccgcacgtctcg
aggcgctgaaagaaaacgggggtgcccgcttggctgagtaccacgcgaaagcgacagaacacctgagcaccttgagc
gaaaaagcgaaaccggcgctggaagatctacgccagggcttattgcctgttcttgagagctttaaagtcagttttctgtcagc
tctggaagaatatactaaaaagctgaatacccag

TABLE 33

Amino acid sequence of MSP1E3D1 (SEQ ID NO:95)

MGHHHHHHHDYDIPTTENLYFQGSTFSKLREQLGPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYLDDFQKKWQEEMELYRQKVEPLRAELQEGARQKLH
ELQEKLSPLGEEMRDRARAHVDALRTHLAPYSDELRQRLAARLEALKENGGARLAEY
HAKATEHLSTLSEKAKPALEDLRQGLLPVLESFKVSFLSALEEYTKKLNTQ

A protein corresponding to, MSP2 with a N-terminal TEV cleavable His-tag has been designed. The coding and amino acid sequences are given in Tables 34 and 35, respectively.

TABLE 34

DNA sequence encoding MSP2TEV (HisTev-H1-H2-H3-H4-H5-H6-H7-H8-H9-H10-GT-H1-H2-
H3-H4-H5-H6-H7-H8-H9-H10) (SEQ ID NO:107)

atgggtcatcatcatcatcatcatcacgattatgatattcctactactgagaatttgtattttcagggtctaaagctccttgacaac
tgggacagcgtgacctccaccttcagcaagctgcgcgaacagctcggccctgtgacccaggagttctgggataacctgg
aaaaggagacagagggcctgaggcaggagatgagcaaggatctggaggaggtgaaggccaaggtgcagccctacc
tggacgacttccagaagaagtggcaggaggagatggagctctaccgccagaaggtggagccgctgcgcgcagagctc
caagagggcgcgcgccagaagctgcacgagctgcaagagaagctgagcccactgggcgaggagatgcgcgaccgc
gcgcgcgcccatgtggacgcgctgcgcacgcatctggccccctacagcgacgagctgcgccagcgcttggccgcgcgc
cttgaggctctcaaggagaacggcggcgccagactggccgagtaccacgccaaggccaccgagcatctgagcacgct
cagcgagaaggccaagcccgcgctcgaggacctccgccaaggcctgctgcccgtgctggagagcttcaaggtcagctt
cctgagcgctctcgaggagtacactaagaagctcaacacccagggtaccctaaagctccttgacaactgggacagcgtg
acctccaccttcagcaagctgcgcgaacagctcggccctgtgacccaggagttctgggataacctggaaaaggagaca
gagggcctgaggcaggagatgagcaaggatctggaggaggtgaaggccaaggtgcagccctacctggacgacttcca
gaagaagtggcaggaggagatggagctctaccgccagaaggtggagccgctgcgcgcagagctccaagagggcgc
gcgccagaagctgcacgagctgcaagagaagctgagcccactgggcgaggagatgcgcgaccgcgcgcgcgcccat
gtggacgcgctgcgcacgcatctggccccctacagcgacgagctgcgccagcgcttggccgcgccttgaggctctca
aggagaacggcggcgccagactggccgagtaccacgccaaggccaccgagcatctgagcacgctcagcgagaagg
ccaagcccgcgctcgaggacctccgccaaggcctgctgcccgtgctggagagcttcaaggtcagcttcctgagcgctctc
gaggagtacactaagaagctcaacacccag

TABLE 35

Amino acid sequence of HisTEV-MSP2 (SEQ ID NO:96)

MGHHHHHHHDYDIPTTENLYFQGLKLLDNWDSVTSTFSKLREQLGPVTQEFWDNLEKETEGL
RQEMSKDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLSTLSEKA
KPALEDLRQGLLPVLESFKVSFLSALEYTKKLNTQGTLKLLDNWDSVTSTFSKLREQLGPVTQE
FWDNLEKETEGLRQEMKDLEEVKAKVQPYLDDFQKKWQEEMELYRQKVEPLRAELQEGARQ
KLHELQEKLSPLGEEMRDRARAHVDALRTHLAPYSDELRQRLAARLEALKENGGARLAEYHAK
ATEHLSTLSEKAKPALEDLRQGLLPVLESFKVSFLSALEEYTKKLNTQ

New constructs have been designed to produce a which make a "linear dimer" to generate Nanodiscs with only a single polypeptide sequence. These are fusions that make use of our knowledge of the parts of the MSP1 sequences which are important and are thus are "MSP2 derivatives". All have the TEV protease-cleavage His-tag.

TABLE 36

DNA sequence encoding MSP2N1 (HisTev-H0.5-H2-H3-H4-H5-H6-H7-H8-H9-H10-GT-H1/2-H2-H3-H4-H5-H6-H7-H8-H9-H10) (SEQ ID NO:108)

atgggtcatcatcatcatcatcatcacgattatgatattcctactactgagaatttgtattttcagggttctaccttcagtaaacttc
gcgaacaactgggccccgtgacgcaggaattctgggacaacctggaaaaagaaaccgagggactgcgtcaggaaat
gtccaaagatttagaagaggtgaaggccaaggttcagccatatctcgatgactttcagaaaaaatggcaggaagagatg
gaattatatcgtcaaaaggtggaaccgctgcgtgcggaactgcaagaggggcacgccaaaaactccatgagctccaa
gagaagctcagcccattaggcgaagaaatgcgcgatcgcgcccgtgcacatgttgatgcactccggactcatttggcgcc
gtattcggatgaacttcgccagcgtttggccgcacgtctcgaggcgctgaaagaaaacggggtgcccgcttggctgagt
accacgcgaaagcgacagaacacctgagcaccttgagcgaaaaagcgaaaccggcgctggaagatctacgccagg
gcttattgcctgttcttgagagctttaaagtcagttttctgtcagctctggaagaatatactaaaaagctgaatacccagggtac
cttcagtaaacttcgcgaacaactgggccccgtgacgcaggaattctgggacaacctggaaaaagaaaccgagggact
gcgtcaggaaatgtccaaagatttagaagaggtgaaggccaaggttcagccatatctcgatgactttcagaaaaaatggc
aggaagagatggaattatatcgtcaaaaggtggaaccgctgcgtgcggaactgcaagaggggcacgccaaaaactc
catgagctccaagagaagctcagcccattaggcgaagaaatgcgcgatcgcgcccgtgcacatgttgatgcactccgga
ctcatttggcgccgtattcggatgaacttcgccagcgtttggccgcacgtctcgaggcgctgaaagaaaacggggtgccc
gcttggctgagtaccacgcgaaagcgacagaacacctgagcaccttgagcgaaaaagcgaaaccggcgctggaaga
tctacgccagggcttattgcctgttcttgagagctttaaagtcagttttctgtcagctctggaagaatatactaaaaagctgaat
acccag

TABLE 37

Amino acid sequence of MSP2N1 (SEQ ID NO:98)

MGHHHHHHHDYDIPTTENLYFQGSTFSKLREQLGPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYSDELRQRLAARLEALKENGGARLAEYHAKATEHLSTL
SEKAKPALEDLRQGLLPVLESFKVSFLSALEEYTKKLNTQGTFSKLREQLGPVTQEFW
DNLEKETEGLRQEMSKDLEEVKAKVQPYLDDFQKKWQEEMELYRQKVEPLRAELQE
GARQKLHELQEKLSPLGEEMRDRARAHVDALRTHLAPYSDELRQRLAARLEALKENG
GARLAEYHAKATEHLSTLSEKAKPALEDLRQGLLPVLESFKVSFLSALEEYTKKLNTQ

TABLE 38

DNA sequence encoding MSP2N2 (SEQ ID NO:109) (HisTev-H0.5-H2-H3-H4-H5-H6-H7-H8-H9-H10-GT-H2-H3-H4-H5-H6-H7-H8-H9-H10)

atgggtcatcatcatcatcatcatcacgattatgatattcctactactgagaatttgtattttcagggttctaccttcagtaaacttc
gcgaacaactgggccccgtgacgcaggaattctgggacaacctggaaaaagaaaccgagggactgcgtcaggaaat
gtccaaagatttagaagaggtgaaggccaaggttcagccatatctcgatgactttcagaaaaaatggcaggaagagatg
gaattatatcgtcaaaaggtggaaccgctgcgtgcggaactgcaagaggggcacgccaaaaactccatgagctccaa
gagaagctcagcccattaggcgaagaaatgcgcgatcgcgcccgtgcacatgttgatgcactccggactcatttggcgcc
gtattcggatgaacttcgccagcgtttggccgcacgtctcgaggcgctgaaagaaaacggggtgcccgcttggctgagt
accacgcgaaagcgacagaacacctgagcaccttgagcgaaaaagcgaaaccggcgctggaagatctacgccagg
gcttattgcctgttcttgagagctttaaagtcagttttctgtcagctctggaagaatatactaaaaagctgaatacccagggtac
ccccgtgacgcaggaattctgggacaacctggaaaaagaaaccgagggactgcgtcaggaaatgtccaaagatttaga
agaggtgaaggccaaggttcagccatatctcgatgactttcagaaaaaatggcaggaagagatggaattatatcgtcaa
aaggtggaaccgctgcgtgcggaactgcaagaggggcacgccaaaaactccatgagctccaagagaagctcagcc
cattaggcgaagaaatgcgcgatcgcgcccgtgcacatgttgatgcactccggactcatttggcgccgtattcggatgaact TABLE 38-continued DNA sequence encoding MSP2N2 (SEQ ID NO:109) (HisTev-H0.5-H2-H3-H4-H5-H6-H7-H8-
H9-H10-GT-H2-H3-H4-H5-H6-H7-H8-H9-H10)

tcgccagcgtttggccgcacgtctcgaggcgctgaaagaaaacgggggtgcccgcttggctgagtaccacgcgaaagc
gacagaacacctgagcaccttgagcgaaaaagcgaaaccggcgctggaagatctacgccagggcttattgcctgttctt
gagagctttaaagtcagttttctgtcagctctggaagaatatactaaaaagctgaatacccag

TABLE 39

Amino acid sequence of MSP2N2 (SEQ ID NO:99)

MGHHHHHHHDYDIPTTENLYFQGSTFSKLREQLGPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYSDELRQRLAARLEALKENGGARLAEYHAKATEHLSTL
SEKAKPALEDLRQGLLPVLESFKVSFLSALEEYTKKLNTQGTPVTQEFWDNLEKETEG
LRQEMSKDLEEVKAKVQPYLDDFQKKWQEEMELYRQKVEPLRAELQEGARQKLHEL
QEKLSPLGEEMRDRARAHVDALRTHLAPYSDELRQRLAARLEALKENGGARLAEYHA
KATEHLSTLSEKAKPALEDLRQGLLPVLESFKVSFLSALEEYTKKLNTQ

A further MSP2 derivative (MSP2N3 has been designed to include helices 2-10 following the linker part of the H1 helix sequence. The DNA coding and amino acid sequences are given in Tables 40 and 41, respectively.

TABLE 40

DNA sequence encoding MSP2N3 (HisTev-H0.5-H2-H3-H4-H5-H6-H7-H8-H9-H10-GTREQLG-
H2-H3-H4-H5-H6-H7-H8-H9-H10) (SEQ ID NO:110)

Atgggtcatcatcatcatcatcatcacgattatgatattcctactactgagaatttgtattttcagggttctaccttcagtaaacttc
gcgaacaactgggcccgtgacgcaggaattctgggacaacctggaaaaagaaaccgagggactgcgtcaggaaat
gtccaaagatttagaagaggtgaaggccaaggttcagccatatctcgatgactttcagaaaaaatggcaggaagagatg
gaattatatcgtcaaaaggtggaaccgctgcgtgcggaactgcaagaggggggcacgccaaaaactccatgagctccaa
gagaagctcagcccattaggcgaagaaatgcgcgatcgcgcccgtgcacatgttgatgcactccggactcatttggcgcc
gtattcggatgaacttcgccagcgtttggccgcacgtctcgaggcgctgaaagaaaacgggggtgcccgcttggctgagt
accacgcgaaagcgacagaacacctgagcaccttgagcgaaaaagcgaaaccggcgctggaagatctacgccagg
gcttattgcctgttcttgagagctttaaagtcagttttctgtcagctctggaagaatatactaaaaagctgaatacccagggtac
ccgcgaacaactgggcccgtgacgcaggaattctgggacaacctggaaaaagaaaccgagggactgcgtcaggaa
atgtccaaagatttagaagaggtgaaggccaaggttcagccatatctcgatgactttcagaaaaaatggcaggaagaga
tggaattatatcgtcaaaaggtggaaccgctgcgtgcggaactgcaagaggggggcacgccaaaaactccatgagctcc
aagagaagctcagcccattaggcgaagaaatgcgcgatcgcgcccgtgcacatgttgatgcactccggactcatttggcg
ccgtattcggatgaacttcgccagcgtttggccgcacgtctcgaggcgctgaaagaaaacgggggtgcccgcttggctga
gtaccacgcgaaagcgacagaacacctgagcaccttgagcgaaaaagcgaaaccggcgctggaagatctacgccag
ggcttattgcctgttcttgagagctttaaagtcagttttctgtcagctctggaagaatatactaaaaagctgaatacccagtaag
ctt

TABLE 41

Amino acid sequence of MSP2N3 (SEQ ID NO:111)

MGHHHHHHHDYDIPTTENLYFQGSTFSKLREQLGPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYSDELRQRLAARLEALKENGGARLAEYHAKATEHLSTL
SEKAKPALEDLRQGLLPVLESFKVSFLSALEEYTKKLNTQGTREQLGPVTQEFWDNLE
KETEGLRQEMSKDLEEVKAKVQPYLDDFQKKWQEEMELYRQKVEPLRAELQEGARQ
KLHELQEKLSPLGEEMRDRARAHVDALRTHLAPYSDELRQRLAARLEALKENGGARLA
EYHAKATEHLSTLSEKAKPALEDLRQGLLPVLESFKVSFLSALEEYTKKLNTQ

Unlike MSP2 and MSP2TEV these proteins self-assemble with lipids at 300:1 to 400:1 molar ratios with preferable formation of significantly bigger particles (Stokes diameter approximately 15.5 nm, corresponding to a calculated diameter assuming discoidal shape of about 17 nm).

New dimer sequences (i.e., tandem repeat MSP) have been designed with the fusion region to be composed of two different linkers which have high propensity to form beta-turns (Creighton, Proteins, p. 226). These scaffold proteins are specifically designed to promote the anti-parallel helix-turn-helix structure in Nanodiscs. The constituent scaffold proteins include MSP1T3, as well as the specially designed new scaffold proteins as described herein, MSP1N1 and the circularly permuted MSP2N5 which has a modified sequence of amphipathic helices to optimize the salt bridges formed between two scaffold proteins in the antiparallel helix-turn-helix structure.

The general scheme for a tandem repeat MSP is MSP—Linker—MSP, where linker may be either the Linker 1 or Linker 2 sequence defined below and MSP may be any of the monomeric membrane scaffold proteins previously defined. Linker 1 (Lb1) is composed of 4 amino acids, preferably the sequence Asn-Pro-Gly-Thr (SEQ ID NO:104). Linker 2 (Lb2) is composed of 6 amino acids with one additional residue on both ends to provide more flexibility, preferably the sequence Ser-Asn-Pro-Gly-Thr-Gln (SEQ ID NO:136).

TABLE 42

DNA sequence encoding MSP2N4 (His-TEV-H2S-H3-H4-H5-H6-H7-H8-H9-H10-NPGT-H2-H3-H4-H5-H6-H7-H8-H9-H10) (SEQ ID NO:112)

atgggtcatcatcatcatcatcatcacgattatgatattcctactactgagaatttgtattttcagggttccgtgac
gcaggaattctgggacaacctggaaaaagaaaccgagggactgcgtcaggaaatgtccaaagatttagaagagg
tgaaggccaaggttcagccatatctcgatgactttcagaaaaaatggcaggaagagatggaattatatcgtcaaaag
gtggaaccgctgcgtgcggaactgcaagagggggcacgccaaaaactccatgagctccaagagaagctcagcc
cattaggcgaagaaatgcgcgatcgcgcccgtgcacatgttgatgcactccggactcatttggcgccgtattcggatg
aacttcgccagcgtttggccgcacgtctcgaggcgctgaaagaaaacgggggtgcccgcttggctgagtaccacgc
gaaagcgacagaacacctgagcaccttgagcgaaaaagcgaaaccggcgctggaagatctacgccagggcttat
tgcctgttcttgagagctttaaagtcagttttctgtcagctctggaagaatatactaaaaagctgaatacccagaatccag
gtaccccgtgacgcaggaattctgggacaacctggaaaaagaaaccgagggactgcgtcaggaaatgtccaaa
gatttagaagaggtgaaggccaaggttcagccatatctcgatgactttcagaaaaaatggcaggaagagatggaatt
atatcgtcaaaaggtggaaccgctgcgtgcggaactgcaagagggggcacgccaaaaactccatgagctccaag
agaagctcagcccattaggcgaagaaatgcgcgatcgcgcccgtgcacatgttgatgcactccggactcatttggcg
ccgtattcggatgaacttcgccagcgtttggccgcacgtctcgaggcgctgaaagaaaacgggggtgcccgcttggct
gagtaccacgcgaaagcgacagaacacctgagcaccttgagcgaaaaagcgaaaccggcgctggaagatctac
gccagggcttattgcctgttcttgagagctttaaagtcagttttctgtcagctctggaagaatatactaaaaagctgaatac
ccag

TABLE 43

Amino acid sequence of MSP2N4 (SEQ ID NO:113)

MGHHHHHHHDYDIPTTENLYFQGSVTQEFWDNLEKETEGLRQEMSKDLEEVKAKVQ
PYLDDFQKKWQEEMELYRQKVEPLRAELQEGARQKLHELQEKLSPLGEEMRDRARA
HVDALRTHLAPYSDELRQRLAARLEALKENGGARLAEYHAKATEHLSTLSEKAKPALE
DLRQGLLPVLESFKVSFLSALEEYTKKLNTQNPGTPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYSDELRQRLAARLEALKENGGARLAEYHAKATEHLSTL
SEKAKPALEDLRQGLLPVLESFKVSFLSALEEYTKKLNTQ

TABLE 44

DNA sequence encoding MSP2N5 (His-TEV-H2S-H3-H4-H4-H5-H6-H7-H8-H9-NPGT-H3-H4-H4-H5-H6-H7-H8-H9-H2) (SEQ ID NO:114)

atgggtcatcatcatcatcatcatcacgattatgatattcctactactgagaatttgtattttcagggttccgtgacgcaggaattc
tgggacaacctggaaaaagaaaccgagggactgcgtcaggaaatgtccaaagatttagaagaggtgaaggccaaggt
tcagccatatctcgatgactttcagaaaaaatggcaggaagagatggaattatatcgtcaaaaggtggaaccatatctcga
tgactttcagaaaaaatggcaggaagagatggaattatatcgtcaaaaggtggaaccgctgcgtgcggaactgcaagag
ggggcacgccaaaaactccatgagctccaagagaagctcagcccattaggcgaagaaatgcgcgatcgcgcccgtgc
acatgttgatgcactccggactcatttggcgccgtattcggatgaacttcgccagcgtttggccgcacgtctcgaggcgctga
agaaaacgggggtgcccgcttggctgagtaccacgcgaaagcgacagaacacctgagcaccttgagcgaaaaagc
gaaaccggcgctggaagatctacgccagggcttattgaatccaggtaccaaagatttagaagaggtgaaggccaaggtt
cagccatatctcgatgactttcagaaaaaatggcaggaagagatggaattatatcgtcaaaaggtggaaccatatctcgat
gactttcagaaaaaatggcaggaagagatggaattatatcgtcaaaaggtggaaccgctgcgtgcggaactgcaagag
ggggcacgccaaaaactccatgagctccaagagaagctcagcccattaggcgaagaaatgcgcgatcgcgcccgtgc
acatgttgatgcactccggactcatttggcgccgtattcggatgaacttcgccagcgtttggccgcacgtctcgaggcgctga
agaaaacgggggtgcccgcttggctgagtaccacgcgaaagcgacagaacacctgagcaccttgagcgaaaaagc
gaaaccggcgctggaagatctacgccagggcttattgcccgtgacgcaggaattctgggacaacctggaaaaagaaac
cgagggactgcgtcaggaaatgtcc

TABLE 45

Amino acid sequence of MSP2N5 (SEQ ID NO:115)

MGHHHHHHHDYDIPTTENLYFQGSVTQEFWDNLEKETEGLRQEMSKDLEEVKAKVQ
PYLDDFQKKWQEEMELYRQKVEPLYDDFQKKWQEEMELYRQKVEPLRAELQEGARQ
KLHELQEKLSPLGEEMRDRARAHVDALRTHLAPYSDELRQRLAARLEALKENGGARLA
EYHAKATEHLSTLSEKAKPALEDLRQGLLNPGTKDLEEVKAKVQPYLDDFQKKWQEE
MELYRQKVEPLYDDFQKKWQEEMELYRQKVEPLRAELQEGARQKLHELQEKLSPLGE
EMRDRARAHVDALRTHLAPYSDELRQRLAARLEALKENGGARLAEYHAKATEHLSTLS
EKAKPALEDLRQGLLPVTQEFWDNLEKETEGLRQEMS

TABLE 46

DNA sequence encoding MSP2N6 (His-TEV-H2S-H3-H4-H4-H5-H6-H7-H8-H9-SNPGTQ-H3-H4-H4-H5-H6-H7-H8-H9-H2) (SEQ ID NO:116)

```
atgggtcatcatcatcatcatcatcacgattatgatattcctactactgagaatttgtattttcagggttccgtgacgcaggaattc
tgggacaacctggaaaagaaaccgagggactgcgtcaggaaatgtccaaagatttagaagaggtgaaggccaaggt
tcagccatatctcgatgactttcagaaaaaatggcaggaagagatggaattatatcgtcaaaaggtggaaccatatctcga
tgactttcagaaaaaatggcaggaagagatggaattatatcgtcaaaaggtggaaccgctgcgtgcggaactgcaagag
ggggcacgccaaaaactccatgagctccaagagaagctcagcccattaggcgaagaaatgcgcgatcgcgcccgtgc
acatgttgatgcactccggactcatttggcgccgtattcggatgaacttcgccagcgtttggccgcacgtctcgaggcgctga
aagaaaacgggggtgcccgcttggctgagtaccacgcgaaagcgacagaacacctgagcaccttgagcgaaaaagc
gaaaccggcgctggaagatctacgccagggcttattgtccaatccaggtacccaaaaagatttagaagaggtgaaggcc
aaggttcagccatatctcgatgactttcagaaaaaatggcaggaagagatggaattatatcgtcaaaaggtggaaccata
tctcgatgactttcagaaaaaatggcaggaagagatggaattatatcgtcaaaaggtggaaccgctgcgtgcggaactgc
aagaggggcacgccaaaaactccatgagctccaagagaagctcagcccattaggcgaagaaatgcgcgatcgcgc
ccgtgcacatgttgatgcactccggactcatttggcgccgtattcggatgaacttcgccagcgtttggccgcacgtctcgagg
cgctgaaagaaaacgggggtgcccgcttggctgagtaccacgcgaaagcgacagaacacctgagcaccttgagcgaa
aaagcgaaaccggcgctggaagatctacgccagggcttattgcccgtgacgcaggaattctgggacaacctggaaaaa
gaaaccgagggactgcgtcaggaaatgtcc
```

TABLE 47

Amino acid sequence MSP2N6 (SEQ ID NO:117)

```
MGHHHHHHHDYDIPTTENLYFQGSVTQEFWDNLEKETEGLRQEMSKDLEEVKAKVQ
PYLDDFQKKWQEEMELYRQKVEPYLDDFQKKWQEEMELYRQKVEPLRAELQEGARQ
KLHELQEKLSPLGEEMRDRARAHVDALRTHLAPYSDELRQRLAARLEALKENGGARLA
EYHAKATEHLSTLSEKAKPALEDLRQGLLSNPGTQKDLEEVKAKVQPYLDDFQKKWQ
EEMELYRQKVEPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPALEDLRQGLLPVTQEFWDNLEKETEGLRQEMS
```

Fusion constructs of membrane scaffold proteins have been constructed with other proteins and peptides. Fusions with cytochrome P450 reductase (CPR) include the following:

TABLE 48

DNA sequence encoding MSP2CPR (MSP2-linker-CPR, linker amino acid sequence is VD and CPR is the rat cytochrome P450 reductase complete sequence) (SEQ ID NO:118)

```
atgggtcatcatcatcatcatcacattgagggacgtctgaagctgttggacaattgggactctgttacgtctaccttcagtaaa
cttcgcgaacaactgggccccgtgacgcaggaattctgggacaacctggaaaaagaaaccgagggactgcgtcagga
aatgtccaaagatttagaagaggtgaaggccaaggttcagccatatctcgatgactttcagaaaaaatggcaggaagag
atggaattatatcgtcaaaaggtggaaccgctgcgtgcggaactgcaagaggggcacgccaaaaactccatgagctc
caagagaagctcagcccattaggcgaagaaatgcgcgatcgcgcccgtgcacatgttgatgcactccggactcatttggc
gccgtattcggatgaacttcgccagcgtttggccgcacgtctcgaggcgctgaaagaaaacgggggtgcccgcttggctg
agtaccacgcgaaagcgacagaacacctgagcaccttgagcgaaaaagcgaaaccggcgctggaagatctacgcca
gggcttattgcctgttcttgagagctttaaagtcagttttctgtcagctctggaagaatatactaaaaagctgaatacccaggt
accctgaagctgttggacaattgggactctgttacgtctaccttcagtaaacttcgcgaacaactgggccccgtgacgcagg
aattctgggacaacctggaaaagaaaccgagggactgcgtcaggaaatgtccaaagatttagaagaggtgaaggcc
aaggttcagccatatctcgatgactttcagaaaaaatggcaggaagagatggaattatatcgtcaaaaggtggaaccgct
gcgtgcggaactgcaagaggggcacgccaaaaactccatgagctccaagagaagctcagcccattaggcgaagaa
atgcgcgatcgcgcccgtgcacatgttgatgcactccggactcatttggcgccgtattcggatgaacttcgccagcgtttggc
cgcacgtctcgaggcgctgaaagaaaacgggggtgcccgcttggctgagtaccacgcgaaagcgacagaacacctga
gcaccttgagcgaaaaagcgaaaccggcgctggaagatctacgccagggcttattgcctgttcttgagagctttaaagtca
gttttctgtcagctctggaagaatatactaaaaagctgaatacccagtcgaccatgggagactctcacgaagacaccagtg
ccaccatgcctgaggccgtggctgaagaagtgtctctattcagcacgacggacatggttctgttttctctcatcgtgggggtcc
tgacctactggttcatcttagaaagaagaaagaagagataccggagttcagcaagatccaaacaacggcccccaccgt
caaagagagcagcttcgtggaaaagatgaagaaaacgggaaggaacattatcgtattctatggctcccagacgggaac
cgctgaggagttttgccaaccggctgtccaaggatgcccaccgctacggggatgcggggcatgtccgcagaccctgaaga
gtatgacttggccgacctgagcagcctgcctgagatcgacaagtcccctggtagtcttctgcatggccacatacggagaggg
cgaccccacggacaatgcgcaggacttctatgactggctgcaggagactgacgtggacctcactgggtcaagtttgctgt
atttggtcttgggaacaagacctatgagcacttcaatgccatgggcaagtatgtggaccagcggctggagcagcttggcgc
ccagcgcatctttgagttgggccttggtgatgatgacgggaacttggaagaggatttcatcacgtggagggagcagttctgg
ccagctgtgtgcagttctttggggtagaagccactggggaggtacgcattcgccagtatgagctcgtggtccacgaa
gacatggacgtagccaaggtgtacacgggtgagatgggccgtctgaagagctacgagaaccagaaaccccccttcgat
gctaagaatccattcctggctgctgtcaccgccaaccggaagctgaaccaaggcactgagcggcatctaatgcacctgg
agttggacatctcagactccaagatcaggtatgaatctggagatcacgtggctgtgtacccagccaatgactcagcctgg
tcaaccagattggggagatcctgggagctgacctggatgtcatcatgtctctaaacaatctcgatgaggagtcaaacaaga
agcatccgttccctgccccaccacctaccgcacggccctcacctactacctggacatcactaacccgcacgcaccaat
```

TABLE 48-continued

DNA sequence encoding MSP2CPR (MSP2-linker-CPR, linker amino acid sequence
is VD and CPR is the rat cytochrome P450 reductase complete sequence)
(SEQ ID NO:118)

```
gtgctctacgaactggcacagtacgcctcagagccctcggagcaggagcacctgcacaagatggcgtcatcctcaggcg
agggcaaggagctgtacctgagctgggtggtggaagcccggaggcacatcctagccatcctccaagactacccatcact
gcggccacccatcgaccacctgtgtgagctgctgccacgcctgcaggcccgatactactccattgcctcatcctccaaggt
ccaccccaactccgtgcacatctgtgccgtggccgtggagtacgaagcgaagtctggccgagtgaacaaggggtggc
cactagctggcttcgggccaaggaaccagcaggcgagaatggcggccgcgccctggtacccatgttcgtgcgcaaatct
cagttccgcttgcctttcaagtccaccacacctgtcatcatggtgggccccggcactgggattgcccctttcatgggcttcatc
caggaacgagcttggcttcgagagcaaggcaaggaggtgggagagacgctgctatactatggctgccggcgctcggat
gaggactatctgtaccgtgaagagctagcccgcttccacaaggacggtgcctcacgcagcttaatgtggccttttcccgg
gagcaggcccacaaggtctatgtccagcaccttctgaagagagacagggaacacctgtggaagctgatccacgagggc
ggtgcccacatctatgtgtgcggggatgctcgaaatatggccaaagatgtgcaaaacacattctatgacattgtggctgagt
tcgggcccatggagcacacccaggctgtggactatgttaagaagctgatgaccaagggccgctactcactagatgtgtgg
agc
```

TABLE 49

Amino acid sequence of MSP2CPR (SEQ ID NO:119)

```
MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPALEDLRQGLLPVLESFKVSFLSALEEYTKKLNTQGTLKLLDNWDSVTSTFS
KLREQLGPVTQEFWDNLEKETEGLRQEMSKDLEEVKAKVQPYLDDFQKKWQEEMEL
YRQKVEPLRAELQEGARQKLHELQEKLSPLGEEMRDRARAHVDALRTHLAPYSDELR
QRLAARLEALKENGGARLAEYHAKATEHLSTLSEKAKPALEDLRQGLLPVLESFKVSFL
SALEEYTKKLNTQSTMGDSHEDTSATMPEAVAEEVSLFSTTDMVLFSLIVGVLTYWFIF
RKKKEEIPEFSKIQTTAPPVKESSFVEKMKKTGRNIIVFYGSQTGTAEEFANRLSKDAH
RYGMRGMSADPEEYDLADLSSLPEIDKSLVVFCMATYGEGDPTDNAQDFYDWLQETD
VDLTGVKFAVFGLGNKTYEHFNAMGKYVDQRLEQLGAQRIFELGLGDDDGNLEEDFIT
WREQFWPAVCEFFGVEATGEESSIRQYELVVHEDMDVAKVYTGEMGRLKSYENQKP
PFDAKNPFLAAVTANRKLNQGTERHLMHLELDISDSKIRYESGDHVAVYPANDSALVN
QIGEILGADLDVIMSLNNLDEESNKKHPFPCPTTYRTALTYYLDITNPPRTNVLYELAQY
ASEPSEQEHLHKMASSSGEGKELYLSWVVEARRHILAILQDYPSLRPPIDHLCELLPRL
QARYYSIASSSKVHPNSVHICAVAVEYEAKSGRVNKGVATSWLRAKEPAGENGGRAL
VPMFVRKSQFRLPFKSTTPVIMVGPGTGIAPFMGFIQERAWLREQGKEVGETLLYYGC
RRSDEDYLYREELARFHKDGALTQLNVAFSREQAHKVYVQHLLKRDREHLWKLIHEG
GAHIYVCGDARNMAKDVQNTFYDIVAEFGPMEHTQAVDYVKKLMTKGRYSLDVWS
```

Fusions have been prepared with fluorescent proteins (FP) and MSP sequences. All constructs of the form His-TEV2-(FP)-MSP1T2 or His-TEV-MSP1T2-GT-(FP), where (FP) is the enhanced green fluorescent protein (EGFP), the enhanced yellow fluorescent protein (EYFP) or cyan fluorescent protein (CFP).

The overall N-terminal sequences are of the form: His-TEV2 (which have been modified to incorporate a BamH1 restriction site into the sequence). The modified His-TEV2 DNA sequence is atgggtcatcatcatcatcatcatcac-gattatgatattcctactactgagaatttgtattttcagggatcc (SEQ ID NO:120), and the modified His-TEV2 Protein sequence is MGHHHHHHHDYDIPTTENLYFQGS (SEQ ID NO:121).

The fluorescent proteins have the following DNA and protein sequences:

TABLE 50

DNA sequence encoding EGFP (SEQ ID NO:122)

```
gtgagcaagggcgaggagctgttcaccggggtggtgcccatcctggtcgagctggacggcgacgtaaacggccacaag
ttcagcgtgtccggcgagggcgagggcgatgccacctacggcaagctgaccctgaagttcatctgcaccaccggcaagc
tgcccgtgccctggcccaccctcgtgaccaccctgacctacggcgtgcagtgcttcagccgctaccccgaccacatgaag
cagcacgacttcttcaagtccgccatgcccgaaggctacgtccaggagcgcaccatcttcttcaaggacgacggcaacta
caagacccgcgccgaggtgaagttcgagggcgacaccctggtgaaccgcatcgagctgaagggcatcgacttcaagg
aggacggcaacatcctggggcacaagctggagtacaactacaacagccacaacgtctatatcatggccgacaagcag
aagaacggcatcaaggtgaacttcaagatccgccacaacatcgaggacggcagcgtgcagctcgccgaccactacca
gcagaacacccccatcggcgacggccccgtgctgctgcccgacaaccactacctgagcacccagtccgccctgagca
aagaccccaacgagaagcgcgatcacatggtcctgctggagttcgtgaccgccgccgggatcactctcggcatggacg
agctgtacaag
```

TABLE 51

Amino acid sequence of EGFP (SEQ ID NO:123)

VSKGEELFTGVVPILVELDGDVNGHKFSVSGEGEGDATYGKLTLKFICTTGKLPVPWP
TLVTTLTYGVQCFSRYPDHMKQHDFFKSAMPEGYVQERTIFFKDDGNYKTRAEVKFE
GDTLVNRIELKGIDFKEDGNILGHKLEYNYNSHNVYIMADKQKNGIKVNFKIRHNIEDGS
VQLADHYQQNTPIGDGPVLLPDNHYLSTQSALSKDPNEKRDHMVLLEFVTAAGITLGM
DELYK

TABLE 52

DNA sequence encoding EYFP (SEQ ID NO:124)

gtgagcaagggcgaggagctgttcaccggggtggtgcccatcctggtcgagctggacggcgacgtaaacggccacaag
ttcagcgtgtccggcgagggcgagggcgatgccacctacggcaagctgaccctgaagttcatctgcaccaccggcaagc
tgcccgtgccctggcccaccctcgtgaccaccttcggctacggcctgcagtgcttcgcccgctaccccgaccacatgaagc
agcacgacttcttcaagtccgccatgcccgaaggctacgtccaggagcgcaccatcttcttcaaggacgacggcaactac
aagacccgcgccgaggtgaagttcgagggcgacaccctggtgaaccgcatcgagctgaagggcatcgacttcaagga
ggacggcaacatcctggggcacaagctggagtacaactacaacagccacaacgtctatatcatggccgacaagcaga
agaacggcatcaaggtgaacttcaagatccgccacaacatcgaggacggcagcgtgcagctcgccgaccactaccag
cagaacacccccatcggcgacggccccgtgctgctgcccgacaaccactacctgagctaccagtccgccctgagcaaa
gaccccaacgagaagcgcgatcacatggtcctgctggagttcgtgaccgccgccgggatcactctcggcatggacgagc
tgtacaag

TABLE 53

Amino acid sequence of EYFP (SEQ ID NO:125)

VSKGEELFTGVVPILVELDGDVNGHKFSVSGEGEGDATYGKLTLKFICTTGKLPVPWP
TLVTTFGYGLQCFARYPDHMKQHDFFKSAMPEGYVQERTIFFKDDGNYKTRAEVKFE
GDTLVNRIELKGIDFKEDGNILGHKLEYNYNSHNVYIMADKQKNGIKVNFKIRHNIEDGS
VQLADHYQQNTPIGDGPVLLPDNHYLSYQSALSKDPNEKRDHMVLLEFVTAAGITLGM
DELYK

TABLE 54

DNA sequence encoding ECFP (SEQ ID NO:126)

gtgagcaagggcgaggagctgttcaccggggtggtgcccatcctggtcgagctggacggcgacgtaaacggccacaag
ttcagcgtgtccggcgagggcgagggcgatgccacctacggcaagctgaccctgaagttcatctgcaccaccggcaagc
tgcccgtgccctggcccaccctcgtgaccaccctgacctggggcgtgcagtgcttcagccgctaccccgaccacatgaag
cagcacgacttcttcaagtccgccatgcccgaaggctacgtccaggagcgcaccatcttcttcaaggacgacggcaacta
caagacccgcgccgaggtgaagttcgagggcgacaccctggtgaaccgcatcgagctgaagggcatcgacttcaagg
aggacggcaacatcctggggcacaagctggagtacaactacatcagccacaacgtctatatcaccgccgacaagcag
aagaacggcatcaaggccaacttcaagatccgccacaacatcgaggacggcagcgtgcagctcgccgaccactacca
gcagaacacccccatcggcgacggccccgtgctgctgcccgacaaccactacctgagcacccagtccgccctgagca
aagaccccaacgagaagcgcgatcacatggtcctgctggagttcgtgaccgccgccgggatcactctcggcatggacg
agctgtacaagtaa

TABLE 55

Amino acid sequence of ECFP (SEQ ID NO:127)

VSKGEELFTGVVPILVELDGDVNGHKFSVSGEGEGDATYGKLTLKFICTTGKLPVPWP
TLVTTLTWGVQCFSRYPDHMKQHDFFKSAMPEGYVQERTIFFKDDGNYKTRAEVKFE
GDTLVNRIELKGIDFKEDGNILGHKLEYNYISHNVYITADKQKNGIKANFKIRHNIEDGSV
QLADHYQQNTPIGDGPVLLPDNHYLSTQSALSKDPNEKRDHMVLLEFVTAAGITLGMD
ELYK

TABLE 56

DNA sequence encoding His-TEV-MSP1T2-GT (SEQ ID NO:128)

atgggtcatcatcatcatcatcatcacgattatgatattcctactactgagaatttgtattttcagggtctacctttcagtaaacttc
gcgaacaactgggccccgtgacgcaggaattctgggacaacctggaaaagaaaccgagggactgcgtcaggaaat
gtccaaagatttagaagaggtgaaggccaaggttcagccatatctcgatgactttcagaaaaaatggcaggaagagatg
gaattatatcgtcaaaaggtggaaccgctgcgtgcggaactgcaagaggggggcacgccaaaaactccatgagctccaa
gagaagctcagcccattaggcgaagaaatgcgcgatcgcgcccgtgcacatgttgatgcactccggactcatttggcgcc

TABLE 56-continued

DNA sequence encoding His-TEV-MSP1T2-GT (SEQ ID NO:128)

```
gtattcggatgaacttcgccagcgtttggccgcacgtctcgaggcgctgaaagaaaacgggggtgcccgcttggctgagt
accacgcgaaagcgacagaacacctgagcaccttgagcgaaaaagcgaaaccggcgctggaagatctacgccagg
gcttattgcctgttcttgagagctttaaagtcagttttctgtcagctctggaagaatatactaaaaagctgaatacccagggtac
c
```

TABLE 57

Amino acid sequence of His-TEV-MSP1T2-GT (SEQ ID NO:129)

```
MGHHHHHHHDYDIPTTENLYFQGSTFSKLREQLGPVTQEFWDNLEKETEGLRQEMSK
DLEEVKAKVQPYLDDFQKKWQEEMELYRQKVEPLRAELQEGARQKLHELQEKLSPLG
EEMRDRARAHVDALRTHLAPYSDELRQRLAARLEALKENGGARLAEYHAKATEHLSTL
SEKAKPALEDLRQGLLPVLESFKVSFLSALEEYTKKLNTQGT
```

MSP derivatives have been prepared with the incorporation of cysteine residues into the scaffold proteins by point mutation. DNA coding and amino acid sequences are given in Tables 58 and 59, respectively. In MSP1RC12' a cysteine residue is incorporated at the last residue in the Factor X recognition site. This mutant is used to prepare fluorescently labeled discs and attach to surfaces or matrices. In MSP1K90C, Lysine90 is replaced by a cysteine. See Tables 60 and 61 for coding and amino acid sequences respectively. In MSP1K152C, Lysine 152 is replaced by cysteine; see Tables 62 and 63.

TABLE 58

DNA sequence encoding MSP1RC12' (SEQ ID NO:130)

```
Atgggtcatcatcatcatcatcacattgagggatgtctgaagctgttggacaattgggactctgttacgtctaccttcagtaaa
cttcgcgaacaactgggccccgtgacgcaggaattctgggacaacctggaaaaagaaaccgagggactgcgtcagga
aatgtccaaagatttagaagaggtgaaggccaaggttcagccatatctcgatgactttcagaaaaaatggcaggaagag
atggaattatatcgtcaaaaggtggaaccgctgcgtgcggaactgcaagaggggcacgccaaaaaactccatgagctc
caagagaagctcagcccattaggcgaagaaatgcgcgatcgcgcccgtgcacatgttgatgcactccggactcatttggc
gccgtattcggatgaacttcgccagcgtttggccgcacgtctcgaggcgctgaaagaaaacgggggtgcccgcttggctg
agtaccacgcgaaagcgacagaacacctgagcaccttgagcgaaaaagcgaaaccggcgctggaagatctacgcca
gggcttattgcctgttcttgagagctttaaagtcagttttctgtcagctctggaagaatatactaaaaagctgaatacccag
```

TABLE 59

MSP1RC12' Protein Sequence (SEQ ID NO:131)

```
MGHHHHHHIEGCLKLLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHAKATEHLS
TLSEKAKPALEDLRQGLLPVLESFKVSFLSALEEYTKKLNTQ
```

TABLE 60

DNA sequence encoding MSP1K90C (SEQ ID NO:132)

```
atgggtcatcatcatcatcatcacattgagggacgtctgaagctgttggacaattgggactctgttacgtctaccttcagtaaa
cttcgcgaacaactgggccccgtgacgcaggaattctgggacaacctggaaaaagaaaccgagggactgcgtcagga
aatgtccaaagatttagaagaggtgaaggccaaggttcagccatatctcgatgactttcagaaaaaatggcaggaagag
atggaattatatcgtcaaaaggtggaaccgctgcgtgcggaactgcaagaggggcacgccaatgtctccatgagctcc
aagagaagctcagcccattaggcgaagaaatgcgcgatcgcgcccgtgcacatgttgatgcactccggactcatttggcg
ccgtattcggatgaacttcgccagcgtttggccgcacgtctcgaggcgctgaaagaaaacgggggtgcccgcttggctga
gtaccacgcgaaagcgacagaacacctgagcaccttgagcgaaaaagcgaaaccggcgctggaagatctacgccag
ggcttattgcctgttcttgagagctttaaagtcagttttctgtcagctctggaagaatatactaaaaagctgaatacccag
```

TABLE 61

MSP1K90C Protein sequence (SEQ ID NO:133)

```
MGHHHHHHIEGRLKLLLDNWDSVTSTFSKLREQLGPVTQEFWDNLEKETEGLRQEMS
KDLEEVKAKVQPYLDDFQKKWQEEMELYRQKVEPLRAELQEGARQCLHELQEKLSPL
```

TABLE 61-continued

MSP1K90C Protein sequence (SEQ ID NO:133)

GEEMRDRARAHVDALRTHLAPYSDELRQRLAARLEALKENGGARLAEYHAKATEHLS
TLSEKAKPALEDLRQGLLPVLESFKVSFLSALEEYTKKLNTQ

TABLE 62

DNA sequence encoding MSP1K152C (SEQ ID NO:134)

```
atgggtcatcatcatcatcatcacattgagggacgtctgaagctgttggacaattgggactctgttacgtctaccttcagtaaa
cttcgcgaacaactgggccccgtgacgcaggaattctgggacaacctggaaaaagaaaccgagggactgcgtcagga
aatgtccaaagatttagaagaggtgaaggccaaggttcagccatatctcgatgactttcagaaaaaatggcaggaagag
atggaattatatcgtcaaaaggtggaaccgctgcgtgcggaactgcaagaggggcacgccaaaaactccatgagctc
caagagaagctcagcccattaggcgaagaaatgcgcgatcgcgcccgtgcacatgttgatgcactccggactcatttggc
gccgtattcggatgaacttcgccagcgtttggccgcacgtctcgaggcgctgaaagaaaacgggggtgcccgcttggctg
agtaccacgcatgcgcgacagaaacacctgagcaccttgagcgaaaaagcgaaaccggcgctggaagatctacgcca
gggcttattgcctgttcttgagagctttaaagtcagttttctgtcagctctggaagaatatactaaaaagctgaatacccag
```

TABLE 63

MSP1K152C Protein sequence (SEQ ID NO:135)

MGHHHHHHIEGRLKLLDNWDSVTSTFSKLREQLGPVTQEFWDNLEKETEGLRQEMS
KDLEEVKAKVQPYLDDFQKKWQEEMELYRQKVEPLRAELQEGARQKLHELQEKLSPL
GEEMRDRARAHVDALRTHLAPYSDELRQRLAARLEALKENGGARLAEYHACATEHLS
TLSEKAKPALEDLRQGLLPVLESFKVSFLSALEEYTKKLNTQ

The mutations in MSP1K90C and in MSP1K152C are located on inter-helical interfaces. Discs were formed in the presence of DTT. The discs are more stable toward temperature-induced irreversible degradation. These are our variants of the "Milano" mutations.

In addition to these sequences, there are two fusion protein constructs of reference. These are composed of two MSP1 constructs linked by a Gly-Ser linker: MSP2 (MSP1-Gly-Thr-MSP1, SEQ ID NO:17) and MSP2D1D1 (MSP1T3-Gly-Thr-H2-H3-H4-H5-H6-H7-H8-H9-H10, SEQ ID NO:86).

Other constructs that can be readily produced include permutations of the above, i.e. MSP1 or MSP2 or MSP2a with any combination of the following: hinge deletion, hinge replacement, half-repeat deletion, histidine tag, different linkers for MSP2 analogs.

Example 3

Expression of Recombinant MSPs

To express MSP proteins, the nucleic acid constructs were inserted between the NcoI and HindIII sites in the pET28 expression vector and transformed into *E. coli* BL21 (DE3). Transformants were grown on LB plates using kanamycin for selection. Colonies were used to inoculate 5 ml starter cultures grown in LB broth containing 30 μg/ml kanamycin. For overexpression, cultures were inoculated by adding 1 volume overnight culture to 100 volumes LB broth containing 30 μg/ml kanamycin and grown in shaker flasks at 37° C. When the optical density at 600 nm reached 0.6-0.8, isopropyl-β-D-thiogalactopyranoside (IPTG) was added to a concentration of 1 mM to induce expression and cells were grown 3-4 hours longer before harvesting by centrifugation. Cell pellets were flash frozen and stored at −80° C.

Example 4

Purification of Recombinant MSPs

Purification of histidine-tagged MSPs was carried out as follows. A frozen cell pellet from 1 liter of expression culture was resuspended in 25 milliliters of 20 mM Tris HCl pH 7.5 containing 1 mM phenylmethylsulfonyl fluoride. Triton X-100 (t-octylphenoxypolyethoxyethanol) was added from a 10% (w/v) stock in distilled H2O to a final concentration of 1%. The resuspended cells were sonicated on ice at 50% duty cycle at a power setting of 5 for four cycles of 1 minute on, 5 minutes off with a Branson probe sonifier. The resulting lysate was centrifuged for 30 minutes at 30,000 rpm in a Beckman Ti 45 rotor in a ultracentrifuge. The resulting supernatant was filtered through a 0.22 μm nylon syringe filter. The salt concentration was adjusted to 0.5 M from a 4 M NaCl stock in water and applied to a 5 ml Hi-Trap nickel loaded column (Pharmacia, Piscataway, N.J.).

For His-tagged-MSP1, the column is washed with 20 ml buffer (10 mM Tris pH 8, 0.5 M NaCl) containing 1% Triton X-100, followed by 20 ml buffer+50 mM sodium cholate, and then 20 ml buffer and 20 ml 100 mM imidazole in buffer. The His-tagged polypeptide is eluted with 15 ml 0.5 M imidazole in buffer.

For His-tagged-MSP2, the column is washed with 20 ml buffer (10 mM Tris pH 8, 0.5 M NaCl) containing 1% Triton X-100; 20 ml buffer+50 mM cholate; 20 ml buffer; 20 ml 35 mM imidazole in buffer. The His-tagged polypeptide is then eluted with 15 ml 0.5 M imidazole in buffer, and the purified protein is dialyzed against 10 mM Tris pH 8, 0.15 M NaCl using a 10,000 MW cutoff cellulose dialysis membrane.

Example 5

Production of MSP-containing Nanoscale Particles

To reconstitute MSP proteins of the present invention with lipid, purified MSP was concentrated in a pressurized ultrafiltration device (Amicon) using a 10,000 MW cutoff filter to ~2-6 mg protein/ml. Concentration of protein was determined by bicinchoninic acid assay (Pierce Chemical, Rockford, Ill.) or measurement of A280 using theoretical absorption coefficient. Phospholipid (dipalmitoyl phosphatidylcholine in this case, however different phosphatidylcholines and mixtures of phosphatidylcholine and other lipids can be used) in chloroform stock solution was dried under a stream of nitrogen and placed in vacuo overnight. Phosphate analysis was performed to determine the concentration of chloroform stock solutions. The dried lipid film was resuspended in buffer 10 mM Tris HCl pH 8.0 or pH 7.5 containing 0.15 M NaCl and 50 mM sodium cholate to give a final lipid concentration of 25 mM. The suspension was vortexed and heated to 50° C. to obtain a clear solution. Phospholipid solution was added to solution of MSP (2-6 mg/ml protein) to give molar ratios for MSP1:lipid of 2:200 and for MSP2 of 1:200. The mixture was incubated overnight at 37° C. and then dialyzed against 1000 volumes of buffer without cholate with 4 changes of buffer over 2-3 days.

Example 6

Tissue Factor Incorporation

Tissue Factor (TF) is a representative membrane protein. In order to demonstrate the value of MSP technology for a tethered membrane protein, recombinant human TF was incorporated into MSP-supported Nanodiscs. The recombinant protein consists of an extracellular domain, the transmembrane anchor and a truncated cytosolic domain. The truncation increases the homogeneity of the protein by removing the C-terminal portions of the protein which are subject to proteolysis by bacterial enzymes. This modification does not affect TF activity. Additional modifications to the protein include an N-terminal trafficking peptide and an HPC4 epitope tag. The trafficking peptide directs the expressed protein to the intermembrane space of the recombinant $E.\ coli$ host cell, in which space the peptide sequence is cleaved. The HPC4 epitope allows for affinity purification with $Ca^{2+}$ dependent antibody (Rezaie et al., 1992) and does not affect TF activity.

A 25 mM lipid mixture containing 80% phosphatidyl choline and 20% phosphatidyl serine was solubilized with 50 mM cholate in 10 mM Tris Cl, 150 mM NaCl at pH 8.0. TF, MSP1 and lipid (in a ratio of 1:10:1000) were combined and incubated overnight at 37° C. The sample was then dialyzed at 37° C. (10,000 dalton molecular weight cutoff membrane) against buffer containing 10 mM Tris Cl, 150 mM NaCl at pH 8.0 (lacking cholate) for 2 hours. Dialysis was then continued at 4° C. for an additional 6 hours with buffer changes every 2 hours. The approximately 1 ml sample was then concentrated to <250 µl using a YM-10 centrifuge concentrator and injected into a Pharmacia 10/30 Superdex 200 HR gel filtration column. Samples were eluted with buffer identical to that described above (no cholate) at 0.5 ml per minute. Fractions from chromatography were run on an 8-25% gradient SDS polyacrylamide gel to determine apparent size and then checked for coagulation activity. The chromatogram showing elution of TF incorporated into an excess population of MSP1 Nanodiscs is shown in FIG. 16A-16B.

The activity of TF in several disk fractions was determined by coagulation assays with human serum. Activity was monitored in fractions 25-28 as the inverse of coagulation time. Activity was highest in fraction 25 at 40 $hr^{-1}$ and decreased through fraction 28 at 30 $hr^{-1}$. This is expected from the size chromatogram in that the leading edge of the Nanodisc peak has a larger effective mass due to the incorporation of TF in the MSP-supported bilayer. This assay thus demonstrates that TF is incorporated into Nanodiscs in an active conformation and that the membrane environment of the Nanodisc closely mimics that of the native membrane system.

Cytochrome b5 is a membrane anchored heme protein having a single membrane anchor domain that penetrates the membrane bilayer. Cytochrome b5 solubilized from its native membrane exists as large aggregates in the absence of detergent and appears as a smear rather than a discrete band on native polyacrylamide gel electrophoresis. Formation of Nanodiscs through a self-assembly process wherein cytochrome b5 is added to the preparation of MSP and phospholipid results in the incorporation of cytochrome b5 into Nanodisc structures. This is verified by the intense heme staining of the band corresponding to Nanodiscs. The data show that cytochrome b5 can be successfully solubilized using MSP technology and that disc complexes containing cytochrome b5 can be chromatographically separated and purified away from the undesired aggregated material. The optical absorption properties of the heme chromophore of the purified material demonstrate that the heme active site in a native conformation.

Nanodiscs can also be formed by mixing 20 µl of MSP1 (10 mg/ml), 6.6 µl cytochrome b5 (0.5 mM) and 50 µl egg phosphatidylcholine/sodium cholate (11.2 egg PC, 6.2 mg/ml sodium cholate), incubating overnight at 4° C., followed by dialysis to remove cholate. Purification was accomplished using a Pharmacia MonoQ FPLC anion exchange column equilibrated in 25 mM Tris Cl, pH 8.0. A linear gradient was run at 0.5 ml/min from 0-1 M NaCl in 20 min.

As an alternative to incorporating tethered membrane proteins into Nanodiscs from solubilized, purified proteins, the tethered membrane proteins can be incorporated into Nanodiscs with MSPs using membrane or membrane fragment preparations containing those tethered membrane proteins of interest.

Example 7

Embedded Membrane Protein Incorporation

Cytochrome P450 2B4 from rabbit liver microsomes, cytochrome P450 3A4 found in nature in human liver microsomes and cytochrome P450 6B1 from insect microsomes are representative of embedded membrane proteins.

Cytochrome P450 2B4 was isolated from rabbit liver microsomes after induction with phenobarbital. Formation of 2B4 Nanodiscs is as follows. Cytochrome P450 2B4 was reconstituted into disks by the detergent dialysis method. The buffer consisted of 10 mM Tris-HCl pH 8.0, 0.1 M NaCl, 10% (v/v) glycerol. The mixture of apo A-I, cholate and phospholipid (1:220:110 mole ratio) was incubated for 8 hours at 37° C. followed by addition of P450 (1:0.5, apo A-I:P450 mole ratio) and incubation overnight at room temperature. The mixture was dialyzed using a 10,000 MW cutoff slide-a-lyzer (Pierce Chemical Co., Rockford, Ill.) at room temperature for two hours followed by a change of buffer and continued dialysis at 4° C. It was found that 82% of the P450 content could be recovered under these conditions. After dialysis, the mixture was injected onto a Superdex 200 HR10/30 gel filtration column (Pharmacia, Uppsala, SE) equilibrated in reconstitution buffer at room temperature at a flow rate of 0.25 ml/minute with collection of 0.5 ml fractions. Fractions were assayed using native polyacrylamide gradient gel electrophoresis on 8-25% gradient native gels and Coomassie staining using the Phastgel system (Pharmacia, Uppsala, Sweden).

Human cytochrome P450 3A4, normally from liver microsomes, has also been cloned, expressed in *E. coli*, purified and incorporated into MSP-supported bilayer Nanodiscs. Ten nanomoles of MSP2, one micromole of lipid, five nanomoles of cytochrome P450 3A4 protein and two micromoles cholic acid were incubated together at 37° C. for 2 hours. The incubated mixture was then dialyzed in a 10K Slide-A-lyzer Dialysis Cassette (Pierce Chemical Co., Rockford, Ill.). The dialysis was carried out with 10 mM potassium phosphate (pH 7.4) 150 mM NaCl buffer. The sample was dialyzed at 37° C. for 6 hours followed by a buffer change, and dialysis continued at 4° C. with two buffer changes at 12 hour intervals. The samples were then fractionated on a Superdex 200 HR 10/30 column (Pharmacia, Uppsala, SE) equilibrated in dialysis buffer at room temperature at a flow rate of 0.5 ml/min.

Cytochrome P450 6B1 is another model embedded membrane protein; it has been isolated from *Papilio polyxenes*, the black swallowtail. These butterflies feed exclusively on plants producing furanocoumarins, plant metabolites that are phototoxic to most organisms. Cytochrome 6B1 catalyzes the detoxification of furanocoumarins.

In order to show the utility of the MSP methodology of the present invention, we demonstrated that isolated membranes containing their repertoire of membrane proteins and natural lipids could be used as a source for incorporating membrane proteins into Nanodiscs. An important illustrative embodiment is the use of the common insect cell (Sf9)-baculovirus expression system which is used widely as a heterologous expression system. Thus, we used an insect cell line co-infected such that a microsomal preparation containing overexpressed insect CYP6B1 and also overexpressed insect NADPH cytochrome P450 reductase. In these experiments we not only demonstrate that MSP Nanodiscs can be used to incorporate another cytochrome P450 system into soluble monodisperse particles but also that the source of this P450 could be simply whole membranes containing this protein.

A standard baculovirus expression system was used to obtain microsomal preparations with overexpressed insect cytochrome CYP6B1 and insect NADPH P450 reductase. Construction of the recombinant CYP6B1 baculovirus expression vector and infection of *Spodoptera frugiperda* (Sf9) was performed as previously described (Chen et al., 2002). Typically, 32 plates containing $6 \times 10^7$ baculovirus-infected cells each (MOI of 2) were collected 72 hours post-infection. Microsomal membranes were homogenized in 2 ml grinding buffer (pH 7.8) composed of 0.1 M sodium phosphate buffer (pH 7.8), 1.1 mM EDTA, 20% glycerol, 0.5 mM PMSF, 0.1 mM DTT, and 5 µg/ml (w/v) leupeptin. Membranes were frozen in liquid nitrogen and stored at −80° C.

To assemble Nanodiscs comprising CYP6B1 from the microsomal membrane preparation, the protein concentration of the membranes was determined using a BCA™ protein assay kit from Pierce (Rockford, Ill.). We assumed a 1:1 mass relationship of protein:lipid in the membranes and an average molecular weight of phospholipids of 750 grams/mole. The membranes were detergent-solubilized with 0.5 M cholic acid (neutralized) and mixed with MSP in the approximate ratio of 1:25:50 to 1:2000:1000, preferably 1:75:150 in at least some cases, for MSP:lipid:detergent. Typically, reconstitution samples include approximately 100 nmol scaffold protein, 10 µmol lipid, and 20 µmol neutralized cholic acid and were pre-incubated for 1.5 hours at 4° C. The temperature chosen is higher than the phase transition temperature for the lipids. Detergent was removed by incubating with Biobeads® SM-2 Adsorbent from BioRad Laboratories (Hercules, Calif.) (0.4 grams Biobeads per 1 ml of reconstitution mixture) for 1.5 hours at 4° C. followed by centrifugation at 11,750×g for 5 minutes. His6-tagged MSP particles were purified by incubating with 1 ml of Ni-NTA agarose from Qiagen, Inc. (Valencia, Calif.) per 7.5 mg of His6-tagged MSP for 1 hour at 4° C., followed by centrifugation at 11,750×g for 5 minutes. MSP particles bound to the Ni-NTA agarose were washed with three sequential resin volumes of 0.1 M sodium phosphate buffer (pH 7.4) containing 0.3 M NaCl, 0.15 M NaCl, and no NaCl, respectively. To maintain the integrity of the CYP6B1 protein, MSP particles were eluted with 0.1 M sodium phosphate buffer (pH 7.4) containing 0.25 M EDTA (to chelate trace metal ions) rather than the 50 mM imidazole used in previous MSP purifications.

Figure 9:
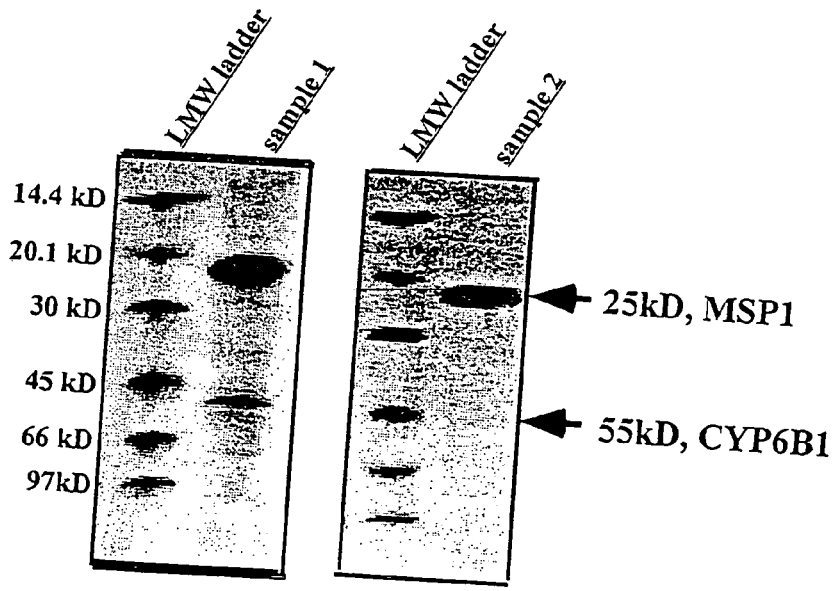
FIG. 9 illustrates the results of PAGE with sample 1 (Nanodiscs prepared with microsomal membranes from cells coexpressing cytochrome P450 6B1 and NADPH P450 reductase). Sample 2 was prepared from microsome lacking expression of CYP6B1.
Figure 10:
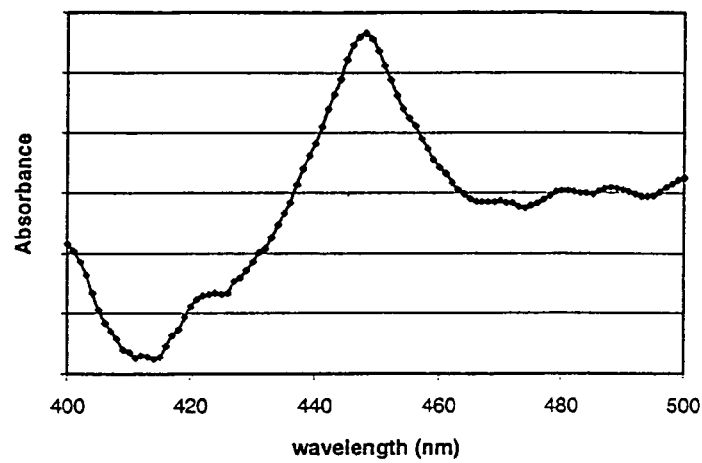
FIG. 10 provides a characteristic optical spectrum of active cytochrome P450 6B1 incorporated within Nanodiscs; the characteristic peak is at 450 nm. Such spectra indicate a correct thiolate heme ligation and no evidence for the presence of an inactive "P420" form of the cytochrome in the solubilized membrane bilayer system.
Figure 11:
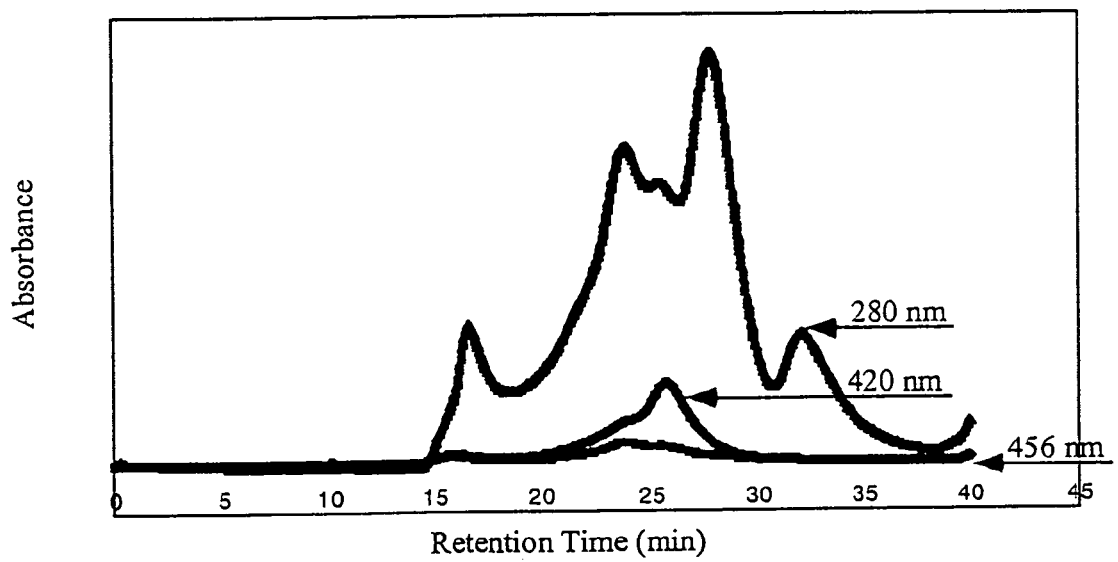
FIG. 11 depicts a chromatogram of sample separated by a Superdex sizing column. Retention times indicated rHDL particles 10 nm in size.
Figure 12:
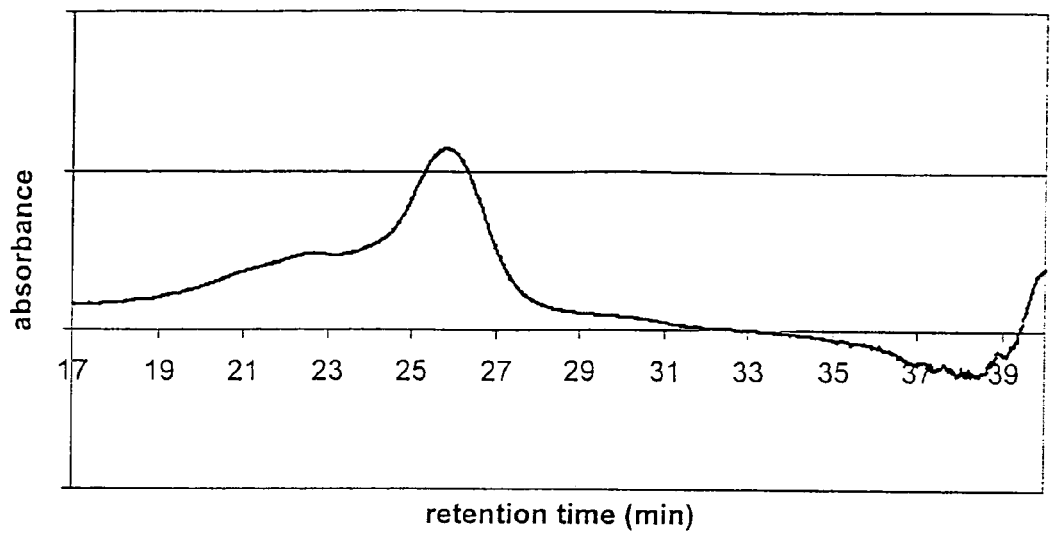
FIG. 12 illustrates co-incorporation of cytochrome P450 reductase and cytochrome P450 6B1 in MSP Nanodiscs. The ratio of absorbances at 456 nm (predominantly reductase) to that at 420 nm (predominantly P450) is plotted as a function of retention time. The peak at about 26 min indicates a Nanodisc population containing both reductase and cytochrome.

Based on the lipid concentration contained in the microsomal preparations, MSP technology was used to assemble microsomal proteins into nanoparticle discs using a ratio of 110:1:220 lipid:MSP1:cholate. The microsomal sample was detergent solubilized with neutralized cholate and mixed with MSP1. The sample was incubated at 4° C. for 2 hours. The detergent can be removed by dialysis or adsorption to hydrophobic beads. In this experiment Biobeads (hydrophobic beads, trademark of BioRad, Hercules, Calif.) were added in excess (0.25 g per 1 ml disc mixture) and incubated for 2 hours at 4° C. for 2 hours to remove detergent. The sample was removed from the beads and the $His_6$-tagged MSP was isolated by using a batch purification method with $Ni^{2+}$ resin. The MSP disks were then isolated by Superdex sizing column chromatography (FIG. 9). Incorporation of P450 into the $His_6$-tagged discs was followed by CO difference spectroscopy of nickel affinity column purified and sizing column-purified fractions (FIG. 10). SDS-PAGE was performed using 8-25% gradient gels stained with Coomassie blue to verify incorporation of cytochrome P450 6B1 into discs (FIG. 10).

The endogenous (natural) ratio of cytochrome P450 to reductase is about 10-20. To obtain activity of the cytochrome P450 6B1 after reconstitution into discs, it is preferred that an excess of reductase be added to the reconstitution mixture, such that a P450 molecule and reductase molecule both partition into a single disc. Supplementation of the microsomal preparation with exogenously added reductase has been successfully demonstrated.

Figure 13:
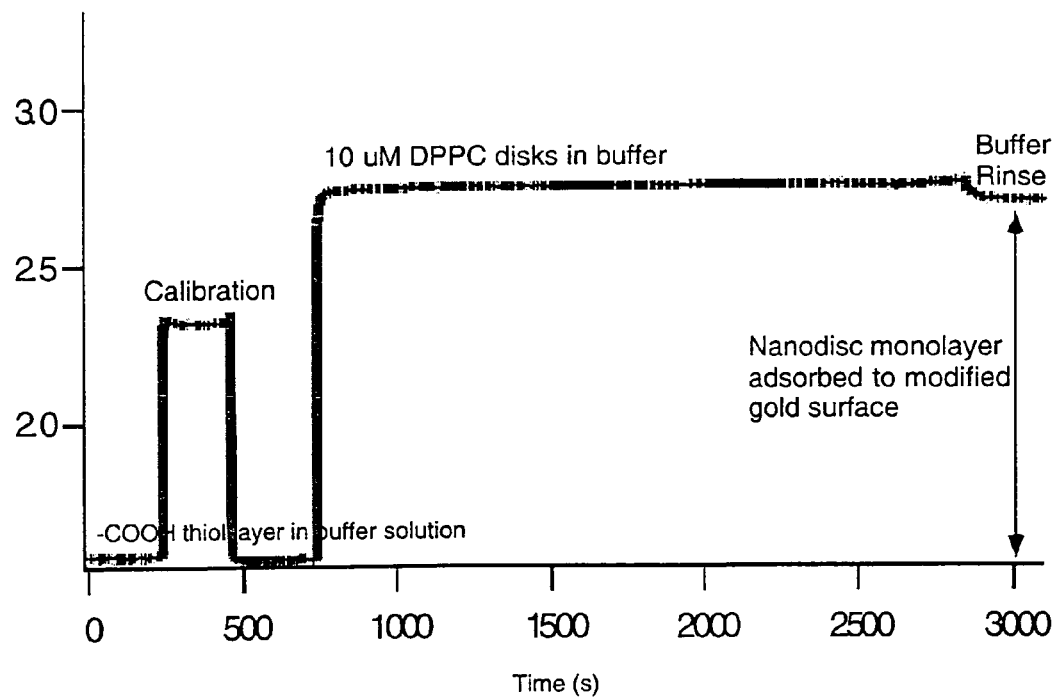
FIG. 13 illustrates the binding of DPPC Nanodiscs containing carboxyl terminated thiols to a gold surface, as monitored by surface plasmon resonance.

The protocol for making discs using microsomal preparations was used with one modification. Exogenous rat reductase was added after the solubilization step of the microsomal preparation with sodium cholate and before the addition of MSP1. Otherwise identical disc assembly and purification procedures were followed. The sample was separated by a Superdex sizing column, where absorbance at 280 nm indicates the presence of MSP1, absorbance at 420 and 456 nm indicates the presence of ferric species, and absorbance at 456 nm also indicates presence of reductase. A ratio plot of 456 to 420 nm was made; it showed positions on the chromatogram where the absorbance at 456 nm was above that associated with cytochrome P450 6B1 and, therefore, could be attributed to absorbance by reductase. Retention times reflected the presence of 10 nm particles containing cytochrome P450 6B1 and reductase (FIG. 13).

MSP-supported Nanodiscs with purified proteins, membrane fragments or disrupted membranes can be used in high throughput screening ventures, for example, to identify new pharmaceuticals and other biologically active molecules.

Example 8

Integral Membrane Protein Incorporation

Bacteriorhodopsin (BR) is a model integral membrane protein, and a model seven transmembrane domain protein. BR was incorporated into nanoscale structures using the following procedure, which is a protocol useful for other proteins as well. BR was obtained as lyophilized purple membrane from Sigma (St. Louis, Mo.). 1 mg BR was suspended in 1 ml 25 mM potassium phosphate, pH 6.9. 1 ml 90 mM n-octyl β-D-glucopyranoside in the same buffer was added and the sample placed in the dark at 24° C. overnight. This treatment produces a detergent-solubilized monomeric form (Dencher et al., 1982). BR was quantitated assuming a molar extinction coefficient at 550 nm of 63,000. BR (7.8 µM) was mixed with MSP1 (97 µM) or MSP2 (110 µM) and cholate (50 mM) to give final molar ratios of MSP1:BR of 10:1 or MSP2:BR of 5:1 and a cholate concentration of approximately 8 mM. For reconstitution with phospholipid, the lipid is solubilized as above in the presence of 50 mM cholate and mixed with MSP1 at a mole ratio of 1 MSP1:110 lipids:0.1 BR. The mixture was incubated at room temperature for ~3 hours followed by dialysis overnight against 1000 volumes of buffer using 10,000 MW cutoff dialysis devices (Slide-a-lyzer, Pierce Chemical). Dialysis was continued at 4 degrees for 2 days with several changes of buffer. 10 mM HEPES, pH 7.5, 0.15 M NaCl buffer can be used. Tris buffer pH 7.5 or pH 8 has also been used successfully.

The human 5-hydroxytryptamine 1A G protein coupled receptor has been incorporated into MSP-containing nanoparticles. A commercially available insect cell expression system that provides a membrane fraction containing the human 5-hydroxytryptamine 1A (5-HT-1A) GPCR was used as a source of this GPCR to prepare Nanodiscs. Briefly, the 5-HT-1A receptor containing membrane preparation was mixed with phospholipids (phosphatidyl choline, phosphatidylethanolamine, phosphatidyl serine) at a ratio of 45:45:10, MSP1 and cholate (neutralized cholic acid).

5-HT-1A receptors overexpressed in a commercially available Sf9 insect cell membrane preparation (Sigma Chemical Co., St. Louis, Mo.) were solubilized using the following protocol. POPC, POPS and POPE (Avanti Phospholipids) in chloroform were mixed in a 45:10:45 mole ratio and dried down under a stream of nitrogen, then placed under vacuum for several hours to remove residual solvent. The phospholipids were dispersed in 50 mM Tris pH 7.4, 0.2 M NaCl, 50 mM sodium cholate buffer at a concentration of 25 mM phospholipid. Five microliters of the Sf9 membrane preparation (0.2 mg/ml protein), 1.62 microliters of phospholipid in buffer, 2.4 microliters of MSP1 (4.2 mg/ml) and 0.28 microliters 4 M NaCl were mixed and left for 1 hour on ice. The mixture was diluted to 100 microliters total volume with 50 mM Tris pH 7.4 and dialyzed in a mini slide-a-lyzer (Pierce Chemical) against 50 mM Tris pH 7.4 at 4° C. (two one-liter changes of buffer).

To determine the amount of 5-HT-1A receptor associated with Nanodiscs, a radiolabeled ligand was bound to the receptor and disk-receptor-ligand complexes were isolated using the 6-histidine tag present in the MSP1 according to the following protocol. After dialysis, the mixture was diluted to 200 microliters total volume with 50 mM Tris pH 7.4. Ninety-five microliters of the diluted mixture were placed into each of two tubes. One hundred five microliters of stock reagent were added to give final concentrations of 50 mM Tris pH 7.4, 10 mM $MgSO_4$, 0.5 mM EDTA, 0.1% ascorbic acid in a final volume of 200 microliters. Tritium-labeled 8-hydroxy-DAT (specific activity 135000 Ci/mole) was added to each tube to give a concentration of 1.5 nM. As a control, unlabeled metergoline (final concentration 100 micromolar) was added to one of the tubes as a competitive ligand. After 1 hour on ice, the mixture was applied to 200 microliters of Ni-chelating resin to specifically bind receptor associated with His-tagged MSP1 disks. The resin was washed three times with 0.5 ml of cold 50 mM Tris pH 7.4 to remove non-specifically bound ligand. Specifically bound radiolabeled 8-hydroxy-DAT bound to receptor/disk complexes were eluted with 0.5 ml 0.5 M imidazole in 10 mM Tris pH 7.4, 0.5 M NaCl. Scintillation cocktail was mixed with the eluate and specifically bound radioligand was determined by scintillation counting. Between five and fifteen percent of the receptor initially present in the Sf9 membrane was found to bind ligand in receptor associated with MSP1 Nanodiscs.

The particles into which the 5-HT-1A GPCR had incorporated were dialyzed. Functionality (in terms of ligand binding) was tested by incubation with buffer containing tritiated 8-OH-DAT, an agonist of this receptor. The particles were then run over a Ni-NTA column to bind via the histidine tag on the MSP1 and to separate the particles from 8-OH-DAT which had not bound to the particles, and the material bound to the column was then eluted. Association of the tritium labeled agonist was demonstrated, showing that the incorporated GPCR retained its ability to bind agonist.

As discussed above for the tethered membrane proteins, the integral and embedded membrane proteins can be incorporated into Nanodiscs using MSPs and solubilized membrane preparations, rather than purified, solubilized proteins. The naturalistic presentation of the proteins within the Nanodiscs is maintained, regardless of whether the proteins were purified or whether they were directly derived from membrane preparations.

Example 9

Analysis of MSP-Supported Nanodisc Phospholipid Assemblies

The particles resulting from self-assembly of membrane scaffold proteins and phospholipids, either with or without an additional target protein, were analyzed as follows.

Bacteriorhodopsin-containing particles were dialyzed, and the resulting mixture was injected onto a Superdex 200 HR10/30 gel filtration column (Pharmacia) and eluted with buffer at 0.5 ml/min at room temperature. Absorbance was monitored at 280 nm for protein and 550 nm for BR. 0.5 ml fractions were collected. The column was calibrated using a mixture of thyroglobulin (669 kDa, Stoke's diameter 170 A), ferritin (440 kDa, Stoke's diameter 122 A), catalase (232 kDa, Stoke's diameter 92 A), lactate dehydrogenase (140 kDa, Stoke's diameter 82 A), bovine serum albumin (66 kDa, Stoke's diameter 71 A), and horse heart cytochrome c (12.4 kDa, Stoke's diameter 35.6 A).

Atomic Force Microscopy was performed with a Digital Instruments Nanoscope IIIa in contact mode with sharpened silicon nitride probes under buffer. MSP1 and MSP2 dipalmitoyl phosphatidylcholine particles were treated with 1:50 Factor Xa:MSP protein by mass in 10 mM Tris pH 8, 0.15 M NaCl, 2 mM $CaCl_2$ for 8 hours. 2-10 ml sample was placed on a freshly cleaved mica surface along with 20 ml imaging buffer (10 mM Tris pH 8, 0.15 M NaCl, 10 mM $MgCl_2$) and incubated for 30 minutes or longer before mounting sample in the fluid cell. Several milliliters of buffer were flushed through the fluid cell to remove unadsorbed material.

Phosphate analysis of the nanoscale particles was carried out as follows. Phosphate assay procedures were adapted from Chen et al. (1956) and Fiske and Subbarow (1925). Samples containing roughly 40 nmoles lipid phosphate were dried down in glass tubes. 75 µl 8.9 N $H_2SO_4$ was added to each tube and heated to 210° C. for 30 minutes. 1 drop 30% $H_2O_2$ was added to each tube and heated for 30 minutes. Tubes were cooled, 0.65 ml $H_2O$ was added followed by 83.3 µl 2.5% w/v ammonium molybdate tetrahydrate followed by vortexing and the addition of 83.3 µl 10% w/v ascorbic acid. After mixing, the tubes were placed in a boiling water bath for 7 minutes. Absorbance was read at 820 nm. Absorbance was calibrated using potassium phosphate standards from 0 to 100 nmol phosphate. Buffer blanks from column chromatography were included for MSP proteins.

Example 10

MSP-supported Structures on Surfaces

Nanodiscs comprising MSPs and a protein of interest can be assembled onto a gold surface or other solid surface (solid support). The utility of this relates to the resulting epitaxial presentation of a target incorporated into a Nanodisc assembly to the solution. This offers an ideal system for quantitating binding of other macromolecules or small molecules tagged with dielectric contrast agents to the target protein. A common method of accomplishing such measurements uses surface plasmon resonance (SPR) technology. SPR is a common technique used to monitor biomolecular interactions at surfaces. The ability of SPR to rapidly detect and quantitate unlabeled protein interactions on gold surfaces is useful for creating high through put chip assays for diverse membrane proteins (embedded and solubilized) on discs.

Discs consisting of the phospholipid DPPC either with or without an additional thiolated lipid and MSP1 protein were prepared as follows. A 25 mM lipid mixture containing phosphatidylcholine was solubilized with 50 mM cholate in 10 mM Tris Cl, 150 mM NaCl at pH 8.0 were combined and incubated overnight at 37° C. For thiolated discs, 90% phosphatidylcholine and 10% thiolated lipid (ATA-TEG-DSPA, Northern Lipids, Vancouver, BC, Calif.) was solubilized in 3.3 mM Tris Cl, 66.7 mM borate, 150 mM NaCl at pH 9.0 in order to unmask the thiols in the thiolated lipids. MSP1 and lipid (1:100) were combined and incubated overnight at 37° C. The sample was then dialyzed at 37° C. (10,000 MW cutoff membrane) against buffer containing 10 mM Tris Cl, 150 mM NaCl at pH 8.0 without cholate for 2 hours. Dialysis was then continued at 4° C. for an additional 6 hours with buffer changes every 2 hours. The approximately 1 ml sample was concentrated to <250 µl using a YM-10 centrifuge concentrator and injected onto a Pharmacia 10/30 Superdex 200 HR gel filtration column. Samples were eluted from the column using the stated buffer without cholate at flow rates of 0.5 ml/min. Fractions from chromatography were analyzed by polyacrylamide gel electrophoresis using 8-25% gradient polyacrylamide gel to determine apparent size.

The Nanodisc samples (3-20 µM) prepared as described were injected into an SPR instrument to determine if the discs would bind to the gold surface. Both the DPPC and 10% thiolated lipid discs adsorbed to a gold surface and a modified gold surface covered with a monolayer of methyl terminated thiol (nonanethiol) or carboxyl terminated thiol (11-mercaptoundecanoic acid). Thiolated discs were injected using a buffer consisting of 3.3 mM Tris, 66.7 mM borate, 150 mM NaCl, pH 9.0. DPPC discs were injected using a buffer of 10 mM Tris, 150 mM NaCl, pH 7.5 or pH 8.0. In all cases, the discs could not be removed even under harsh conditions (0.5 M HCl). Surface coverage was shown to increase with increasing concentration of discs injected (3 µM vs. 19 µM). Discs do not form perfectly packed monolayers; accordingly, surface coverage is limited by the jamming limit (theoretical maximum coverage based on random sequential absorption to the surface modeling discs as identical non-overlapping hard spheres) of 0.547. The coverage for a full monolayer of discs was calculated based on an assumption of disc height of 5.5 nm and a refractive index between 1.45 and 1.5. The full monolayer values were multiplied by the jamming limit to determine the maximum coverage that was then used to determine percent coverage based on experimental values. When the disc concentration was at least 10 µM, the estimated coverages were between about 62 and about 103%. The resultant SPR trace demonstrating association of the Nanodiscs to the gold surface is shown in FIG. 14.

Nanodiscs comprising MSPs and a protein of interest can be attached to a solid support via the His tag on the MSP where the support is coated with Ni-NTA or a His tag-specific antibody, commercially available from BD Biosciences Clontech, Palo Alto, Calif., for example, or to Ni-NTA agarose beads, commercially available from Qiagen, Valencia, Calif., for example, or other solid support, including beads, chips, plates and microtiter dishes.

Example 11

General Techniques

For SDS-PAGE, microliter samples were separated on 8-25% gradient polyacrylamide gels (Pharmacia) and stained with Coomassie blue.

Sizing column chromatography purification was carried out as follows. The nickel affinity-purified sample mixture was injected onto a Superdex (Trademark of Pharmacia, Piscataway, N.J.) 200 HR10/30 gel filtration column (Pharmacia) equilibrated in 0.1M sodium phosphate buffer (pH 7.4) at a flow rate of 0.5 ml/min. Fractions containing CYP6B1 were concentrated using a Centricon YM-30 centrifugal filter device (Millipore Corporation, Billerica, Mass.) and re-injected onto the Superdex 200 HR10/30 gel filtration column under the same buffer conditions.

Lipids were extracted by the Folch method (Folch-Pi et al. (1957)), where the sample was homogenized with 2:1 chloroform-methanol (v/v) and washed with ¼ volume 0.88% KCl in water. The solution was mixed vigorously and the phases were completely separated by centrifugation (3,000× g) for 5 minutes.

Nanodisc assembly is generally carried out as follows. The protein concentration of the membranes was determined using a BCA™ (bicinchoninic acid) protein assay kit from Pierce (Rockford, Ill.). We assumed a 1:1 mass relationship of protein: lipid in the membranes with an average molecular weight of phospholipids of 750 grams/mole. The membranes were detergent solubilized with 0.5 M cholic acid (neutralized) and mixed with MSP in the approximate ratio of 1:25:50 to 1:2000:1000 with 1:75:150 preferable. The membranes were detergent solubilized with 0.5 M cholic acid (neutralized) and mixed with MSP in the approximate ratio of 1:100: 200 for MSP:lipid:detergent. Typically, reconstitution samples include approximately 100 nmol membrane scaffold protein, 10 µmol lipid, and 20 µmol cholate and were pre-incubated for 1.5 hours at 4° C. Detergent was removed by incubating with Biobeads® SM-2 Adsorbent from BioRad Laboratories (Hercules, Calif.) (0.4 grams Biobeads per 1 ml of reconstitution mixture) for 1.5 hours at 4° C. followed by centrifugation at 11,750×g for 5 minutes. His6-tagged MSP particles were purified by incubating with 1 ml of Ni-NTA agarose from Qiagen, Inc. (Valencia, Calif.) per 7.5 milligrams of His6-tagged MSP for 1 hour at 4° C., followed by centrifugation at 11,750×g for 5 minutes. MSP particles bound to the Ni-NTA agarose were washed with three sequential resin volumes of 0.1 M sodium phosphate buffer (pH 7.4) containing 0.3 M NaCl, 0.15 M NaCl, and no NaCl, respectively. To maintain the integrity of the CYP6B1 protein, MSP particles were eluted with 0.1 M sodium phosphate buffer (pH 7.4) containing 0.25 M EDTA rather than the 50 mM imidazole used in previous MSP purifications.

Thin-Layer Chromatography (TLC) is carried out as follows. Samples were spotted onto preparative silica gel stationary phase TLC plates purchased from EM Science (Hawthorne, N.Y.) alongside phospholipid standards purchased from Avant (Alabaster, Ala.) and developed using a mobile phase of chloroform/methanol/ammonium hydroxide (65:25:4). TLC plates were exposed to iodine vapor for visualization, scanned using a Hewlett Packard ScanJet, and quantified on a Macintosh computer using the public domain NIH Image program developed at the U.S. National Institutes of Health (available on the internet at the website entitled rsb.info.nih.gov/nih-image).

Example 12

Substrate Binding

The CYP6B1-containing population of Nanodiscs collected after Superdex size fractionation was concentrated to an enzyme concentration of 50 nM. A microtiter plate was arranged with wells A1-A5 and wells B1-B5 each containing 200 µl Nanodisc samples and wells C1-C5 each containing 200 µl buffer (0.1 M sodium phosphate, pH 7.4). To rows A and C, a 20 mM stock concentration of xanthotoxin (Sigma Chemical Co.) in methanol was added to yield final concentrations of 0 µM (column 1), 10 µM (column 2), 20 µM (column 3), 50 µM (column 4), and 150 µM (column 5). This dilution was such that the total organic solvent content did not exceed 1% when added to the Nanodisc samples. To row B, 0 µl, 0.1 µl, 0.2 µl, 0.5 µl, and 1.5 µl methanol were added.

The contents of each microtiter well were scanned at 1 nm increments using a SpectraMAX® Plus microplate spectrophotometer (Molecular Devices, Sunnyvale, Calif.) and were corrected for the background buffer absorbance (defined in row C) and Nanodisc absorbance (well A1).

Example 13

Nanodiscs with Larger MSPs

The relatively larger Nanodiscs (the "extended" membrane scaffold protein sequences) are useful in controlling the oligomerization state of 7-Tm receptors or other hydrophobic or partially hydrophobic proteins which are particularly large or which tend to oligomerize incorporated into Nanodiscs. As specifically exemplified, a bacteriorhodopsin trimer is self-assembled in larger nanodiscs using the longer MSPs.

Purple membrane was isolated from *Halobacterium salinarum* JW-3 cultures as described (Oesterhelt and Stoeckenius 1974). Sucrose was removed by centrifugation at 35,000 rpm in a Beckman Ti-45 rotor for 15 minutes followed by resuspension in water. This process was repeated three times, the sample was aliquoted, lyophilized and stored at −20° C. Concentrations of MSPs were determined from absorbance at 280 nm using extinction coefficients of 24740 $M^{-1}$ $cm^{-1}$ for MSP1 and 31720 $M^{-1}$ $cm^{-1}$ for the other MSPs based on calculated extinction coefficient (Gill and von Hippel 1989). The extinction coefficient in nanodisc buffer for MSP1E1, MSP1E2 and MSP1E3 was found to be equal to the calculated value in 20 mM phosphate buffer, 6 M guanidine HCl pH 6.5. DMPC was obtained from Avanti Polar Lipids, Inc., dissolved in chloroform and quantitated by phosphate analysis (Chen, Toribara et al. 1956). Buffer consisted of 10 mM Tris HCl pH 7.4, 0.1 M NaCl, 0.01% $NaN_3$ unless stated otherwise. Water was purified with a Milli-Q system (Millipore). All other materials were high-quality reagents.

To self-assemble nanodiscs with bacteriorhodopsin and extended MSPs, bacteriorhodopsin was initially solubilized with 4% w/v Triton X-100 as described (Dencher and Heyn 1978). MSP stock solutions (200-400 µM) and a DMPC/cholate mixture (200/400 mM in buffer) were added to bR in eppendorf tubes or Falcon tubes (typically about 190 µM) to give MSP to bR molar ratios of 2:3 and different phospholipid ratios. After one hour at room temperature, detergent was removed by treatment for 3-4 hours with 400 mg wet Biobeads SM-2 (BioRad) per ml of solution, with gentle agitation to keep the beads suspended (Levy, Bluzat et al. 1990). Beads were removed by centrifuging the suspension through a pinhole made in the bottom of the tubes.

Self-assembled Nanodisc mixtures were filtered through 0.22 micron filters and injected onto a size exclusion chromatography column (Superdex 200 HR 10/30 column) run at 0.5 ml/min at room temperature with collection of one minute fractions. Peak elution was monitored at 280 and 560 nm.

Figure 20:
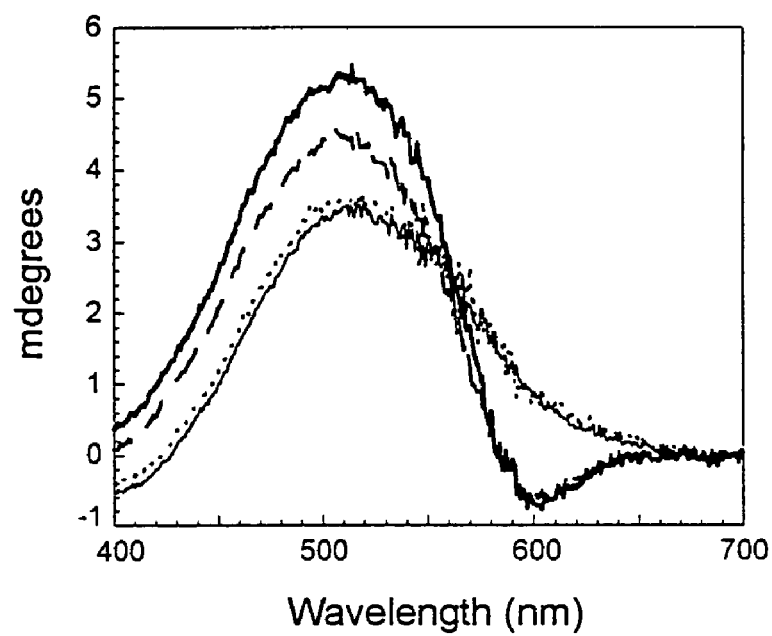
FIG. 20 shows size exclusion chromatography elution profiles for the Nanodiscs self-assembled with: A—MSP1—DPPC; B—MSP1E1—DPPC; C—MSP1E2—DPPC; D—MSP1E3—DPPC. Curve E shows the elution profile of the set of calibration proteins: 1—Bovine serum albumin, 2—Bovine liver catalase, Stokes diameter 10.4 nm; 3—Ferritin, diameter 12.2 nm; 4—Thyroglobulin.

Nanodiscs were analyzed by SDS-PAGE, protein was quantified, and lipid stoichiometry was determined. Samples containing MSP1E3 and different amounts of bR as calibration standards were separated on 20% SDS-PAGE using a Phastgel system (Pharmacia) along with gel-filtration purified samples of MSP1E3-bR nanodiscs. After staining with Brilliant blue R-250, gels were scanned and bands quantitated using the computer program NIH image to determine the ratio of bR to MSP1E3 in nanodiscs. The amount of lipid per bR in MSP1E3 disks was determined using the extinction coefficient $\epsilon_{560}$=56,600±1200 $M^{-1}$ $cm^{-1}$ for bR in MSP1E3 nanodiscs measured by the method of retinal titration and phospholipid content was determined by phosphate analysis (Chen, Toribara et al. 1956; Rehorek and Heyn 1979). Circular dichroism spectra were measured with a Jasco J-720 spectrapolarimeter at ambient temperature at a sample OD of approximately 2.

bR-MSP mixtures at a 3 to 2 ratio were titrated with lipid to determine optimal ratios for bR solubilization as assessed by gel filtration chromatography. The optimal ratio is chosen as the ratio at which the main peak of solubilized bR is the major component with a minimum amount of larger species. At less than optimal ratios, species of smaller size appear. The optimal ratios for MSP1, E1, E2, and E3 determined in this manner are 10:1, 10:1, 55:1 and 80:1, respectively with main peak being approximately 80% of total bR injected. The results of reinjection of the pooled main peaks are shown in FIG. 19. The sizes based on calibration of the column with a set of standard proteins are 11, 11.4, 12.2, 12.8 nm in diameter for MSP1EI, MSP1E2, and MSP1E3, respectively.

bR in purple membrane exhibits excitonic interactions between bR retinal chromophores in trimers which give rise to a positive and a negative peak in the CD spectrum. The monomeric forms of bR show a single positive peak arising from interaction of retinal with the protein environment. CD spectra of bR solubilized by MSP's at the optimal lipid ratios are shown in FIG. 20. Only MSP1E2 and MSP1E3 have a negative peak at 600 nm, indicating assembly of a trimeric form of bR in the nanoscale discoidal particles.

Example 14

Amphotericin B-loaded Nanodiscs

Two Nanodisc preparations, one containing Amphotericin B (AmB) and one without (as control) are made. The ratio of MSP1T2/POPC/AmB in AmB particles is 2:130:1, and the ratio of MSP1T2/POPC in the control particle preparation is 1:65.

Synthetic 1-Palmitoyl-2-Oleoyl-sn-Glycero-3-Phosphocholine (POPC) is obtained from Avanti Polar Lipids (Alabaster, Ala.) and prepared as a 75 mM (a concentration within the range of 70 to 80 mM is acceptable) stock in chloroform and stored at −20° C. The lipid concentration is determined by quantifying total phosphorus using the method of Chen et al. (1956). Amphotericin B (AmB) powder is obtained from Sigma (St. Louis, Mo.) and prepared as 2 mM stock in DMSO, protected from light and stored at −20° C. MSP1T2 is expressed and purified as described by Denisov et al. (2004).

AmB is added to POPC lipid solution to give a lipid:AmB molar ratio of 65:1. The solution is dried under a stream of nitrogen and placed under vacuum overnight to remove residual solvent. Manipulations of samples containing AmB were protected from light whenever possible. The mixture is resuspended by the addition of 100 mM cholate in standard buffer (10 mM Tris-HCl (pH 7.4), 0.1M NaCl, 1 mM EDTA) to yield a lipid concentration of 50 mM. The tubes are vortexed, sonicated, and heated briefly in a 37° C. water bath, until the mixture is completely solubilized.

MSP1T2 protein is added to the lipid/AmB/cholate solution to give a protein/lipid/AmB ratio of 2:130:1. The final lipid concentration is approximately 15 mM. The mixture is incubated for 2 h at 4° C., near the phase transition temperature for POPC. BioBeads are added to remove cholate, and the sample is incubated for an additional 2 h at 4° C. Samples are separated by size exclusion chromatography on a Superdex 200 HR 10/30 column (Amersham Biosciences, Piscataway, N.J.), and the 10 nm fractions were retained. Concentration of Amphotericin B is determined by comparing the $A_{405}$ to a standard curve of Amphotericin B constructed from 1 to 20 µg/ml. Nanodisc concentration is determined by measuring $A_{280}$ (MSP1T2 $\epsilon_{280}$=21,000 $M^{-1}$ $cm^{-1}$).

Example 15

Ketoconazole-loaded Nanodiscs

Nanodiscs containing the small molecule antifungal ketoconazole were prepared by incubating MSP1T2, ketoconazole, DMPC, and cholate at a molar ratio of 1:10:80:160, respectively. The mixture was incubated at 25° C. for 45 min, BioBeads were added (50% w/v), and incubation was continued for an additional 45 min. Incubation with BioBeads removed cholate, and resulted in the self assembly of Nanodiscs and the partitioning of lipophilic ketoconazole to the bilayer environment of nascent Nanodiscs. The ketoconazole containing Nanodiscs were purified by nickel affinity chromatography and the column eluate was concentrated by diafiltration with Standard Buffer (20 mM Tris-HCl (pH 7.4), 0.1 M NaCl, 0.5 mM EDTA).

Figure 21A:
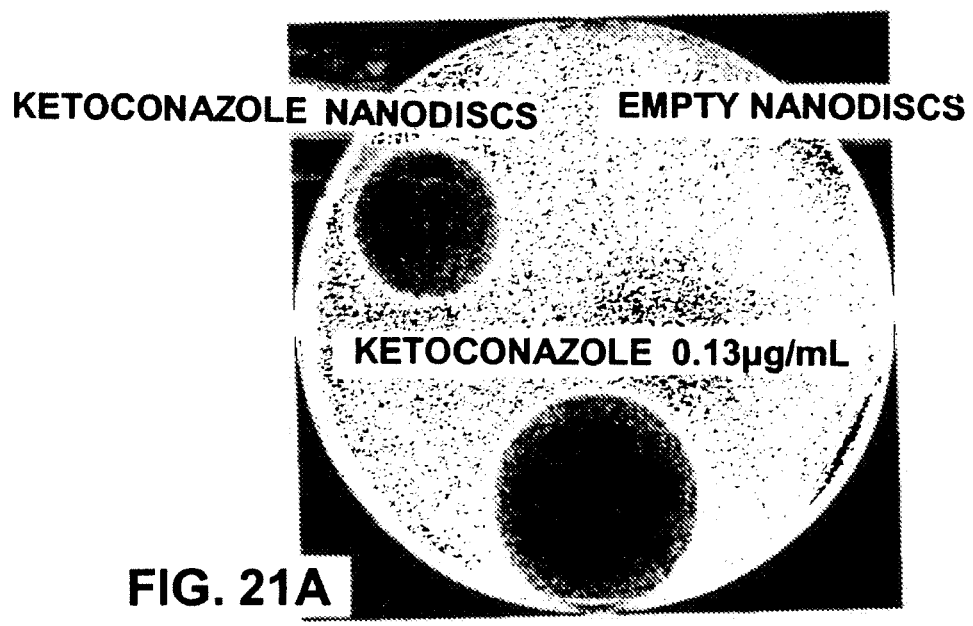
FIG. 21A shows the inhibition of *Candida albicans* by Nanodiscs loaded with ketoconazole and by a solution of ketoconazole in 1% DMS. There was no inhibition by "empty" Nanodiscs.
Figure 21B:
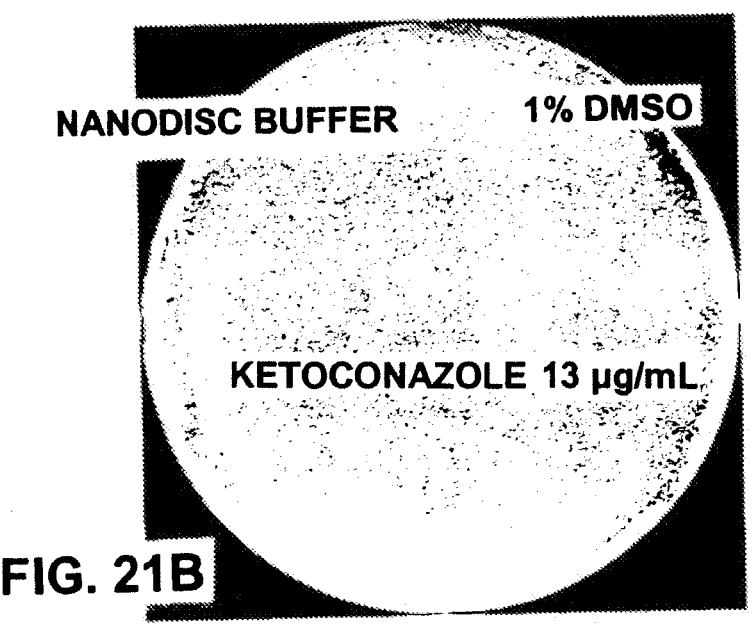
FIG. 21B shows that there is no growth inhibition by the Nanodisc buffer, 1% DMSO or by the lower amount of ketoconazole.

Antifungal activity of the ketoconazole-containing Nanodisc preparation was qualitatively assayed against a lawn of *Candida albicans* grown on Yeast Potato Dextrose (YPD) agar. A colony of freshly grown *C. albicans* was mixed in sterile water, and 1 ml of the cell suspension was evenly applied to the surface of a YPD-agar plate. The excess cell liquid was decanted and 20 µl aliquots of Nanodiscs containing ketoconazole, Nanodiscs prepared without ketoconazole (empty Nanodiscs), and 13 µg/ml ketoconazole solution in 1% DMSO were spotted separately onto the surface of the plate (FIG. 21A). The plate was incubated for 18 hr at 35° C. Nanodiscs containing ketoconazole inhibited the growth of the *C. albicans* in a manner consistent with the ketoconazole control, whereas empty Nanodiscs showed no effect of fungal growth. This result demonstrates that the ketoconazole antifungal activity co-purified with the Nanodiscs and indicates that ketoconazole was associated with the Nanodiscs following self-assembly. Application of 20 µl aliquots of Standard Buffer or 1% DMSO showed no antifungal activity (FIG. 21B). Addition of 20 µl of a 0.13 µg/ml solution of ketoconazole did not visibly inhibit growth, indicating that the application of this 100-fold lower concentration of the drug was too dilute to affect the fungi at the cell density present on the plate.

Example 16

Gadolinium-containing Nanodiscs

Nanodiscs containing an amphiphilic gadolinium chelate can be made by incorporating phospholipid or other type of lipid having a chelating group as the polar headgroup portion of the amphiphilic lipid. One such phospholipid is synthesized by reacting phosphatidylethanolamine with the dianhydride of diethylenetriaminepentaacetic acid (DTPA) to yield a tetradentate chelating phospholipid which can be loaded with $Gd^{3+}$ either before or after assembly of nanodiscs. The chelating lipid with or without bound $Gd^{3+}$ can be mixed with or without other types of phospholipid in organic solution followed by removal of solvent and formation of nanodiscs by the usual methods.

Another chelating agent suitable for gadolinium cations is 1,2-dipalmitoyl-sn-glycero-3-phosphoethanolamine-N-diethylenetriaminepentaacetate (DPPE-DTPA). An ethylenediaminetetraacetate (EDTA) derivative can be used in place of the DTPA group. Dimyristoyl and distearoyl can substitute for the dipalmitoyl moieties. The relatively long chain fatty acids attached to the remainder of the chelating molecule facilitate uptake of the gadolinium or other ion of interest (including but not limited to trivalent cations of iridium, technecium, and lanthanides in general) into the Nanodisc particles. DTPA phospholipids are useful. See Urizzi et al. (1996) Tetrahedron Lett. 37:4685-4688 for a discussion of lipophilic chelating agents.

Example 17

Nanodiscs Containing Photodynamic Compounds

Nanodiscs containing a photodynamic compound, especially a therapeutic photodynamic compound are prepared essentially as described herein above for Amphotericin B and ketoconazole but with the use of the photodynamic compound, such as a psoralen, phthalacyanin or porphyrin, with the modification that stock solutions, assembly reactions and Nanodisc preparations are protected from light.

Example 18

Fluorescently Labeled Nanodiscs

The methodology for preparation of Nanodiscs containing small organic molecules, in particular fluorescent labels is as follows.

All glassware involved in this procedure is to be washed with 1M KOH and sonicated for 15 minutes when possible.

Two Nanodisc preparations, one labeled and one unlabeled are described. The ratio of MSP1/DPPC/DiI in the labeled prep is 1/100/.05 with 0.5 mg of MSP1 used, and the ratio of MSP1/DPPC in the unlabeled prep is 1/100 with 2 mg of MSP1 used. DPPC is obtained from stock solutions dissolved in chloroform. Appropriate amounts of DPPC are delivered to two glass tubes. DiI in ethanol is added to the labeled disc prep tube. Solvent is dried down using nitrogen, and samples are placed in a vacuum dessicator overnight to remove residual solvent.

50 mM cholate in standard buffer (10 mM Tris-HCl pH 7.4, 0.1M NaCl, 1 mM EDTA, 0.01% $NaN_3$) is added to the dried lipid samples to yield 25 mM final lipid concentration. The tubes are vortexed, heated, and sonicated until lipid is completely in solution. 0.5 mg of MSP1 in buffer at 37° C. is added to the sample to be labeled, and 2 mg of MSP1 in buffer at 37° C. is added to the unlabeled sample. The samples are incubated at 37° C. for 4 hours. Dialysis is then performed to remove the sodium cholate. Dialysis is done at 37° C. in standard buffer for 24 hours with 3 buffer changes.

Both samples are concentrated to about 0.3 ml, filtered, and subjected to size exclusion chromatography on a Superdex column. Fractions are collected, combining and saving those which contain particles with a diameter of about 10 nm. Concentration of the Nanodiscs is determined by measuring absorption at 280 nm ($A_{280}$ of 1 mg/ml MSP1 is 1.0). Absorption of DiI at 280 nm is assumed to be negligible in the labeled disc sample.

BIBLIOGRAPHY

Angrand, M. et al. (1997) *Eur. J. Biochem.* 250:168-76.
Atkinson, D. and Small, D. M. (1986) *Ann. Rev. Biophys. Chem.* 15: 403-456.
Bayburt, T. H. et al. (1998) *J. Struct. Biol.* 123: 37-44.
Bayburt, T. H. et al. (2000) *Langmuir* 16: 5993-5997.
Bayburt, T. H. et al. (2002) *Nano Letters* 2:853-856.
Boguski, M. S. et al. (1986) *J. of Lipid Research* 27: 1011-1034.
Borhani, D. W. et al. (1997) *Proc. Natl. Acad. Sci. USA* 94: 12291-12296.
Brouillette, C. G. et al. (1984) *Biochemistry* 23: 359-367.
Brouillette, C. et al. (2001) *Biochim. Biophys. Acta* 1531:4-46.
Carlson, J. W. et al. (2000) *Langmuir* 16: 3927-3931.
Carlson, J. W. et al. (1997) *Biophys. J.* 73: 1184-1189.
Chen et al. (1956) *Anal. Chem.* 28:1756-1758.
Chen, J. S. et al. (2002) *Insect Molecular Biology* 11:175-186.
Dalton, M. B. and Swaney, J. B. (1993) *J. Biol. Chem.* 268: 19274-19283.
Dencher, N. A. and Heyn, M. P. (1982) *Methods Enz.* 88:, 5-10.
Denisov, I. G., Grinkova, Y. V., Lazarides, A. A. and Sligar, S. G. (2004) *J. Am. Chem Soc.* 126: 3477-3487.
Drake et al. (1989) *Am. J. Pathol.* 134: 1087-1097.
Durbin, D. M. and Jonas, A. (1999) *J. Lipid Research* 40: 2293-2302.
Estabrook, R. W., and J. Werringloer. (1978) *Meth. Enzymol.*52:212-20.
Fidge, N. H. (1999) *J. Lipid Research* 40: 187-201.
Fielding, P. E. and Fielding, C. J. (1991) *Biochemistry of Lipids, Lipoproteins, and Membranes*. D. E. Vance and J. Vance. Amsterdam, Elsevier Press: 427-459.
Fiske and Subbarow (1925) *J. Biol. Chem.* 66:374-389.
Folch-Pi, J. et al. (1957) *J. Biol. Chem.* 226:497-509.
Forte, T. M. et al. (1971) *Biochim. Biophys. Acta* 248: 381-386.
Frank, P. G. et al. (1997) *Biochemistry* 36: 1798-1806.
Friis, E. P. et al. (1999) *Proc. Natl Acad. Sci. USA* 96: 1379-84.
Glomset, J. A. (1968) *J. Lipid Research* 9: 155-167.
Higuchi, R. et al. (1988) *Nucl. Acids Res.* 16: 7351.
Holvoet, P. et al. (1995) *Biochemistry* 34: 13334-13342.
Imaoka, S. et al. (1992) *Biochemistry* 31:6063-9.
Jonas, A. (1986) *Methods Enzymol.* 128: 553-582.
Jonas, A. (1991) *Biochim. Biophys. Acta* 1084: 205-220.
Jonas, A. et al. (1989) *J. Biol. Chem.* 264: 4818-4824.
Kirilovsky, J. et al. (1985) *FEBS Letters* 183:75-80.
Koppaka, V. et al. (1999) *J. Biol. Chem.* 274: 14541-14544.
Ma, R. et al. (1994) *Arch. Biochem. Biophys.* 310:332-40.
Marheineke, K. er al. (1998) *FEBS Letters* 441:49-52.
Miller, J. P. et al. (1996) *Biochemistry* 35: 1466-1474.
Mukhopadhyay, R. et al. (2000) *J. Inorg. Biochem.* 78: 251-254.
Nemerson, Y. and Repke, D. (1985) *Thromb. Res.* 40:350-358.
Omura, T., and R. Sato. (1964) *J. Biol. Chem.* 239:2370-8.
Phillips, J. C. et al. (1997) *Biophysics Journal* 73: 2337-2346.
Rezaie et al. (1992) *Protein Expression and Purification* 3: 453-460.
Robinson, C. R. and Sauer, R. T. (1998) *Proc. Natl Acad. Sci. USA* 95(11):5929-34.
Rogers, D. P. et al. (1998) *Biochemistry* 37: 945-955.
Rogers, D. P. et al. (1998) *Biochemistry* 37: 11714-11725.
Savelli, G. et al. (2000) *Curr. Opin. Colloid & Interface Science* 5:111-117.
Schafmeister et al. (1993) *Science* 262:734-738.
Segrest, J. P. et al. (1999) *J. Biol. Chem.* 274: 31755-31758.
Shaw, A. W., McLean, M. A. and Sligar, S. G. (2004) FEBS Lett. 556: 260-264
Tocanne, J.-F. et al. (1994) *Chemistry and Physics of Lipids* 73: 139-158.
Wald, J. H. et al. (1990) *J. Biol. Chem.* 265: 20044-20050.
Wald, J. H. et al. (1990) *J. Biol. Chem.* 265: 20037-20043.
Wang, M. et al. (1997) *Proc. Natl. Acad. Sci. USA* 94: 8411-8416.
Wlodawer, A. et al. (1979) *FEBS Lett.* 104: 231-2 Segr35.

What is claimed is:

1. An immunogenic composition comprising stable, soluble nanoscale discoid particles, which particles comprise a membrane scaffold protein, at least one hydrophobic or partially hydrophobic antigen molecule from a virus, a bacterium, fungus, protozoan, parasite, a human neoplastic cell or an animal neoplastic, tumor or cancer cell, and at least one phospholipid, wherein said immunogenic composition optionally further comprises an immunological adjuvant, and wherein said membrane scaffold protein is a derivative or a truncated form of human apolipoprotein A1, is amphipathic and wherein said membrane scaffold protein forms at least one alpha helix, and lacks the N-terminal globular domain of human apolipoprotein A1 (amino acids 8-50 of SEQ ID NO:2) and wherein the membrane scaffold protein is that of SEQ ID NO:6 or SEQ ID NO:9.

2. The immunogenic composition of claim 1, wherein the hydrophobic or partially hydrophobic antigen molecule is from a solubilized membrane preparation or a solubilized membrane fragment preparation.

3. The immunogenic composition of claim 1, wherein said hydrophobic or partially hydrophobic antigen molecule is a protein, a lipoprotein, lipopolysaccharide, lipooligosaccharide, glycoprotein, or a glycolipid.

4. The immunogenic composition of claim 1, wherein said artificial membrane scaffold protein comprises the amino acid sequence as set forth in SEQ ID NO: 6.

5. The immunogenic composition of claim 1, wherein the bacterium is a rickettsia or a mycoplasma.

6. The immunogenic composition of claim 1, wherein the antigenic molecule is selected from the group consisting of gp120 of Human Immunodeficiency Virus, an envelope glycoprotein of Herpes simplex virus, an envelope glycoprotein of measles virus, a "spike" protein of SARS virus, a hemagglutinin of influenza virus, a hemagglutinin of parainfluenza virus, an M6 protein of *Streptococcus pyogenes*, a fimbrillin of *Porphoryomonas gingivalis*, an InIB protein of *Listeria monocytogenes*, an ActA protein of *Listeria monocytogenes*, a YadA protein of *Yersinia enterocolitica*, an IcsA protein of *Shigella flexneri*, an invasin of *Yersinia pseudotuberculosis*, at least one acf gene product of *Vibrio cholerae*, capsular material comprising the poly-D-glutamate polypeptide of *Bacillus anthracis*, a fibrinogen/fibrin binding protein of *Staphylococcus aureus*, V and/or W antigens of *Yersinia pestis*, *Yersinia enterocolitica* or *Yersinia pseudotuberculosis*, flagellin of *Campylobacter jejuni*, a porin of *Campylobacter jejuni*, and an O antigen of *Salmonella typhi, Salmonella choleraesuis* or *Salmonella enteritidis*.

7. The immunogenic composition of claim 1, wherein the human neoplastic cell or animal neoplastic cell is a malignant melanoma cell, a gastrointestinal carcinoma cell, a neuroblastoma cell, an osteosarcoma cell, a renal carcinoma cell, a breast carcinoma cell, a lung carcinoma cell, a leukemia cell, a lymphoma cell or a myeloma cell.

8. The immunogenic composition of claim 1, wherein the nanoscale particle further comprises a molecule which targets said nanoscale particle to a cell surface.

9. The immunogenic composition of claim 8, wherein the cell surface is a mucosal cell surface.

10. The immunogenic composition of claim 9, wherein said mucosal cell surface is an intestinal mucosal cell surface.

11. The immunogenic composition of claim 8, wherein the cell surface is an epithelial cell surface.

12. The immunogenic composition of claim 1, wherein the at least one phospholipid is phosphatidyl choline, phosphatidyl ethanolamine, phosphatidyl inositol, dipalmitoyl-phosphatidylcholine, dimyristoyl phosphatidyl choline, 1-palmitoyl-2-oleoyl-phosphatidyl choline, 1-palmitoyl-2-oleoyl-phosphatidyl serine, 1-palmitoyl-2-oleoyl-phosphatidyl ethanolamine, dihexanoyl phosphatidyl choline, dipalmitoyl phosphatidyl ethanolamine, dipalmitoyl phosphatidyl inositol, dimyristoyl phosphatidyl ethanolamine, dimyristoyl phosphatidyl inositol, dihexanoyl phosphatidyl ethanolamine, dihexanoyl phosphatidyl inositol, 1-palmitoyl-2-oleoyl-phosphatidyl ethanolamine and 1-palmitoyl-2-oleoyl-phosphatidyl inositol.

13. The immunogenic composition of claim 1, wherein said artificial membrane scaffold protein comprises the amino acid sequence as set forth in SEQ ID NO: 9.

* * * * *